(12) United States Patent
Brenner

(10) Patent No.: US 9,393,292 B2
(45) Date of Patent: *Jul. 19, 2016

(54) METHODS FOR INDUCING SELECTIVE APOPTOSIS

(71) Applicant: Baylor College of Medicine, Houston, TX (US)

(72) Inventor: Malcolm K. Brenner, Bellaire, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/743,384

(22) Filed: Jun. 18, 2015

(65) Prior Publication Data

US 2015/0366954 A1 Dec. 24, 2015

Related U.S. Application Data

(63) Continuation of application No. 13/112,739, filed on May 20, 2011, now Pat. No. 9,089,520.

(60) Provisional application No. 61/347,154, filed on May 21, 2010.

(51) Int. Cl.

| | |
|---|---|
| *A61K 35/12* | (2015.01) |
| *C12N 5/10* | (2006.01) |
| *A61K 38/52* | (2006.01) |
| *A61K 35/17* | (2015.01) |
| *A61K 35/28* | (2015.01) |
| *A61K 35/545* | (2015.01) |
| *A61K 39/00* | (2006.01) |
| *C12N 5/0783* | (2010.01) |
| *C12N 5/0775* | (2010.01) |
| *A61K 38/48* | (2006.01) |

(52) U.S. Cl.
CPC ............. *A61K 38/52* (2013.01); *A61K 35/17* (2013.01); *A61K 35/28* (2013.01); *A61K 35/545* (2013.01); *A61K 38/4873* (2013.01); *A61K 39/001* (2013.01); *C12N 5/0636* (2013.01); *C12N 5/0663* (2013.01); *A61K 2039/5156* (2013.01); *A61K 2039/5158* (2013.01); *C07K 2319/00* (2013.01); *C12N 2501/48* (2013.01); *C12N 2510/00* (2013.01); *C12Y 304/22062* (2013.01); *C12Y 502/01008* (2013.01)

(58) Field of Classification Search
None
See application file for complete search history.

(56) References Cited

U.S. PATENT DOCUMENTS

| | | | |
|---|---|---|---|
| 4,514,506 A | 4/1985 | Braatz et al. | |
| 5,384,253 A | 1/1995 | Krzyzek et al. | |
| 5,538,880 A | 7/1996 | Lundquist et al. | |
| 5,550,214 A | 8/1996 | Eberlein et al. | |
| 5,550,318 A | 8/1996 | Adams et al. | |
| 5,589,343 A | 12/1996 | Marchand et al. | |
| 5,610,042 A | 3/1997 | Chang et al. | |
| 5,645,992 A | 7/1997 | Lott et al. | |
| 5,648,226 A | 7/1997 | Van Den Eynde et al. | |
| 5,709,995 A | 1/1998 | Chisari et al. | |
| 5,719,054 A | 2/1998 | Boursnell et al. | |
| 5,741,899 A | 4/1998 | Capon et al. | |
| 5,750,395 A | 5/1998 | Fikes et al. | |
| 5,780,036 A | 7/1998 | Chisari | |
| 5,830,462 A | 11/1998 | Crabtree et al. | |
| 5,834,266 A | 11/1998 | Crabtree et al. | |
| 5,840,839 A | 11/1998 | Wang et al. | |
| 5,869,337 A | 2/1999 | Crabtree et al. | |
| 5,869,608 A | 2/1999 | Caldwell et al. | |
| 5,871,753 A | 2/1999 | Crabtree et al. | |
| 5,925,565 A | 7/1999 | Berlioz et al. | |
| 5,935,819 A | 8/1999 | Eichner et al. | |
| 5,955,596 A | 9/1999 | Zagursky et al. | |
| 5,965,242 A | 10/1999 | Patton et al. | |
| 5,994,313 A | 11/1999 | Crabtree et al. | |
| 6,010,878 A | 1/2000 | Dixit et al. | |
| 6,011,018 A | 1/2000 | Crabtree et al. | |
| 6,043,082 A | 3/2000 | Crabtree et al. | |
| 6,046,047 A | 4/2000 | Crabtree et al. | |
| 6,046,158 A | 4/2000 | Ariizumi et al. | |
| 6,054,436 A | 4/2000 | Crabtree et al. | |
| 6,403,765 B1 | 6/2002 | Alnemri | |
| 6,497,876 B1 | 12/2002 | maraskovsky et al. | |
| 6,558,951 B1 | 5/2003 | Tomai et al. | |

(Continued)

FOREIGN PATENT DOCUMENTS

| | | |
|---|---|---|
| EP | 0 273 085 | 7/1988 |
| EP | 0 510 691 | 10/1996 |

(Continued)

OTHER PUBLICATIONS

Quintarelli et al., Co-expression of cytokine and suicide genes to enhance the activity and safety of tumor-specific cytotoxic T lymphocytes. Blood, Oct. 15, 2007_vol. 110, No. 8, p. 2793-2802.*
"Sipuleucel-T:APC 8015, APC-8015, prostate cancer vaccine—Dendreon." Drugs R D. 2006;7(3):197-201.
Adam et al., "Cross-linking of the p55 Tumor Necrosis Factor Receptor Cytoplasmic Domain by a Dimeric Ligand Induces nuclear Factor-kB and Mediates Cell Death," The Journal of Biological Chemistry vol. 270, No. 29, Jul. 21, 1995, pp. 17482-17487.
Adema et al., "A dendritic-cell-deprived C-C chemokine that preferentially attracts naïve T cells." Nature. Jun. 12, 1997;387(6634):713-717.

(Continued)

*Primary Examiner* — Scott Long
*Assistant Examiner* — Arthur S Leonard
(74) *Attorney, Agent, or Firm* — Grant IP, Inc.

(57) ABSTRACT

Provided herein are methods for cell therapy by modifying transfused cells to express an inducible caspase 9 protein, so that the cells may be selectively killed if the patient experiences dangerous side effects. Provided also within relates in part to methods for preventing or treating Graft versus Host Disease by modifying T cells before administration to a patient, so that they may be selectively killed if GvHD develops in the patient.

34 Claims, 54 Drawing Sheets

(56) References Cited

U.S. PATENT DOCUMENTS

| | | | |
|---|---|---|---|
| 6,670,186 B1 | 12/2003 | Nair et al. | |
| 6,943,245 B2 | 9/2005 | Killary et al. | |
| 7,404,950 B2 | 7/2008 | Spencer | |
| 2002/0160975 A1 | 10/2002 | Alnemri et al. | |
| 2003/0082163 A1 | 5/2003 | Shu | |
| 2003/0091593 A1 | 5/2003 | Bachmann et al. | |
| 2003/0092132 A1 | 5/2003 | Rodgers | |
| 2003/0108527 A1 | 6/2003 | Seya et al. | |
| 2003/0153518 A1 | 8/2003 | Foxwell et al. | |
| 2003/0206917 A1 | 11/2003 | Tykocinski et al. | |
| 2003/0232055 A1 | 12/2003 | Medzhitov | |
| 2004/0019195 A1 | 1/2004 | Scholm et al. | |
| 2004/0209836 A1 | 10/2004 | Spencer | |
| 2005/0215472 A1 | 9/2005 | Schulke et al. | |
| 2006/0263368 A1 | 11/2006 | Rosenblum et al. | |
| 2007/0081963 A1 | 4/2007 | Oh et al. | |
| 2008/0269160 A1 | 10/2008 | Spencer et al. | |
| 2008/0274140 A1 | 11/2008 | Weiner et al. | |
| 2008/0300202 A1 | 12/2008 | Kentros | |
| 2009/0175880 A1 | 7/2009 | Keler et al. | |
| 2009/0191159 A1 | 7/2009 | Sakurada et al. | |
| 2009/0263852 A1 | 10/2009 | Sperandio et al. | |
| 2009/0299763 A1 | 12/2009 | Sakurada | |
| 2009/0311183 A1 | 12/2009 | Devy et al. | |
| 2010/0196336 A1 | 8/2010 | Park et al. | |
| 2010/0203067 A1 | 8/2010 | Spencer et al. | |
| 2011/0023137 A1 | 1/2011 | Chu et al. | |
| 2011/0033383 A1 | 2/2011 | Spencer et al. | |
| 2011/0286980 A1 | 11/2011 | Brenner | |
| 2011/0287038 A1 | 11/2011 | Slawin et al. | |
| 2013/0323834 A1 | 12/2013 | Brenner et al. | |
| 2014/0255360 A1 | 9/2014 | Spencer et al. | |
| 2015/0328292 A1 | 11/2015 | Spencer et al. | |

FOREIGN PATENT DOCUMENTS

| | | |
|---|---|---|
| WO | WO 94/09699 | 5/1994 |
| WO | WO 96/12796 | 5/1996 |
| WO | WO 01/83551 | 11/2001 |
| WO | WO 02/36769 | 5/2002 |
| WO | WO 2004/073641 | 9/2004 |
| WO | WO 2006/133398 | 12/2006 |
| WO | WO 2008/006087 | 1/2008 |
| WO | WO 2008/049113 | 4/2008 |
| WO | WO 2010/033949 | 3/2010 |
| WO | WO 2011/035018 | 3/2011 |
| WO | WO 2011/130566 | 12/2011 |
| WO | WO 2014/164348 | 10/2014 |
| WO | WO 2014/197638 | 12/2014 |
| WO | WO 2015/134877 | 9/2015 |

OTHER PUBLICATIONS

Adema et al., "Migration of dendritic cell based cancer vaccines: in vivo veritas?" Curr Opin Immunol. Apr. 2005;17(2):170-174.
Albert et al., "Dendritic cell maturation is required for the cross-tolerization of CD8+ T cells." Nat Immunol. Nov. 2001;2(11):1010-1017.
Amara et al, "A versatile synthetic dimerizer for the regulation of protein-protein interactions." PNAS 1997;94:10618-10623.
Amrolia et al., "Adoptive immunotherapy with allodepleted donor T-cells improves immune reconstitution after haploidentical stem cell transplantation." Blood. Sep. 15, 2006;108(6):1797-808.
Amrolia et al., "Selective depletion of donor alloreactive T cells without loss of antiviral or antileukemic responses." Blood. Sep. 15, 2003;102(6):2292-9.
Anasetti et al., Donor Buffy Coat Cell Infusion After Marrow Transplantation for Aplastic Anemia. Blood, 1988, 72: 1099-1100.
Anderson et al., "A homologue of the TNF receptor and its ligand enhance T-cell growth and dendritic-cell function." Nature. Nov. 13, 1997;390(6656):175-179.
Andre-Schmutz et al., "Immune reconstitution without graft-versus-host disease after haemopoietic stem-cell transplantation: a phase 1/2 study." Lancet. Jul. 13, 2002;360(9327):130-7.
Arcone et al., "Identification of sequences responsible for acute-phase induction of human C-reactive protein." Nucleic Acids Res. Apr. 25, 1988;16(8):3195-3207.
Ardeshna et al., "The PI3 kinase, p38 SAP kinase, and NF-kappaB signal transduction pathways are involved in the survival and maturation of lipopolysaccharide-stimulated human monocyte-derived dendritic cells." Blood. Aug. 1, 2000;96(3):1039-1046.
ARGENT™ Regulated Homodimerization Kit Instructions. Version 2.0 ARIAD Pharmaceuticals, Inc. Cambridge, MA. Sep. 9, 2002, p. 1-15.
Aversa et al., "Full haplotype-mismatched hematopoietic stem-cell transplantation: a phase II study in patients with acute leukemia at high risk of relapse." J Clin Oncol. May 20, 2005;23(15):3447-54.
Aversa et al., "Treatment of high-risk acute leukemia with T-cell-depleted stem cells from related donors with one fully mismatched HLA haplotype." N Engl J Med. Oct. 22, 1998;339(17):1186-93.
Banchereau et al., "Dendritic cells and the control of immunity." Nature. Mar. 19, 1998;392(6673):245-252.
Banchereau et al., "Dendritic cells as therapeutic vaccines against cancer." Nat Rev Immunol. Apr. 2005;5(4):296-306.
Banchereau et al., "Dendritic cells: controllers of the immune system and a new promise for immunotherapy." Ann NY Acad Sci. Apr. 2003;987:180-187.
Banchereau et al., "Immunobiology of dendritic cells." Annu Rev Immunol. 2000; 18:767-811.
Bander et al., "Phase I trial of 177lutetium-labeled J591, a monoclonal antibody to prostate-specific membrane antigen, in patients with androgen-independent prostate cancer." J Clin Oncol. Jul. 20, 2005;23(21):4591-601.
Belshaw et al. (Sep. 1996). "Controlling programmed cell death with a cyclophilin-cyclosporin-based chemical inducer of dimerization." Chemistry & Biology. 3(9): pp. 731-738.
Bennett et al., "Apoptosis of rat vascular smooth muscle cells is regulated by p53-dependent and -independent pathways." Circ Res. Aug. 1995;77(2):266-273.
Bennett et al., "Help for cytotoxic-T-cell response is mediated by CD40 signalling." Nature. Jun. 4, 1998;393(6684):478-480.
Berger et al., "Pharmacologically regulated Fas-mediated death of adoptively transferred T cells in a nonhuman primate model." Blood. Feb. 15, 2004;103(4):1261-9.
Bernard et al., "HIV-specific cytotoxic T-lymphocyte activity in immunologically normal HIV-infected persons." AIDS. Nov. 12, 1998;12(16):2125-2139.
Beutler B., "Inferences, questions and possibilities in Toll-like receptor signalling." Nature. Jul. 8, 2004;430(6996):257-263.
Bianco FJ, et al., "Natural History of Biochemically-Recurrent Castrate-Resistant Disease in Men treated with maximal androgen blockage for a Rising PSA after Radical Prostatectomy," Cancer Symposium: Abstract 278, 2005.
Bisping et al., "Targeting receptor kinases by a novel indolinone derivative in multiple myeloma: abrogation of stroma-derived interleukin-6 secretion and induction of apoptosis in cytogenetically defined subgroups." Blood. Mar. 1, 2006;107(5):2079-2089.
Blau et al., "A proliferation switch for genetically modified cells." Proc Natl Acad Sci USA. Apr. 1, 1997;94(7):3076-3081.
Bleakley M, Riddell Sr., "Molecules and mechanisms of the graft-versus-leukaemia effect." Nat Rev Cancer. May 2004;4(5):371-80.
Bloom, J.D. and F.H. Arnold, In the light of directed evolution: pathways of adaptive protein evolution. Proc Natl Acad Sci U S A, 2009. 106 Suppl 1: p. 9995-10000.
Boatright, K.M. and G.S. Salvesen, Mechanisms of Caspase activation. Curr Opin Cell Biol, 2003. 15(6): p. 725-31.
Boatright, K.M., et al., A unified model for apical Caspase activation. Mol Cell, 2003. 11(2): p. 529-41.
Bojak et al., "Muscle specific versus ubiquitous expression of Gag based HIV-1 DNA vaccines: a comparative analysis." Vaccine. May 6, 2002;20(15):1975-1979.
Boldin et al., "Involvement of MACH, a Novel MORT1/FADD-Interacting Protease, in Fas/APO-1- and TNF Receptor-Induced Cell Death," Cell vol. 85, 803-815, Jun. 14, 1996.
Bollard et al., "Cytotoxic T lymphocyte therapy for Epstein-Barr virus+ Hodgkin's disease." J Exp Med. Dec. 20, 2004;200(12):1623-33.

(56) References Cited

OTHER PUBLICATIONS

Bonini et al., "HSV-TK gene transfer into donor lymphocytes for control of allogeneic graft-versus-leukemia." Science. Jun. 13, 1997;276(5319):1719-24.
Bonnert et al., GeneBank: AAC50954.1; GI: 1814020; Feb. 2, 1997.
Boss, W.F., et al., Basal signaling regulates plant growth and development. Plant Physiol, 2010. 154(2): p. 439-43.
Bowie et al, "Deciphering the message in protein sequences: tolerance to amino acid substitutions." Science Mar. 1990; 247:1306-1310.
Brady, S.C., L.A. Allan, and P.R. Clarke, Regulation of caspase-9 through phosphorylation by protein kinase C zeta in response to hyperosmotic stress. Mol Cell Biol, 2005. 25(23): p. 10543-55.
Breitbach et al., "Potential risks of bone marrow cell transplantation into infarcted hearts." Blood. Aug. 15, 2007;110(4):1362-9.
Cardone, M.H., et al., Regulation of cell death protease caspase-9 by phosphorylation. Science, 1998. 282(5392): p. 1318-21.
Carter et al., "Prostate-specific membrane antigen is a hydrolase with substrate and pharmacologic characteristics of a neuropeptidase." Proc Natl Acad Sci USA. Jan. 23, 1996;93(2):749-53.
Caux et al., "CD34+ hematopoietic progenitors from human cord blood differentiate along two independent dendritic cell pathways in response to GM-CSF+TNF alpha." Adv Exp Med Biol. 1997;417:21-25.
Caux et al., "In vitro regulation of development and function of dendritic cells." Hematol Cell Ther. Oct. 1996;38(5):463.
Cazeaux et al., "Comparative study of immune responses induced after immunization with plasmids encoding the HIV-1 Nef protein under the control of the CMV-IE or the muscle-specific desmin promoter." Vaccine. Sep. 10, 2002;20(27-28):3322-31.
Chamberlain et al., "Concise review: mesenchymal stem cells: their phenotype, differentiation capacity, immunological features, and potential for homing." Stem Cells. Nov. 2007;25(11):2739-49.
Chan et al., "A Domain in TNF Receptors that mediates ligand-independent receptor assembly and signaling," Science 288, 2351-2354, (2001).
Chan, Francis Ka-Ming, "Three is Better Than One: Pre-Ligand Receptor Assembly in the Regulation of TNF Receptor Signaling," Cytokine, Feb. 2007; 37(2) 101-107.
Chang et al., "Metastatic renal cell carcinoma neovasculature expresses prostate-specific membrane antigen." Urology. Apr. 2001;57(4):801-5.
Chang et al., "Proarrhythmic potential of mesenchymal stem cell transplantation revealed in an in vitro coculture model." Circulation. Apr. 18, 2006;113(15):1832-41.
Chang et al., "Prostate-specific membrane antigen is produced in tumor-associated neovasculature." Clin Cancer Res. Oct. 1999;5(10):2674-81.
Chang, W.C., et al., Modifying ligand-induced and constitutive signaling of the human 5-HT4 receptor. PLoS One, 2007. 2(12): p. e1317.
Chao, Y., et al., Engineering a dimeric Caspase-9: a re-evaluation of the induced proximity model for Caspase activation. PLoS Biol, 2005. 3(6): p. e183. 1079-1087.
Chatterjee et al., "Strategies for efficient gene transfer into hematopoietic cells. The use of adeno-associated virus vectors in gene therapy." Ann NY Acad Sci. Dec. 29, 1995;770:79-90.
Chen C, Okayama H., "High-efficiency transformation of mammalian cells by plasmid DNA." Mol Cell Biol. Aug. 1987;7(8):2745-2752.
Chen et al., "A testicular antigen aberrantly expressed in human cancers detected by autologous antibody screening." Proc Natl Acad Sci USA. Mar. 4, 1997;94(5):1914-1918.
Cheung et al., "Plasmid encoding papillomavirus Type 16 (HPV16) DNA constructed with codon optimization improved the immunogenicity against HPV infection." Vaccine. Dec. 16, 2004;23(5):629-638.
Chiodoni et ai, "Dendritic Cells Infiltrating Tumors Cotransduced with Granulocyte/Macrophage Colony-Stimulating factor (GM-CSF) and CD40 Ligand Genes Take Up and Present Endo-genous Tumor-Associated Antigens, and Prime Naive Mice for a Cytotoxic T Lymphocyte Response," J. Exp. Med. vol. 190, No. 1, Jul. 5, 1999. pp. 125-133.
Choe et al., "Crystal structure of human toll-like receptor 3 (TLR3) ectodomain" Science. Jul. 22, 2005;309(5734):581-585.
Christiansen et al., "N-glycosylation and microtubule integrity are involved in apical targeting of prostate-specific membrane antigen: implications for immunotherapy." Mol Cancer Ther. May 2005;4(5):704-14.
Ciceri, F., et al., "Infusion of suicide-gene-engineered donor lymphocytes after family haploidentical haemopoietic stem-cell transplantation for leukaemia (the TK007 trial): a non-randomised phase I-II study," Lancet Oncol. 2009, vol. 10, No. 5, pp. 489-500.
Cisco et al., "Induction of human dendritic cell maturation using transfection with RNA encoding a dominant positive toll-like receptor 4." J Immunol. Jun. 1, 2004;172(11):7162-7168.
Clackson et al., "Redesigning an FKBP-ligand interface to generate chemical dimerizers with novel specificity." Proc Natl Acad Sci USA. Sep. 1, 1998;95(18):10437-10442.
Clackson T., "Dissecting the functions of proteins and pathways using chemically induced dimerization." Chem Biol Drug Des. Jun. 2006;67(6):440-442.
Clackson, T. , "Controlling Protein-Protein interactions Using Chemical inducers and Disrupters of Dimerization" Chapter 4.2, pp. 227-249 in Chemical Biology: From Small Molecules to Systems Biology and Drug Design (Schreiber, s., et al., eds., Wiley, 2007)).
Clarke et al., "Randomized phase II trial of chemoradiotherapy followed by either dose-dense or metronomic temozolomide for newly diagnosed glioblastoma." J Clin Oncol. Aug. 10, 2009;27(23):3861-7.
Clarke Sr., "The critical role of CD40/CD40L in the CD4-dependent generation of CD8+ T cell immunity." J Leukoc Biol. May 2000;67(5):607-614.
Clarke, S.J., et al., "A phase I, pharmacokinetic (PK), and preliminary efficacy assessment of ALD518, a humanized anti-IL-6 antibody, in patients with advanced cancer ," 2009, J. Clin. Oncol. 27:15s (suppl.; abstr. 3025).
Coffin "Molecular Mechanisms of Nucleic Acid Integration," Journal of Mecical Virology, 31:43-19 (1990).
Cohen et al., "Nucleotide sequence of the cDNA encoding human tyrosinase-related protein." Nucleic Acids Res. May 11, 1990;18(9):2807-2808.
Contin et al., "Membrane-anchored CD40 is processed by the tumor necrosis factor-alpha-converting enzyme. Implications for CD40 signaling." J Biol Chem. Aug. 29, 2003;278(35):32801-32809.
Coupar et al., "A general methods for the construction of recombinant vaccinia viruses expressing multiple foreign genes." Gene. Aug. 15, 1988;68(1):1-10.
Cranmer et al., "Clinical applications of dendritic cell vaccination in the treatment of cancer." Cancer Immunol Immunother. Apr. 2004;54(4):275-306.
Crawford et al., "A controlled trial of leuprolide with and without flutamide in prostatic carcinoma." N Engl J Med. Aug. 17, 1989;321(7):419-424, w/, erratum N Engl J Med Nov. 16, 1989;321(20):1420.
Cremer et al., "Long-lived immature dendritic cells mediated by TRANCE-RANK interaction." Blood. Nov. 15, 2002;100(10):3646-3655.
Cristofanilli et al., "Circulating tumor cells, disease progression, and survival in metastatic breast cancer." N Engl J Med. Aug. 19, 2004;351(8):781-91.
Cyster JG., "Chemokines and cell migration in secondary lymphoid organs." Science. Dec. 10, 1999;286(5447):2098-2102.
Dallal RM, Lotze MT., "The dendritic cell and human cancer vaccines." Curr Opin Immunol. Oct. 2000;12(5):583-588.
Davis et al., "Crystal structure of prostate-specific membrane antigen, a tumor marker and peptidase." Proc Natl Acad Sci USA. Apr. 26, 2005;102(17):5981-5986.
De Becker et al., "The adjuvant monophosphoryl lipid A increases the function of antigen-presenting cells." Int Immunol. Jun. 2000;12(6):807-815.
de Gruijl et al, "Prolonged Maturation and Enhanced Transduction of Dendritic Cells Migrated from Human Skin Explants After In Situ

(56) References Cited

OTHER PUBLICATIONS

Delivery of CD40-Targeted Adenoviral Vectors," The Journal of Immunology vol. 169,2002 PQS 5322-5331.
de la Thille et al., "Detection of prostate-specific membrane antigen expressing cells in blood obtained from renal cancer patients: a potential biomarker of vascular invasion." Cancer Detect Prev. 2000;24(6):579-88.
De Vries et al., "Effective migration of antigen-pulsed dendritic cells to lymph nodes in melanoma patients is determined by their maturation state." Cancer Res. Jan. 1, 2003;63(1):12-17.
de Witte et al., "An inducible caspase 9 safety switch can halt cell therapy-induced autoimmune disease." J Immunol. May 1, 2008;180(9):6365-73.
Deml et al. "Multiple effects of codon usage optimization on expression and immunogenicity of DNA candidate vaccines encoding the human immunodeficiency virus type 1 Gag protein," 2001. J. Virol. 75:10991-11001.
Denault et al., "Caspase 3 attenuates XIAP(X-linked inhibitor of apoptosis protein)-mediated inhibition of Caspase 9" Biochem. J. (2007) 11-19.
Deonarain, "Ligand-targeted receptor-mediated vectors for gene delivery," 1998, Expert Opin. Ther. Pat., vol. 8, pp. 53-69.
Dey BR, Spitzer TR., "Current status of haploidentical stem cell transplantation." Br J Haematol. Nov. 2006;135(4):423-37.
Di Stasi, A., et al., Inducible apoptosis as a safety switch for adoptive cell therapy. N Engl J Med, 2011. 365(18): p. 1673-83.
Diehl et al., "CD40 activation in vivo overcomes peptide-induced peripheral cytotoxic T-lymphocyte tolerance and augments anti-tumor vaccine efficacy." Nat Med. Jul. 1999;5(7):774-779.
Dominici et al., "Minimal criteria for defining multipotent mesenchymal stromal cells. The International Society for Cellular Therapy position statement." Cytotherapy. 2006;8(4):315-7.
Donnelly et al., "DNA vaccines." Annu Rev Immunol. 1997;15:617-48.
Dudley et al., "Adoptive cell transfer therapy following non-myeloablative but lymphodepleting chemotherapy for the treatment of patients with refractory metastic melanoma." J Clin Oncol. Apr. 1, 2005;23(10):2346-2357.
Dudley et al., "Cancer regression and autoimmunity in patients after clonal repopulation with antitumor lymphocytes." Science. Oct. 25, 2002;298(5594):850-4.
Elgueta et al., "Molecular mechanism and function of CD40/CD40L engagement in the immune system," Immunological Reviews, 229, (2009) 152-172.
Evel-Kabler et al., "SOCS1 restricts dendritic cells' ability to break self tolerance and induce antitumor immunity by regulating IL-12 production and signaling." J Clin Invest. Jan. 2006;116(1):90-100.
Fan et al., "Improved artificial death switches based on caspases and FADD." Hum Gene Ther. Sep. 20, 1999;10(14):2273-2285.
Farrar et al., "Activation of the Raf-1 kinase cascade by coumermycin-induced dimerization," Nature Sep. 12, 1996;383(6596):178-181.
Fearon et al., "The instructive role of innate immunity in the acquired immune response," Science, Apr. 5, 1996;272(5258):50-53.
Fechheimer et al., "Transfection of mammalian cells with plasmid DNA by scrape loading and sonication loading." Proc Natl Acad Sci USA. Dec. 1987;84(23):8463-8467.
Fernandez et al., "Dendritic cells directly trigger NK cell functions: cross-talk relevant in innate anti-tumor immune responses in vivo." Nat Med. Apr. 1999;5(4):405-411.
Ferrari et al., "Second-strand synthesis is a rate-limiting step for efficient transduction by recombinant adeno-associated virus vectors." J Virol. May 1996;70(5):3227-3234.
Fisher et al., "Transduction with recombinant adeno-associated virus for gene therapy is limited by leading-strand synthesis." J Virol. Jan. 1996;70(1):520-532.
Flotte et al., "Stable in vivo expression of the cystic fibrosis transmembrane conductance regulator with an adeno-associated virus vector." Proc Natl Acad Sci USA. Nov. 15, 1993;90(22):10613-10617.

Flotte TR, Carter BJ. "Adeno-associated virus vectors for gene therapy." Gene Ther. Aug. 1995;2(6):357-362.
Flotte, "Prospects for Virus-Based Gene Therapy for Cystic Fibrosis," Journal of Bioenergetics and Bioinformatics, vol. 25, No. 1, 1993, p. 37-42.
Freeman et al., "The role of (111)in Capromab Pendetide (ProstaScintR) immunoscintigraphy in the management of prostate cancer." Q J Nucl Med. Jun. 2002;46(2):131-7.
Freytag et al., "Phase I study of replication-competent adenovirus-mediated double suicide gene therapy for the treatment of locally recurrent prostate cancer." Cancer Res. Sep. 1, 2002;62(17):4968-76.
Fujio Y, Walsh K., "Akt mediates cytoprotection of endothelial cells by vascular endothelial growth factor in an anchorage-dependent manner." J Biol Chem. Jun. 4, 1999;274(23):16349-16354.
Galbiati et al., "N-terminal fatty acylation of the alpha-subunit of the G-protein Gi1: only the myristoylated protein is a substrate for palmitoylation." Biochem J. Nov. 1, 1994;303(Pt 3):697-700.
Gauthier-Campbell et al., "Regulation of dendritic branching and pilopodia formation in hippocampal neurons by specific acylated protein motifs." Mol Biol Cell. May 2004;15(5):2205-2217.
Gefter et al., "A simple method for polyethylene glycol-promoted hybridization of mouse myeloma cells." Somatic Cell Genet. Mar. 1977;3(2):231-236.
GenBank Accession No. M29540, Nov. 1, 1994.
Gestwicki JE, Marinec PS., Chemical control over protein-protein interactions: beyond inhibitors. Comb Chem High Throughput Screen. Sep. 2007;10(8):667-675.
Ghetie et al., "The GLP large scale preparation of immunotoxins containing deglycosylated ricin a chain and a hindered disulfide bond." J Immunol Methods. Sep. 13, 1991;142(2):223-30.
Gilboa E, Vieweg J., "Cancer immunotherapy with mRNA-transfected dendritic cells." Immunol Rev. Jun. 2004;199:251-263.
Gilboa E., "The promise of cancer vaccines." Nat Rev Cancer. May 2004;4(5):401-411.
Gittes RF., "Carcinoma of the prostate." N Engl J Med. Jan. 24, 1991;324(4):236-245.
Goodman et al., "Recombinant adeno-associated virus-mediated gene transfer into hematopoietic progenitor cells." Blood. Sep. 1, 1994;84(5):1492-1500.
Goodwin et al., "Suppression of human T-cell mitogenesis by prostaglandin. Existence of a prostaglandin-producing suppressor cell." J Exp Med. Dec. 1, 1977;146(6):1719-1734.
Goodwin JS., "Immunomodulation by eicosanoids and anti-anflammatory drugs." Curr Opin Immunol. Dec. 1989;2(2):264-268.
Gopal TV., "Gene transfer method for transient gene expression, stable transformation, and cotransformation of suspension cell cultures." Mol Cell Biol. May 1985;5(5):1188-1190.
Gossen et al., "Transcriptional activation by tetracyclines in mammalian cells." Science. Jun. 23, 1995;268(5218):1766-1769.
Gossen M, Bujard H., "Tight control of gene expression in mammalian cells by tetracycline-responsive promoters." Proc Natil Acad Sci USA. Jun. 15, 1992;89(12):5547-5551.
Gottschalk et al., "Post-transplant lymphoproliferative disorders." Annu Rev Med. 2005;56:29-44.
Graham FL, van der Eb AJ., "A new technique for the assay of infectivity of human adenovirus 5 DNA." Virology. Apr. 1973;52(2):456-467.
Granucci et al., "Eerly events in dendritic cell maturation induced by LPS." Microbes Infect. Nov. 1999;1(13):1079-1084.
Granucci et al., "Inducible IL-2 production by dendritic cells revealed by global gene expression analysis." Nat Immunol. Sep. 2001;2(9):882-888.
Granucci et al., "Modulation of cytokine expression in mouse dendritic cell clones." Eur J Immunol. Oct. 1994;24(10):2522-2526.
Grewal IS, Flavell RA., "CD40 and CD154 in cell-mediated immunity." Annu Rev Immunol. 1998;16:111-135.
Hall et al., "Mesenchymal stem cells in cancer: tumor-associated fibroblasts and cell-based delivery vehicles." Int J Hematol. Jul. 2007;86(1):8-16.
Hammad et al., "Monocyte-derived dendritic cells induce a house dust mite-specific Th2 allergic inflammation in the lung of humanized SCID mice:involvement of CCR7." J Immunol. Aug. 1, 2002;169(3):1524-1534.

(56) References Cited

OTHER PUBLICATIONS

Hanks B.A., et al.. "Re-engineered CD40 receptor enables potent pharmacological activation of dendritic-cell cancer vaccines in vivo" Nature Medicine, vol. 11, No. 2. 2005 pp. 130-137.
Harbury et al., "Crystal structure of an isoleucine-zipper trimer," Nature, vol. 371, Sep. 1, 1994, 80-83.
Hauer et al., "TNF receptor (TNFR)-associated factor (TRAF) 3 serves as an Inhibitor of TRAF2 5-mediated activation of the noncanonical NF-B pathway by TRAF-binding TNFRs." PNAS, vol. 102, No. 8, Feb. 22, 2005; pp. 2874-2879.
Hay et al., "Replication of Adenovirus Mini-Chromasomes," J. Mol. Biol. (1984) 175, 493-510.
He et al., "A simplified system for generating recombinant adenoviruses." Proc Natl Acad Sci USA. Mar. 3, 1998;95(5):2509-2514.
Hearing et al., "Identification of a repeated sequence element required for efficient encapsidation of the adenovirus type 5 chromosome." J Virol. Aug. 1987;61(8):2555-2558.
Hearing P, Shenk T., "Functional analysis of the nucleotide sequence surrounding the cap site for adenovirus type 5 region E1A messenger RNAs." J Mol Biol. Jul. 15, 1983;167(4):809-822.
Hermans et al., "CD8+ T cell-dependent elimination of dendritic cells in vivo limits the induction of antitumor immunity." J Immunol. Mar. 15, 2000;164(6):3095-3101.
Ho et al., "Dimeric ligands define a role for transcriptional activation domains in reinitiation." Nature. Aug. 29, 1996;382(6594):822-826.
Hodge et al., "Vector-based delivery of tumor-associated antigens and T-cell co-stimulatory molecules in the induction of immune responses and anti-tumor immunity," Cancer Detect Prevent 2002; 26;275-291.
Holler et al., "Development of improved soluble inhibitors of FasL and CD40L based on oligomerized receptors," Journal of Immunolgial Methods 237(2000) 159-173.
Hollstein et al., "Database of p53 gene somatic mutations in human tumors and cell lines." Nucleic Acids Ress. Sep. 1994;22(17):3551-3555.
Holsinger et al., "Signal transduction in T lymphocytes using a conditional allele of Sos." Proc Natl Acad Sci USA. Oct. 10, 1995;92(21):9810-9814.
Hong, T., et al., A simple theoretical framework for understanding heterogeneous differentiation of CD4+ T cells. BMC Syst Biol, 2012. 6: p. 66.
Horng et al., PNAS 98(22):12654-12658, 2001.
Horwitz et al., "Fludarabine-based nonmyeloablative stem cell transplantation for sickle cell disease with and without renal failure: clinical outcome and pharmacokinetics." Biol Blood Marrow Transplant. Dec. 2007;13(12):1422-6.
Horwitz et al., "Isolated allogeneic bone marrow-derived mesenchymal cells engraft and stimulate growth in children with osteogenesis imperfecta: Implications for cell therapy of bone." Proc Natl Acad Sci U S A. Jun. 25, 2002;99(13):8932-7.
Horwitz et al., "Transplantability and therapeutic effects of bone marrow-derived mesenchymal cells in children with osteogenesis imperfecta." Nat Med. Mar. 1999;5(3):309-13.
Hoshino et al., "Cutting edge:Toll-like receptor 4(TLR4)-deficient mice are hyporesponsive to lipopolysaccharide: evidence for TLR4 as the Lps gene product." J Immunol. Apr. 1, 1999;162(7):3749-3752.
Hou WS, Van Parijs L., "A Bcl-2-dependent molecular timer regulates the lifespan and immunogenicity of dendritic cells." Nat Immunol. Jun. 2004;5(6):583-589.
Hsiao, E.C., et al., Constitutive Gs activation using a single-construct tetracycline-inducible expression system in embryonic stem cells and mice. Stem Cell Res Ther, 2011. 2(2): p. 11.
Huang et al., "Donor lymphocyte infusion for the treatment of leukemia relapse after HLA-mismatched/haploidentical T-cell-replete hematopoietic stem cell transplantation." Haematologica. Mar. 2007;92(3):414-7.
Huang et al., "Modified donor lymphocyte infusion after HLA-mismatched/haploidentical T cell-replete hematopoietic stem cell transplantation for prophylaxis of relapse of leukemia in patients with advanced leukemia." J Clin Immunol. May 2008;28(3):276-83.
Hurley et al., "National Marrow Donor Program HLA-matching guidelines for unrelated marrow transplants." Biol Blood Marrow Transplant. Oct. 2003;9(10):610-5.
Introna et al., "Genetic modification of human T cells with CD20: a strategy to purify and lyse transduced cells with anti-CD20 antibodies." Hum Gene Ther. Mar. 1, 2000;11(4):611-20.
Ismaili et al., "Monophosphoryl lipid a activates both human dendritic cells and T cells." J Immunol. Jan. 15, 2002;168(2):926-932.
Israeli et al., "Expression of the prostate-specific membrane antigen." Cancer Res. Apr. 1, 1994;54(7):1807-11.
Israeli et al., "Sensitive nested reverse transcription polymerase chain reaction detection of circulating prostatic tumor cells: comparison of prostate-specific membrane antigen and prostate-specific antigen-based assays." Cancer Res. Dec. 15, 1994;54(24):6306-10.
Israeli et al., Molecular cloning of a complementary DNA encoding a prostate-specific membrane antigen. Cancer Res. Jan. 15, 1993;53(2):227-230.
Iuliucci et al., "Intravenous safety and pharmacokinetics of a novel dimerizer drug, AP1903, in healthy volunteers." J Clin Pharmacol. Aug. 2001;41(8):870-9.
Jackson et al., "A second tyrosinase-related protein, TRP-2, maps to and is mutated at the mouse slaty locus." EMBO J. Feb. 1992;11(2):527-535.
Jacquot et al, "CD154/CD40 and CD70/CD27 interactions have different and sequential functions in T cell-dependent B cell responses: enhancement of plasma cell differentiation by CD27 signaling," J Immunol 1997; 159: 2652-2657.
Janeway et al., "Approaching the asymptote? Evolution and revolution in immunology." Cold Spring Harb Symp Quant Biol. 1989;54 Pt 1:1-13.
Jemal et al., "Cancer statastics, 2008." CA Cancer J Clin. Mar.-Apr. 2008;58(2):71-96.
Josien et al., "TRANCE, a tumor necrosis factor family member, enhances the longevity and adjuvant properties of dendritic cells in vivo." J Exp Med. Feb. 7, 2000;191(3):495-502.
Junker et al., "Kinetics of cell death in T lymphocytes genetically modified with two novel suicide fusion genes." Gene Ther. Jul. 2003;10(14):1189-97.
Kadowaki N. et al., "Subsets of human dendritic cell precursors express different toll-like receptors and respond to different microbial antigens," J Exp Med. 2001, vol. 194, pp. 863-869.
Kagan JC, Medzhitov R., "Phosphoinositide-mediated adaptor recruitment controls Toll-like receptor signaling." Cell. Jun. 2, 2006;125(5):943-955.
Kageyama et al., "Differing utilization of homologous transcription initiation sites of rat K and T kininogen genes under inflammation condition." J Biol Chem. Feb. 15, 1987;262(5):2345-2351.
Kalams et al., "The critical need for CD4 help in maintaining effective cytotoxic T lymphocyte responses." J Exp Med. Dec. 21, 1998;188(12):2199-2204.
Kalinski et al., "Dendritic cells, obtained from peripheral blood precursors in the presence of PGE2, promote Th2 responses." Adv Exp Med Biol. 1997;417:363-367.
Kalinski et al., "Prostaglandin E(2) is a selective inducer of interleukin-12 p40 (IL-12p40) production and an inhibitor of bioactive IL-12p70 heterodimer." Blood. Jun. 1, 2001;97(11):3466-3469.
Kandel ES, Hay N., "The regulation and activities of the multifunctional serine/threonine kinase Akt/PKB." Exp Cell Res. Nov. 25, 1999;253(1):210-229.
Kanto et al., "Ceramide mediates tumor-induced dendritic cell apoptosis." J Immunol. Oct. 1, 2001;167(7):3773-3784.
Kantoff et al., "Overall survival analysis of a phase II randomized controlled trial of a Poxviral-based PSA-targeted immunotherapy in metastatic castration-resistant prostate cancer." J Clin Oncol. Mar. 1, 2010;28(7):1099-105.
Kantoff et al., "Sipuleucel-T immunotherapy for castration-resistant prostate cancer." N Engl J Med. Jul. 29, 2010;363(5):411-22.
Kaplitt et al., "Long-term gene expression and phenotypic correction using adeno-associated virus vectors in the mammalian brain." Nat Genet. Oct. 1994;8(2):148-154.

(56) References Cited

OTHER PUBLICATIONS

Kaplitt et al., "Long-term gene transfer in porcine myocardium after coronary infusion of an adeno-associated virus vector." Ann Thorac Surg. Dec. 1996;62(6):1669-76.

Kawakami et al., "Identification of a human melanoma antigen recognized by tumor-infiltrating lymphocytes associated with in vivo tumor rejection." Proc Natl Acad Sci USA. Jul. 5, 1994;91(14):6458-6462.

Kawakami et al., "Identification of the immunodominant peptides of the MART-1 human melanoma antigen recognized by the majority of HLA-A2-restricted tumor infiltrating lymphocytes." J Exp Med. Jul. 1, 1994;180(1):347-352.

Kehry, Marilyn R., "CD40-Mediated Signaling in B Cells, Balancing Cell Survival, Growth and Death," The American Association of Immunologists, 1996, 2345-2348.

Kelly WK, Slovin SF., "Chemotherapy for androgen-independent prostate cancer: myth or reality." Curr Oncol Rep. Sep. 2000;2(5):394-401.

Kempf et al, "Improved stimulation of human dendritic cells by receptor engagement with surface-modified microparticles," J Drug Target vol. 11 No. 1, Jan. 2003 pp. 11-18.

Kessler et al., "Gene delivery to skeletal muscle results in sustained expression and systemic delivery of a therapeutic protein." Proc Natl Acad Sci USA. Nov. 26, 1996;93(24):14082-14087.

Kikuchi et al., "Dendritic cells genetically modified to express CD40 ligand and pulsed with antigen can initiate antigen-specific humoral immunity independent of CD4+ T cells." Nat Med. Oct. 2000;6(10):1154-1159.

Klein et al., "High-velocity microprojectiles for delivering nucleic acids into living cells," (1987) Nature, 327,70-73.

Kobayashi et al., "IRAK-M is a negative regulator of Toll-like receptor signaling." Cell. Jul. 26, 2002;110(2):191-202.

Koeberl et al., "Persistent expression of human clotting factor Ix from mouse liver after intravenous injection of adeno-associated virus vectors." Proc Natl Acad Sci USA. Feb. 18, 1997;94(4):1426-1431.

Kohler G, Milstein C., "Continuous cultures of fused cells secreting antibody of predefined specificity." Nature. Aug. 7, 1975;256(5517):495-497.

Kohler G, Milstein C., "Derivation of specific antibody-producing tissue culture and tumor lines by cell fusion." Eur J Immunol. Jul. 1976;6(7):511-519.

Kolb et al., "Graft-versus-leukemia reactions in allogeneic chimeras." Blood. Feb. 1, 2004;103(3):767-76.

Kopytek et al., "Chemically induced dimerization of dihydrofolate reductase by a homobifunctional dimer of methotrexate." Chem Biol. May 2000;7(5):313-321.

Korst et al., "Effect of adenovirus gene transfer vectors on the immunologic functions of mouse dendritic cells." Mol Ther. Mar. 2002;5(3):307-315.

Kouskoff, V., et al., B cell receptor expression level determines the fate of developing B lymphocytes: receptor editing versus selection. Proc Natl Acad Sci U S A, 2000. 97(13): p. 7435-9.

Kraaij et al., "Prostate specific membrane antigen (PSMA) is a tissue-specific target for adenoviral transduction of prostate cancer in vitro." Prostate. Feb. 15, 2005;62(3):253-9.

Kumar et al., "Immunogenicity testing of a novel engineered HIV-1 envelope gp140 DNA vaccine construct." DNA Cell Biol. Jul. 2006;25(7):383-392.

Kutzler et al., "Coimmunization with an optimized IL-15 plasmid results in enhanced function and longevity of CD8 T cells that are partially independent of CD4 T cell help." J Immunol. Jul. 1, 2005;175(1):112-123.

Kutzler MA, Weiner DB., "DNA vaccines: ready for prime time?" Nat Rev Genet. Oct. 2008;9(10):776-788.

Kwon et al., "Isolation and sequence of a cDNA clone for human tyrosinase that maps at the mouse c-albino locus." Proc Natl Acad Sci USA. Nov. 1987;84(21):7473-7477.

Labeur et al., "Generation of tumor immunity by bone marrow-derived dendritic cells correlates with dendritic cell maturation stage." J Immunol. Jan. 1, 1999;162(1):168-175.

Laddy et al., "Heterosubtypic protection against pathogenic human and avian influenza viruses via in vivo electroporation of synthetic consensus DNA antigens." PLoS One. Jun. 25, 2008;3(6):e2517.

Lang et al., "Long-term outcome after haploidentical stem cell transplantation in children." Blood Cells Mol Dis. Nov.-Dec. 2004;33(3):281-7.

Langenkamp et al., "Kinetics of dendritic cell activation: impact on priming of TH1, TH1 and nonpolarized T cells." Nat Immunol. Oct. 2000;1(4):311-316.

Lanzavecchia A, Sallusto F., "Regulation of T cell immunity by dendritic cells." Cell. Aug. 10, 2001;106(3):263-266.

Lanzavecchia et al., "Dynamics of T lymphocyte responses: intermediates, effectors, and memory cells." Science. Oct. 6, 2000;290(5489):92-97.

Lapointe et al., "Human dendritic cells require multiple activation signals for the efficient generation of tumor antigen-specific T lymphocytes." Eur J Immunol. Nov. 2000;30(11):3291-3298.

Lapteva et al., "Development of Novel CD4-Independent iCD40-Dendritic Cell Vaccine for HIV-1 Immunotherapy," vol. 17, no. Suppl 1, May 2009, 12th Annual Meeting of the American Society of Gene Therapy: San Diego, CA, May 27-30, 2009.

Lapteva et al., "Enhance Activation of Human Dendritic Cells by inducible CD40 and Toll-like Receptor-4 Ligation," Cancer Research 2007, 67; (21) Nov. 1, 2007, pp. 10528-10537.

Le Blanc et al., "Mesenchymal stem cells for treatment of steroid-resistant, severe, acute graft-versus-host disease: a phase II study." Lancet. May 10, 2008;371(9624):1579-86.

Lee et al., "A clinical grade cocktail of cytokines and PGE2 results in uniform maturation of human monocyte-derived dendritic cells: implications for immunotherapy." Vaccine. Dec. 19, 2002;20 Suppl 4:A8-A22.

Lee et al., "Cytoplasmic domain-mediated dimerizations of toll-like receptor 4 observed by beta-lactamase enzyme fragment complementation." J Biol Chem. Mar. 12, 2004;279(11):10564-10574.

Lee et al., "Multipotent stromal cells from human marrow home to and promote repair of pancreatic islets and renal glomeruli in diabetic NOD/scid mice." Proc Natl Acad Sci U S A. Nov. 14, 2006;103(46):17438-43.

Leo et al., "Partition coefficients and their uses." Chem Rev. Dec. 1971;71(6):525-616.

Levrero et al., "Defective and nondefective adenovirus vectors for expressing foreign genes in vitro and in vivo." Gene. May 30, 1991;101(2):195-202.

Li et al., "A novel conditional Akt 'survival+A185 switch' reversibly protects cells from apoptosis." Gene Ther. Feb. 2002;9(4):233-244.

Li et al., "The HIV-1 Env protein signal sequence retards its cleavage and down-regulates the glycoprotein folding." Virology. Jul. 5, 2000;272(2):417-428.

Liu et al., "Constitutive and antibody-induced internalization of prostate-specific membrane antigen." Cancer Res. Sep. 15, 1998;58(18):4055-60.

Liu et al., "Differential regulation of interleukin (IL)-12 p35 and p40 gene expression and interferon (IFN)-gamma-primed IL-12 production by Ifn regulatory factor 1." J Exp Med. Oct. 2003;198(8):1265-1276.

Liu et al., "Monoclonal antibodies to the extracellular domain of prostate-specific membrane antigen also react with tumor vascular endothelium." Cancer Res. Sep. 1, 1997;57(17):3629-34.

Livak et al., "Analysis of relative gene expression data using real-time quantitative PCR and the 2(-Delta Delta C(T)) Method." Methods. Dec. 2001;25(4):402-408.

Lodge et al., Dendridic Cell-based Immunotherapy of Prostate Cancer: Immune Monitoring of a Phase II Clincal Trial, Cancer Res. 60:829-833, 2000.

Loiarro et al., "Peptide-mediated interference of TIR domain dimerization in MyD88 inhibits interleukin-1-dependent activation of NF-{kappa}B." J Biol. Chem. Apr. 22, 2005;280(16):15809-15814.

Luft et al., "Functionally distinct dendritic cell (DC) populations induced by physiologic stimuli: prostaglandin E(2) regulates the migratory capacity of specific DC subsets." Blood. Aug. 15, 2002;100(4):1362-1372.

(56) References Cited

OTHER PUBLICATIONS

Luning Prak, E.T., M. Monestier, and R.A. Eisenberg, B cell receptor editing in tolerance and autoimmunity. Ann N Y Acad Sci, 2011. 1217: p. 96-121.
Luo et al., "Oligomerization activates c-RAF-1 through a Ras-dependent mechanism." Nature. Sep. 12, 1996;383(6596):181-185.
MacCorkle et al., "Synthetic activation of caspases: artificial death switches." Proc Natl Acad Sci USA. Mar. 31, 1998;95(7):3655-3660.
Macejak DG, Sarnow P., "Internal initiation of translation mediated by the 5' leader of a cellular mRNA." Nature. Sep. 5, 1991;353(6339):90-94.
Machiels et al., "Prospective randomized study comparing docetaxel, estramustine, and prednisone with docetaxel and prednisone in metastatic hormone-refractory prostate cancer." J Clin Oncol. Nov. 10, 2008;26(32):5261-8.
Malin et al., "Vaccinia expression of Mycobacterium tuberculosis-secreted proteins: tissue plasminogen activator signal sequence enhances expression and immunogenicity of M. tuberculosis Ag85." Microbes Infect. Nov. 2000;2(14):1677-1685.
Malissen B, Ewbank JJ., "'TaiLoRing' the response of dendritic cells to pathogens." Nat Immunol. Aug. 2005;6(8):750-769.
Mann et al., "Construction of a retrovirus packaging mutant and its use to produce helper-free defective retrovirus." Cell. May 1983;33(1):153-159.
Marijt et al., "Hematopoiesis-restricted minor histocompatibility antigens HA-1- or HA-2-specific T cells can induce complete remissions of relapsed leukemia." Proc Natl Acad Sci U S A. Mar. 4, 2003;100(5):2742-7.
Marsland et al., "CCL19 and CCL21 induce a potent proinflammatory differentiation program in licensed dendritic cells." Immunity. Apr. 2005;22(4):493-505.
Martin, M.C., et al., Protein kinase A regulates Caspase-9 activation by Apaf-1 downstream of cytochrome c. J Biol Chem, 2005. 280(15): p. 15449-55.
Martln-Fontecha et al., "Regulation of dendritic cell migration to the draining lymph node: impact on T lymphocyte traffic and priming." J Exp Med. Aug. 18, 2003;198(4):615-621.
Mazouz et al., "CD40 triggering increases the efficiency of dendritic cells for antitumoral immunization." Cancer Immun. Mar. 27, 2002;2:2.
McCown et al., "Differential and persistent expression patterns of CNS gene transfer by an adeno-associated virus (AAV) vector." Brain Res. Mar. 25, 1996;713(1-2):99-107.
McIlroy et al., "Histamine and prostaglandin E up-regulate the production of Th2-attracting chemokines (CCL17 and CCL22) and down-regulate IFN-gamma-induced CXCL10 production by immature human dendritic cells." Immunology. Apr. 2006;117(4):507-516.
McWhirter et al., "Crystallographic analysis of CD40 recognition and signaling by human TRAF2." Proc Natl Acad Sci USA. Jul. 20, 1999;96(15):8408-8413.
Medema et al., "Expression of the serpin serine protease inhibitor 6 protects dendritic cells from cytotoxic T lymphocyte-induced apoptosis: differential modulation by T helper type 1 and type 2 cells." J Exp Med. Sep. 3, 2001;194(5):657-667.
Medzhitov et al., "A human homologue of the *Drosophila* Toll protein signals activation of adaptive immunity." Nature. Jul. 24, 1997;388(6640):394-397.
Megiovanni et al., "Double-stranded RNA stimulation of CD40 ligation of monocyte-derived dendritic cells as models to study their activation and maturation process." Eur Cytokine Netw. Apr.-Jun. 2004;15(2):126-134.
Melief et al., "Effective therapeutic anticancer vaccines based on preCision guiding of cytolytic T lymphocytes" Immunol Rev. vol. 188, Oct. 2002, pp. 177-182.
Meyer et al., "Cutting edge: cyclooxygenase-2 activation suppresses Th1 polarization in response to helicobacter pylori." J Immunol. Oct. 15, 2003;171(8):3913-3917.
Meylan et al., "Intracellular pattern recognition receptors in the host response." Nature. Jul. 6, 2006;442(7098):39-44.

Miga et al., "Dendritic cell longevity and T cell persistence is controlled by CD154-CD40 interactions." Eur J Immunol. Mar. 2001;31(3):959-965.
Mizukami et al., "Adeno-associated virus type 2 binds to a 150-kilodalton cell membrane glycoprotein." Virology. Mar. 1, 1996;217(1):124-130.
Mochizuki et al., "Akt protein kinase inhibits non-apoptotic programmed cell death induced by ceramide." J Biol Chem. Jan. 25, 2002;277(4):2790-2797.
Molldrem et al., "A PR1-human leukocyte antigen-A2 tetramer can be used to isolate low-frequency cytotoxic T lymphocytes from healthy donors that selectively lyse chronic myelogenous leukemia." Cancer Res. Jun. 1, 1999;59(11):2675-81.
Montgomery et al., "Heterologous and homologous protection against influenza A by DNA vaccination: optimization of DNA vectors." DNA Cell Biol. Nov. 1993;12(9):777-783.
Morgan et al., "Cancer regression in patients after transfer of genetically engineered lymphocytes." Science. Oct. 6, 2006;314(5796):126-129.
Morgan et al., "Case report of a serious adverse event following the administration of T cells transduced with a chimeric antigen receptor recognizing ERBB2." Mol Ther. Apr. 2010;18(4):843-51.
Morse et al., "Migration of human dendritic cells after injection in patients with metastic malignancies." Cancer Res. Jan. 1, 1999;5((1):56-58.
Mukherjee et al., "Lipid-dependent recruitment of neuronal Src to lipid rafts in the brain." J Biol Chem. Oct. 17, 2003;278(42):40806-40814.
Nabel et al., "Recombinant gene expression in vivo within endothelial cells of the arterial wall." Science. Jun. 16, 1989;244(4910):1342-1344.
Nakagami et al., "Safety and efficacy of docetaxel, estramustine phosphate and hydrocortisone in hormone-refractory prostate cancer patients." Int J Urol. Jul. 2010;17(7):629-34.
Napolitanl et al., "Selected Toll-like receptor agonist combinations synergistically trigger a T helper type 1-polarizing program in dendrinic cells," Nat Immunol. Aug. 2005; vol. 6. No. 8, pp. 769-776.
Narayanan et al. A composite MyD88/CD40 switch synergistically activates mouse and human dendritic cells for enhanced antitumor efficacy. J Clin Invest. 2011, vol. 121(4), p. 1524-1529.
Narum et al., "Codon optimization of gene fragments encoding Plasmodium falciparum merzoite proteins enhances DNA vaccine protein expression and immunogenicity in mice." Infect Immun. Dec. 2001;69(12):7250-7253.
Nauta AJ, Fibbe WE., "Immunomodulatory properties of mesenchymal stromal cells." Blood. Nov. 15, 2007;110(10):3499-506.
Nestle et al., "Dendritic cells: on the move from bench to bedside." Nat Med. Jul. 2001;7(7):761-765.
Ni et al., "Molecular basis for CD40 signaling mediated by TRAF3." Proc Natl Acad Sci USA. Sep. 12, 2000;97(19):10395-10399.
Nicolau et al., "Liposomes as carriers for in vivo gene transfer and expression." Methods Enzymol. 1987;149:157-176.
Nociari et al., "A novel one-step, highly sensitive fluorometric assay to evaluate cell-mediated cytotoxicity." J Immunol Methods. Apr. 15, 1998;213(2):157-167.
Nopora A, Brocker T., "Bcl-2 controls dendritic cell longevity in vivo." J Immunol. Sep. 15, 2002;169(6):3006-3014.
Oehm et al., "Purification and Molecular Cloning of the APO-1 Cell Surface Antigen, a Member of the Tumor Necrosis Factorperve Growth Factor Receptor Superfamily, Sequence Identity With the Fas Antigen," The Journal of Biological Chemistry, vol. 267, No. 15, May 25, 1992 10709-10715.
Ohshima et al., "Expression and function of OX40 ligand on human dendritic cells." J Immunol. Oct. 15, 1997;159(8):3838-3848.
Oliviero et al., "The human haptoglobin gene: transcriptional regulation during development and acute phase induction." EMBO J. Jul. 1987;6(7):1905-1912.
O'Neill et al., "Manipulating dendritic cell biology for the active immunotherapy of cancer." Blood. Oct. 15, 2004;104(8):2235-2246.
O'Sullivan B, Thomas R., "CD40 and dendritic cell function." Crit Rev Immunol. 2003;23(1-2):83-107.

(56) References Cited

OTHER PUBLICATIONS

Ozinsky et al., "The repertoire for pattern recognition of pathogens by the innate immune system is defined by cooperation between toll-like receptors." Proc Natl Acad Sci USA. Dec. 5, 2000;97(25):13766-13771.

Page et al., "A nonisotopic method for the measurement of cell membrane integrity." Anticancer Res. Jul.-Aug. 1998;18(4A):2313-2316.

Palecek et al., "Integrin-ligand binding properties govern cell migration speed through cell-substratum adhesiveness." Nature. Feb. 6, 1997;385(6616):537-540.

Papworth, C., Bauer, J. C., Braman, J. and Wright, D. A., Site-directed mutagenesis in one day with >80% efficiency. Strategies, 1996. 9(3): p. 3-4.

Park et al., "Cutting Edge: CpG DNA inhibits dendritic cell apoptosis by up-regulating cellular inhibitor of apoptosis proteins through the phosphatidylinositide-3'-OH kinase pathway." J Immunol. Jan. 1, 2002;168(1):5-8.

Pasare C, Medzhitov R., "Toll pathway-dependent blockade of CD4+CD25+ T cell-mediated suppression by dendritic cells." Science. Feb. 14, 2003;299(5609):1033-1036.

Paskind et al., "Dependence of Moloney murine leukemia virus production on cell growth." Virology. Sep. 1975;67(1):242-248.

Pelletier J, Sonenberg N., "Internal initiation of translation of eukaryotic mRNA directed by a sequence derived from poliovirus RNA." Nature. Jul. 28, 1988;334(6180):320-325.

Perales et al., "Gene transfer in vivo: sustained expression and regulation of genes introduced into the liver by receptor-targeted uptake." Proc Natl Acad Sci USA. Apr. 26, 1994;91(9):4086-4090.

Phinney DG, Prockop DJ., "Concise review: mesenchymal stem/multipotent stromal cells: the state of transdifferentiation and modes of tissue repair—current views." Stem Cells. Nov. 2007;25(11):2896-902.

Ping et al., "Altered beta-adrenergic receptor signaling in heart failure, in vivo gene transfer via adeno and adeno-associated virus." Microcirculation. Jun. 1996;3(2):225-228.

Pinto et al., "Prostate-specific membrane antigen: a novel folate hydrolase in human prostatic carcinoma cells." Clin Cancer Res. Sep. 1996;2(9):1445-51.

Pittenger et al., "Multilineage potential of adult human mesenchymal stem cells." Science. Apr. 2, 1999;284(5411):143-7.

Poli V, Cortese R., "Interleukin 6 induces a liver-specific nuclear protein that binds to the promoter of acute-phase genes." Proc Natl Acad Sci USA. Nov. 1989;86(21):8202-8206.

Potter et al., "Enhancer-dependent expression of human kappa immunoglobulin genes introduced into mouse pre-B lymphocytes by electroporation." Proc Natl Acad Sci USA. Nov. 1984;81(22):7161-7165.

Prins et al., "The TLR-7 agonist, imiquimod, enhances dendritic cell survival and promotes tumor antigen-specific T cell priming: relation to central nervous system antitumor immunity." J Immunol. Jan. 1, 2006;176(1):157-164.

Prockop DJ., "Marrow stromal cells as stem cells for nonhematopoietic tissues." Science. Apr. 4, 1997;276(5309):71-4.

Prowse KR, Baumann H., "Hepatocyte-stimulating factor, beta 2 interferon, and interleukin-1 enhance expresson of the rat alpha 1-acid glycoprotein gene via a distal upstream regulatory region." Mol Cell Biol. Jan. 1988;8(1):42-51.

Pruschy et al., "Mechanistic Sutdies of a Signaling Pathway Activated by the Organic Dimerizer FK1012," Chemistry and biology 1994 vol. 1, No. 3, 164-172.

Przepiorka et al., "1994 Consensus Conference on Acute GVHD Grading." Bone Marrow Transplant. Jun. 1995;15(6):825-8.

Puccetti et al., "Effects of IL-12 and IL-23 on antigen-presenting cells at the interface between innate and adaptive immunity." Crit Rev Immunol. 2002;22(5-6):373-390.

Pule et al., "Artificial T-cell receptors." Cytotherapy. 2003;5(3):211-26.

Pullen et al., "CD40 signaling through tumor necrosis factor receptor-associated factors (TRAFs). Binding site specificity and activation of downstream pathways by distinct TRAFs." J Biol Chem. May 14, 1999;274(20):14246-14254.

Raina, D., et al., c-Abl tyrosine kinase regulates caspase-9 autocleavage in the apoptotic response to DNA damage. J Biol Chem, 2005. 280(12): p. 11147-51.

Ramos et al., "An Inducible Caspase 9 Suicide Gene to Improve the Safety of Mesenchymal Stromal Cell Therapies," Stem Cells, Translational and Clinical Research, Apr. 15, 2010, pp. 1-16.

Randall, K.L., et al., Dock8 mutations cripple B cell immunological synapses, germinal centers and long-lived antibody production. Nat Immunol, 2009. 10(12): p. 1283-91.

Re F, Strominger JL., "Toll-lke receptor 2(TLR2) and TLR4 differentially activate human dendritic cells." J Biol Chem. Oct. 5, 2001;276(40):37692-37699.

Reis e Sousa C., "Dendritic cells as sensors of infection." Immunity. May 2001;14(5):495-498.

Renan MJ., "Cancer genes: current status, future prospects, and applications in radiotherapy/oncology." Radiother Oncol. Nov. 1990;19(3):197-218.

Renatus, M., et al., Dimer formation drives the activation of the cell death protease Caspase-9. Proc Natl Acad Sci USA, 2001. 98(25): p. 14250-5.

Rescigno et al., "Dendritic cell survival and maturation are regulated by different signaling pathways." J Exp Med. Dec. 7, 1998;188(11):2175-2180.

Rezvani et al., "Functional leukemia-associated antigen-specific memory CD8+ T cells exist in healthy individuals and in patients with chronic myelogenous leukemia before and after stem cell transplantation." Blood. Oct. 15, 2003;102(8):2892-900.

Rezvani et al., "T-cell responses directed against multiple HLA-A*0201-restricted epitopes derived from Wilms' tumor 1 protein in patients with leukemia and healthy donors: identification, quantification, and characterization." Clin Cancer Res. Dec. 15, 2005;11(24 Pt 1):8799-807.

Richard et al, "Expansion of Genetically modified Primary Human HemopOietic cells Using Chemical Inducers of Dimerization," Blood vol. 95, 2000 pp. 430-436.

Riddell et al., "T-cell mediated rejection of gene-modified HIV-specific cytotoxic T lymphocytes in HIV-infected patients." Nat Med. Feb. 1996;2(2):216-23.

Ridge et al., "A conditioned dendritic cell can be a temporal bridge between a CD4+ T-helper and a T-Killer cell." Nature. Jun. 4, 1998;393(6684):474-478.

Ridgway D., "The first 1000 dendritic cell vaccinees." Cancer Invest. 2003;21(6):873-886.

Riol-Blanco et al., "The chemokine receptor CCR7 activates in dendritic cells two signaling modules that independently regulate chemotaxis and migratory speed." J Immunol. Apr. 1, 2005;174(7):4070-4080.

Rippe et al., "DNA-mediated gene transfer into adult rat hepatocytes in primary culture." Mol Cell Biol. Feb. 1990;10(2):689-695.

Rivera et al., "A humanized system for pharmacologic control of gene expression." Nat Med. Sep. 1996;2(9):1028-1032.

Rivera, V.M., "Controlling Gene Expression USing SynthetiC Ligands," Methods: A companion to Methods in Enzymology vol. 14,1998 pp. 421-429.

Ron et al., "Angiotensinogen gene-nducible enhancer-binding protein 1, a member of a new family of large nuclear proteins that recognize nuclear factor kappa B-binding sites through a zinc finger motif." Mol Cell Biol. May 1991;11(5):2887-2895.

Rooney et al., "Infusion of cytotoxic T cells for the prevention and treatment of Epstein-Barr virus-induced lymphoma in allogeneic transplant recipients." Blood. Sep. 1, 1998;92(5):1549-55.

Roose, J.P., et al., T cell receptor-independent basal signaling via Erk and Abl kinases suppresses RAG gene expression. PLoS Biol, 2003. 1(2): p. E53.

Rosenberg SA., "A new era for cancer immunotherapy based on the genes that encode cancer antigens." Immunity. Mar. 1999;10(3):281-287.

Roux et al., "A versatile and potentially general approach to the targeting of specific cell types by retrovirus: application to the infec-

(56) References Cited

OTHER PUBLICATIONS tion of human cells by means of major histocompatibility complex class I and class II antigens by mouse ecotropic murine leukemia virus-derived viruses." Proc Natl Acad Sci USA. Dec. 1989;86(23):9079-9083.
Rudd, M.L., A. Tua-Smith, and D.B. Straus, Lck SH3 domain function is required for T-cell receptor signals regulating thymocyte development. Mol Cell Biol, 2006. 26(21): p. 7892-900.
Rudinger, Peptide Hormones Jun. 1976; pp. 1-7.
Sale GE, Storb R., "Bilateral diffuse pulmonary ectopic ossification after marrow allograft in a dog. Evidence for allotransplantation of hemopoietic and mesenchymal stem cells." Exp Hematol. Nov. 1983;11(10):961-6.
Salkowski et al., "Lipopolysaccharide and monophosphoryl lipid A differentially regulate interleukin-12, gamma interferon, and interleukin-10 mRNA production in murine macrophages." Infect Immun. Aug. 1997;65(8):3239-3247.
Sallusto et al., "Rapid and coordinated switch in chemokine receptor expression during dendritic cell maturation." Eur J Immunol. Sep. 1998;28(9):2760-2769.
Samulski et al., "A recombinant plasmid from which an infectious adeno-associated virus genome can be excised in vitro and its use to study viral replication." J Virol. Oct. 1987;61(10):3096-3101.
Sanchez-Sanchez et al., "The multiple personalities of the chemokine receptor CCR7 in dendritic cells." J Immunol. May 1, 2006;176(9):5153-5159.
Sato et al., "Combination of monocyte-derived dendrinic cells and activated T cells which express CD40 ligand an new approach to cancer Immunotherapy," Cancer Imminol Immunther, vol. 53, No. 1, Jan. 2004, pp. 53-61.
Scandella et al., "CCL19/CCL21-triggered signal transduction and migration of dendritic cells requires prostaglandin E2." Blood. Mar. 1, 2004;103(5):1595-1601.
Scandella et al., "Prostaglandin E2 is a key factor for CCR7 surface expression and migration of monocyte-derved dendritic cells." Blood. Aug. 15, 2002;100(4):1354-1361.
Schellhammer et al., "Prostate specific antigen decreases after withdrawal of antiandrogen therapy with bicalutamide or flutamide in patients receiving combined androgen blockade." J Urol. May 1997;157(5):1731-1735.
Scher et al., "Clinical trials in relapsed prostate cancer: defining the target." J Natl Cancer Inst. Nov. 20, 1996;88(22):1623-1634.
Scher et al., "Design and end points of clinical trials for patients with progressive prostate cancer and castrate levels of testosterone: recommendations of the Prostate Cancer Clinical Trials Working Group." J Clin Oncol. Mar. 1, 2008;26(7):1148-59.
Scher Hi, Kelly WK., "Flutamide withdrawal syndrome: its impact on clinical trials in hormone-refractory prostate cancer." J Clin Oncol. Aug. 1993;11(8):1566-1572.
Schneider et al., "Inactivation of the human immunodeficiency virus type 1 inhibitory elements allows Rev-independent expression of Gag and Gag/protease and particle formation." J Virol. Jul. 1997;71(7):4892-4903.
Schoenberger et al., "T-cell help for cytotoxic T lymphocytes is mediated by CD40-CD40L interactions." Nature. Jun. 4, 1998;393(6684):480-483.
Schram, B.R., et al., B cell receptor basal signaling regulates antigen-induced Ig light chain rearrangements. J Immunol, 2008. 180(7): p. 4728-41.
Schuler et al., "The use of dendritic cells in cancer immunotherapy." Curr Opin Immunol. Apr. 2003; 15(2):138-147.
Schumacher TN., "T-cell-receptor gene therapy." Nat Rev Immunol. Jul. 2002;2(7):512-9.
Schuster, et al., "ALD518, a humanized anti-IL-6 antibody, treats anemia in patients with advanced non-small cell lung cancer (NSCLC): Results of a phase II, randomized, double-blind, placebo-controlled trial," 2010, J. Clin. Oncol. 28-7s (suppl.; abstr. 7631).
Schweitzer BA, Kool ET., "Aromatic Nonpolar Nucleosides as Hydrophobic Isosteres of Pyrimidine and Purine Nucleosides." J Org Chem. Dec. 1, 1994;59(24):7238-7242.

Seifert, R. and K. Wenzel-Seifert, Constitutive activity of G-protein-coupled receptors: cause of disease and common property of wild-type receptors. Naunyn Schmiedebergs Arch Pharmacol, 2002. 366(5): p. 381-416.
Shaffer et al., "Circulating tumor cell analysis in patients with progressive castration-resistant prostate cancer." Clin Cancer Res. Apr. 1, 2007;13(7):2023-9.
Shen et al., "Silencing of SOCS1 enhances antigen presentation by dendritic cells and antigen-specific anti-tumor immunity." Nat Biotechnol. Dec. 2004;22(12):1546-1553.
Shi, Y., Mechanisms of Caspase activation and inhibition during apoptosis. Mol Cell, 2002. 9(3): p. 459-70.
Shiozaki, E.N., et al., Mechanism of XIAP-mediated inhibition of caspase-9. Mol Cell, 2003. 11(2): p. 519-27.
Shiozaki, E.N., J. Chai, and Y. Shi, Oligomerization and activation of caspase-9, induced by Apaf-1 CARD. Proc Natl Acad Sci U S A, 2002. 99(7): p. 4197-202.
Silver et al., "Prostate-specific membrane antigen expression in normal and malignant human tissues." Clin Cancer Res. Jan. 1997;3(1):81-5.
Simpson et al., "Consequences of Fas-ligand and perforin expression by colon T cells in a mouse model of inflammatory bowel disease." Gastroenterology. Oct. 1998; 115(4):849-855.
Small EJ, Srinivas S., "The antiandrogen withdrawal syndrome. Experience in a large cohort of unselected patients with advanced prostate cancer." Cancer. Oct. 15, 1995;76(8):1428-1434.
Small EJ, Vogelzang NJ., "Second-line hormonal therapy for advanced prostate cancer: a shifting paradigm." J Clin Oncol. Jan. 1997;15(1):382-388.
Smith et al., "Cognate CD4(+) T cell licensing of dendritic cells in CD8(+) T cell immunity." Nat Immunol. Nov. 2004;5(11):1142-1148.
Smith et al., "DNA/MVA vaccine for HIV type 1:effects of codon-optimization and the expression of aggregates or virus-like particles on the immunogenicity of the DNA prime." AIDS Res Hum Retroviruses. Dec. 2004;20(12):1335-1347.
Snyder et al., "Prostaglandins modulate macrophage Ia expression." Nature. Sep. 9, 1982;299(5879):163-165.
Solomon et al., "Selective depletion of alloreactive donor lymphocytes: a novel method to reduce the severity of graft-versus-host disease in older patients undergoing matched sibling donor stem cell transplantation." Blood. Aug. 1, 2005;106(3):1123-9.
Sorensen et al., "Endostatin reduces cascularization, blood flow, and growth in a rat gliosarcoma." Neuro Oncol. Jan. 2002;4(1):1-8.
Sorkin, A. and M. von Zastrow, Endocytosis and signalling: intertwining molecular networks. Nat Rev Mol Cell Biol, 2009. 10(9): p. 609-22.
Spencer et al., "A general strategy for producing conditional alleles of Src-like tyrosine kinases." Proc Natl Acad Sci USA Oct. 10, 1995;92(21):9805-9809.
Spencer et al., "Controlling signal transduction with synthetic ligands." Science. Nov. 12, 1993;262(5136):1019-1024.
Spencer et al., "Functional analysis of Fas signaling in vivo using synthetic inducers of dimerization." Curr Biol. Jul. 1, 1996;6(7):839-847.
Spiegel, A.M., Defects in G protein-coupled signal transduction in human disease. Annu Rev Physiol, 1996. 58: p. 143-70.
Spitzer, TM. "Haploidentical Stem Cell Transplantation: the Always Present but overlooked Donor," Hematology, 2005, 1:390-395.
Sporri R, Reis e Sousa C., "Inflammatory mediators are insufficient for full dendritic cell activation and promote expansion of CD4+ T cell populations lacking helper function." Nat Immunol. Feb. 2005;6(2):163-170.
Srinivasula et al., "A conserved XIAP-interactionmotif in caspase-9 and Smac/DIABLO regulates caspase activity and apoptosis," Nature 410, 112-116.
Steinman et al., "Tolerogenic dendritic cells." Annu Rev Immunol. 2003;21:685-711.
Steinman RM, Pope M., "Exploiting dendritic cells to improve vaccine efficacy." J Clin Invest. Jun. 2002;109(12):1519-1526.
Stennicke, H.R., et al., Caspase-9 can be activated without proteolytic processing. J Biol Chem, 1999. 274(13): p. 8359-62.

(56) References Cited

OTHER PUBLICATIONS

Straathof et al., "An inducible caspase 9 safety switch for T-cell therapy." Blood. Jun. 1, 2005;105(11):4247-54.
Strasser et al., "Integrin Activation by Regulated Dimerization and Oligomerization of Platelet Endothelial Cell Adhesion Molecule (PECAM)-1 from Within the Cell," Immunity Review 30, Feb. 20, 2009, 180-192.
Strober et al., "Signalling pathways and molecular interactions of NOD1 and NOD2." Nat Rev Immunol. Jan. 2006;6(1):9-20.
Studeny et al., "Bone marrow-derived mesenchymal stem cells as vehicles for interferon-beta delivery into tumors." Cancer Res. Jul. 1, 2002;62(13):3603-8.
Studeny et al., "Mesenchymal stem cells: potential precursors for tumor stroma and targeted-delivery vehicles for anticancer agents." J Natl Cancer Inst. Nov. 3, 2004;96(21):1593-603.
Su et al., "Alternatively spliced variants of prostate-specific membrane antigen RNA: ratio of expression as a potential measurement of progression." Cancer Res. Apr. 1, 1995;55(7):1441-1443.
Su et al., "Telomerase mRNA-transfected dendritic cells stimulate antigen-specific CD8+ and CD4+ T cell responses in patients with metastatic prostate cancer." J Immunol. Mar. 15, 2005;174(6):3798-3807.
Suarez-Alvarez et al, Epigenetic Mechanisms Regulate MHC and Antigen Processing Moleculers in Human Embryonic and Induced Pluripotent Stem Cells. PLoS One (April) 5(4):e10192, 2010, pp. 1-12.
Suda et al., "Molecular Cloning and Expression of the Fas Ligand, a Novel Member of the Tumor Necrosis Factor Family," Cell vol. 75, 1169-1176 Dec. 17, 1993.
Tai et al., "Mechanisms by which SGN-40, a Humanized Anti-CD40 Antibody, Induces Cytotoxicity in Human Multiple Myeloma Celis: Clinical Implications," Cancer Research, Apr. 15, 2004, vol. 64, pp. 2846-2852.
Tao, Y.X., Constitutive activation of G protein-coupled receptors and diseases: insights into mechanisms of activation and therapeutics. Pharmacol Ther, 2008. 120(2): p. 129-48.
ten Klooster JP, Hordijk PL., "Targeting and localized signalling by small GTPases." Biol Cell. Jan. 2007;99(1):1-12.
Tepler et al., "The gene for the rat mast cell high affinity IgE receptor alpha chain. Structure and alternative mRNA splicing patterns." J Biol Chem. Apr. 5, 1989;264(10):5912-5915.
Termeer et al., "Oligosaccharides of hyaluronan are potent activators of dendritic cells." J Immunol. Aug. 15, 2000;165(4):1863-1870.
Tey et al., Inducible Caspase 9 Suicide Gene to Improve the Safety of Allodepleted T Cells after Haploidentical Stem Cell Transplantation. Bio Blood & Marrow Transplant. 13:913-924 (2007).
Thomis et al., "A Fas-based suicide switch in human T cells for the treatment of graftversus-host disease." Blood. Mar. 1, 2001;97(5):1249-57.
Thompson et al., "The low-toxicity versions of LPS, MPL adjuvant and RC529, are efficient adjuvants for CD4+ T Cells." J Leukoc Biol. Dec. 2005;78(6):1273-1280.
Tibbetts C., "Viral DNA sequence from incomplete particles of human adenovirus type 7." Cell. Sep. 1977;12(1):243-249.
Tiberghien et al., "Administration of herpes simplex-thymidine kinase-expressing donor T cells with a T-cell-depleted allogeneic marrow graft." Blood. Jan. 1, 2001;97(1):63-72.
Tolar et al., "Sarcoma derived from cultured mesenchymal stem cells." Stem Cells. Feb. 2007;25(2):371-9.
Tone M . et al., "Regulation of CD40 function by its isoforms generated through alternative splicing," PNAS. Feb. 13, 2001, vol. 98, No. 4, pp. 1751-1756.
Tong et al, "Prospects for CD40-directed Experimental Therapy of Human Cancer," Cancer Gene Therapy vol. 10, 2003,pp. 1-13.
Troyer et al., "Detection and characterization of the prostate-specific membrane antigen (PSMA) in tissue extracts and body fluids." Int J Cancer. Sep. 4, 1995;62(5):552-8.
Tur-Kaspa et al., "Use of electroporation to introduce biologically active foreign genes into primary rat hepatocytes." Mol Cell Biol. Feb. 1986;6(2):716-718.

Tyndall A, Uccelli A., "Multipotent mesenchymal stromal cells for autoimmune diseases: teaching new dogs old tricks." Bone Marrow Transplant. Jun. 2009;43(11):821-8.
Tze, L.E., et al., Basal immunoglobulin signaling actively maintains developmental stage in immature B cells. PLoS Biol, 2005. 3(3): p. e82.
van der Pouw Krann T.C., et al., "Prostaglandin E2 is a potent inhibitor of human interleukin12 production," J Exp Med., 1995, vol. 181, pp. 775-779.
Vassiliou et al., "Prostaglandin E2 promotes the survival of bone marrow-derived dendritic cells." J Immunol. Dec. 1, 2004;173(11):6955-6964.
Vidalain et al., "CD40 signaling in human dendritic cells is initiated within membrane rafts." EMBO J. 2000; 19:3304-3313.
Vieweg J, Jackson A., "Modulation of antitumor responses by dendritic cells." Springer Semin Immunopathol. Jan. 2005;26(3):329-341.
Vincent et al., "Targeting of proteins to membranes through hedgehog auto-processing." Nat Biotechnol. Aug. 2003;21(8):936-940.
Vonderheide et al., "CD40 activation of carcinoma cells increases expression of adhesion and major histocompatibility molecules but fails to induce either CD80/CD86 expression or T cell alloreactivity." Int J Oncol. Oct. 2001;19(4):791-798.
Wagner et al., "A strategy for treatment of Epstein-Barr virus-positive Hodgkin's disease by targeting interleukin 12 to the tumor environment using tumor antigen-specific T cells." Cancer Gene Ther. Feb. 2004;11(2):81-91.
Wagner et al., "Transferrin-polycation conjugates as carriers for DNA uptake into cells." Proc Natl Acad Sci USA. May 1990;87(9):3410-3414.
Waldner, C., et al., Double conditional human embryonic kidney cell line based on FLP and PhiC31 mediated transgene integration. BMC Res Notes, 2011. 4: p. 420.
Walter et al., "Reconstitution of cellular immunity against cytomegalovirus in recipients of allogeneic bone marrow by transfer of T-cell clones from the donor." N Engl J Med. Oct. 19, 1995;333(16):1038-44.
Wang et al., "Relative contributions of codon usage, promoter efficiency and leader sequence to the antigen expression and immunogenicity of HIV-1 Env DNA vaccine." Vaccine. May 22, 2006;24(21):4531-4540.
Werneburg et al., "Molecular Characterization of CD40 Signaling Intermediates," The Journal of Biological Chemistry, vol. 276, Nov. 16, 2001, 43334-43342.
Werts et al., "TIR, CARD and PYRIN: three domains for an antimicrobial triad." Cell Death Differ. May 2006;14(5):798-815.
Wesemann et al., "Suppressor of cytokine signaling 1 inhibits cytokine induction of CD40 expression in macrophages." J Immunol. Sep. 1, 2002;169(5):2354-2360.
Wilson et al., "A 58-base-par region of the human C3 gene confers synergistic inducibility by interleukin-1 and interleukin-6." Mol Cell Biol. Dec. 1990;10(12):6181-6191.
Wilson et al., "Implantation of vascular grafts lined with genetically modified endothelial cells." Science. Jun. 16, 1989;244(4910):1344-1346.
Woltman et al., "Rapamycin specifically interferes with GM-CSF signaling in human dendritic cells, leading to apoptosis via increased p27KIP1 expression." Blood. Feb. 15, 2003;101(4):1439-1445.
Wong et al., "Fas Antigen and p55 TNF Receptor Signal Apoptosis Through Distinct Pathways," Journal of Immunology, 1994, 152: pp. 1751-1755.
Wong P, Famer EG., "Feedback regulation of pathogen-specific T cell priming." Immunity. Apr. 2003;18(4):499-511.
Wright et al., "Upregulation of prostate-specific membrane antigen after androgen-deprivation therapy." Urology. Aug. 1996;48(2):326-34.
Wu and Wu, "Liver-directed gene delivery," Adv Drug Delivery Rev, 1993;12:159-167.
Wu et al., "Codon optimization reveals critical factors for high level expression of two rare codon genes in *Escherichia coli*: RNA stability and secondary structure but not tRNA abundance." Biochem Biophys Res Commun. Jan. 2, 2004;313(1):89-96.

(56) References Cited

OTHER PUBLICATIONS

Wu Gy, Wu Ch., "Receptor-mediated in vitro gene transformation by a soluble DNA carrier system." J Biol Chem. Apr. 5, 1987;262(10):4429-32.
Xiao et al., "Efficient long-term gene transfer into muscle tissue of immunocompetent mice by adeno-associated virus vector." J Virol. Nov. 1996;70(11):8098-8108.
Xiao et al., "Establishment of a Cell Model Based on FKBP12 Dimerization for Screening of FK506-like Neurotrophic small Molecular Compounds." J Biomol Screen. Apr. 2006;11(3):225-235.
Xie et al., "Adenovirus-mediated tissue-targeted expression of a caspase-9-based artificial death switch for the treatment of prostate cancer." Cancer Res. Sep. 15, 2001;61(18):6795-6804.
Xu et al., "Optimization of transcriptional regulatory elements for constructing plasmid vectors." Gene. Jul. 11, 2001;272(1-2):149-156.
Yadava A, Ockenhouse CF., "Effect of codon optimization on expression levels of a functionally folded malaria vaccine candidate in prokaryotic and eukaryotic expression systems." Infect Immun. Sep. 2003;71(9):4961-4969.
Yan et al., "Enhanced cellular immune responses elicited by an engineered HIV-1 subtype B consensus-based envelope DNA vaccine." Mol Ther. Feb. 2007;15(2):411-421.
Yanagawa Y, Onoe K., "CCL19 induces rapid dendritic extension of murine dendritic cells." Blood. Sep. 15, 2002;100(6):1948-1956.
Yang et al., "In vivo and in vitro gene transfer to mammalian somatic cells by particle bombardment." Proc Natl Acad Sci USA. Dec. 1990;87(24):9568-9572.
Yang et al., "Induction of inflammation by West Nile virus capsid through the caspase-9 apoptotic pathway." Emerg Infect Dis. Dec. 2002;8(12):1379-1384.
Yoon et al., "Unexpected severe calcification after transplantation of bone marrow cells in acute myocardial infarction." Circulation. Jun. 29, 2004;109(25):3154-7.
Zechner et al., "Recombinant human cachectin/tumor necrosis factor by not interleukin-1 alpha downregulates lipoprotein lipase gene expression at the transcriptional level in mouse 3T3-L1 adipocytes." Mol Cell Biol. Jun. 1988;8(6):2394-2401.
Zhang et al., "Integrin-nucleated Toll-like receptor (TLR) dimerization reveals subcellular targeting of TLRs and distinct mechanisms of TLR4 activation and signaling." FEBS Lett. Dec. 4, 2002;532(1-2):171-176.
Zhang et al., "mRNA secondary structure at start AUG codon is a key limiting factor for human protein expression in *Escherichia coli*." Biochem Biophys Res Commun. Oct. 13, 2006;349(1):69-78.
Zhao et al., "Integrin Activation by Regulated Dimerization and Oligomerization of Platelet Endothelial Cell Adhesion Molecule (PECAM)-1 from Within the Cell," Jan. 8, 2001, Journal of Cell Biology, vol. 152, 65-73.
Zhong et al., "Chimeric antigen receptors combining 4-1BB and CD28 signaling domains augment PI3kinase/AKT/Bcl-XL activation and CD8+ T cell-mediated tumor eradication." Mol Ther. Feb. 2010;18(2):413-20.
Zhou et al., "Multiple RNA splicing and the presence of cryptic RNA splice donor and acceptor sites may contribute to low expression levels and poor immunogenicity of potential DNA vaccines containing the env gene of equine infectious anemia virus (EIAV)." Vet Microbiol. Aug. 25, 2002;88(2):127-151.
Zitvogel et al., "Therapy of murine tumors with tumor peptide-pulsed dendritic cells: dependence on T cells, B7 costimulation, and T helper cell 1-associated cytokines." J Exp Med. Jan. 1, 1996;183(1):87-97.
Zlatkine et al., "Retargeting of cytosolic proteins to the plasma membrane by the Lck protein tyrosine kinase dual acylation motif." J Cell Sci. Mar. 1997;110(Pt5):673-679.
Zou et al., "Regulation of the Apaf-1/Caspase-9 Apoptosome by Caspase-3 and XIAP," The Journal of Biological Chemistry, vol. 278, No. 10, Mar. 7, 2003, pp. 8091-8098.
zur Medege et al., "Expression and immunogenicity of sequence-modified human immunodeficiency virus type 1 subtype B pol and gagpol DNA vaccines." J Virol. Jun. 2003;77(11):6197-6207.
zur Megede, J., et al., "Increased expression and immunogenicity of sequence-modified human immunodeficiency virus type 1 gag gene," 2000. J. Virol. 74:2628-2635.
Office Action dated: Jun. 23, 2014 in U.S. Appl. No. 13/786,672, filed Mar. 6, 2014 and published as: 2013/0323834 on: Dec. 5, 2013.
Office Action dated: Dec. 26, 2014 in U.S. Appl. No. 13/792,135, filed Mar. 10, 2013 and published as: 2014/0255360 on: Sep. 11, 2014.
International Search Report and Written Opinion mailed: Oct. 17, 2011. For International Application No. PCT/US2011/037381, filed May 20, 2011 and published as WO/2011/146862 on Nov. 24, 2011.
Invitation to pay additional fees and, where applicable, protest fee dated: Oct. 24, 2014 in International Application No. PCT/US2014/22004 filed Mar. 7, 2014.
International Search Report and Written Opinion dated: Jan. 7, 2015 in International Application No. PCT/US2014/22004 filed Mar. 7, 2014.
International Search Report and the Written Opinion of the International Searching Authority dated Oct. 31, 2014 in International Application No. PCT/US2014/40964 filed: Jun. 4, 2014.
Ando et al., "A Safeguard System for Induced Pluripotent Stem Cell-Derived Rejuvenated T Cell Therapy" Stem Cell Reports (2015) 5:1-12.
Lim et al., "Lentiviral vector mediated thymidine kinase expression in pluripotent stem cells enables removal of tumorigenic cells" PLoS One (2013) 8(7):e70543.
Wu et al., "Development of an inducible caspase-9 safety switch for pluripotent stem cell-based therapies" Molecular Therapy—Methods Clinical Development 1:14053.
Zhai et al., "Vaccinia virus protein F1L is a caspase-9 inhibitor" J. Biol. Chem. (2010) 285(8):5569-80.
Zhong et al., "Safeguarding nonhuman primate iPS cells with suicide genes" Molecular Therapy (2011) 19(9):1667-1675.
International Search Report and Written Opinion mailed on Aug. 12, 2015 for International Application No. PCT/US2015/019186, filed on Mar. 6, 2015 and published as WO 2015/134877 on Sep. 11, 2015.
International Preliminary Report on Patentability mailed on Sep. 24, 2015 for International Application No. PCT/US2014/022004, filed on Mar. 7, 2014 and published as WO 2014/164348 on Oct. 9, 2014.
Office Action dated May 27, 2015 in U.S. Appl. No. 13/792,135, filed Mar. 10, 2013 and published as U.S. 2014/0255360 on Sep. 11, 2014.
Office Action dated: Feb. 6, 2013 in U.S. Appl. No. 13/112,739, filed May 20, 2011 and published as: 2011/0286980 on Nov. 24, 2011.
Office Action dated: Oct. 23, 2013 in U.S. Appl. No. 13/112,739, filed May 20, 2011 and published as: 2011/0286980 on Nov. 24, 2011.
Office Action dated: Aug. 15, 2014 in U.S. Appl. No. 13/112,739, filed May 20, 2011 and published as: 2011/0286980 on Nov. 24, 2011.
Office Action dated Apr. 2, 2015 in U.S. Appl. No. 13/112,739, filed May 20, 2011 and published as U.S. 2011/0286980 on Nov. 24, 2011.
Office Action dated Apr. 14, 2015 in U.S. Appl. No. 13/786,672, filed Mar. 6, 2014 and published as U.S. 2013/0323834 on Dec. 5, 2013.
Brentjens RJ, Davila ML, Riviere I, et al: CD19-targeted T cells rapidly induce molecular remissions in adults with chemotherapy-refractory acute lymphoblastic leukemia. Sci Transl Med 5:177ra38, 2013.
Carpenito C, Milone MC, Hassan R, et al: Control of large, established tumor xenografts with genetically retargeted human T cells containing CD28 and CD137 domains. Proc Natl Acad Sci U S A 106:3360-5, 2009.
Finney HM, Akbar AN, Lawson AD: Activation of resting human primary T cells with chimeric receptors: costimulation from CD28, inducible costimulator, CD134, and CD137 in series with signals from the TCR zeta chain. J Immunol 172:104-13, 2004.
Guedan S, Chen X, Madar A, et al: ICOS-based chimeric antigen receptors program bipolar TH17/TH1 cells. Blood, 2014, p. 1070-80.
Kalos M, Levine BL, Porter DL, et al: T cells with chimeric antigen receptors have potent antitumor effects and can establish memory in patients with advanced leukemia. Sci Transl Med 3:95ra73, 2011.
Kershaw MH, Westwood JA, Parker LL, et al: A phase I study on adoptive immunotherapy using gene-modified T cells for ovarian cancer. Clin Cancer Res 12:6106-15, 2006.

(56) References Cited

OTHER PUBLICATIONS

Porter DL, Levine BL, Kalos M, et al: Chimeric antigen receptor-modified T cells in chronic lymphoid leukemia. N Engl J Med 365:725-33, 2011.
Pule MA, Savoldo B, Myers GD, et al: Virus-specific T cells engineered to coexpress tumor-specific receptors: persistence and antitumor activity in individuals with neuroblastoma. Nat Med 14:1264-70, 2008.
Song DG, Ye Q, Poussin M, et al: CD27 costimulation augments the survival and antitumor activity of redirected human T cells in vivo. Blood 119:696-706, 2012.
Till BG, Jensen MC, Wang J, et al: CD20-specific adoptive immunotherapy for lymphoma using a chimeric antigen receptor with both CD28 and 4-1BB domains: pilot clinical trial results. Blood 119:3940-50, 2012.
Aliprantis et al., "The apoptotic signaling pathway activated by Toll-like receptor-2" EMBO J. (2000) 19(13):3325-3336.
Bollard CM, et al., "Adapting a transforming growth factor beta-related tumor protection strategy to enhance antitumor immunity" Blood (2002) 99:3179-3187.
Burns et al., "Inhibition of interleukin 1 receptor/Toll-like receptor signaling through the alternatively spliced, short form of MyD88 is due to its failure to recruit IRAK-4" J. Exp. Med (2003) 197(2):263-268.
Horwitz, E. M. et al., "Mesenchymal Stromal Cells" Biol Blood Marrow Transplant (2007) 13:53-57.
Hostager et al., "Different CD40-mediated signaling events require distinct CD40 structural features" J. Immunol. (1996) 157:1047-1053.
Jonuleit et al., "Pro-inflammatory cytokines and prostaglandins induce maturation of potent immunostimulatory dendritic cells under fetal calf serum-free conditions" Eur. J. Immunol. (1997) 27:3135-3142.
Medzhitov et al., "MyD88 is an adaptor protein in the hToll/IL-1 receptor family signaling pathways" Molecular Cell (1998) 2:253-258.
Milone, M.C., et al., "Chimeric receptors containing CD137 signal transduction domains mediate enhanced survival of T cells and increased antileukemic efficacy in vivo" Mol. Ther. (2009) 17:1453-1464.

Nikitina, E. et al., "Versatile prostate cancer treatment with inducible caspase and interleukin-12" Cancer Res. (2005) 65:4309-4319.
Zhang, W., et al., "mRNA secondary structure at start AUG codon is a key limiting factor for human protein expression in *Escherichia coli*." Biochem. Biophys. Res. Commun. (2006) 349:69-78.
Ferraro, B. et al., "Co-delivery of PSA and PSMA DNA vaccines with electroporation induces potent immune responses" Human Vaccines (2011) 7:120-127.
Gaubert and Wengel, "Synthesis of 1-(2'-O-methyl-β-d-ribofuranosyl)-5-nitroindole and its phosphoramidite derivative" Tetrahedron Letters (2004) 45:5629-5632.
Gross, G., and Eshar, Z., "Endowing T cells with antibody specificity using chimeric T cell receptors" FASEB Journal (1992) 6:3370-3378.
Haynes, N.M., et al., "Redirecting mouse CTL against colon carcinoma: superior signaling efficacy of single-chain variable domain chimeras containing TCR-zeta vs Fc epsilon RI-gamma" J. Immunol. (2001) 166:182-7.
Heslop, H.E., "Genetic engineering of T-cell receptors: TCR takes to titin" Blood (2013) 122:853-854.
Sardesai, N.Y., and Weiner, D.B., "Electroporation delivery of DNA vaccines: prospects for success" Current Opinion in Immunol. (2011) 23:421-9.
Zhang, Y., et al., "Transduction of human T cells with a novel T-cell receptor confers anti-HCV reactivity" PLOS Pathogens (2010) 6:e1001018.
International Preliminary Report on Patentability dated Dec. 17, 2015 in International Application No. PCT/US2014/040964, filed on Jun. 4, 2014 and published as WO 2014/197638 on Dec. 11, 2014.
Office Action dated Feb. 26, 2016 in U.S. Appl. No. 13/786,672, filed Mar. 6, 2013 and published as U.S. 2013/0323834 on Dec. 5, 2013.
Kiuru et al., "Genetic control of wayward pluripotent stem cells and their progeny after transplantation" Cell Stem Cell (2009) 4(4):289-300.
Haase et al., "Generation of induced pluripotent stem cells from human cord blood" Cell Stem Cell (2009) 5:434-441.
Addgene product literature Plasmid #15567, Feb. 22, 2016, pp. 1-4, https://www.addgene.org/15567/.
Ariad Pharmaceuticals, Inc., "Argent Regulated Homodimerization Kit" Version 2.0, product brochure, Sep. 9, 2002.
Office Action dated May 3, 2016 in U.S. Appl. No. 13/792,135, filed Mar. 10, 2013 and published as U.S. 2014/0255360 on Sep. 11, 2014.

\* cited by examiner

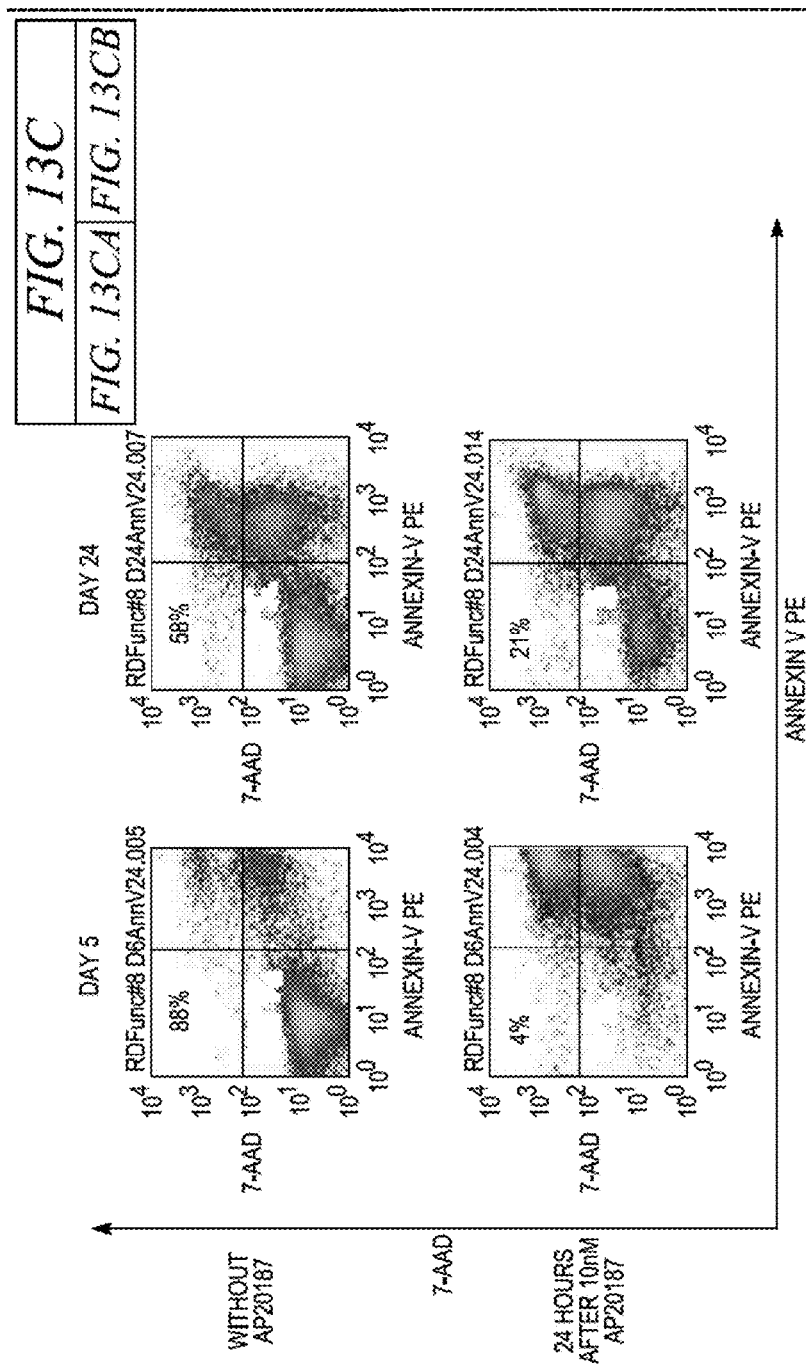

FIG. 19 Panels A-Q

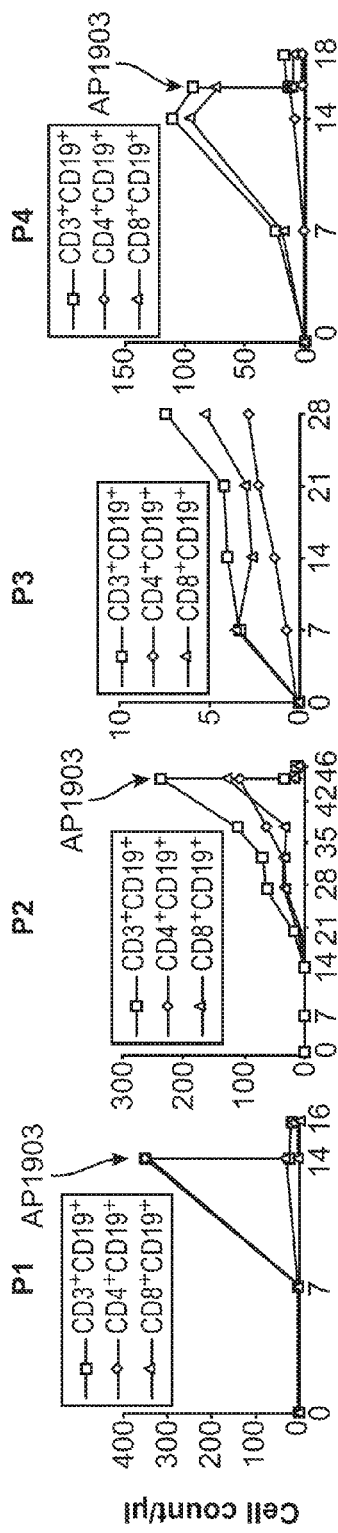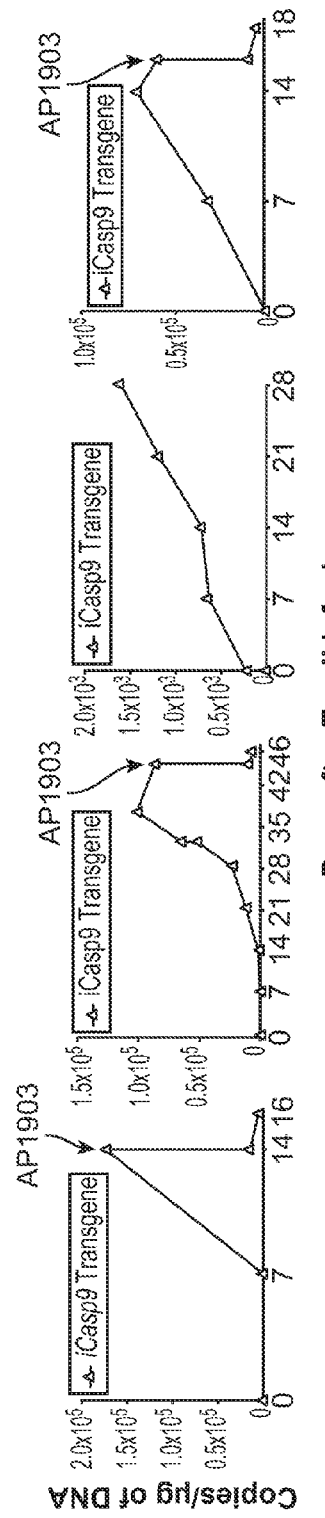

US 9,393,292 B2

METHODS FOR INDUCING SELECTIVE APOPTOSIS

RELATED PATENT APPLICATIONS

This patent application is a continuation application of U.S. patent application Ser. No. 13/112,739, filed May 20, 2011, and entitled METHODS FOR INDUCING SELECTIVE APOPTOSIS, naming Malcolm K. Brenner as inventor, which is a non-provisional patent application claiming priority to U.S. Provisional Patent Application Ser. No. 61/347,154, filed May 21, 2010, and entitled "Method for Inducing Selective Apoptosis," which are all referred to and all incorporated by reference herein in their entirety. This application incorporates by reference the computer readable "Sequence Listing" that was filed on Aug. 8, 2011, in U.S. patent application Ser. No. 13/112,739, filed May 20, 2011.

STATEMENT OF GOVERNMENT SUPPORT

This invention has been developed pursuant to NHLBI grant number U54HL081007. The Government may have rights in this invention.

FIELD

The technology relates in part to methods for cell therapy by modifying transfused cells to express an inducible caspase 9 protein, so that the cells may be selectively killed if the patient experiences dangerous side effects. The technology further relates in part to methods for preventing or treating Graft versus Host Disease by modifying T cells before administration to a patient, so that they may be selectively killed if GvHD develops in the patient.

SEQUENCE LISTING

The instant application contains a Sequence Listing which has been submitted in ASCII format via EFS-Web and is hereby incorporated by reference in its entirety. Said ASCII copy, created on Jul. 5, 2011, is named BEL206UT.txt and is 29,927 bytes in size.

BACKGROUND

There is an increasing use of cellular therapy in which modified or unmodified cells are administered to a patient. An example of a cellular therapy is adoptive T cell transfer after CD34+ stem cell transplantation. Administering T cells after stem cell transfer helps to accelerate the reconstitution of an immune system in the patient recipient. When a matched related or unrelated donor is not available, or the disease is too aggressive for an extensive donor search, the use of an HLA haploidentical family donor may be effective. Such donors may be parents, siblings, or second-degree relatives. Such infusions may enhance immune recovery and thereby reduce virus infections and eliminate relapsing leukemia cells. However, the coexistence of alloreactive T cells in a donor stem cell graft may cause graft-versus-host disease (GvHD) in which the donor cells react against the recipient, which may progressively damage the skin, gut, liver, and other organs of the recipient, often with fatal consequences. The administration of more than $10^5$ T cells/kg recipient weight of unmodified donor T cells has been associated with severe GvHD (Huang, X. J., et al., (2007) Haematoligica 92:414-417; Huang, X. J., et al., (2008) J. Clin. Immunol. 28:276-283). Although the likelihood of GvHD may be reduced by not providing T cells to the patient, this may lead to a high rate of post-transplant infectious complications and a high incidence of disease relapse.

Other examples of cell therapies include using native cells or cells genetically engineered to express a heterologous gene. These treatments are used for many disorders, including blood disorders, but these therapies may have negative side effects. In another method, immature progenitor cells that can differentiate into many types of mature cells, such as, for example, mesenchymal stromal cells, may be used to treat disorders by replacing the function of diseased cells. There is a need for a rapid and effective mechanism to remove possible negative effects of donor cells used in cellular therapy.

SUMMARY

An inducible caspase 9 system has been applied to human T cells, which were then administered to stem cell transplantation patients. This system does not rely on interfering with cell division, or DNA synthesis, thus the system is not restricted to dividing cells. Instead, the system relies on a human-derived gene, which is likely less immunogenic than other safety switches using, for example, a HSV-tk derived gene. Further, the system does not involve the use of an otherwise therapeutic compound such as, for example, gancylovir, allowing the compound to continue to be used for therapy, such as, for example, cancer therapy. Upon exhibiting graft versus host disease (GvHD) symptoms, caspase 9 was activated after the administration of a multimeric ligand, which caused dimerization of the protein and induced apoptosis of the allogeneic activated T cells. These features form the basis of T cell transfusion immunotherapies, providing a safety switch following transfusion, should a negative event occur, such as GvHD. A caspase 9 based apoptotic safety switch has also been applied to progenitor cells, such as mesenchymal stromal cells, before administering them to a patient, to provide the ability to selectively kill the therapeutic cells if the patient experiences negative side effects.

Thus, featured in some embodiments are methods of administering donor T cells to a human patient, comprising transfecting or transducing human donor T cells in a donor cell culture with a nucleic acid including a promoter region and a nucleotide sequence that encodes a chimeric protein comprising a multimeric ligand binding region and a caspase 9 polypeptide; and administering the transduced or transfected donor T cells to the human patient.

Thus, also featured in some embodiments are methods of reducing the effect of graft versus host disease in a human patient following donor T cell transplantation, comprising transfecting or transducing human donor T cells in a donor cell culture with a nucleic acid including a promoter region and a nucleotide sequence that encodes a chimeric protein comprising a multimeric ligand binding region and a caspase 9 polypeptide; administering the transduced or transfected donor T cells to the patient; detecting the presence or absence of graft versus host disease in the patient after; and administering a multimeric ligand that binds to the multimeric ligand binding region to a patient for whom the presence of graft versus host disease is detected.

Thus, also featured in some embodiments are methods of stem cell transplantation, comprising administering a haploidentical stem cell transplant to a human patient; and administering haploidentical donor T cells to the patient, wherein the T cells are transfected or transduced in a haploidentical donor cell culture with a nucleic acid including a promoter region and a nucleotide sequence that encodes a chimeric protein comprising a multimeric ligand binding region and a caspase 9 polypeptide.

Also featured in some embodiments are methods of administering donor T cells to a human patient, comprising transfecting or transducing non-allodepleted human donor T cells in a donor cell culture with a nucleic acid including a promoter region and a nucleotide sequence that encodes a chimeric protein comprising a multimeric ligand binding region and a caspase 9 polypeptide; and administering the transduced or transfected donor T cells to the human patient.

Also featured in some embodiments are methods of reducing the effect of graft versus host disease in a human patient following donor T cell transplantation, comprising transfecting or transducing non-allodepleted human donor T cells in a donor cell culture with a nucleic acid including a promoter region and a nucleotide sequence that encodes a chimeric protein comprising a multimeric ligand binding region and a caspase 9 polypeptide; administering the transduced or transfected donor T cells to the patient; detecting the presence or absence of graft versus host disease in the patient after; and administering a multimeric ligand that binds to the multimeric ligand binding region to a patient for whom the presence of graft versus host disease is detected.

Also featured in some embodiments are methods of stem cell transplantation, comprising administering a haploidentical stem cell transplant to a human patient; and administering non-allodepleted haploidentical donor T cells to the patient, wherein the T cells are transfected or transduced in a haploidentical donor cell culture with a nucleic acid including a promoter region and a nucleotide sequence that encodes a chimeric protein comprising a multimeric ligand binding region and a caspase 9 polypeptide.

In some embodiments, the haploidentical stem cell transplant is a $CD34^+$ haploidentical stem cell transplant. In some embodiments, the human donor T cells are haploidentical to the patient's T cells. In some embodiments, the patient has cancer. In some embodiments, the patient has a solid tumor. In some embodiments, the cancer is present in the blood or bone marrow of the patient. In some embodiments, the patient has a blood or bone marrow disease. In some embodiments, the patient has been diagnosed with any condition or disorder that can be alleviated by stem cell transplantation. In some embodiments, the patient has been diagnosed with sickle cell anemia or metachromatic leukodystrophy.

In some embodiments, the promoter is activated in activated T cells. In some embodiments, the promoter comprises a 5' LTR sequence, for example a polynucleotide in SEQ ID NO: 1, or, for example, the nucleotide sequence of SEQ ID NO: 1. In some embodiments, the chimeric protein further comprises a marker polypeptide, for example, a CD19 polypeptide. In some embodiments, the methods further comprise a selection step, wherein cells that express the marker are selected for administration to the patient. In some embodiments, the cells are selected by immunomagnetic selection.

In some embodiments, the caspase 9 polypeptide is a truncated caspase 9 polypeptide. In some embodiments, the caspase 9 polypeptide lacks the caspase recruitment domain. In some embodiments, the caspase 9 polypeptide comprises the amino acid sequence of SEQ ID NO: 9, or a fragment thereof, or is encoded by the nucleotide sequence of SEQ ID NO: 8, or a fragment thereof.

In some embodiments, the donor cell culture is prepared from a bone marrow sample. In some embodiments, the donor cell culture is prepared from peripheral blood. In some embodiments, the donor cell culture is prepared from donor peripheral blood mononuclear cells. In some embodiments, the donor T cells are allodepleted from the donor cell culture before transfection or transduction. In some embodiments, the transduced or transfected T cells are cultured in the presence of IL-2 before administration to the patient.

In some embodiments, the methods further comprise administering a multimeric ligand that binds to the multimeric ligand binding region. In some embodiments, the multimeric ligand binding region is selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof. In some embodiments, the multimeric ligand binding region is an FKBP12 region. In some embodiments, the multimeric ligand is an FK506 dimer or a dimeric FK506 analog ligand. In some embodiments, the multimeric ligand is AP1903. In some embodiments, the multimeric ligand is administered to treat graft versus host disease. In some embodiments, the patient exhibits graft versus host disease symptoms before the multimeric ligand is administered. In some embodiments, the patient exhibits one or more Stage 0 graft versus host disease symptoms. In some embodiments, the patient exhibits one or more Stage 1 graft versus host disease symptoms. In some embodiments, the patient exhibits one or more Stage 2 graft versus host disease symptoms. In some embodiments, the patient exhibits one or more Stage 3 graft versus host disease symptoms. In some embodiments, the patient exhibits one or more Stage 4 graft versus host disease symptoms. In some embodiments, more than one dose of the multimeric ligand is administered. In some embodiments, after administration of the multimeric ligand, the number of alloreactive T cells is reduced. In some embodiments, the alloreactive T cells express the marker and CD3. In some embodiments, the number of alloreactive T cells is reduced by from about 60% to 99%, about 70% to 95%, from 80% to 90% or about 90% or more after administration of the multimeric ligand. In some embodiments, after administration of the multimeric ligand, donor T cells survive in the patient that are able to expand and are reactive to viruses and fungi. In some embodiments, after administration of the multimeric ligand, donor T cells survive in the patient that are able to expand and are reactive to tumor cells in the patient.

In some embodiments, the patients have received haplo-CD34+ stem cell transplants before or at the same time as administration of the donor T cells. In some embodiments, the donor T cells are transduced or transfected with a retroviral vector. In some embodiments, the retroviral vector is a murine leukemia virus vector. In some embodiments, the retroviral vector is an SFG vector. In some embodiments, the transfected or transduced cells are further transfected or transduced with a gene expression vector.

In some embodiments, the methods further comprise determining whether to administer an additional dose or additional doses of the multimeric ligand to the patient based upon the appearance of graft versus host disease symptoms in the patient. In some embodiments, the methods further comprise determining whether to administer an additional dose or additional doses of the multimeric ligand to the patient, wherein the determination is based upon the amount or concentration of marker and CD3 positive T cells in the patient.

In some embodiments, at least $1 \times 10^6$ transduced or transfected donor T cells are administered to the patient. In some embodiments, at least $1 \times 10^7$ transduced or transfected donor T cells are administered to the patient. In some embodiments, at least $1 \times 10^8$ transduced or transfected donor T cells are administered to the patient.

In some embodiments, the methods further comprise identifying the presence, absence or stage of graft versus host disease in the patient, and administering a multimeric ligand that binds to the multimeric ligand binding region, maintaining a subsequent dosage of the multimeric ligand, or adjusting a subsequent dosage of the multimeric ligand to the patient based on the presence, absence or stage of the graft versus host disease identified in the patient. In some embodiments, the methods further comprise identifying the presence, absence or stage of graft versus host disease in the patient, and determining whether a multimeric ligand that binds to the multimeric ligand binding region should be administered to the patient, or the dosage of the multimeric ligand subsequently administered to the patient is adjusted based on the presence, absence or stage of the graft versus host disease identified in the patient. In some embodiments, the methods further comprise receiving information comprising the presence, absence or stage of graft versus host disease in the patient; and administering a multimeric ligand that binds to the multimeric ligand binding region, maintaining a subsequent dosage of the multimeric ligand, or adjusting a subsequent dosage of the multimeric ligand to the patient based on the presence, absence or stage of the graft versus host disease identified in the patient. In some embodiments, the methods further comprise identifying the presence, absence or stage of graft versus host disease in the patient, and transmitting the presence, absence or stage of the graft versus host disease to a decision maker who administers a multimeric ligand that binds to the multimeric ligand binding region, maintains a subsequent dosage of the multimeric ligand, or adjusts a subsequent dosage of the multimeric ligand administered to the patient based on the presence, absence or stage of the graft versus host disease identified in the subject. In some embodiments, the methods further comprise identifying the presence, absence or stage of graft versus host disease in the patient, and transmitting an indication to administer a multimeric ligand that binds to the multimeric binding region, maintain a subsequent dosage of the multimeric ligand or adjust a subsequent dosage of the multimeric ligand administered to the patient based on the presence, absence or stage of the graft versus host disease identified in the subject.

Featured in some embodiments are methods of controlling the survival of transplanted therapeutic cells in a patient, comprising preparing or obtaining therapeutic cells; transfecting or transducing the therapeutic cells with a nucleic acid including a promoter region and a nucleotide sequence that encodes a chimeric protein comprising a multimeric ligand binding region and a caspase 9 polypeptide; transplanting the transduced or transfected therapeutic cells into the patient; and after step administering a multimeric ligand to the patient, wherein the multimeric ligand binds to the multimeric ligand binding region, wherein transplanted therapeutic cells that express the caspase 9 polypeptide are killed following administration of the multimeric ligand.

Also featured in some embodiments are methods of transplanting therapeutic cells in a human patient, comprising preparing or obtaining cells for transplantation; transfecting or transducing the cells with a nucleic acid including a promoter region and a nucleotide sequence that encodes a chimeric protein comprising a multimeric ligand binding region and a caspase 9 polypeptide; and transplanting the transduced or transfected therapeutic cells into the human patient.

Also featured in some embodiments are methods of preparing progenitor therapeutic cells for transplantation in a patient, comprising preparing or obtaining cells for transplantation; and transfecting or transducing the cells with a nucleic acid including a promoter region and a nucleotide sequence that encodes a chimeric protein comprising a multimeric ligand binding region and a caspase 9 polypeptide.

In some embodiments, the patient is a human patient. In some embodiments, a multimeric ligand is administered to the patient, wherein the multimeric ligand binds to the multimeric ligand binding region. In some embodiments, the multimeric ligand is administered to kill transplanted therapeutic cells. In some embodiments, the therapeutic cells are obtained or prepared from bone marrow. In some embodiments, the therapeutic cells are obtained or prepared from umbilical cord blood. In some embodiments, the therapeutic cells are obtained or prepared from peripheral blood. In some embodiments, the therapeutic cells are obtained or prepared from peripheral blood mononuclear cells. In some embodiments, the therapeutic cells are progenitor cells. In some embodiments, the therapeutic cells are hematopoietic progenitor cells. In some embodiments, the therapeutic cells are selected from the group consisting of mesenchymal stromal cells, embryonic stem cells, and inducible pluripotent stem cells. In some embodiments, the promoter is developmentally regulated and the caspase 9 polypeptide is expressed in developmentally differentiated cells. In some embodiments, the therapeutic cells are modified by transfection or transduction of a heterologous gene, in some embodiments the modified therapeutic cells are T cells. In some embodiments, the promoter is tissue specific and the caspase 9 polypeptide is expressed in the specific tissue. In some embodiments, the patient has cancer. In some embodiments, the patient has a solid tumor. In some embodiments, the cancer is present in the blood or bone marrow of the patient. In some embodiments, the patient has a blood or bone marrow disease. In some embodiments, the patient has any condition or disorder that can be alleviated by stem cell transplantation. In some embodiments, the patient has been diagnosed with sickle cell anemia or metachromatic leukodystrophy.

In some embodiments, the chimeric protein further comprises a marker polypeptide. In some embodiments, the marker polypeptide is a CD19 polypeptide. In some embodiments, the methods further comprise a selection step, wherein cells that express the marker are selected for administration to the patient. In some embodiments, the cells are selected by immunomagnetic selection. In some embodiments, the caspase 9 polypeptide is a truncated caspase 9 polypeptide. In some embodiments, the caspase 9 polypeptide lacks the caspase recruitment domain. In some embodiments, the caspase 9 polypeptide comprises the amino acid sequence of SEQ ID NO: 9, or a fragment thereof, or is encoded by a nucleotide sequence SEQ ID NO: 8, or a fragment thereof.

In some embodiments, the multimeric ligand binding region is selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof. In some embodiments, the multimeric ligand binding region is an FKBP12 region. In some embodiments, the multimeric ligand is an FK506 dimer or a dimeric FK506 analog ligand. In some embodiments, more than one dose of the multimeric ligand is administered. In some embodiments, the therapeutic cells are transduced or transfected with a retroviral vector. In some embodiments, the retroviral vector is a murine leukemia virus vector. In some embodiments, the retroviral vector is an SFG vector. In some embodiments, the transfected or transduced cells are further transfected or transduced with a gene expression vector.

In some embodiments, the methods further comprise identifying a presence or absence of a condition in the patient that requires the removal of transfected or transduced therapeutic cells from the patient; and administering a multimeric ligand that binds to the multimeric ligand binding region, maintaining a subsequent dosage of the multimeric ligand, or adjusting a subsequent dosage of the multimeric ligand to the patient based on the presence or absence of the condition identified in the patient. In some embodiments, the methods further comprise identifying a presence or absence of a condition in the patient that requires the removal of transfected or transduced therapeutic cells from the patient; and determining whether a multimeric ligand that binds to the multimeric ligand binding region should be administered to the patient, or the dosage of the multimeric ligand subsequently administered to the patient is adjusted based on the presence or absence of the condition identified in the patient. In some embodiments, the methods further comprise receiving information comprising presence or absence of a condition in the patient that requires the removal of transfected or transduced therapeutic cells from the patient; and administering a multimeric ligand that binds to the multimeric ligand binding region, maintaining a subsequent dosage of the multimeric ligand, or adjusting a subsequent dosage of the multimeric ligand to the patient based on the presence or absence of the condition identified in the patient. In some embodiments, the methods further comprise identifying a presence or absence of a condition in the patient that requires the removal of transfected or transduced therapeutic cells from the patient; and transmitting the presence, absence or stage of the condition identified in the patient to a decision maker who administers a multimeric ligand that binds to the multimeric ligand binding region, maintains a subsequent dosage of the multimeric ligand, or adjusts a subsequent dosage of the multimeric ligand administered to the patient based on the presence, absence or stage of the condition identified in the patient. In some embodiments, the methods further comprise identifying a presence or absence of a condition in the patient that requires the removal of transfected or transduced therapeutic cells from the patient; and transmitting an indication to administer a multimeric ligand that binds to the multimeric ligand binding region, maintains a subsequent dosage of the multimeric ligand, or adjusts a subsequent dosage of the multimeric ligand administered to the patient based on the presence, absence or stage of the condition identified in the patient.

Also featured in some embodiments is a cell, comprising a nucleic acid including a promoter region and a nucleotide sequence that encodes a chimeric protein comprising a multimeric ligand binding region and a caspase 9 polypeptide, wherein the cell is obtained or prepared from bone marrow or umbilical cord blood.

In some embodiments, the cell is a human cell. In some embodiments, the cell is a progenitor cell. In some embodiments, the cell is a hematopoietic progenitor cell. In some embodiments, the cell is selected from the group consisting of mesenchymal stromal cells, embryonic stem cells, and inducible pluripotent stem cells. In some embodiments, the promoter is developmentally regulated and the caspase 9 polypeptide is expressed in developmentally differentiated cells. In some embodiments, the promoter is tissue-specific and the caspase 9 polypeptide is expressed in the specific tissue. In some embodiments, the chimeric protein further comprises a marker polypeptide. In some embodiments, the marker polypeptide is a CD19 polypeptide. In some embodiments, the caspase 9 polypeptide is a truncated caspase 9 polypeptide. In some embodiments, the caspase 9 polypeptide lacks the caspase recruitment domain. In some embodiments, the caspase 9 polypeptide comprises the amino acid sequence of SEQ ID NO: 9, or a fragment thereof, or is encoded by the nucleotide sequence of SEQ ID NO: 8, or a fragment thereof.

In some embodiments, the multimeric ligand binding region is selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof. In some embodiments, the multimeric ligand binding region is an FKBP12 region. In some embodiments, the cells are transduced or transfected with a retroviral vector. In some embodiments, the retroviral vector is a murine leukemia virus vector. In some embodiments, the retroviral vector is an SFG vector. In some embodiments, the transfected or transduced cells are further transfected or transduced with a gene expression vector.

In some embodiments, the chimeric protein comprises a caspase polypeptide, or a truncated or modified caspase polypeptide, wherein the caspase is caspase 1, 3, or 8.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 1A discloses "Ser-Gly-Gly-Gly-Ser" as SEQ ID NO: 21. FIG. 1B illustrates a representative western blot of full length and truncated caspase 9 protein produced by the expression vectors shown in FIG. 1A.

FIG. 2A illustrates levels of cell surface markers in transduced and nontransduced cells. FIG. 2B illustrates levels of secretion of Th1 and Th2 type cytokines upon antigen stimulation in transduced and nontransduced cells. FIG. 2C illustrates levels of cytolytic activity against autologous EVB-transformed lymphoblastoid B-cell line (LCL), HLA-mismatched LCL, and HSB-2 in transduced and nontransduced cells. FIG. 2D illustrates the persistence of antigen dependence on iCasp9 transduced cell lines. Note the steady decline of T cells after antigen stimulation is discontinued. Further discussion of experimental conditions and results are presented in the Examples.

FIG. 3A illustrates FACS plots of cells after treatment with CID or carrier. FACS plots are presented for unselected cells (top row of FIG. 3A) and cells selected for high GFP expression (bottom row of FIG. 3A). FIG. 3B illustrates the results of overnight treatment of iCasp9 transduced cells with CID. The treated panel clearly shows cells exhibiting characteristics of apoptosis. FIG. 3C illustrates the results of CID treated and untreated cells stained for Annexin-V and 7-ADD. FIG. 3D shows a dose response curve for the CID AP20187. Further discussion of experimental conditions and results are presented in the Examples.

FIG. 4A show the results of cell population selection based on GFP expression. FIG. 4B illustrates the results of cells treated overnight with CID treated and stained for Annexin-V and 7-ADD. FIG. 4C show the results of selected T cells that were mixed 1:1 with non-transduced T-cells and incubated with 10 nM CID following antigenic stimulation. Indicated is the percentage of residual GFP-positive T-cells on day 7. Further discussion of experimental conditions and results are presented in the Examples.

FIG. 5A illustrates the results of cells transduced with an iFas or iCasp9 expression construct and sorted according to GFP expression. FIG. 5B illustrates the results of GFP expression measurements after treatment with CID. FIG. 5C shows the results of expression studies performed in the human derived cell lines Jurkat and MT-2. The cell lines were stained with Annexin-V and 7-ADD. Further discussion of experimental conditions and results are presented in the Examples.

FIG. 8A discloses "S-G-G-G-S" as SEQ ID NO: 21. FIG. 8B illustrates the protocol used to produce the cell product expression iCasp9 in allodepleted cells. Further discussion of experimental conditions and results are presented in the Examples.

FIG. 11A shows the interferon-γ secretion in response to viral antigens as assessed by ELISPOT. FIG. 11B shows the results of a cytotoxicity assay after allodepleted cells were stimulated with EBV-LCLs. FIG. 11C illustrates the frequency of T cells specific for HLA-B8-RAKFKQLL, (SEQ ID NO: 20), an epitope from an EBV lytic antigen (BZLF1).

FIG. 12A shows the levels of Foxp3 expression. FIG. 12B illustrates the results of the functional assay performed to show that addition of CD4+/CD25+ gene modified depleted cells significantly reduced cell proliferation. Further discussion of experimental conditions and results are presented in the Examples.

FIG. 13A shows representative FACS analysis of cells stained with Annexin-V and 7-ADD. FIG. 13B graphically illustrates the results of reactivation of T cells on killing when AP20187 is administered. FIGS. 13CA and 13CB show representative FACS plots showing the effect of extended culture and T cell activation on suicide gene function. Further discussion of experimental conditions and results are presented in the Examples.

FIG. 14A shows the results for EBV-specific T cells. FIG. 14A discloses "RAKFKQLL" as SEQ ID NO: 20. FIG. 14B shows the results for CMV-specific T cells. FIG. 14B discloses "NLVPMVATV" as SEQ ID NO: 23. Cells were quantified by pentamer analysis before allostimulation, after allosimulation and after treatment of allostimulated cells with dimerizer. Further discussion of experimental conditions and results are presented in the Examples.

FIG. 15A shows the mononuclear adherent fraction isolated from bone marrow was homogenously positive for CD73, CD90 and CD105 and was negative for hematopoietic markers. FIG. 15B illustrate analysis showing the cells were able to differentiate into other cell lineages. Further discussion of experimental conditions and results are presented in the Examples.

FIG. 16A illustrates the percentage of CD19 positive cells (e.g., an indicator of successful transduction of iCasp9) remains substantially constant for more than 2 weeks. FIG. 16B shows that successfully transduced and non-transduced cells retain the characteristic MSC surface phenotype. Further discussion of experimental conditions and results are presented in the Examples.

FIG. 17A shows the results of FACS analysis of cells treated with CID for 24 hours. FIG. 17B shows the results of magnetic purification of iCasp9+/CD19+ cells. Further discussion of experimental conditions and results are presented in the Examples.

FIG. 21A shows the results of whole animal imaging. FIG. 21B graphically shows a time course of the killing of iCasp9+ cells after exposure to CID. FIG. 21C shows the results of serial examination of animals after subcutaneous inoculation of MSC. Further discussion of experimental conditions and results are presented in the Examples.

FIG. 25 discloses "SGGGS" as SEQ ID NO: 21. Further discussion of experimental conditions and results are presented in the Examples.

FIGS. 27A-27H provide graphs showing the detection of iCasp9-transduced T cells in the peripheral blood of patients. FIGS. 27A-27D are graphs of cell count/microliter and FIGS. 27E-27H are graphs of copies/microgram of DNA following FACS analysis for iCasp9-transduced T cells (CD3$^+$ CD19$^+$, CD4$^+$ CD19$^+$, or CD8$^+$ CD19$^+$) from four patients (P1-P4) receiving cellular therapy following HLA-haploidentical stem cell transplantation for relapsed leukemia. Patients 1, 2, and 4 developed skin/liver GvHD and received a single dose of the dimerizing drug AP1903.

FIG. 30A is a graph depicting the normalization of bilirubin concentration in patient 1 within 24 hours post-treatment. FIGS. 30B and 30C provide photographs showing the disappearance of skin rash from patient 2 pre treatment (FIG. 30B) and within 24 hours post treatment (FIG. 30C).

FIG. 32 also pictorially illustrates a patient exhibiting symptoms of GvHD.

DETAILED DESCRIPTION

Figure 1A:
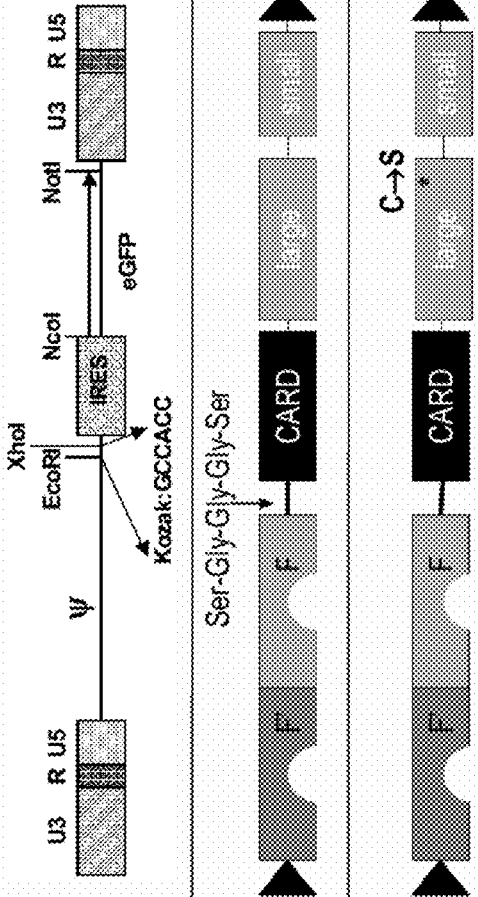
FIGS. 1A-1B illustrate various iCasp9 expression vectors as discussed herein.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

The term "allogeneic" as used herein, refers to HLA or MHC loci that are antigenically distinct.

Thus, cells or tissue transferred from the same species can be antigenically distinct. Syngeneic mice can differ at one or more loci (congenics) and allogeneic mice can have the same background.

The term "antigen" as used herein is defined as a molecule that provokes an immune response. This immune response may involve either antibody production, or the activation of specific immunologically-competent cells, or both.

The term "cancer" as used herein is defined as a hyperproliferation of cells whose unique trait—loss of normal controls—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

Donor: The term "donor" refers to a mammal, for example, a human, that is not the patient recipient. The donor may, for example, have HLA identity with the recipient, or may have partial or greater HLA disparity with the recipient.

Haploidentical: The term "haploidentical" as used with reference to cells, cell types and/or cell lineages, herein refers to cells sharing a haplotype or cells having substantially the same alleles at a set of closely linked genes on one chromosome. A haploidentical donor does not have complete HLA identity with the recipient, there is a partial HLA disparity.

Blood disease: The terms "blood disease", "blood disease" and/or "diseases of the blood" as used herein, refers to conditions that affect the production of blood and its components, including but not limited to, blood cells, hemoglobin, blood proteins, the mechanism of coagulation, production of blood, production of blood proteins, the like and combinations thereof. Non-limiting examples of blood diseases include anemias, leukemias, lymphomas, hematological neoplasms, albuminemias, haemophilias and the like.

Bone marrow disease: The term "bone marrow disease" as used herein, refers to conditions leading to a decrease in the production of blood cells and blood platelets. In some bone marrow diseases, normal bone marrow architecture can be displaced by infections (e.g., tuberculosis) or malignancies, which in turn can lead to the decrease in production of blood cells and blood platelets. Non-limiting examples of bone marrow diseases include leukemias, bacterial infections (e.g., tuberculosis), radiation sickness or poisoning, apnocytopenia, anemia, multiple myeloma and the like.

T cells and Activated T cells (include that this means CD3+ cells): T cells (also referred to as T lymphocytes) belong to a group of white blood cells referred to as lymphocytes. Lymphocytes generally are involved in cell-mediated immunity. The "T" in "T cells" refers to cells derived from or whose maturation is influence by the thymus. T cells can be distinguished from other lymphocytes types such as B cells and Natural Killer (NK) cells by the presence of cell surface proteins known as T cell receptors. The term "activated T cells" as used herein, refers to T cells that have been stimulated to produce an immune response (e.g., clonal expansion of activated T cells) by recognition of an antigenic determinant presented in the context of a Class II major histocompatibility (MHC) marker. T-cells are activated by the presence of an antigenic determinant, cytokines and/or lymphokines and cluster of differentiation cell surface proteins (e.g., CD3, CD4, CD8, the like and combinations thereof). Cells that express a cluster of differential protein often are said to be "positive" for expression of that protein on the surface of T-cells (e.g., cells positive for CD3 or CD 4 expression are referred to as CD3+ or CD4+). CD3 and CD4 proteins are cell surface receptors or co-receptors that may be directly and/or indirectly involved in signal transduction in T cells.

Peripheral blood: The term "peripheral blood" as used herein, refers to cellular components of blood (e.g., red blood cells, white blood cells and platelets), which are obtained or prepared from the circulating pool of blood and not sequestered within the lymphatic system, spleen, liver or bone marrow.

Umbilical cord blood: Umbilical cord blood is distinct from peripheral blood and blood sequestered within the lymphatic system, spleen, liver or bone marrow. The terms "umbilical cord blood", "umbilical blood" or "cord blood", which can be used interchangeably, refers to blood that remains in the placenta and in the attached umbilical cord after child birth. Cord blood often contains stem cells including hematopoietic cells.

By "obtained or prepared" as, for example, in the case of cells, is meant that the cells or cell culture are isolated, purified, or partially purified from the source, where the source may be, for example, umbilical cord blood, bone marrow, or peripheral blood. The terms may also apply to the case where the original source, or a cell culture, has been cultured and the cells have replicated, and where the progeny cells are now derived from the original source.

Allodepletion: The term "allodepletion" as used herein, refers to the selective depletion of alloreactive T cells. The term "alloreactive T cells" as used herein, refers to T cells activated to produce an immune response in reaction to exposure to foreign cells, such as, for example, in a transplanted allograft. The selective depletion generally involves targeting various cell surface expressed markers or proteins, (e.g., sometimes cluster of differentiation proteins (CD proteins)), for removal using immunomagnets, immunotoxins, flow sorting, induction of apoptosis, photodepletion techniques, the like or combinations thereof. In the present methods, the cells may be transduced or transfected with the chimeric protein-encoding vector before or after allodepletion. Also, the cells may be transduced or transfected with the chimeric protein-encoding vector without an allodepletion step, and the non-allodepleted cells may be administered to the patient. Because of the added "safety switch" it is, for example, possible to administer the non allodepleted T cells because an adverse event such as, for example, graft versus host disease, may be alleviated upon the administration of the multimeric ligand.

Graft versus host disease: The terms "graft versus host disease" or "GvHD", refer to a complication often associated with allogeneic bone marrow transplantation and sometimes associated with transfusions of un-irradiated blood to immunocompromised patients. Graft versus host disease sometimes can occur when functional immune cells in the transplanted marrow recognize the recipient as "foreign" and mount an immunologic response. GvHD can be divided into an acute form and a chronic form. Acute GVHD (aGVHD) often is observed within the first 100 days following transplant or transfusion and can affect the liver, skin, mucosa, immune system (e.g., the hematopoietic system, bone marrow, thymus, and the like), lungs and gastrointestinal tract. Chronic GVHD (cGVHD) often begins 100 days or later post transplant or transfusion and can attack the same organs as acute GvHD, but also can affect connective tissue and exocrine glands. Acute GvHD of the skin can result in a diffuse maculopapular rash, sometimes in a lacy pattern.

Donor T cell: The term "donor T cell" as used here refers to T cells that often are administered to a recipient to confer anti-viral and/or anti-tumor immunity following allogeneic stem cell transplantation. Donor T cells often are utilized to inhibit marrow graft rejection and increase the success of alloengraftment, however the same donor T cells can cause an alloaggressive response against host antigens, which in turn can result in graft versus host disease (GVHD). Certain activated donor T cells can cause a higher or lower GvHD response than other activated T cells. Donor T cells may also be reactive against recipient tumor cells, causing a beneficial graft vs. tumor effect.

Mesenchymal stromal cell: The terms "mesenchymal stromal cell" or "bone marrow derived mesenchymal stromal cell" as used herein, refer to multipotent stem cells that can differentiate ex vivo, in vitro and in vivo into adipocytes, osteoblasts and chondroblasts, and may be further defined as a fraction of mononuclear bone marrow cells that adhere to plastic culture dishes in standard culture conditions, are negative for hematopoietic lineage markers and are positive for CD73, CD90 and CD105.

Embryonic stem cell: The term "embryonic stem cell" as used herein, refers to pluripotent stem cells derived from the inner cell mass of the blastocyst, an early-stage embryo of between 50 to 150 cells. Embryonic stem cells are characterized by their ability to renew themselves indefinitely and by their ability to differentiate into derivatives of all three primary germ layers, ectoderm, endoderm and mesoderm. Pluripotent is distinguished from mutipotent in that pluripotent cells can generate all cell types, while multipotent cells (e.g., adult stem cells) can only produce a limited number of cell types.

Inducible pluripotent stem cell: The terms "inducible pluripotent stem cell" or "induced pluripotent stem cell" as used herein refers to adult, or differentiated cells, that are "reprogrammed" or induced by genetic (e.g., expression of genes that in turn activates pluripotency), biological (e.g., treatment viruses or retroviruses) and/or chemical (e.g., small molecules, peptides and the like) manipulation to generate cells that are capable of differentiating into many if not all cell types, like embryonic stem cells. Inducible pluripotent stem cells are distinguished from embryonic stem cells in that they achieve an intermediate or terminally differentiated state (e.g., skin cells, bone cells, fibroblasts, and the like) and then are induced to dedifferentiate, thereby regaining some or all of the ability to generate multipotent or pluripotent cells.

CD34+ cell: The term "CD34+ cell" as used herein refers to a cell expressing the CD34 protein on its cell surface. "CD34" as used herein refers to a cell surface glycoprotein (e.g., sialomucin protein) that often acts as a cell-cell adhesion factor and is involved in T cell entrance into lymph nodes, and is a member of the "cluster of differentiation" gene family. CD34 also may mediate the attachment of stem cells to bone marrow, extracellular matrix or directly to stromal cells. CD34+ cells often are found in the umbilical cord and bone marrow as hematopoietic cells, a subset of mesenchymal stem cells, endothelial progenitor cells, endothelial cells of blood vessels but not lymphatics (except pleural lymphatics), mast cells, a sub-population of dendritic cells (which are factor XIIIa negative) in the interstitium and around the adnexa of dermis of skin, as well as cells in certain soft tissue tumors (e.g., alveolar soft part sarcoma, pre-B acute lymphoblastic leukemia (Pre-B-ALL), acute myelogenous leukemia (AML), AML-M7, dermatofibrosarcoma protuberans, gastrointestinal stromal tumors, giant cell fibroblastoma, granulocytic sarcoma, Kaposi's sarcoma, liposarcoma, malignant fibrous histiocytoma, malignant peripheral nerve sheath tumors, mengingeal hemangiopericytomas, meningiomas, neurofibromas, schwannomas, and papillary thyroid carcinoma).

Gene expression vector: The terms "gene expression vector", "nucleic acid expression vector", or "expression vector" as used herein, which can be used interchangeably throughout the document, generally refers to a nucleic acid molecule (e.g., a plasmid, phage, autonomously replicating sequence (ARS), artificial chromosome, yeast artificial chromosome (e.g., YAC)) that can be replicated in a host cell and be utilized to introduce a gene or genes into a host cell. The genes introduced on the expression vector can be endogenous genes (e.g., a gene normally found in the host cell or organism) or heterologous genes (e.g., genes not normally found in the genome or on extra-chromosomal nucleic acids of the host cell or organism). The genes introduced into a cell by an expression vector can be native genes or genes that have been modified or engineered. The gene expression vector also can be engineered to contain 5' and 3' untranslated regulatory sequences that sometimes can function as enhancer sequences, promoter regions and/or terminator sequences that can facilitate or enhance efficient transcription of the gene or genes carried on the expression vector. A gene expression vector sometimes also is engineered for replication and/or expression functionality (e.g., transcription and translation) in a particular cell type, cell location, or tissue type. Expression vectors sometimes include a selectable marker for maintenance of the vector in the host or recipient cell.

Developmentally regulated promoter: The term "developmentally regulated promoter" as used herein refers to a promoter that acts as the initial binding site for RNA polymerase to transcribe a gene which is expressed under certain conditions that are controlled, initiated by or influenced by a developmental program or pathway. Developmentally regulated promoters often have additional control regions at or near the promoter region for binding activators or repressors of transcription that can influence transcription of a gene that is part of a development program or pathway. Developmentally regulated promoters sometimes are involved in transcribing genes whose gene products influence the developmental differentiation of cells.

Developmentally differentiated cells: The term "developmentally differentiated cells", as used herein refers to cells that have undergone a process, often involving expression of specific developmentally regulated genes, by which the cell evolves from a less specialized form to a more specialized form in order to perform a specific function. Non-limiting examples of developmentally differentiated cells are liver cells, lung cells, skin cells, nerve cells, blood cells, and the like. Changes in developmental differentiation generally involve changes in gene expression (e.g., changes in patterns of gene expression), genetic re-organization (e.g., remodeling or chromatin to hide or expose genes that will be silenced or expressed, respectively), and occasionally involve changes in DNA sequences (e.g., immune diversity differentiation). Cellular differentiation during development can be understood as the result of a gene regulatory network. A regulatory gene and its cis-regulatory modules are nodes in a gene regulatory network that receive input (e.g., protein expressed upstream in a development pathway or program) and create output elsewhere in the network (e.g., the expressed gene product acts on other genes downstream in the developmental pathway or program).

The terms "cell," "cell line," and "cell culture" as used herein may be used interchangeably. All of these terms also include their progeny, which are any and all subsequent generations. It is understood that all progeny may not be identical due to deliberate or inadvertent mutations.

As used herein, the term "icaspase 9 molecule" is defined as an inducible caspase 9. The term "icaspase 9" embraces icaspase 9 nucleic acids, icaspase 9 polypeptides and/or icaspase 9 expression vectors. The term also encompasses either the natural icaspase 9 nucleotide or amino acid sequence, or a truncated sequence that is lacking the CARD domain.

As used herein, the term "icaspase 1 molecule", "icaspase 3 molecule", or "icaspase 8 molecule" is defined as an inducible caspase 1, 3, or 8, respectively. The term icaspase 1, icaspase 3, or icaspase 8, embrases icaspase 1, 3, or 8 nucleic acids, icaspase 1, 3, or 8 polypeptides and/or icaspase 1, 3, or 8 expression vectors, respectively. The term also encompasses either the natural icaspase 1, 3, or 8 nucleotide or amino acid sequence, respectively, or a truncated sequence that is lacking the CARD domain.

As used herein, the term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There are times when the full or partial genomic sequence is used, such as where the non-coding regions are required for optimal expression or where non-coding regions such as introns are to be targeted in an antisense strategy.

As used herein, the term "expression construct" or "transgene" is defined as any type of genetic construct containing a nucleic acid coding for gene products in which part or all of the nucleic acid encoding sequence is capable of being transcribed can be inserted into the vector. The transcript is translated into a protein, but it need not be. In certain embodiments, expression includes both transcription of a gene and translation of mRNA into a gene product. In other embodiments, expression only includes transcription of the nucleic acid encoding genes of interest. The term "therapeutic construct" may also be used to refer to the expression construct or transgene. The expression construct or transgene may be used, for example, as a therapy to treat hyperproliferative diseases or disorders, such as cancer, thus the expression construct or transgene is a therapeutic construct or a prophylactic construct.

As used herein, the term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are discussed infra.

As used herein, the term "ex vivo" refers to "outside" the body. The terms "ex vivo" and "in vitro" can be used interchangeably herein.

As used herein, the term "functionally equivalent," as it relates to caspase 9, or truncated caspase 9, for example, refers to a caspase 9 nucleic acid fragment, variant, or analog, refers to a nucleic acid that codes for a caspase 9 polypeptide, or a caspase 9 polypeptide, that stimulates an apoptotic response. "Functionally equivalent" refers, for example, to a caspase 9 polypeptide that is lacking the CARD domain, but is capable of inducing an apoptotic cell response. When the term "functionally equivalent" is applied to other nucleic acids or polypeptides, such as, for example, CD19, the 5'LTR, the multimeric ligand binding region, or CD3, it refers to fragments, variants, and the like that have the same or similar activity as the reference polypeptides of the methods herein.

As used herein, the term "gene" is defined as a functional protein, polypeptide, or peptide-encoding unit. As will be understood, this functional term includes genomic sequences, cDNA sequences, and smaller engineered gene segments that express, or are adapted to express, proteins, polypeptides, domains, peptides, fusion proteins, and mutants.

The term "immunogenic composition" or "immunogen" refers to a substance that is capable of provoking an immune response. Examples of immunogens include, e.g., antigens, autoantigens that play a role in induction of autoimmune diseases, and tumor-associated antigens expressed on cancer cells.

The term "immunocompromised" as used herein is defined as a subject that has reduced or weakened immune system. The immunocompromised condition may be due to a defect or dysfunction of the immune system or to other factors that heighten susceptibility to infection and/or disease. Although such a categorization allows a conceptual basis for evaluation, immunocompromised individuals often do not fit completely into one group or the other. More than one defect in the body's defense mechanisms may be affected. For example, individuals with a specific T-lymphocyte defect caused by HIV may also have neutropenia caused by drugs used for antiviral therapy or be immunocompromised because of a breach of the integrity of the skin and mucous membranes. An immunocompromised state can result from indwelling central lines or other types of impairment due to intravenous drug abuse; or be caused by secondary malignancy, malnutrition, or having been infected with other infectious agents such as tuberculosis or sexually transmitted diseases, e.g., syphilis or hepatitis.

As used herein, the term "pharmaceutically or pharmacologically acceptable" refers to molecular entities and compositions that do not produce adverse, allergic, or other untoward reactions when administered to an animal or a human.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells presented herein, its use in therapeutic compositions is contemplated. Supplementary active ingredients also can be incorporated into the compositions.

As used herein, the term "polynucleotide" is defined as a chain of nucleotides. Furthermore, nucleic acids are polymers of nucleotides. Thus, nucleic acids and polynucleotides as used herein are interchangeable. Nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. Furthermore, polynucleotides include mutations of the polynucleotides, include but are not limited to, mutation of the nucleotides, or nucleosides by methods well known in the art.

As used herein, the term "polypeptide" is defined as a chain of amino acid residues, usually having a defined sequence. As used herein the term polypeptide is interchangeable with the terms "peptides" and "proteins".

As used herein, the term "promoter" is defined as a DNA sequence recognized by the synthetic machinery of the cell, or introduced synthetic machinery, required to initiate the specific transcription of a gene.

The term "transfection" and "transduction" are interchangeable and refer to the process by which an exogenous DNA sequence is introduced into a eukaryotic host cell. Transfection (or transduction) can be achieved by any one of a number of means including electroporation, microinjection, gene gun delivery, retroviral infection, lipofection, superfection and the like.

As used herein, the term "syngeneic" refers to cells, tissues or animals that have genotypes that are identical or closely related enough to allow tissue transplant, or are immunologically compatible. For example, identical twins or animals of the same inbred strain. Syngeneic and isogeneic can be used interchangeably.

The terms "patient" or "subject" are interchangeable, and, as used herein include, but are not limited to, an organism or animal; a mammal, including, e.g., a human, non-human primate (e.g., monkey), mouse, pig, cow, goat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

As used herein, the term "under transcriptional control" or "operatively linked" is defined as the promoter is in the correct location and orientation in relation to the nucleic acid to control RNA polymerase initiation and expression of the gene.

As used herein, the terms "treatment", "treat", "treated", or "treating" refer to prophylaxis and/or therapy.

As used herein, the term "vaccine" refers to a formulation that contains a composition presented herein which is in a form that is capable of being administered to an animal. Typically, the vaccine comprises a conventional saline or buffered aqueous solution medium in which the composition is suspended or dissolved. In this form, the composition can be used conveniently to prevent, ameliorate, or otherwise treat a condition. Upon introduction into a subject, the vaccine is able to provoke an immune response including, but not limited to, the production of antibodies, cytokines and/or other cellular responses.

In some embodiments, the nucleic acid is contained within a viral vector. In certain embodiments, the viral vector is a retroviral vector.

Hematopoietic Stem Cells and Cell Therapy

Hematopoietic stem cells include hematopoietic progenitor cells, immature, multipotent cells that can differentiate into mature blood cell types. These stem cells and progenitor cells may be isolated from bone marrow and umbilical cord blood, and, in some cases, from peripheral blood. Other stem and progenitor cells include, for example, mesenchymal stromal cells, embryonic stem cells, and inducible pluripotent stem cells.

Bone marrow derived mesenchymal stromal cells (MSCs) have been defined as a fraction of mononuclear bone marrow cells that adhere to plastic culture dishes in standard culture conditions, are negative for hematopoietic lineage markers and positive for CD73, CD90 and CD105, and able to differentiate in vitro into adipocytes, osteoblasts, and chondroblasts. While one physiologic role is presumed to be the support of hematopoiesis, several reports have also established that MSCs are able to incorporate and possibly proliferate in areas of active growth, such as cicatricial and neoplastic tissues, and to home to their native microenvironment and replace the function of diseased cells. Their differentiation potential and homing ability make MSCs attractive vehicles for cellular therapy, either in their native form for regenerative applications, or through their genetic modification for delivery of active biological agents to specific microenvironments such as diseased bone marrow or metastatic deposits. In addition, MSCs possess potent intrinsic immunosuppressive activity, and to date have found their most frequent application in the experimental treatment of graft-versus-host disease and autoimmune disorders (Pittenger, M. F., et al. (1999). Science 284: 143-147; Dominici, M., et al. (2006). Cytotherapy 8: 315-317; Prockop, D. J. (1997). Science 276: 71-74; Lee, R. H., et al. (2006). Proc Natl Acad Sci USA 103: 17438-17443; Studeny, M., et al., (2002). Cancer Res 62: 3603-3608; Studeny, M., et al. (2004). J Natl Cancer Inst 96: 1593-1603; Horwitz, E. M., et al. (1999). Nat Med 5: 309-313; Chamberlain, G., et al., (2007). Stem Cells 25: 2739-2749; Phinney, D. G., and Prockop, D. J. (2007). Stem Cells 25: 2896-2902; Horwitz, E. M., et al. (2002). Proc Natl Acad Sci USA 99: 8932-8937; Hall, B., et al., (2007). Int J Hematol 86: 8-16; Nauta, A. J., and Fibbe, W. E. (2007). Blood 110: 3499-3506; Le Blanc, K., et al. (2008). Lancet 371: 1579-1586; Tyndall, A., and Uccelli, A. (2009). Bone Marrow Transplant).

MSCs have been infused in hundreds of patients with minimal reported side effects. However, follow-up is limited, long term side effects are unknown, and little is known of the consequences that will be associated with future efforts to induce their in vivo differentiation, for example to cartilage or bone, or to genetically modify them to enhance their functionality. Several animal models have raised safety concerns. For instance, spontaneous osteosarcoma formation in culture has been observed in murine derived MSCs. Furthermore, ectopic ossification and calcification foci have been described in mouse and rat models of myocardial infarction after local injection of MSC, and their proarrhythmic potential has also been apparent in co-culture experiments with neonatal rat ventricular myocytes. Moreover, bilateral diffuse pulmonary ossification has been observed after bone marrow transplant in a dog, presumably due to the transplanted stromal components (Horwitz, E. M., et al., (2007). Biol Blood Marrow Transplant 13: 53-57; Tolar, J., et al. (2007). Stem Cells 25: 371-379; Yoon, Y.-S., et al., (2004). Circulation 109: 3154-3157; Breitbach, M., et al. (2007). Blood 110: 1362-1369; Chang, M. G., et al. (2006). Circulation 113: 1832-1841; Sale, G. E., and Storb, R. (1983). Exp Hematol 11: 961-966).

In another example of cell therapy, T cells transduced with a nucleic acid encoding a chimeric antigen receptor have been administered to patients to treat cancer (Zhong, X.-S., (2010) Molecular Therapy 18:413-420). For example, T cells expressing a chimeric antigen receptor based on the humanized monoclonal antibody Trastuzumab (Herceptin) has been used to treat cancer patients. Adverse events are possible, however, and in at least one reported case, the therapy had fatal consequences to the patient (Morgan, R. A., et al., (2010) Molecular Therapy 18:843-851). Transducing the cells with a chimeric caspase 9-based safety switch as presented herein, would provide a safety switch that could stop the adverse event from progressing.

In another example of cell therapy, T cells are modified so that express a non-functional TGF-beta receptor, rendering them resistant to TGF-beta. This allows the modified T cells to avoid the cytotoxicity caused by TGF-beta, and allows the cells to be used in cellular therapy (Bollard, C. J., et al., (2002) Blood 99:3179-3187; Bollard, C. M., et al., (2004) J. Exptl. Med. 200:1623-1633). However, it also could result in a T cell lymphoma, or other adverse effect, as the modified T cells now lack part of the normal cellular control; these therapeutic T cells could themselves become malignant. Transducing these modified T cells with a chimeric caspase 9-based safety switch as presented herein, would provide a safety switch that could avoid this result.

Cells used in cellular therapy, that express a heterologous gene, such as a modified receptor, or a chimeric receptor, may be transduced with nucleic acid that encodes a chimeric caspase 9-based safety switch before, after, or at the same time, as the cells are transduced with the heterologous gene.

Haploidentical Stem Cell Transplantation

While stem cell transplantation has proven an effective means of treating a wide variety of diseases involving hematopoietic stem cells and their progeny, a shortage of histocompatible donors has proved a major impediment to the widest application of the approach. The introduction of large panels of unrelated stem cell donors and or cord blood banks has helped to alleviate the problem, but many patients remain unsuited to either source. Even when a matched donor can be found, the elapsed time between commencing the search and collecting the stem cells usually exceeds three months, a delay that may doom many of the most needy patients. Hence there has been considerable interest in making use of HLA haploidentical family donors. Such donors may be parents, siblings or second-degree relatives. The problem of graft rejection may be overcome by a combination of appropriate conditioning and large doses of stem cells, while graft versus host disease (GvHD) may be prevented by extensive T cell-depletion of the donor graft. The immediate outcomes of such procedures have been gratifying, with engraftment rate >90% and a severe GvHD rate of <10% for both adults and children even in the absence of post transplant immunosuppression. Unfortunately the profound immunosuppression of the grafting procedure, coupled with the extensive T cell-depletion and HLA mismatching between donor and recipient lead to an extremely high rate of post-transplant infectious complications, and contributed to high incidence of disease relapse.

Donor T cell infusion is an effective strategy for conferring anti-viral and anti-tumor immunity following allogeneic stem cell transplantation. Simple addback of T cells to the patients after haploidentical transplantation, however, cannot work;

the frequency of alloreactive T cells is several orders of magnitude higher than the frequency of, for example, virus specific T lymphocytes. Methods are being developed to accelerate immune reconstitution by administrating donor T cells that have first been depleted of alloreactive ceils. One method of achieving this is stimulating donor T cells with recipient EBV-transformed B lymphoblastoid cell lines (LCLs). Alloreactive T cells upregulate CD25 expression, and are eliminated by a CD25 Mab immunotoxin conjugate, RFT5-SMPT-dgA. This compound consists of a murine IgG1 anti-CD25 (IL-2 receptor alpha chain) conjugated via a heterobifunctional crosslinker [N-succinimidyloxycarbonyl-alpha-methyl-d-(2-pyridylthio) toluene] to chemically deglycosylated ricin A chain (dgA).

Treatment with CD25 immunotoxin after LCL stimulation depletes >90% of alloreactive cells. In a phase I clinical study, using CD25 immunotoxin to deplete alloreactive lymphocytes immune reconstitution after allodepleted donor T cells were infused at 2 dose levels into recipients of T-cell-depleted haploidentical SCT. Eight patients were treated at $10^4$ cells/kg/dose, and 8 patients received $10^5$ cells/kg/dose. Patients receiving $10^5$ cells/kg/dose showed significantly improved T-cell recovery at 3, 4, and 5 months after SCT compared with those receiving $10^4$ cells/kg/dose (P<0.05). Accelerated T-cell recovery occurred as a result of expansion of the effector memory (CD45RA(-)CCR-7(-)) population (P<0.05), suggesting that protective T-cell responses are likely to be long lived. T-cell-receptor signal joint excision circles (TRECs) were not detected in reconstituting T cells in dose-level 2 patients, indicating they are likely to be derived from the infused allodepleted cells. Spectratyping of the T cells at 4 months demonstrated a polyclonal Vbeta repertoire. Using tetramer and enzyme-linked immunospot (ELISPOT) assays, cytomegalovirus (CMV)- and Epstein-Barr virus (EBV)-specific responses in 4 of 6 evaluable patients at dose level 2 as early as 2 to 4 months after transplantation, whereas such responses were not observed until 6 to 12 months in dose-level 1 patients. The incidence of significant acute (2 of 16) and chronic graft-versus-host disease (GvHD; 2 of 15) was low. These data demonstrate that allodepleted donor T cells can be safely used to improve T-cell recovery after haploidentical SCT. The amount of cells infused was subsequently escalated to $10^6$ cells/kg without evidence of GvHD.

Although this approach reconstituted antiviral immunity, relapse remained a major problem and 6 patients transplanted for high risk leukemia relapsed and died of disease. Higher T cell doses are therefore useful to reconstitute anti-tumor immunity and to provide the hoped-for anti-tumor effect, since the estimated frequency of tumor-reactive precursors is 1 to 2 logs less than frequency of viral-reactive precursors. However, in some patients, these doses of cells will be sufficient to trigger GvHD even after allodepletion (Hurley C K, et al., Biol Blood Marrow Transplant 2003; 9:610-615; Dey B R, et al., Br. J Haematol. 2006; 135:423-437; Aversa F, et al., N Engl J Med 1998; 339:1186-1193; Aversa F, et al., J Clin. Oncol. 2005; 23:3447-3454; Lang P, Mol. Dis. 2004; 33:281-287; Kolb H J, et al., Blood 2004; 103:767-776; Gottschalk S, et al., Annu. Rev. Med 2005; 56:29-44; Bleakley M, et al., Nat. Rev. Cancer 2004; 4:371-380; Andre-Schmutz I, et al., Lancet 2002; 360:130-137; Solomon S R, et al., Blood 2005; 106:1123-1129; Amrolia P J, et al., Blood 2006; 108:1797-1808; Amrolia P J, et al., Blood 2003; Ghetie V, et al., J Immunol Methods 1991; 142:223-230; Molldrem J J, et al., Cancer Res 1999; 59:2675-2681; Rezvani K, et al., Clin. Cancer Res. 2005; 1 1:8799-8807; Rezvani K, et al., Blood 2003; 102:2892-2900).

Graft versus Host Disease (GvHD)

Graft Versus Host Disease is a Condition that Sometimes Occurs after the Transplantation of Donor immunocompetent cells, for example, T cells, into a recipient. The transplanted cells recognize the recipient's cells as foreign, and attack and destroy them. This condition can be a dangerous effect of T cell transplantation, especially when associated with haploidentical stem cell transplantation. Sufficient T cells should be infused to provide the beneficial effects, such as, for example, the reconstitution of an immune system and the graft anti-tumor effect. But, the number of T cells that can be transplanted can be limited by the concern that the transplant will result in severe graft versus host disease.

Graft versus Host Disease may be staged as indicated in the following tables:

| | Staging | | | | |
|---|---|---|---|---|---|
| | Stage 0 | Stage 1 | Stage 2 | Stage 3 | Stage 4 |
| Skin | No rash | Rash <25% BSA | 25-50% | >50% Generalized erythroderma | Plus bullae and desquamation |
| Gut (for pediatric patients) | <500 mL diarrhea/day | 501-1000 mL/day 5 cc/kg-10 cc/kg/day | 1001-1500 mL/day 10 cc/kg-15 cc/kg/day | >1500 mL/day >15 cc/kg/day | Severe abdominal pain and ileus |
| UGI | | Severe nausea/vomiting | | | |
| Liver | Bilirubins 2 mg/di | 2.1-3 mg/di | 3.1-6 mg/di | 6.1-15 mg/di | >15 mg/di |

Acute GvHD grading may be performed by the consensus conference criteria (Przepiorka D et al., 1994 Consensus Conference on Acute GVHD Grading. Bone Marrow Transplant 1995; 15:825-828).

| | Grading Index of Acute GvHD | | | |
|---|---|---|---|---|
| | Skin | Liver | Gut | Upper GI |
| 0 | None and | None and | None and | None |
| I | Stage 1-2 and | None and | None | None |
| II | Stage 3 and/or | Stage 1 and/or | Stage 1 and/or | Stage 1 |
| III | None-Stage 3 with | Stage 2-3 or | Stage 2-4 | N/A |
| IV | Stage 4 or | Stage 4 | N/A | N/A |

Inducible Caspase 9 as a "Safety Switch" for Cell Therapy and for Genetically Engineered Cell Transplantation By reducing the effect of graft versus host disease is meant, for example, a decrease in the GvHD symptoms so that the patient may be assigned a lower level stage, or, for example, a reduction of a symptom of graft versus host disease by at least 20%, 30%, 40%, 50%, 60%, 70%, 80%, 90%, 95%, or 99%. A reduction in the effect of graft versus host disease may also be measured by detection of a reduction in activated T cells involved in the GvHD reaction, such as, for example, a reduction of cells that express the marker protein, for example CD19, and express CD3 ($CD3^+$ $CD19^+$ cells, for example) by at least 30%, 40%, 50%, 60%, 70%, 75%, 80%, 85%, 90%, 95%, or 99%.

Provided herein is an alternative suicide gene strategy that is based on human proapoptotic molecules fused with an FKBP variant that is optimized to bind a chemical inducer of dimerization (CID) (Clackson T, et al., Proc Natl Acad Sci USA. 1998, 95:10437-10442), m AP1903, a synthetic drug that has proven safe in healthy volunteers (Iuliucci J D, et al., J Clin Pharmacol. 2001, 41:870-879). Administration of this small molecule results in cross-linking and activation of the proapoptotic target molecules. The application of this inducible system in human T lymphocytes has been explored using Fas or the death effector domain (DED) of the Fas-associated death domain-containing protein (FADD) as proapoptotic molecules. Up to 90% of T cells transduced with these inducible death molecules underwent apoptosis after administration of CID (Thomis D C, et al., Blood. 2001, 97:1249-1257; Spencer D M, et al., Curr Biol. 1996, 6: 839-847; Fan L, et al., Hum Gene Ther. 1999, 10: 2273-2285; Berger C, et al., Blood. 2004, 103:1261-1269; Junker K, et al., Gene Ther. 2003, 10:1189-197). This suicide gene strategy may be used in any appropriate cell used for cell therapy including, for example, hematopoietic stem cells, and other progenitor cells, including, for example, mesenchymal stromal cells, embryonic stem cells, and inducible pluripotent stem cells.

Therefore, this safety switch, catalyzed by caspase 9, may be used where there is a condition in the cell therapy patient that requires the removal of the transfected or transduced therapeutic cells. Conditions where the cells may need to be removed include, for example, GvHD, inappropriate differentiation of the cells into more mature cells of the wrong tissue or cell type, and other toxicities. To activate the caspase 9 switch in the case of inappropriate differentiation, it is possible to use tissue specific promoters. For example, where a progenitor cell differentiates into bone and fat cells, and the fat cells are not desired, the vector used to transfect or transduce the progenitor cell may have a fat cell specific promoter that is operably linked to the caspase 9 nucleotide sequence. In this way, should the cells differentiate into fat cells, upon administration of the multimer ligand, apoptosis of the inappropriately differentiated fat cells should result.

The methods may be used, for example, for any disorder that can be alleviated by cell therapy, including cancer, cancer in the blood or bone marrow, other blood or bone marrow borne diseases such as sickle cell anemia and metachromic leukodystrophy, and any disorder that can be alleviated by a stem cell transplantation, for example blood or bone marrow disorders such as sickle cell anemia or metachromal leukodystrophy.

The efficacy of adoptive immunotherapy may be enhanced by rendering the therapeutic T cells resistant to immune evasion strategies employed by tumor cells. In vitro studies have shown that this can be achieved by transduction with a dominant-negative receptor or an immunomodulatory cytokine (Bollard C M, et al., Blood. 2002, 99:3179-3187: Wagner H J, et al., Cancer Gene Ther. 2004, 11:81-91). Moreover, transfer of antigen-specific T-cell receptors allows for the application of T-cell therapy to a broader range of tumors (Pule M, et al., Cytotherapy. 2003, 5:211-226; Schumacher T N, Nat Rev Immunol. 2002, 2:512-519). A suicide system for engineered human T cells was developed and tested to allow their subsequent use in clinical studies. Caspase 9 has been modified and shown to be stably expressed in human T lymphocytes without compromising their functional and phenotypic characteristics while demonstrating sensitivity to CID, even in T cells that have upregulated antiapoptotic molecules. (Straathof, K. C., et al., 2005, Blood 105:4248-54).

In genetically modified cells used for gene therapy, the gene may be a heterologous polynucleotide sequence derived from a source other than the cell that is being used to express the gene. The gene is derived from a prokaryotic or eukaryotic source such as a bacterium, a virus, yeast, a parasite, a plant, or even an animal. The heterologous DNA also is derived from more than one source, i.e., a multigene construct or a fusion protein. The heterologous DNA also may include a regulatory sequence, which is derived from one source and the gene from a different source. Or, the heterologous DNA may include regulatory sequences that are used to change the normal expression of a cellular endogenous gene.

Other Caspase Molecules

Caspase polypeptides other than caspase 9 that may be encoded by the chimeric polypeotides of the current technology include, for example, caspase 1, caspase 3, and caspase 8. Discussions of these caspase polypeptides may be found in, for example, MacCorkle, R. A., et al., Proc. Natl. Acad. Sci. U.S.A. (1998) 95:3655-3660; and Fan, L., et al. (1999) Human Gene Therapy 10:2273-2285).

Engineering Expression Constructs

Expression constructs encode a multimeric ligand binding region and a caspase 9 polypeptide, or, in certain embodiments a multimeric ligand binding region and a caspase 9 polypeptide linked to a marker polypeptide, all operatively linked. In general, the term "operably linked" is meant to indicate that the promoter sequence is functionally linked to a second sequence, wherein, for example, the promoter sequence initiates and mediates transcription of the DNA corresponding to the second sequence. The caspase 9 polypeptide may be full length or truncated. In certain embodiments, the marker polypeptide is linked to the caspase 9 polypeptide. For example, the marker polypeptide may be linked to the caspase 9 polypeptide via a polypeptide sequence, such as, for example, a cleavable 2A-like sequence. The marker polypeptide may be, for example, CD19.

2A-like sequences, or "cleavable" 2A sequences, are derived from, for example, many different viruses, including, for example, from Thosea asigna. These sequences are sometimes also known as "peptide skipping sequences." When this type of sequence is placed within a cistron, between two peptides that are intended to be separated, the ribosome appears to skip a peptide bond, in the case of Thosea asigna sequence, the bond between the Gly and Pro amino acids is omitted. This leaves two polypeptides, in this case the caspase 9 polypeptide and the marker polypeptide. When this sequence is used, the peptide that is encoded 5' of the 2A sequence may end up with additional amino acids at the carboxy terminus, including the Gly residue and any upstream in the 2A sequence. The peptide that is encoded 3' of the 2A sequence may end up with additional amino acids at the amino terminus, including the Pro residue and any downstream in the 2A sequence.

The expression construct may be inserted into a vector, for example a viral vector or plasmid. The steps of the methods provided may be performed using any suitable method, these methods include, without limitation, methods of transducing, transforming, or otherwise providing nucleic acid to the antigen-presenting cell, presented herein. In some embodiments, the truncated caspase 9 polypeptide is encoded by the nucleotide sequence of SEQ ID NO 8, or a functionally equivalent fragment thereof, with or without DNA linkers, or has the amino acid sequence of SEQ ID NO: 9, or a functionally equivalent fragment thereof. In some embodiments, the CD19 polypeptide is encoded by the nucleotide sequence of SEQ ID NO 14, or a functionally equivalent fragment thereof, with or without DNA linkers, or has the amino acid sequence of SEQ ID NO: 15, or a functionally equivalent fragment thereof. A functionally equivalent fragment of the caspase 9 polypeptide has substantially the same ability to induce apoptosis as the polypeptide of SEQ ID NO: 9, with at least 50%, 60%, 70%, 80%, 90%, or 95% of the activity of the polypeptide of SEQ ID NO: 9. A functionally equivalent fragment of the CD19 polypeptide has substantially the same ability as the polypeptide of SEQ ID No: 15, to act as a marker to be used to identify and select transduced or transfected cells, with at least 50%, 60%, 70%, 80%, 90%, or 95% of the marker polypeptide being detected when compared to the polypeptide of SEQ ID NO: 15, using standard detection techniques.

Ligand-Binding Regions

The ligand-binding ("dimerization") domain of the expression construct can be any convenient domain that will allow for induction using a natural or unnatural ligand, for example, an unnatural synthetic ligand. The ligand-binding domain can be internal or external to the cellular membrane, depending upon the nature of the construct and the choice of ligand. A wide variety of ligand-binding proteins, including receptors, are known, including ligand-binding proteins associated with the cytoplasmic regions indicated above. As used herein the term "ligand-binding domain" can be interchangeable with the term "receptor". Of particular interest are ligand-binding proteins for which ligands (for example, small organic ligands) are known or may be readily produced. These ligand-binding domains or receptors include the FKBPs and cyclophilin receptors, the steroid receptors, the tetracycline receptor, the other receptors indicated above, and the like, as well as "unnatural" receptors, which can be obtained from antibodies, particularly the heavy or light chain subunit, mutated sequences thereof, random amino acid sequences obtained by stochastic procedures, combinatorial syntheses, and the like. In certain embodiments, the ligand-binding region is selected from the group consisting of FKBP ligand-binding region, cyclophilin receptor ligand-binding region, steroid receptor ligand-binding region, cyclophilin receptors ligand-binding region, and tetracycline receptor ligand-binding region. Often, the ligand-binding region comprises a Fv'Fvls sequence. Sometimes, the Fv'Fvls sequence further comprises an additional Fv' sequence. Examples include, for example, those discussed in Kopytek, S. J., et al., Chemistry & Biology 7:313-321 (2000) and in Gestwicki, J. E., et al., Combinatorial Chem. & High Throughput Screening 10:667-675 (2007); Clackson T (2006) Chem Biol Drug Des 67:440-2; Clackson, T., in Chemical Biology: From Small Molecules to Systems Biology and Drug Design (Schreiber, s., et al., eds., Wiley, 2007)).

For the most part, the ligand-binding domains or receptor domains will be at least about 50 amino acids, and fewer than about 350 amino acids, usually fewer than 200 amino acids, either as the natural domain or truncated active portion thereof. The binding domain may, for example, be small (<25 kDa, to allow efficient transfection in viral vectors), monomeric, nonimmunogenic, have synthetically accessible, cell permeable, nontoxic ligands that can be configured for dimerization.

The receptor domain can be intracellular or extracellular depending upon the design of the expression construct and the availability of an appropriate ligand. For hydrophobic ligands, the binding domain can be on either side of the membrane, but for hydrophilic ligands, particularly protein ligands, the binding domain will usually be external to the cell membrane, unless there is a transport system for internalizing the ligand in a form in which it is available for binding. For an intracellular receptor, the construct can encode a signal peptide and transmembrane domain 5' or 3' of the receptor domain sequence or may have a lipid attachment signal sequence 5' of the receptor domain sequence. Where the receptor domain is between the signal peptide and the transmembrane domain, the receptor domain will be extracellular.

The portion of the expression construct encoding the receptor can be subjected to mutagenesis for a variety of reasons. The mutagenized protein can provide for higher binding affinity, allow for discrimination by the ligand of the naturally occurring receptor and the mutagenized receptor, provide opportunities to design a receptor-ligand pair, or the like. The change in the receptor can involve changes in amino acids known to be at the binding site, random mutagenesis using combinatorial techniques, where the codons for the amino acids associated with the binding site or other amino acids associated with conformational changes can be subject to mutagenesis by changing the codon(s) for the particular amino acid, either with known changes or randomly, expressing the resulting proteins in an appropriate prokaryotic host and then screening the resulting proteins for binding.

Antibodies and antibody subunits, e.g., heavy or light chain, particularly fragments, more particularly all or part of the variable region, or fusions of heavy and light chain to create high-affinity binding, can be used as the binding domain. Antibodies that are contemplated include ones that are an ectopically expressed human product, such as an extracellular domain that would not trigger an immune response and generally not expressed in the periphery (i.e., outside the CNS/brain area). Such examples, include, but are not limited to low affinity nerve growth factor receptor (LNGFR), and embryonic surface proteins (i.e., carcinoembryonic antigen). Yet further, antibodies can be prepared against haptenic molecules, which are physiologically acceptable, and the individual antibody subunits screened for binding affinity. The cDNA encoding the subunits can be isolated and modified by deletion of the constant region, portions of the variable region, mutagenesis of the variable region, or the like, to obtain a binding protein domain that has the appropriate affinity for the ligand. In this way, almost any physiologically acceptable haptenic compound can be employed as the ligand or to provide an epitope for the ligand. Instead of antibody units, natural receptors can be employed, where the binding domain is known and there is a useful ligand for binding.

Oligomerization

The transduced signal will normally result from ligand-mediated oligomerization of the chimeric protein molecules, i.e., as a result of oligomerization following ligand-binding, although other binding events, for example allosteric activation, can be employed to initiate a signal. The construct of the chimeric protein will vary as to the order of the various domains and the number of repeats of an individual domain.

For multimerizing the receptor, the ligand for the ligand-binding domains/receptor domains of the chimeric surface membrane proteins will usually be multimeric in the sense that it will have at least two binding sites, with each of the binding sites capable of binding to the ligand receptor domain. By "multimeric ligand binding region" is meant a ligand binding region that binds to a multimeric ligand. The term "multimeric ligands" include dimeric ligands. A dimeric ligand will have two binding sites capable of binding to the ligand receptor domain. Desirably, the subject ligands will be a dimer or higher order oligomer, usually not greater than about tetrameric, of small synthetic organic molecules, the individual molecules typically being at least about 150 Da and less than about 5 kDa, usually less than about 3 kDa. A variety of pairs of synthetic ligands and receptors can be employed. For example, in embodiments involving natural receptors, dimeric FK506 can be used with an FKBP12 receptor, dimerized cyclosporin A can be used with the cyclophilin receptor, dimerized estrogen with an estrogen receptor, dimerized glucocorticoids with a glucocorticoid receptor, dimerized tetracycline with the tetracycline receptor, dimerized vitamin D with the vitamin D receptor, and the like. Alternatively higher orders of the ligands, e.g., trimeric can be used. For embodiments involving unnatural receptors, e.g., antibody subunits, modified antibody subunits, single chain antibodies comprised of heavy and light chain variable regions in tandem, separated by a flexible linker domain, or modified receptors, and mutated sequences thereof, and the like, any of a large variety of compounds can be used. A significant characteristic of these ligand units is that each binding site is able to bind the receptor with high affinity and they are able to be dimerized chemically. Also, methods are available to balance the hydrophobicity/hydrophilicity of the ligands so that they are able to dissolve in serum at functional levels, yet diffuse across plasma membranes for most applications.

In certain embodiments, the present methods utilize the technique of chemically induced dimerization (CID) to produce a conditionally controlled protein or polypeptide. In addition to this technique being inducible, it also is reversible, due to the degradation of the labile dimerizing agent or administration of a monomeric competitive inhibitor.

The CID system uses synthetic bivalent ligands to rapidly crosslink signaling molecules that are fused to ligand-binding domains. This system has been used to trigger the oligomerization and activation of cell surface (Spencer, D. M., et al., Science, 1993. 262: p. 1019-1024; Spencer D. M. et al., Curr Biol 1996, 6:839-847; Blau, C. A. et al., Proc Natl Acad. Sci. USA 1997, 94:3076-3081), or cytosolic proteins (Luo, Z. et al., Nature 1996, 383:181-185; MacCorkle, R. A. et al., Proc Natl Acad Sci USA 1998, 95:3655-3660), the recruitment of transcription factors to DNA elements to modulate transcription (Ho, S. N. et al., Nature 1996, 382:822-826; Rivera, V. M. et al., Nat. Med. 1996, 2:1028-1032) or the recruitment of signaling molecules to the plasma membrane to stimulate signaling (Spencer D. M. et al., Proc. Natl. Acad. Sci. USA 1995, 92:9805-9809; Holsinger, L. J. et al., Proc. Natl. Acad. Sci. USA 1995, 95:9810-9814).

The CID system is based upon the notion that surface receptor aggregation effectively activates downstream signaling cascades. In the simplest embodiment, the CID system uses a dimeric analog of the lipid permeable immunosuppressant drug, FK506, which loses its normal bioactivity while gaining the ability to crosslink molecules genetically fused to the FK506-binding protein, FKBP12. By fusing one or more FKBPs to caspase 9, one can stimulate caspase 9 activity in a dimerizer drug-dependent, but ligand and ectodomain-independent manner. This provides the system with temporal control, reversibility using monomeric drug analogs, and enhanced specificity. The high affinity of third-generation AP20187/AP1903 CIDs for their binding domain, FKBP12, permits specific activation of the recombinant receptor in vivo without the induction of non-specific side effects through endogenous FKBP12. FKBP12 variants having amino acid substitutions and deletions, such as FKBP12V$_{36}$, that bind to a dimerizer drug, may also be used. In addition, the synthetic ligands are resistant to protease degradation, making them more efficient at activating receptors in vivo than most delivered protein agents.

The ligands used are capable of binding to two or more of the ligand-binding domains. The chimeric proteins may be able to bind to more than one ligand when they contain more than one ligand-binding domain. The ligand is typically a non-protein or a chemical. Exemplary ligands include, but are not limited to FK506 (e.g., FK1012).

Other ligand binding regions may be, for example, dimeric regions, or modified ligand binding regions with a wobble substitution, such as, for example, FKBP12(V36): The human 12 kDa FK506-binding protein with an F36 to V substitution, the complete mature coding sequence (amino acids 1-107), provides a binding site for synthetic dimerizer drug AP1903 (Jemal, A. et al., CA Cancer J. Clinic. 58, 71-96 (2008); Scher, H. I. and Kelly, W. K., Journal of Clinical Oncology 11, 1566-72 (1993)). Two tandem copies of the protein may also be used in the construct so that higher-order oligomers are induced upon cross-linking by AP1903.

F36V'-FKBP: F36V'-FKBP is a codon-wobbled version of F36V-FKBP. It encodes the identical polypeptide sequence as F36V-FKPB but has only 62% homology at the nucleotide level. F36V'-FKBP was designed to reduce recombination in retroviral vectors (Schellhammer, P. F. et al., J. Urol. 157, 1731-5 (1997)). F36V'-FKBP was constructed by a PCR assembly procedure. The transgene contains one copy of F36V'-FKBP linked directly to one copy of F36V-FKBP.

In some embodiments, the ligand is a small molecule. The appropriate ligand for the selected ligand-binding region may be selected. Often, the ligand is dimeric, sometimes, the ligand is a dimeric FK506 or a dimeric FK506 analog. In certain embodiments, the ligand is AP1903 (CAS Index Name: 2-Piperidinecarboxylic acid, 1-[(2S)-1-oxo-2-(3,4,5-trimethoxyphenyl)butyl]-, 1,2-ethanediylbis[imino(2-oxo-2,1-ethanediyl)oxy-3,1-phenylene[(1R)-3-(3,4-dimethoxyphenyl)propylidene]]ester, [2S-[1(R*),2R[S[S*[1(R*), 2R*]]]]]-(9Cl) CAS Registry Number: 195514-63-7; Molecular Formula: C78H98N4O20 Molecular Weight: 1411.65). In certain embodiments, the ligand is AP20187. In certain embodiments, the ligand is an AP20187 analog, such as, for example, AP1510. In some embodiments, certain analogs will be appropriate for the FKBP12, and certain analogs appropriate for the wobbled version of FKBP12. In certain embodiments, one ligand binding region is included in the chimeric protein. In other embodiments, two or more ligand binding regions are included. Where, for example, the ligand binding region is FKBP12, where two of these regions are included, one may, for example, be the wobbled version.

Other dimerization systems contemplated include the coumermycin/DNA gyrase B system. Coumermycin-induced dimerization activates a modified Raf protein and stimulates the MAP kinase cascade. See Farrar et al., 1996.

AP1903 for Injection

AP1903 API is manufactured by Alphora Research Inc. and AP1903 Drug Product for Injection is made by Formatech Inc. It is formulated as a 5 mg/mL solution of AP1903 in a 25% solution of the non-ionic solubilizer Solutol HS 15 (250 mg/mL, BASF). At room temperature, this formulation is a clear, slightly yellow solution. Upon refrigeration, this formulation undergoes a reversible phase transition, resulting in a milky solution. This phase transition is reversed upon re-warming to room temperature. The fill is 2.33 mL in a 3 mL glass vial (~10 mg AP1903 for Injection total per vial).

AP1903 is removed from the refrigerator the night before the patient is dosed and stored at a temperature of approximately 21° C. overnight, so that the solution is clear prior to dilution. The solution is prepared within 30 minutes of the start of the infusion in glass or polyethylene bottles or non-DEHP bags and stored at approximately 21° C. prior to dosing.

All study medication is maintained at a temperature between 2 degrees C. and 8 degrees C., protected from excessive light and heat, and stored in a locked area with restricted access.

Upon determining a need to administer AP1903 and induce the inducible caspase 9 polypeptide, patients may be, for example, administered a single fixed dose of AP1903 for Injection (0.4 mg/kg) via IV infusion over 2 hours, using a non-DEHP, non-ethylene oxide sterilized infusion set. The dose of AP1903 is calculated individually for all patients, and is not be recalculated unless body weight fluctuates by ≥10%. The calculated dose is diluted in 100 mL in 0.9% normal saline before infusion.

In a previous Phase I study of AP1903, 24 healthy volunteers were treated with single doses of AP1903 for Injection at dose levels of 0.01, 0.05, 0.1, 0.5 and 1.0 mg/kg infused IV over 2 hours. AP1903 plasma levels were directly proportional to dose, with mean Cmax values ranging from approximately 10-1275 ng/mL over the 0.01-1.0 mg/kg dose range. Following the initial infusion period, blood concentrations demonstrated a rapid distribution phase, with plasma levels reduced to approximately 18, 7, and 1% of maximal concentration at 0.5, 2 and 10 hours post-dose, respectively. AP1903 for Injection was shown to be safe and well tolerated at all dose levels and demonstrated a favorable pharmacokinetic profile. Iuliucci J D, et al., J Clin Pharmacol. 41: 870-9, 2001.

The fixed dose of AP1903 for injection used, for example, may be 0.4 mg/kg intravenously infused over 2 hours. The amount of AP1903 needed in vitro for effective signaling of cells is 10-100 nM (1600 Da MW). This equates to 16-160 µg/L or ~0.016-1.6 mg/kg (1.6-160 µg/kg). Doses up to 1 mg/kg were well-tolerated in the Phase I study of AP1903 described above. Therefore, 0.4 mg/kg may be a safe and effective dose of AP1903 for this Phase I study in combination with the therapeutic cells.

Selectable Markers

In certain embodiments, the expression constructs contain nucleic acid constructs whose expression is identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as herpes simplex virus thymidine kinase (tk) are employed. Immunologic surface markers containing the extracellular, non-signaling domains or various proteins (e.g. CD34, CD19, LNGFR) also can be employed, permitting a straightforward method for magnetic or fluorescence antibody-mediated sorting. The selectable marker employed is not believed to be important, so long as it is capable of being expressed simultaneously with the nucleic acid encoding a gene product. Further examples of selectable markers include, for example, reporters such as GFP, EGFP, beta-gal or chloramphenicol acetyltransferase (CAT). In certain embodiments, the marker protein, such as, for example, CD19, is used for selection of the cells for transfusion, such as, for example, in immunomagnetic selection.

Control Regions

1. Promoters

Various promoters are available that are capable of directing the expression of the polynucleotide in the targeted cell. Thus, where a human cell is targeted the polynucleotide sequence-coding region may, for example, be placed adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it is desirable to prohibit or reduce expression of one or more of the transgenes. Examples of transgenes that are toxic to the producer cell line are pro-apoptotic and cytokine genes. Several inducible promoter systems are available for production of viral vectors where the transgene products are toxic (add in more inducible promoters).

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of *Drosophila*, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter, which drives expression of the gene of interest, is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that may be useful is the Tet-Off™ or Tet-On™ system (Clontech, Palo Alto, Calif.) originally developed by Gossen and Bujard (Gossen and Bujard, Proc. Natl. Acad. Sci. USA, 89:5547-5551, 1992; Gossen et al., Science, 268:1766-1769, 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system may be used so that the producer cells could be grown in the presence of tetracycline or doxycycline and prevent expression of a potentially toxic transgene, but when the vector is introduced to the patient, the gene expression would be constitutively on.

In some circumstances, it is desirable to regulate expression of a transgene in a gene therapy vector. For example, different viral promoters with varying strengths of activity are utilized depending on the level of expression desired. In mammalian cells, the CMV immediate early promoter is often used to provide strong transcriptional activation. The CMV promoter is reviewed in Donnelly, J. J., et al., 1997. Annu. Rev. Immunol. 15:617-48. Modified versions of the CMV promoter that are less potent have also been used when reduced levels of expression of the transgene are desired. When expression of a transgene in hematopoietic cells is desired, retroviral promoters such as the LTRs from MLV or MMTV are often used. Other viral promoters that are used depending on the desired effect include SV40, RSV LTR, HIV-1 and HIV-2 LTR, adenovirus promoters such as from the E1A, E2A, or MLP region, AAV LTR, HSV-TK, and avian sarcoma virus.

In other examples, promoters may be selected that are developmentally regulated and are active in particular differentiated cells. Thus, for example, a promoter may not be active in a pluripotent stem cell, but, for example, where the pluripotent stem cell differentiates into a more mature cell, the promoter may then be activated.

Similarly tissue specific promoters are used to effect transcription in specific tissues or cells so as to reduce potential toxicity or undesirable effects to non-targeted tissues. These promoters may result in reduced expression compared to a stronger promoter such as the CMV promoter, but may also result in more limited expression, and immunogenicity (Bojak, A., et al., 2002. Vaccine. 20:1975-79; Cazeaux., N., et al., 2002. Vaccine 20:3322-31). For example, tissue specific promoters such as the PSA associated promoter or prostate-specific glandular kallikrein, or the muscle creatine kinase gene may be used where appropriate.

Examples of tissue specific or differentiation specific promoters include, but are not limited to, the following: B29 (B cells); CD14 (monocytic cells); CD43 (leukocytes and platelets); CD45 (hematopoietic cells); CD68 (macrophages); desmin (muscle); elastase-1 (pancreatic acinar cells); endoglin (endothelial cells); fibronectin (differentiating cells, healing tissues); and Flt-1 (endothelial cells); GFAP (astrocytes).

In certain indications, it is desirable to activate transcription at specific times after administration of the gene therapy vector. This is done with such promoters as those that are hormone or cytokine regulatable. Cytokine and inflammatory protein responsive promoters that can be used include K and T kininogen (Kageyama et al., (1987) J. Biol. Chem., 262, 2345-2351), c-fos, TNF-alpha, C-reactive protein (Arcone, et al., (1988) Nucl. Acids Res., 16(8), 3195-3207), haptoglobin (Oliviero et al., (1987) EMBO J., 6, 1905-1912), serum amyloid A2, C/EBP alpha, IL-1, IL-6 (Poli and Cortese, (1989) Proc. Nat'l Acad. Sci. USA, 86, 8202-8206), Complement C3 (Wilson et al., (1990) Mol. Cell. Biol., 6181-6191), IL-8, alpha-1 acid glycoprotein (Prowse and Baumann, (1988) Mol Cell Biol, 8, 42-51), alpha-1 antitrypsin, lipoprotein lipase (Zechner et al., Mol. Cell. Biol., 2394-2401, 1988), angiotensinogen (Ron, et al., (1991) Mol. Cell. Biol., 2887-2895), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 anti-chymotrypsin. Other promoters include, for example, SV40, MMTV, Human Immunodeficiency Virus (MV), Moloney virus, ALV, Epstein Barr virus, Rous Sarcoma virus, human actin, myosin, hemoglobin, and creatine.

It is envisioned that any of the above promoters alone or in combination with another can be useful depending on the action desired. Promoters, and other regulatory elements, are selected such that they are functional in the desired cells or tissue. In addition, this list of promoters should not be construed to be exhaustive or limiting; other promoters that are used in conjunction with the promoters and methods disclosed herein.

2. Enhancers

Enhancers are genetic elements that increase transcription from a promoter located at a distant position on the same molecule of DNA. Early examples include the enhancers associated with immunoglobulin and T cell receptors that both flank the coding sequence and occur within several introns. Many viral promoters, such as CMV, SV40, and retroviral LTRs are closely associated with enhancer activity and are often treated like single elements. Enhancers are organized much like promoters. That is, they are composed of many individual elements, each of which binds to one or more transcriptional proteins. The basic distinction between enhancers and promoters is operational. An enhancer region as a whole stimulates transcription at a distance and often independent of orientation; this need not be true of a promoter region or its component elements. On the other hand, a promoter has one or more elements that direct initiation of RNA synthesis at a particular site and in a particular orientation, whereas enhancers lack these specificities. Promoters and enhancers are often overlapping and contiguous, often seeming to have a very similar modular organization. A subset of enhancers are locus-control regions (LCRs) that can not only increase transcriptional activity, but (along with insulator elements) can also help to insulate the transcriptional element from adjacent sequences when integrated into the genome.

Any promoter/enhancer combination (as per the Eukaryotic Promoter Data Base EPDB) can be used to drive expression of the gene, although many will restrict expression to a particular tissue type or subset of tissues (reviewed in, for example, Kutzler, M. A., and Weiner, D. B., 2008. Nature Reviews Genetics 9:776-88). Examples include, but are not limited to, enhancers from the human actin, myosin, hemoglobin, muscle creatine kinase, sequences, and from viruses CMV, RSV, and EBV. Appropriate enhancers may be selected for particular applications. Eukaryotic cells can support cytoplasmic transcription from certain bacterial promoters if the appropriate bacterial polymerase is provided, either as part of the delivery complex or as an additional genetic expression construct.

3. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the present methods, and any such sequence is employed such as human or bovine growth hormone and SV40 polyadenylation signals and LTR polyadenylation signals. Non-limiting examples include the 3'LTR, and the SV40 polyadenylation signal present in the pCEP3 plasmid (Invitrogen, Carlsbad, Calif.). Also contemplated as an element of the expression cassette is a terminator. These elements can serve to enhance message levels and to minimize read through from the cassette into other sequences. Termination or poly(A) signal sequences may be, for example, positioned about 11-30 nucleotides downstream from a conserved sequence (AAUAAA) at the 3' end of the mRNA (Montgomery, D. L., et al., 1993. DNA Cell Biol. 12:777-83; Kutzler, M. A., and Weiner, D. B., 2008. Nature Rev. Gen. 9:776-88).

4. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. The initiation codon is placed in-frame with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements is used to create multigene, or polycistronic messages. IRES elements are able to bypass the ribosome-scanning model of 5' methylated cap-dependent translation and begin translation at internal sites (Pelletier and Sonenberg, Nature, 334:320-325, 1988). IRES elements from two members of the picornavirus family (polio and encephalomyocarditis) have been discussed (Pelletier and Sonenberg, 1988), as well an IRES from a mammalian message (Macejak and Sarnow, Nature, 353:90-94, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Sequence Optimization

Protein production may also be increased by optimizing the codons in the transgene. Species specific codon changes may be used to increase protein production. Also, codons may be optimized to produce an optimized RNA, which may result in more efficient translation. By optimizing the codons to be incorporated in the RNA, elements such as those that result in a secondary structure that causes instability, secondary mRNA structures that can, for example, inhibit ribosomal binding, or cryptic sequences that can inhibit nuclear export of mRNA can be removed (Kutzler, M. A., and Weiner, D. B., 2008. Nature Rev. Gen. 9:776-88; Yan., J. et al., 2007. Mol. Ther. 15:411-21; Cheung, Y. K., et al., 2004. Vaccine 23:629-38; Narum., D. L., et al., 2001. 69:7250-55; Yadava, A., and Ockenhouse, C. F., 2003. Infect. Immun. 71:4962-69; Smith., J. M., et al., 2004. AIDS Res. Hum. Retroviruses 20:1335-47; Zhou, W., et al., 2002. Vet. Microbiol. 88:127-51; Wu, X., et al., 2004. Biochem. Biophys. Res. Commun. 313:89-96; Zhang, W., et al., 2006. Biochem. Biophys. Res. Commun. 349:69-78; Deml, L. A., et al., 2001. J. Virol. 75:1099-11001; Schneider, R. M., et al., 1997. J. Virol. 71:4892-4903; Wang, S. D., et al., 2006. Vaccine 24:4531-40; zur Megede, J., et al., 2000. J. Virol. 74:2628-2635). For example, the FBP12, the caspase polypeptide, and the CD19 sequences may be optimized by changes in the codons.

Leader Sequences

Leader sequences may be added to enhance the stability of mRNA and result in more efficient translation. The leader sequence is usually involved in targeting the mRNA to the endoplasmic reticulum. Examples include, the signal sequence for the HIV-1 envelope glycoprotein (Env), which delays its own cleavage, and the IgE gene leader sequence (Kutzler, M. A., and Weiner, D. B., 2008. Nature Rev. Gen. 9:776-88; Li, V., et al., 2000. Virology 272:417-28; Xu, Z. L., et al. 2001. Gene 272:149-56; Malin, A. S., et al., 2000. Microbes Infect. 2:1677-85; Kutzler, M. A., et al., 2005. J. Immunol. 175:112-125; Yang., J. S., et al., 2002. Emerg. Infect. Dis. 8:1379-84; Kumar., S., et al., 2006. DNA Cell Biol. 25:383-92; Wang, S., et al., 2006. Vaccine 24:4531-40). The IgE leader may be used to enhance insertion into the endoplasmic reticulum (Tepler, I, et al. (1989) J. Biol. Chem. 264:5912).

Expression of the transgenes may be optimized and/or controlled by the selection of appropriate methods for optimizing expression. These methods include, for example, optimizing promoters, delivery methods, and gene sequences, (for example, as presented in Laddy, D. J., et al., 2008. PLoS. ONE 3 e2517; Kutzler, M. A., and Weiner, D. B., 2008. Nature Rev. Gen. 9:776-88).

Nucleic Acids

A "nucleic acid" as used herein generally refers to a molecule (one, two or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid." Nucleic acids may be, be at least, be at most, or be about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length.

Nucleic acids herein provided may have regions of identity or complementarity to another nucleic acid. It is contemplated that the region of complementarity or identity can be at least 5 contiguous residues, though it is specifically contemplated that the region is, is at least, is at most, or is about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous nucleotides.

As used herein, "hybridization", "hybridizes" or "capable of hybridizing" is understood to mean forming a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but preclude hybridization of random sequences. Stringent conditions tolerate little, if any, mismatch between a nucleic acid and a target strand. Such conditions are known, and are often used for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.5 M NaCl at temperatures of about 42 degrees C. to about 70 degrees C. It is understood that the temperature and ionic strength of a desired stringency are determined in part by the length of the particular nucleic acid(s), the length and nucleobase content of the target sequence(s), the charge composition of the nucleic acid(s), and the presence or concentration of formamide, tetramethylammonium chloride or other solvent(s) in a hybridization mixture.

It is understood that these ranges, compositions and conditions for hybridization are mentioned by way of non-limiting examples only, and that the desired stringency for a particular hybridization reaction is often determined empirically by comparison to one or more positive or negative controls. Depending on the application envisioned varying conditions of hybridization may be employed to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20 degrees C. to about 50 degrees C. The low or high stringency conditions may be further modified to suit a particular application.

Nucleic Acid Modification

Any of the modifications discussed below may be applied to a nucleic acid. Examples of modifications include alterations to the RNA or DNA backbone, sugar or base, and various combinations thereof. Any suitable number of backbone linkages, sugars and/or bases in a nucleic acid can be modified (e.g., independently about 5%, 10%, 15%, 20%, 25%, 30%, 35%, 40%, 45%, 50%, 55%, 60%, 65%, 70%, 75%, 80%, 85%, 90%, 95%, up to 100%). An unmodified nucleoside is any one of the bases adenine, cytosine, guanine, thymine, or uracil joined to the 1' carbon of beta-D-ribofuranose.

A modified base is a nucleotide base other than adenine, guanine, cytosine and uracil at a 1' position. Non-limiting examples of modified bases include inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e. g., 5-methylcytidine), 5-alkyluridines (e. g., ribothymidine), 5-halouridine (e. g., 5-bromouridine) or 6-azapyrimidines or 6-alkylpyrimidines (e. g. 6-methyluridine), propyne, and the like. Other non-limiting examples of modified bases include nitropyrrolyl (e.g., 3-nitropyrrolyl), nitroindolyl (e.g., 4-, 5-, 6-nitroindolyl), hypoxanthinyl, isoinosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, difluorotolyl, 4-fluoro-6-methylbenzimidazole, 4-methylbenzimidazole, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenyl, tetracenyl, pentacenyl and the like.

In some embodiments, for example, a nucleic acid may comprise modified nucleic acid molecules, with phosphate backbone modifications. Non-limiting examples of backbone modifications include phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl modifications. In certain instances, a ribose sugar moiety that naturally occurs in a nucleoside is replaced with a hexose sugar, polycyclic heteroalkyl ring, or cyclohexenyl group. In certain instances, the hexose sugar is an allose, altrose, glucose, mannose, gulose, idose, galactose, talose, or a derivative thereof. The hexose may be a D-hexose, glucose, or mannose. In certain instances, the polycyclic heteroalkyl group may be a bicyclic ring containing one oxygen atom in the ring. In certain instances, the polycyclic heteroalkyl group is a bicyclo[2.2.1]heptane, a bicyclo[3.2.1]octane, or a bicyclo[3.3.1]nonane.

Nitropyrrolyl and nitroindolyl nucleobases are members of a class of compounds known as universal bases. Universal bases are those compounds that can replace any of the four naturally occurring bases without substantially affecting the melting behavior or activity of the oligonucleotide duplex. In contrast to the stabilizing, hydrogen-bonding interactions associated with naturally occurring nucleobases, oligonucleotide duplexes containing 3-nitropyrrolyl nucleobases may be stabilized solely by stacking interactions. The absence of significant hydrogen-bonding interactions with nitropyrrolyl nucleobases obviates the specificity for a specific complementary base. In addition, 4-, 5- and 6-nitroindolyl display very little specificity for the four natural bases. Procedures for the preparation of 1-(2'-O-methyl-.beta.-D-ribofuranosyl)-5-nitroindole are discussed in Gaubert, G.; Wengel, J. Tetrahedron Letters 2004, 45, 5629. Other universal bases include hypoxanthinyl, isoinosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, and structural derivatives thereof.

Difluorotolyl is a non-natural nucleobase that functions as a universal base. Difluorotolyl is an isostere of the natural nucleobase thymine. But unlike thymine, difluorotolyl shows no appreciable selectivity for any of the natural bases. Other aromatic compounds that function as universal bases are 4-fluoro-6-methylbenzimidazole and 4-methylbenzimidazole. In addition, the relatively hydrophobic isocarbostyrilyl derivatives 3-methyl isocarbostyrilyl, 5-methyl isocarbostyrilyl, and 3-methyl-7-propynyl isocarbostyrilyl are universal bases which cause only slight destabilization of oligonucleotide duplexes compared to the oligonucleotide sequence containing only natural bases. Other non-natural nucleobases include 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenyl, tetracenyl, pentacenyl, and structural derivates thereof. For a more detailed discussion, including synthetic procedures, of difluorotolyl, 4-fluoro-6-methylbenzimidazole, 4-methylbenzimidazole, and other non-natural bases mentioned above, see: Schweitzer et al., J. Org. Chem., 59:7238-7242 (1994);

In addition, chemical substituents, for example cross-linking agents, may be used to add further stability or irreversibility to the reaction. Non-limiting examples of cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

A nucleotide analog may also include a "locked" nucleic acid. Certain compositions can be used to essentially "anchor" or "lock" an endogenous nucleic acid into a particular structure. Anchoring sequences serve to prevent disassociation of a nucleic acid complex, and thus not only can prevent copying but may also enable labeling, modification, and/or cloning of the endogeneous sequence. The locked structure may regulate gene expression (i.e. inhibit or enhance transcription or replication), or can be used as a stable structure that can be used to label or otherwise modify the endogenous nucleic acid sequence, or can be used to isolate the endogenous sequence, i.e. for cloning.

Nucleic acid molecules need not be limited to those molecules containing only RNA or DNA, but further encompass chemically-modified nucleotides and non-nucleotides. The percent of non-nucleotides or modified nucleotides may be from 1% to 100% (e.g., about 5, 10, 15, 20, 25, 30, 35, 40, 45, 50, 55, 60, 65, 70, 75, 80, 85, 90 or 95%).

Nucleic Acid Preparation

In some embodiments, a nucleic acid is provided for use as a control or standard in an assay, or therapeutic, for example. A nucleic acid may be made by any technique known in the art, such as for example, chemical synthesis, enzymatic production or biological production. Nucleic acids may be recovered or isolated from a biological sample. The nucleic acid may be recombinant or it may be natural or endogenous to the cell (produced from the cell's genome). It is contemplated that a biological sample may be treated in a way so as to enhance the recovery of small nucleic acid molecules. Generally, methods may involve lysing cells with a solution having guanidinium and a detergent.

Nucleic acid synthesis may also be performed according to standard methods. Non-limiting examples of a synthetic nucleic acid (e.g., a synthetic oligonucleotide), include a nucleic acid made by in vitro chemical synthesis using phosphotriester, phosphite, or phosphoramidite chemistry and solid phase techniques or via deoxynucleoside H-phosphonate intermediates. Various different mechanisms of oligonucleotide synthesis have been disclosed elsewhere.

Nucleic acids may be isolated using known techniques. In particular embodiments, methods for isolating small nucleic acid molecules, and/or isolating RNA molecules can be employed. Chromatography is a process used to separate or isolate nucleic acids from protein or from other nucleic acids. Such methods can involve electrophoresis with a gel matrix, filter columns, alcohol precipitation, and/or other chromatography. If a nucleic acid from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

Methods may involve the use of organic solvents and/or alcohol to isolate nucleic acids. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column is effective for such isolation procedures.

A nucleic acid isolation processes may sometimes include: a) lysing cells in the sample with a lysing solution comprising guanidinium, where a lysate with a concentration of at least about 1 M guanidinium is produced; b) extracting nucleic acid molecules from the lysate with an extraction solution comprising phenol; c) adding to the lysate an alcohol solution for form a lysate/alcohol mixture, wherein the concentration of alcohol in the mixture is between about 35% to about 70%; d) applying the lysate/alcohol mixture to a solid support; e) eluting the nucleic acid molecules from the solid support with an ionic solution; and, f) capturing the nucleic acid molecules. The sample may be dried down and resuspended in a liquid and volume appropriate for subsequent manipulation.

Methods of Gene Transfer

In order to mediate the effect of the transgene expression in a cell, it will be necessary to transfer the expression constructs into a cell. Such transfer may employ viral or non-viral methods of gene transfer. This section provides a discussion of methods and compositions of gene transfer.

A transformed cell comprising an expression vector is generated by introducing into the cell the expression vector. Suitable methods for polynucleotide delivery for transformation of an organelle, a cell, a tissue or an organism for use with the current methods include virtually any method by which a polynucleotide (e.g., DNA) can be introduced into an organelle, a cell, a tissue or an organism.

A host cell can, and has been, used as a recipient for vectors. Host cells may be derived from prokaryotes or eukaryotes, depending upon whether the desired result is replication of the vector or expression of part or all of the vector-encoded polynucleotide sequences. Numerous cell lines and cultures are available for use as a host cell, and they can be obtained through the American Type Culture Collection (ATCC), which is an organization that serves as an archive for living cultures and genetic materials.

An appropriate host may be determined. Generally this is based on the vector backbone and the desired result. A plasmid or cosmid, for example, can be introduced into a prokaryote host cell for replication of many vectors. Bacterial cells used as host cells for vector replication and/or expression include DH5alpha, JM109, and KC8, as well as a number of commercially available bacterial hosts such as SURE® Competent Cells and SOLOPACK Gold Cells (STRATAGENE®, La Jolla, Calif.). Alternatively, bacterial cells such as E. coli LE392 could be used as host cells for phage viruses. Eukaryotic cells that can be used as host cells include, but are not limited to yeast, insects and mammals. Examples of mammalian eukaryotic host cells for replication and/or expression of a vector include, but are not limited to, HeLa, NIH3T3, Jurkat, 293, COS, CHO, Saos, and PC12. Examples of yeast strains include, but are not limited to, YPH499, YPHSO0 and YPHSO1.

Nucleic acid vaccines may include, for example, non-viral DNA vectors, "naked" DNA and RNA, and viral vectors. Methods of transforming cells with these vaccines, and for optimizing the expression of genes included in these vaccines are known and are also discussed herein.

Examples of Methods of Nucleic Acid or Viral Vector Transfer

1. Ex Vivo Transformation

Various methods are available for transfecting vascular cells and tissues removed from an organism in an ex vivo setting. For example, canine endothelial cells have been genetically altered by retroviral gene transfer in vitro and transplanted into a canine (Wilson et al., Science, 244:1344-1346, 1989). In another example, Yucatan minipig endothelial cells were transfected by retrovirus in vitro and transplanted into an artery using a double-balloon catheter (Nabel et al., Science, 244(4910):1342-1344, 1989). Thus, it is contemplated that cells or tissues may be removed and transfected ex vivo using the polynucleotides presented herein. In particular aspects, the transplanted cells or tissues may be placed into an organism.

2. Injection

In certain embodiments, an antigen presenting cell or a nucleic acid or viral vector may be delivered to an organelle, a cell, a tissue or an organism via one or more injections (i.e., a needle injection), such as, for example, subcutaneous, intradermal, intramuscular, intravenous, intraprotatic, intratumor, intraperitoneal, etc. Methods of injection include, foe example, injection of a composition comprising a saline solution. Further embodiments include the introduction of a polynucleotide by direct microinjection. The amount of the expression vector used may vary upon the nature of the antigen as well as the organelle, cell, tissue or organism used. Intradermal, intranodal, or intralymphatic injections are some of the more commonly used methods of DC administration. Intradermal injection is characterized by a low rate of absorption into the bloodstream but rapid uptake into the lymphatic system. The presence of large numbers of Langerhans dendritic cells in the dermis will transport intact as well as processed antigen to draining lymph nodes. Proper site preparation is necessary to perform this correctly (i.e., hair is clipped in order to observe proper needle placement). Intranodal injection allows for direct delivery of antigen to lymphoid tissues. Intralymphatic injection allows direct administration of DCs.

3. Electroporation

In certain embodiments, a polynucleotide is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference).

Transfection of eukaryotic cells using electroporation has been quite successful. Mouse pre-B lymphocytes have been transfected with human kappa-immunoglobulin genes (Potter et al., (1984) Proc. Nat'l Acad. Sci. USA, 81, 7161-7165), and rat hepatocytes have been transfected with the chloramphenicol acetyltransferase gene (Tur-Kaspa et al., (1986) Mol. Cell Biol., 6, 716-718) in this manner.

4. Calcium Phosphate

In other embodiments, a polynucleotide is introduced to the cells using calcium phosphate precipitation. Human KB cells have been transfected with adenovirus 5 DNA (Graham and van der Eb, (1973) Virology, 52, 456-467) using this technique. Also in this manner, mouse L(A9), mouse C127, CHO, CV-1, BHK, NIH3T3 and HeLa cells were transfected with a neomycin marker gene (Chen and Okayama, Mol. Cell Biol., 7(8):2745-2752, 1987), and rat hepatocytes were transfected with a variety of marker genes (Rippe et al., Mol. Cell Biol., 10:689-695, 1990).

5. DEAE-Dextran

In another embodiment, a polynucleotide is delivered into a cell using DEAE-dextran followed by polyethylene glycol. In this manner, reporter plasmids were introduced into mouse myeloma and erythroleukemia cells (Gopal, T. V., Mol Cell Biol. 1985 May; 5(5):1188-90).

6. Sonication Loading

Additional embodiments include the introduction of a polynucleotide by direct sonic loading. LTK-fibroblasts have been transfected with the thymidine kinase gene by sonication loading (Fechheimer et al., (1987) Proc. Nat'l Acad. Sci. USA, 84, 8463-8467).

7. Liposome-Mediated Transfection

In a further embodiment, a polynucleotide may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, (1991) In: Liver Diseases, Targeted Diagnosis and Therapy Using Specific Receptors and Ligands. pp. 87-104). Also contemplated is a polynucleotide complexed with Lipofectamine (Gibco BRL) or Superfect (Qiagen).

8. Receptor Mediated Transfection

Still further, a polynucleotide may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity. Certain receptor-mediated gene targeting vehicles comprise a cell receptor-specific ligand and a polynucleotide-binding agent. Others comprise a cell receptor-specific ligand to which the polynucleotide to be delivered has been operatively attached. Several ligands have been used for receptor-mediated gene transfer (Wu and Wu, (1987) J. Biol. Chem., 262, 4429-4432; Wagner et al., Proc. Natl. Acad. Sci. USA, 87(9):3410-3414, 1990; Perales et al., Proc. Natl. Acad. Sci. USA, 91:4086-4090, 1994; Myers, EPO 0273085), which establishes the operability of the technique. Specific delivery in the context of another mammalian cell type has been discussed (Wu and Wu, Adv. Drug Delivery Rev., 12:159-167, 1993; incorporated herein by reference). In certain aspects, a ligand is chosen to correspond to a receptor specifically expressed on the target cell population.

In other embodiments, a polynucleotide delivery vehicle component of a cell-specific polynucleotide-targeting vehicle may comprise a specific binding ligand in combination with a liposome. The polynucleotide(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a polynucleotide to cells that exhibit upregulation of the EGF receptor.

In still further embodiments, the polynucleotide delivery vehicle component of a targeted delivery vehicle may be a liposome itself, which may, for example, comprise one or more lipids or glycoproteins that direct cell-specific binding. For example, lactosyl-ceramide, a galactose-terminal asialoganglioside, have been incorporated into liposomes and observed an increase in the uptake of the insulin gene by hepatocytes (Nicolau et al., (1987) Methods Enzymol., 149, 157-176). It is contemplated that the tissue-specific transforming constructs may be specifically delivered into a target cell in a similar manner.

9. Microprojectile Bombardment

Microprojectile bombardment techniques can be used to introduce a polynucleotide into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., (1987) Nature, 327, 70-73). There are a wide variety of microprojectile bombardment techniques known in the art, many of which are applicable to the present methods. In this microprojectile bombardment, one or more particles may be coated with at least one polynucleotide and delivered into cells by a propelling force. Several devices for accelerating small particles have been developed. One such device relies on a high voltage discharge to generate an electrical current, which in turn provides the motive force (Yang et al., (1990) Proc. Nat'l Acad. Sci. USA, 87, 9568-9572). The microprojectiles used have consisted of biologically inert substances such as tungsten or gold particles or beads. Exemplary particles include those comprised of tungsten, platinum, and, in certain examples, gold, including, for example, nanoparticles. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

Examples of Methods of Viral Vector-Mediated Transfer

In certain embodiments, a transgene is incorporated into a viral particle to mediate gene transfer to a cell. Typically, the virus simply will be exposed to the appropriate host cell under physiologic conditions, permitting uptake of the virus. The present methods are advantageously employed using a variety of viral vectors, as discussed below.

1. Adenovirus

Adenovirus is particularly suitable for use as a gene transfer vector because of its mid-sized DNA genome, ease of manipulation, high titer, wide target-cell range, and high infectivity. The roughly 36 kb viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, M. J. (1990) Radiother Oncol., 19, 197-218). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence, which makes them useful for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present methods, it is possible to achieve both these goals while retaining the ability to manipulate the therapeutic constructs with relative ease.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay, R. T., et al., J Mol Biol. 1984 Jun. 5; 175(4):493-510). Therefore, inclusion of these elements in an adenoviral vector may permits replication.

In addition, the packaging signal for viral encapsulation is localized between 194-385 by (0.5-1.1 map units) at the left end of the viral genome (Hearing et al., J. (1987) Virol., 67, 2555-2558). This signal mimics the protein recognition site in bacteriophage lambda DNA where a specific sequence close to the left end, but outside the cohesive end sequence, mediates the binding to proteins that are required for insertion of the DNA into the head structure. E1 substitution vectors of Ad have demonstrated that a 450 by (0-1.25 map units) fragment at the left end of the viral genome could direct packaging in 293 cells (Levrero et al., Gene, 101:195-202, 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element derives from the packaging function of adenovirus.

It has been shown that a packaging signal for adenovirus exists in the left end of the conventional adenovirus map (Tibbetts et. al. (1977) Cell, 12, 243-249). Later studies showed that a mutant with a deletion in the E1A (194-358 bp) region of the genome grew poorly even in a cell line that complemented the early (E1A) function (Hearing and Shenk, (1983) J. Mol. Biol. 167, 809-822). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved toward the interior of the Ad5 DNA molecule (Hearing et al., J. (1987) Virol., 67, 2555-2558).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals is packaged selectively when compared to the helpers. If the preference is great enough, stocks approaching homogeneity may be achieved.

To improve the tropism of ADV constructs for particular tissues or species, the receptor-binding fiber sequences can often be substituted between adenoviral isolates. For example the Coxsackie-adenovirus receptor (CAR) ligand found in adenovirus 5 can be substituted for the CD46-binding fiber sequence from adenovirus 35, making a virus with greatly improved binding affinity for human hematopoietic cells. The resulting "pseudotyped" virus, Ad5f35, has been the basis for several clinically developed viral isolates. Moreover, various biochemical methods exist to modify the fiber to allow re-targeting of the virus to target cells. Methods include use of bifunctional antibodies (with one end binding the CAR ligand and one end binding the target sequence), and metabolic biotinylation of the fiber to permit association with customized avidin-based chimeric ligands. Alternatively, one could attach ligands (e.g. anti-CD205 by heterobifunctional linkers (e.g. PEG-containing), to the adenovirus particle.

2. Retrovirus

The retroviruses are a group of single-stranded RNA viruses characterized by an ability to convert their RNA to double-stranded DNA in infected cells by a process of reverse-transcription (Coffin, (1990) In: Virology, ed., New York: Raven Press, pp. 1437-1500). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed psi, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and psi components is constructed (Mann et al., (1983) Cell, 33, 153-159). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas, J. F., and Rubenstein, J. L. R., (1988) In: Vectors: a Survey of Molecular Cloning Vectors and Their Uses, Rodriquez and Denhardt, Eds.). Nicolas and Rubenstein; Temin et al., (1986) In: Gene Transfer, Kucherlapati (ed.), New York: Plenum Press, pp. 149-188; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., (1975) Virology, 67, 242-248). An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, may this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., (1989) Proc. Nat'l Acad. Sci. USA, 86, 9079-9083). Using antibodies against major histocompatibility complex class I and class II antigens, the infection of a variety of human cells that bore those surface antigens was demonstrated with an ecotropic virus in vitro (Roux et al., 1989).

3. Adeno-Associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low-level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., J. Virol., 61:3096-3101 (1987)), or by other methods, including but not limited to chemical or enzymatic synthesis of the terminal repeats based upon the published sequence of AAV. It can be determined, for example, by deletion analysis, the minimum sequence or part of the AAV ITRs which is required to allow function, i.e., stable and site-specific integration. It can also be determined which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, (1995) Ann. N.Y. Acad. Sci., 770; 79-90; Chatteijee, et al., (1995) Ann. N.Y. Acad. Sci., 770, 79-90; Ferrari et al., (1996) J. Virol., 70, 3227-3234; Fisher et al., (1996) J. Virol., 70, 520-532; Flotte et al., Proc. Nat'l Acad. Sci. USA, 90, 10613-10617, (1993); Goodman et al. (1994), Blood, 84, 1492-1500; Kaplitt et al., (1994) Nat'l Genet., 8, 148-153; Kaplitt, M. G., et al., Ann Thorac Surg. 1996 December; 62(6):1669-76; Kessler et al., (1996) Proc. Nat'l Acad. Sci. USA, 93, 14082-14087; Koeberl et al., (1997) Proc. Nat'l Acad. Sci. USA, 94, 1426-1431; Mizukami et al., (1996) Virology, 217, 124-130).

AAV-mediated efficient gene transfer and expression in the lung has led to clinical trials for the treatment of cystic fibrosis (Carter and Flotte, 1995; Flotte et al., Proc. Nat'l Acad. Sci. USA, 90, 10613-10617, (1993)). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., (1996) J. Virol., 70, 520-532; Flotte et al., 1993; Kaplitt et al., 1994; 1996; Koeberl et al., 1997; McCown et al., (1996) Brain Res., 713, 99-107; Ping et al., (1996) Microcirculation, 3, 225-228; Xiao et al., (1996) J. Virol., 70, 8098-8108).

4. Other Viral Vectors

Other viral vectors are employed as expression constructs in the present methods and compositions. Vectors derived from viruses such as vaccinia virus (Ridgeway, (1988) In: Vectors: A survey of molecular cloning vectors and their uses, pp. 467-492; Baichwal and Sugden, (1986) In, Gene Transfer, pp. 117-148; Coupar et al., Gene, 68:1-10, 1988) canary poxvirus, and herpes viruses are employed. These viruses offer several features for use in gene transfer into various mammalian cells.

Once the construct has been delivered into the cell, the nucleic acid encoding the transgene are positioned and expressed at different sites. In certain embodiments, the nucleic acid encoding the transgene is stably integrated into the genome of the cell. This integration is in the cognate location and orientation via homologous recombination (gene replacement) or it is integrated in a random, non-specific location (gene augmentation). In yet further embodiments, the nucleic acid is stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

Methods for Treating a Disease

The present methods also encompass methods of treatment or prevention of a disease where administration of cells by, for example, infusion, may be beneficial.

Cells, such as, for example, progenitor cells, such as, for example, mesenchymal stromal cells, stem cells, pluripotent stem cells, and embryonic stem cells may be used for cell therapy. The cells may be from a donor, or may be cells obtained from the patient. The cells may, for example, be used in regeneration, for example, to replace the function of diseased cells. The cells may also be modified to express a heterologous gene so that biological agents may be delivered to specific microenvironments such as, for example, diseased bone marrow or metastatic deposits. Mesenchymal stromal cells have also, for example, been used to provide immunosuppressive activity, and may be used in the treatment of graft versus host disease and autoimmune disorders. The cells provided in the present application contain a safety switch that may be valuable in a situation where following cell therapy, the cells need to be removed. For example, where progenitor cells are provided to the patient, in some situations there may be an adverse event, such as inappropriate differentiation of the cell into a more mature cell type, or an undesired invitation into another tissue, for example, where it is necessary to remove the therapeutic cells. In such cases, where the cells have a negative effect, the present methods may be used to remove the therapeutic cells through selective apoptosis.

In other examples, T cells are used to treat various diseases and conditions, and as a part of stem cell transplantation. An adverse event that may occur after haploidentical T cell transplantation is graft versus host disease. The likelihood of GvHD occurring increases with the increased number of T cells that are transplanted. This limits the number of T cells that may be infused. By having the ability to selectively remove the infused T cells in the event of GvHD in the patient, a greater number of T cells may be infused, increasing the number to greater than $10^6$, greater than $10^7$, greater than $10^8$, or greater than $10^9$ cells. The number of T cells/kg body weight that may be administered may be, for example, from about $1 \times 10^4$ T cells/kg body weight to about $9 \times 10^7$ T cells/kg body weight, for example about 1, 2, 3, 4, 5, 6, 7, 8, or $9 \times 10^4$; about 1, 2, 3, 4, 5, 6, 7, 8, or $9 \times 10^5$; about 1, 2, 3, 4, 5, 6, 7, 8, or $9 \times 10^6$; or about 1, 2, 3, 4, 5, 6, 7, 8, or $9 \times 10^7$ T cells/kg body weight.

The term "unit dose" as it pertains to the inoculum refers to physically discrete units suitable as unitary dosages for mammals, each unit containing a predetermined quantity of pharmaceutical composition calculated to produce the desired immunogenic effect in association with the required diluent. The specifications for the unit dose of an inoculum are dictated by and are dependent upon the unique characteristics of the pharmaceutical composition and the particular immunologic effect to be achieved.

An effective amount of the pharmaceutical composition, such as the multimeric ligand presented herein, would be the amount that achieves this selected result of selectively removing the cells that include the caspase 9 vector, such that over 60%, 70%, 80%, 85%, 90%, 95%, or 97% of the caspase 9 expressing cells are killed. The term is also synonymous with "sufficient amount."

The effective amount for any particular application can vary depending on such factors as the disease or condition being treated, the particular composition being administered, the size of the subject, and/or the severity of the disease or condition. One can empirically determine the effective amount of a particular composition presented herein without necessitating undue experimentation.

The terms "contacted" and "exposed," when applied to a cell, tissue or organism, are used herein to describe the process by which the pharmaceutical composition and/or another agent, such as for example a chemotherapeutic or radiotherapeutic agent, are delivered to a target cell, tissue or organism or are placed in direct juxtaposition with the target cell, tissue or organism. To achieve cell killing or stasis, the pharmaceutical composition and/or additional agent(s) are delivered to one or more cells in a combined amount effective to kill the cell(s) or prevent them from dividing. The administration of the pharmaceutical composition may precede, be co-current with and/or follow the other agent(s) by intervals ranging from minutes to weeks. In embodiments where the pharmaceutical composition and other agent(s) are applied separately to a cell, tissue or organism, one would generally ensure that a significant period of time did not expire between the times of each delivery, such that the pharmaceutical composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the pharmaceutical composition. In other aspects, one or more agents may be administered within of from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition presented herein and one or more agents may be employed.

Optimized and Personalized Therapeutic Treatment

The induction of apoptosis after administration of the dimer, may be optimized by determining the stage of graft versus host disease, or the number of undesired therapeutic cells that remain in the patient.

For example, determining that a patient has GvHD, and the stage of the GvHD, provides an indication to a clinician that it may be necessary to induce caspase 9 associated apoptosis by administering the multimeric ligand. In another example, determining that a patient has a reduced level of GvHD after treatment with the multimeric ligand may indicate to the clinician that no additional dose of the multimeric ligand is needed. Similarly, after treatment with the multimeric ligand, determining that the patient continues to exhibit GvHD symptoms, or suffers a relapse of GvHD may indicate to the clinician that it may be necessary to administer at least one additional dose of multimeric ligand. The term "dosage" is meant to include both the amount of the dose and the frequency of administration, such as, for example, the timing of the next dose An indication of adjusting or maintaining a subsequent drug dose, such as, for example, a subsequence dose of the multimeric ligand, and/or the subsequent drug dosage, can be provided in any convenient manner. An indication may be provided in tabular form (e.g., in a physical or electronic medium) in some embodiments. For example, the graft versus host disease observed symptoms may be provided in a table, and a clinician may compare the symptoms with a list or table of stages of the disease. The clinician then can identify from the table an indication for subsequent drug dose. In certain embodiments, an indication can be presented (e.g., displayed) by a computer, after the symptoms or the GvHD stage is provided to the computer (e.g., entered into memory on the computer). For example, this information can be provided to a computer (e.g., entered into computer memory by a user or transmitted to a computer via a remote device in a computer network), and software in the computer can generate an indication for adjusting or maintaining a subsequent drug dose, and/or provide the subsequent drug dose amount.

Once a subsequent dose is determined based on the indication, a clinician may administer the subsequent dose or provide instructions to adjust the dose to another person or entity. The term "clinician" as used herein refers to a decision maker, and a clinician is a medical professional in certain embodiments. A decision maker can be a computer or a displayed computer program output in some embodiments, and a health service provider may act on the indication or subsequent drug dose displayed by the computer. A decision maker may administer the subsequent dose directly (e.g., infuse the subsequent dose into the subject) or remotely (e.g., pump parameters may be changed remotely by a decision maker).

Methods as presented herein include without limitation the delivery of an effective amount of an activated cell, a nucleic acid. or an expression construct encoding the same. An "effective amount" of the pharmaceutical composition, generally, is defined as that amount sufficient to detectably and repeatedly to achieve the stated desired result, for example, to ameliorate, reduce, minimize or limit the extent of the disease or its symptoms. Other more rigorous definitions may apply, including elimination, eradication or cure of disease. In some embodiments there may be a step of monitoring the biomarkers to evaluate the effectiveness of treatment and to control toxicity.

Formulations and Routes for Administration to Patients

Where clinical applications are contemplated, it will be necessary to prepare pharmaceutical compositions—expression constructs, expression vectors, fused proteins, transfected or transduced cells, in a form appropriate for the intended application. Generally, this will entail preparing compositions that are essentially free of pyrogens, as well as other impurities that could be harmful to humans or animals.

The multimeric ligand, such as, for example, AP1903, may be delivered, for example at doses of about 0.1 to 10 mg/kg subject weight, of about 0.1 to 5 mg/kg subject weight, of about 0.2 to 4 mg/kg subject weight, of about 0.3 to 3 mg/kg subject weight, of about 0.3 to 2 mg/kg subject weight, or about 0.3 to 1 mg/kg subject weight, for example, about 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, or 10 mg/kg subject weight. In some embodiments, the ligand is provided at 0.4 mg/Kg per dose, for example at a concentration of 5 mg/mL. Vials or other containers may be provided containing the ligand at, for example, a volume per vial of about 0.25 ml to about 10 ml, for example, about 0.25, 0.5, 1, 1.5, 2, 2.5, 3, 3.5, 4, 4.5, 5, 5.5, 6, 6.5, 7, 7.5, 8, 8.5, 9, 9.5, or 10 ml, for example, about 2 ml.

One may generally desire to employ appropriate salts and buffers when recombinant cells are introduced into a patient. The phrase "pharmaceutically or pharmacologically acceptable" refers to molecular entities and compositions that do not produce adverse, allergic, or other untoward reactions when administered to an animal or a human. A pharmaceutically acceptable carrier includes any and all solvents, dispersion media, coatings, antibacterial and antifungal agents, isotonic and absorption delaying agents and the like. The use of such media and agents for pharmaceutically active substances is known. Except insofar as any conventional media or agent is incompatible with the vectors or cells, its use in therapeutic compositions is contemplated. Supplementary active ingredients also can be incorporated into the compositions.

The active compositions may include classic pharmaceutical preparations. Administration of these compositions will be via any common route so long as the target tissue is available via that route. This includes, for example, oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, discussed herein.

The pharmaceutical forms suitable for injectable use include sterile aqueous solutions or dispersions and sterile powders for the extemporaneous preparation of sterile injectable solutions or dispersions. In all cases the form is sterile and is be fluid to the extent that easy syringability exists. It is stable under the conditions of manufacture and storage and is preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In certain examples, isotonic agents, for example, sugars or sodium chloride may be included. Prolonged absorption of the injectable compositions can be brought about by the use in the compositions of agents delaying absorption, for example, aluminum monostearate and gelatin.

For oral administration, the compositions may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including, for example: gels, pastes, powders and slurries. The active ingredient may be added in a therapeutically effective amount to a paste dentifrice that may include, for example, water, binders, abrasives, flavoring agents, foaming agents, and humectants.

The compositions may be formulated in a neutral or salt form. Pharmaceutically-acceptable salts include, for example, the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution may be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media can be employed. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations may meet sterility, pyrogenicity, and general safety and purity standards as required by FDA Office of Biologics standards.

EXAMPLES

The examples set forth below illustrate certain embodiments and do not limit the technology.

Mechanisms for selectively ablating the donor cells have been studied as safety switches for cellular therapies, but there have been complications. Some experience with safety-switch genes to date has been in T lymphocytes since immunotherapy with these cells has proved efficacious as treatment for viral infections and malignancies (Walter, E. A., et al., N. Engl. J. Med. 1995, 333:1038-44; Rooney, C. M., et al., Blood. 1998, 92:1549-55; Dudley, M. E., et al., Science 2002, 298:850-54; Marjit, W. A., et al., Proc. Natl. Acad. Sci. USA 2003, 100:2742-47). The herpes simplex virus I-derived thymidine kinase (HSVTK) gene has been used as an in vivo suicide switch in donor T-cell infusions to treat recurrent malignancy and Epstein Barr virus (EBV) lymphoproliferation after hematopoietic stem cell transplantation (Bonini C, et al., Science. 1997, 276:1719-1724; Tiberghien P, et al., Blood. 2001, 97:63-72). However, destruction of T cells causing graft-versus-host disease was incomplete, and the use of gancyclovir (or analogs) as a pro-drug to activate HSV-TK precludes administration of gancyclovir as an antiviral drug for cytomegalovirus infections. This mechanism of action also requires interference with DNA synthesis, relying on cell division, so that cell killing may be protracted over several days and incomplete, producing a lengthy delay in clinical benefit (Ciceri, F., et al., Lancet Oncol. 2009, 262:1019-24). Moreover, HSV-TK-directed immune responses have resulted in elimination of HSV-TK-transduced cells, even in immunosuppressed human immunodeficiency virus and bone marrow transplant patients, compromising the persistence and hence efficacy of the infused T cells. HSV-TK is also virus-derived, and therefore potentially immunogenic (Bonini C, et al., Science. 1997, 276:1719-1724; Riddell S R, et al., Nat Med. 1996, 2:216-23). The *E coli*-derived cytosine deaminase gene has also been used clinically (Freytag S O, et al., Cancer Res. 2002, 62:4968-4976), but as a xenoantigen it may be immunogenic and thus incompatible with T-cell-based therapies that require long-term persistence. Transgenic human CD20, which can be activated by a monoclonal chimeric anti-CD20 antibody, has been proposed as a nonimmunogenic safety system (Introna M, et al., Hum Gene Ther. 2000, 11: 611-620).

The following section provides examples of method of providing a safety switch in cells used for cellular therapy, using a caspase 9 chimeric protein.

Example 1

Construction and Evaluation of Caspase 9 Suicide Switch Expression Vectors

Vector Construction and Confirmation of Expression

A safety switch that can be stably and efficiently expressed in human T cells is presented herein. The system includes human gene products with low potential immunogenicity that have been modified to interact with a small molecule dimerizer drug that is capable of causing the selective elimination of transduced T cells expressing the modified gene. Additionally the inducible caspase 9 maintains function in T cells overexpressing antiapoptotic molecules.

Expression vectors suitable for use as a therapeutic agent were constructed that included a modified human caspase 9 activity fused to a human FK506 binding protein (FKBP). The caspase 9/FK506 hybrid activity can be dimerized using a small molecule pharmaceutical. Full length, truncated, and modified versions of the caspase 9 activity were fused to FK506, and inserted into the retroviral vector MSCV.IRES.GRP, which also allows expression of the fluorescent marker, GFP. FIG. 1A illustrates the full length, truncated and modified caspase 9 expression vectors constructed and evaluated as a suicide switch for induction of apoptosis.

The full-length inducible caspase 9 molecule (F'-F-C-Casp9) includes 2 FK506 binding proteins (FKBPs) linked with a Ser-Gly-Gly-Gly-Ser linker (SEQ ID NO: 21) to the small and large subunit of the caspase molecule (see FIG. 1A). Full-length inducible caspase 9 (F'F-C-Casp9.I.GFP) has a full-length caspase 9, also includes a caspase recruitment domain (CARD; GenBank NM001 229) linked to 2

12-kDa human FK506 binding proteins (FKBP12; GenBank AH002 818) that contain an F36V mutation (FIG. 1A). The amino acid sequence of one of the FKBPs (F') was codon-wobbled (e.g., the $3^{rd}$ nucleotide of each amino acid codon was altered by a silent mutation that maintained the originally encoded amino acid) to prevent homologous recombination when expressed in a retrovirus. F'F-C-Casp9C3S includes a cysteine to serine mutation at position 287 that disrupts its activation site. In constructs F'F-Casp9, F-C-Casp9, and F'-Casp9, either the caspase activation domain (CARD), one FKBP, or both, were deleted, respectively. All constructs were cloned into MSCV.IRES.GFP as EcoRI-XhoI fragments.

293T cells were transfected with each of these constructs and 48 hours after transduction expression of the marker gene GFP was analyzed by flow cytometry. In addition, 24 hours after transfection, 293T cells were incubated overnight with 100 nM CID and subsequently stained with the apoptosis marker annexin V. The mean and standard deviation of transgene expression level (mean GFP) and number of apoptotic cells before and after exposure to the chemical inducer of dimerization (CID) (% annexin V within GFP~ cells) from 4 separate experiments are shown in the second through fifth columns of the table in FIG. 1A. In addition to the level of GFP expression and staining for annexin V, the expressed gene products of the full length, truncated and modified caspase 9 were also analyzed by western blot to confirm the caspase 9 genes were being expressed and the expressed product was the expected size. The results of the western blot are presented in FIG. 1B.

Coexpression of the inducible caspase 9 constructs of the expected size with the marker gene GFP in transfected 293T cells was demonstrated by Western blot using a caspase 9 antibody specific for amino acid residues 299-318, present both in the full-length and truncated caspase molecules as well as a GFP-specific antibody. Western blots were performed as presented herein.

Transfected 293T cells were resuspended in lysis buffer (50% Tris/Gly, 10% sodium dodecyl sulfate [SDS], 4% beta-mercaptoethanol, 10% glycerol, 12% water, 4% bromophenol blue at 0.5%) containing aprotinin, leupeptin, and phenylmethylsulfonyl fluoride (Boehringer, Ingelheim, Germany) and incubated for 30 minutes on ice. After a 30-minute centrifugation, supernatant was harvested, mixed 1:2 with Laemmli buffer (Bio-Rad, Hercules, Calif.), boiled and loaded on a 10% SDS-polyacrylamide gel. The membrane was probed with rabbit anti-caspase 9 (amino acid residues 299-3 18) immunoglobulin G (IgG; Affinity BioReagents, Golden, Colo.; 1:500 dilution) and with mouse anti-GFP IgG (Covance, Berkeley, Calif.; 1:25,000 dilution). Blots were then exposed to appropriate peroxidase-coupled secondary antibodies and protein expression was detected with enhanced chemiluminescence (ECL; Amersham, Arlington Heights, Ill.). The membrane was then stripped and reprobed with goat polyclonal antiactin (Santa Cruz Biotechnology; 1:500 dilution) to check equality of loading.

Figure 1B:
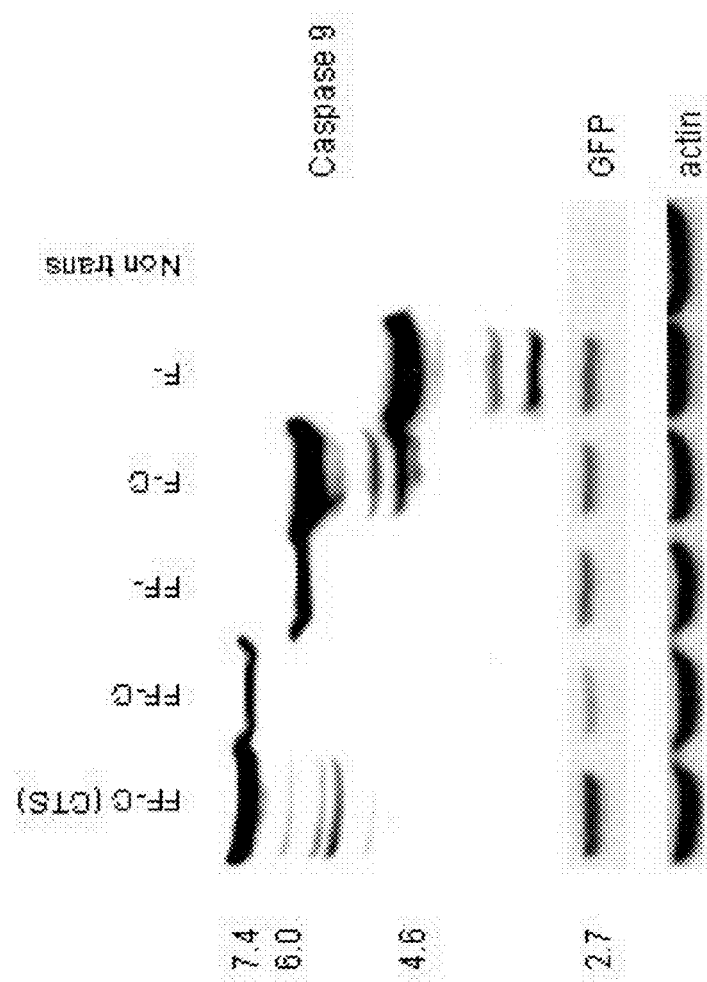

Additional smaller size bands, seem in FIG. 1B, likely represent degradation products. Degradation products for the F'F-C-Casp9 and F'F-Casp9 constructs may not be detected due to a lower expression level of these constructs as a result of their basal activity. Equal loading of each sample was confirmed by the substantially equal amounts of actin shown at the bottom of each lane of the western blot, indicating substantially similar amounts of protein were loaded in each lane.

Evaluation of Caspase 9 Suicide Switch Expression Constructs.

Cell Lines

B 95-8 EBV transformed B-cell lines (LCLs), Jurkat, and MT-2 cells (kindly provided by Dr S. Marriott, Baylor College of Medicine, Houston, Tex.) were cultured in RPMI 1640 (Hyclone, Logan, Utah) containing 10% fetal bovine serum (FBS; Hyclone). Polyclonal EBV-specific T-cell lines were cultured in 45% RPMI/45% Clicks (Irvine Scientific, Santa Ana, Calif.)/10% FBS and generated as previously reported. Briefly, peripheral blood mononuclear cells ($2\times10^6$ per well of a 24-well plate) were stimulated with autologous LCLs irradiated at 4000 rads at a responder-to-stimulator (R/S) ratio of 40:1. After 9 to 12 days, viable cells were restimulated with irradiated LCLs at an R/S ratio of 4:1. Subsequently, cytotoxic T cells (CTLs) were expanded by weekly restimulation with LCLs in the presence of 40 U/mL to 100 U/mL recombinant human interleukin-2 (rhIL-2; Proleukin; Chiron, Emeryville, Calif.).

Retrovirus Transduction

For the transient production of retrovirus, 293T cells were transfected with iCasp9/iFas constructs, along with plasmids encoding gag-pol and RD 114 envelope using GeneJuice transfection reagent (Novagen, Madison, Wis.). Virus was harvested 48 to 72 hours after transfection, snap frozen, and stored at ~80° C. until use. A stable FLYRD 18-derived retroviral producer line was generated by multiple transductions with VSV-G pseudotyped transient retroviral supernatant. FLYRD18 cells with highest transgene expression were single-cell sorted, and the clone that produced the highest virus titer was expanded and used to produce virus for lymphocyte transduction. The transgene expression, function, and retroviral titer of this clone was maintained during continuous culture for more than 8 weeks. For transduction of human lymphocytes, a non-tissue-culture-treated 24-well plate (Becton Dickinson, San Jose, Calif.) was coated with recombinant fibronectin fragment (FN CH-296; Retronectin; Takara Shuzo, Otsu, Japan; 4 mg/mL in PBS, overnight at 4° C.) and incubated twice with 0.5 mL retrovirus per well for 30 minutes at 37° C. Subsequently, $3\times10^5$ to $5\times10^5$ T cells per well were transduced for 48 to 72 hours using 1 mL virus per well in the presence of 100 U/mL IL-2. Transduction efficiency was determined by analysis of expression of the coexpressed marker gene green fluorescent protein (GFP) on a FACScan flow cytometer (Becton Dickinson). For functional studies, transduced CTLs were either non-selected or segregated into populations with low, intermediate, or high GFP expression using a MoFlo cytometer (Dako Cytomation, Ft Collins, Colo.) as indicated.

Induction and Analysis of Apoptosis

CID (AP20187; ARIAD Pharmaceuticals) at indicated concentrations was added to transfected 293T cells or transduced CTLs. Adherent and nonadherent cells were harvested and washed with annexin binding buffer (BD Pharmingen, San Jose, Calif.). Cells were stained with annexin-V and 7-amino-actinomycin D (7-AAD) for 15 minutes according to the manufacturer's instructions (BD Pharmingen). Within 1 hour after staining, cells were analyzed by flow cytometry using CellQuest software (Becton Dickinson).

Cytotoxicity Assay

The cytotoxic activity of each CTL line was evaluated in a standard 4-hour $^{51}Cr$ release assay, as previously presented. Target cells included autologous LCLs, human leukocyte antigen (HLA) class I-mismatched LCLs and the lymphokine-activated killer cell-sensitive T-cell lymphoma line HSB-2.

Target cells incubated in complete medium or 1% Triton X-100 (Sigma, St Louis, Mo.) were used to determine spontaneous and maximum $^{51}Cr$ release, respectively. The mean percentage of specific lysis of triplicate wells was calculated as 100×(experimental release −spontaneous release)/(maximal release−spontaneous release).

Phenotyping

Cell-surface phenotype was investigated using the following monoclonal antibodies: CD3, CD4, CD8 (Becton Dickinson) and CD56 and TCR-α/β (Immunotech, Miami, Fla.). ΔNGFR-iFas was detected using anti-NGFR antibody (Chromaprobe, Aptos, Calif.). Appropriate matched isotype controls (Becton Dickinson) were used in each experiment. Cells were analyzed with a FACSscan flow cytometer (Becton Dickinson).

Analysis of Cytokine Production

The concentration of interferon-γ (IFN-γ), IL-2, IL-4, IL-5, IL-10, and tumor necrosis factor-α (TNFα) in CTL culture supernatants was measured using the Human Th1/Th2 cytokine cytometric Bead Array (BD Pharmingen) and the concentration of IL-12 in the culture supernatants was measured by enzyme-linked immunosorbent assay (ELISA; R&D Systems, Minneapolis, Minn.) according to the instructions of the manufacturer.

In Vivo Experiments

Non-obese diabetic severe combined immunodeficient (NOD/SCID) mice, 6 to 8 weeks of age, were irradiated (250 rad) and injected subcutaneously in the right flank with $10 \times 10^6$ to $15 \times 10^6$ LCLs resuspended in Matrigel (BD Bioscience). Two weeks later mice bearing tumors that were approximately 0.5 cm in diameter were injected into the tail vein with a 1:1 mixture of nontransduced and iCasp9.I.GFPhigh-transduced EBV CTLs (total $15 \times 10^6$). At 4 to 6 hours prior and 3 days after CTL infusion, mice were injected intraperitoneally with recombinant hIL-2 (2000 U; Proleukin; Chiron). On day 4, the mice were randomly segregated in 2 groups: 1 group received CID (50 µg AP20187, intraperitoneally) and 1 group received carrier only (16.7% propanediol, 22.5% PEG400, and 1.25% Tween 80, intraperitoneally). On day 7, all mice were killed. Tumors were homoge-nized and stained with antihuman CD3 (BD Pharmingen). By FACS analysis, the number of GFP+ cells within the gated CD3+ population was evaluated. Tumors from a control group of mice that received only nontransduced CTLs (total $15 \times 10^6$) were used as a negative control in the analysis of CD3+/GFP+ cells.

Optimization of Expression and Function of Inducible Caspase 9

Caspases 3, 7, and 9 were screened for their suitability as inducible safety-switch molecules both in transfected 293T cells and in transduced human T cells. Only inducible caspase 9 (iCasp9) was expressed at levels sufficient to confer sensitivity to the chosen CID (e.g., chemical inducer of dimerization). An initial screen indicated that the full length iCasp9 could not be maintained stably at high levels in T cells, possibly due to transduced cells being eliminated by the basal activity of the transgene. The CARD domain is involved in physiologic dimerization of caspase 9 molecules, by a cytochrome C and adenosine triphosphate (ATP)-driven interaction with apoptotic protease-activating factor 1 (Apaf-1). Because of the use of a CID to induce dimerization and activation of the suicide switch, the function of the CARD domain is superfluous in this context and removal of the CARD domain was investigated as a method of reducing basal activity. Given that only dimerization rather than multimerization is required for activation of caspase 9, a single FKBP domain also was investigated as a method to effect activation.

The activity of the resultant truncated and/or modified forms of caspase 9 (e.g., the CARD domain, or one of the 2 FKBP domains, or both, are removed) were compared. A construct with a disrupted activation site, F'F-C-Casp9$_{C->S}$, provided a nonfunctional control (see FIG. 1A). All constructs were cloned into the retroviral vector MSCV[26] in which retroviral long terminal repeats (LTRs) direct transgene expression and enhanced GFP is coexpressed from the same mRNA by use of an internal ribosomal entry site (IRES). In transfected 293T cells, expression of all inducible caspase 9 constructs at the expected size as well as coexpression of GFP was demonstrated by Western blot (see FIG. 1B). Protein expression (estimated by mean fluorescence of GFP and visualized on Western blot) was highest in the nonfunctional construct F'F-C-Casp9$_{C->S}$ and greatly diminished in the full-length construct F'F-C-Casp9. Removal of the CARD (F'F-Casp9), one FKBP (F-C-Casp9), or both (F-Casp9) resulted in progressively higher expression of both inducible caspase 9 and GFP, and correspondingly enhanced sensitivity to CID (see FIG. 1A). Based on these results, the F-Casp9 construct (henceforth referred to as iCasp9$_M$) was used for further study in human T lymphocytes.

Stable Expression of iCasp9$_M$ in Human T Lymphocytes

The long-term stability of suicide gene expression is of utmost importance, since suicide genes must be expressed for as long as the genetically engineered cells persist. For T-cell transduction, a FLYRD18-derived retroviral producer clone that produces high-titer RD114-pseudotyped virus was generated to facilitate the transduction of T cells. iCasp9$_M$ expression in EBV-specific CTL lines (EBV-CTL) was evaluated since EBV-specific CTL lines have well-characterized function and specificity and are already being used as in vivo therapy for prevention and treatment of EBV-associated malignancies. Consistent transduction efficiencies of EBV-CTLs of more than 70% (mean, 75.3%; range, 71.4%-83.0% in 5 different donors) were obtained after a single transduction with retrovirus. The expression of iCasp9$_M$ in EBV-CTLs was stable for at least 4 weeks after transduction without selection or loss of transgene function.

iCasp9$_M$ does not Alter Transduced T-Cell Characteristics

Figure 2A:
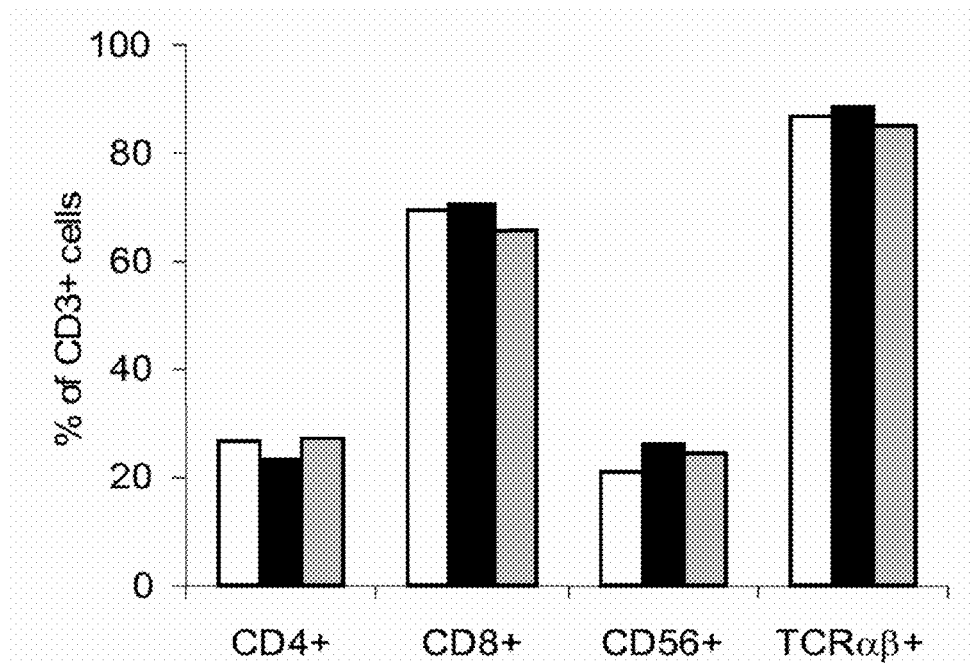
FIGS. 2A-2D graphically present results of experiments performed to evaluate the effect of expression of iCasp9 expression constructs on the phenotype of cells transduced with various iCasp9 expression vectors.
Figure 2B:
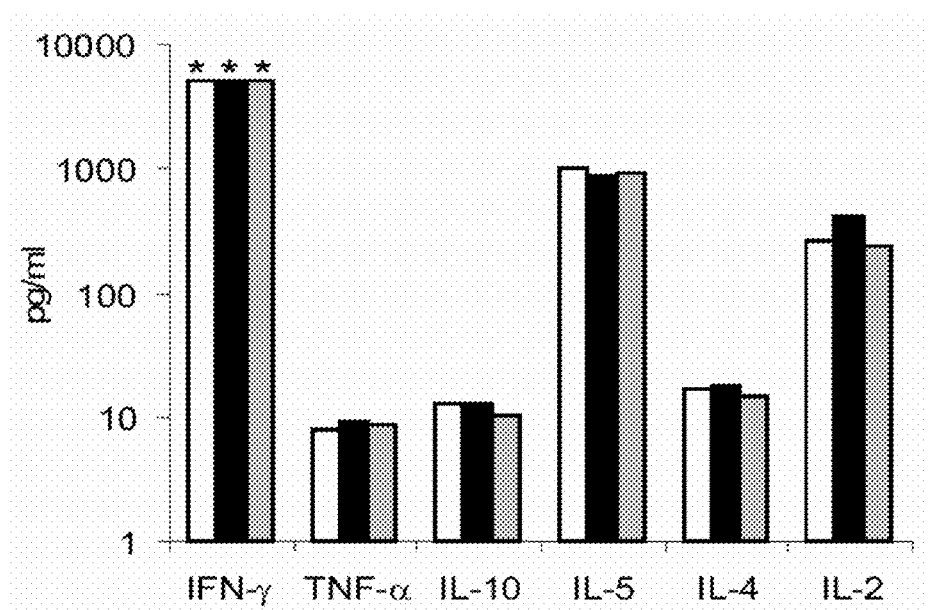
Figure 2C:
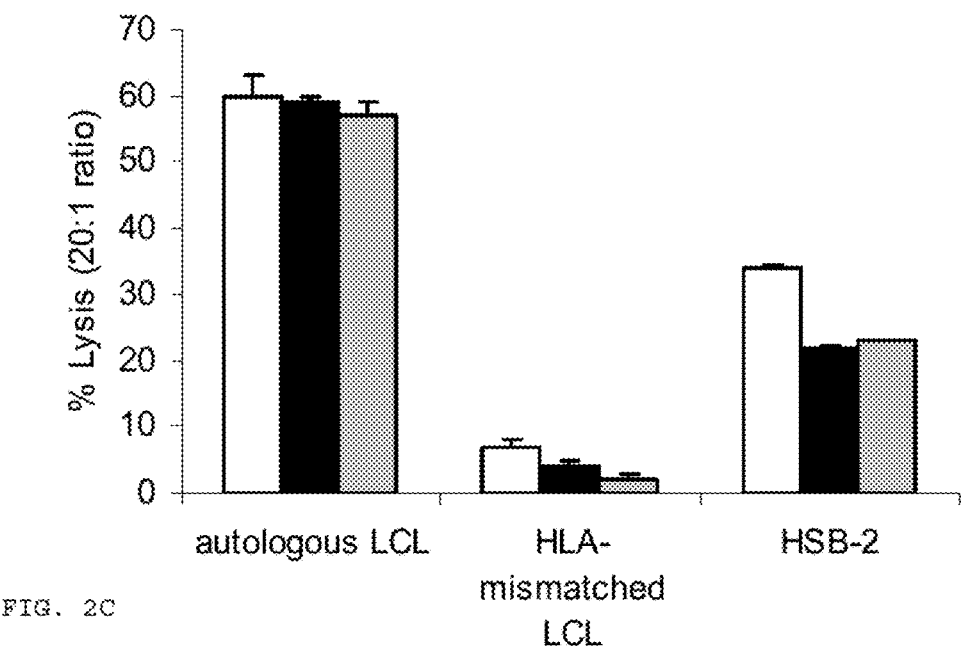
Figure 2D:
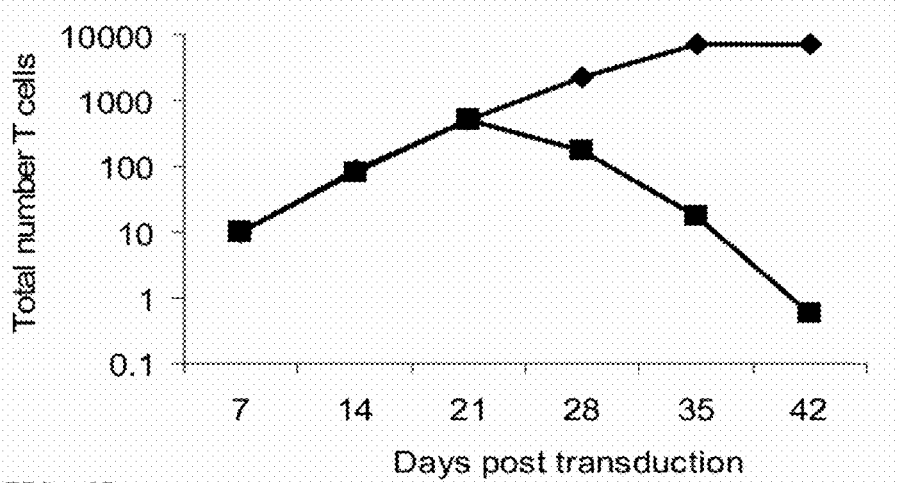

To ensure that expression of iCasp9$_M$ did not alter T-cell characteristics, the phenotype, antigen-specificity, proliferative potential, and function of nontransduced or nonfunctional iCasp9$_{C->S}$-transduced EBV-CTLs was compared with that of iCasp9$_M$-transduced EBV-CTLs. In 4 separate donors, transduced and nontransduced CTLs consisted of equal numbers of CD4+, CD8+, CD56+, and TCR α/β+ cells (see FIG. 2A). Similarly, production of cytokines including IFN-γ, TNFα, IL-10, IL-4, IL-5, and IL-2 was unaltered by iCasp9$_M$ expression (see FIG. 2B). iCasp9$_M$-transduced EBV-CTLs specifically lysed autologous LCLs comparable to nontransduced and control-transduced CTLs (see FIG. 2C). Expression of iCasp9M did not affect the growth characteristics of exponentially growing CTLs, and importantly, dependence on antigen and IL-2 for proliferation was preserved (see FIG. 2D). FIGS. 2A and 2B graphically phenotypic and secretion data of type TH1 and TH2 cytokines upon antigen stimulation. FIG. 2C graphically illustrates the level of cytotoxic activity against autologous EBV-transformed lymphoblastoid B-cell line (LCL), HLA-mismatched LCL, and HSB-2 (a LAK cell target) were compared in nontransduced (white bars), F-Casp9$_M$-transduced (black bars), and F'F-C-Casp9$_{C->S}$-transduced (stipled bars) EBV-specific CTLs (EBV-CTLs) on day 15 to day 18 after transduction (2 antigenic stimulations after transduction). The mean and standard deviation of triplicate wells are shown. Examples of experiments using EBV-CTLs from 4 different donors are shown. FIG. 2D graphically illustrates the antigen dependence of iCasp9$_M$-transduced CTLs. On day 21 after transduction the normal weekly antigenic stimulation with autologous LCLs and IL-2 was continued (black diamonds) or discontinued (black squares). Discontinuation of antigen stimulation resulted in a steady decline of T cells.

Figure 3A:
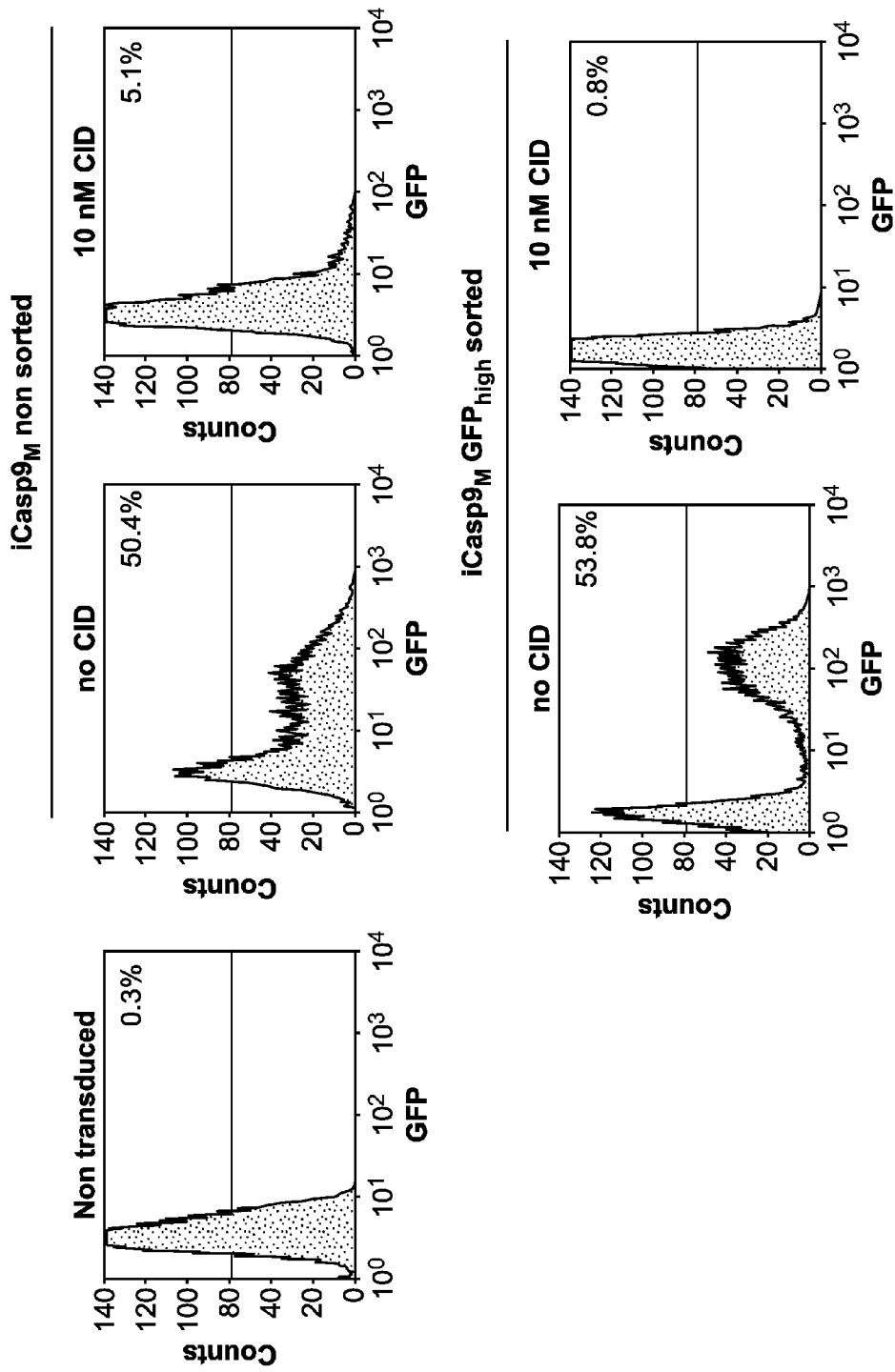
FIGS. 3A-3D illustrate the results of various experiments performed to determine the efficacy of a chemical inducer of dimerization (CID), in cells expressing iCasp9 expression constructs.

Elimination of More than 99% of T Lymphocytes Selected for High Transgene Expression In Vitro Inducible iCasp9$_M$ proficiency in CTLs was tested by monitoring loss of GFP-expressing cells after administration of CID; 91.3% (range, 89.5%-92.6% in 5 different donors) of GFP+ cells were eliminated after a single 10-nM dose of CID (see FIG. 3A). Similar results were obtained regardless of exposure time to CID (range, 1 hour-continuous). In all experiments, CTLs that survived CID treatment had low transgene expression with a 70% (range, 55%-82%) reduction in mean fluorescence intensity of GFP after CID. No further elimination of the surviving GFP+ T cells could be obtained by an antigenic stimulation followed by a second 10-nM dose of CID. Therefore, the non-responding CTLs most likely expressed insufficient iCasp9$_M$ for functional activation by CID. To investigate the correlation between low levels of expression and CTL non-response to CID, CTLs were sorted for low, intermediate, and high expression of the linked marker gene GFP and mixed 1:1 with nontransduced CTLs from the same donor to allow for an accurate quantitation of the number of transduced T cells responding to CID-induced apoptosis.

Figure 4A:
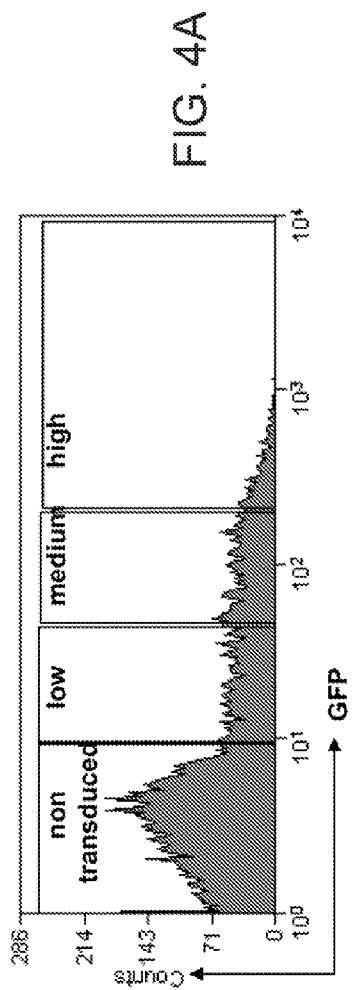
FIGS. 4A-4C illustrate the results of various experiments performed to measure the correlation between transgene expression level and function of iCasp9.
Figure 4B:
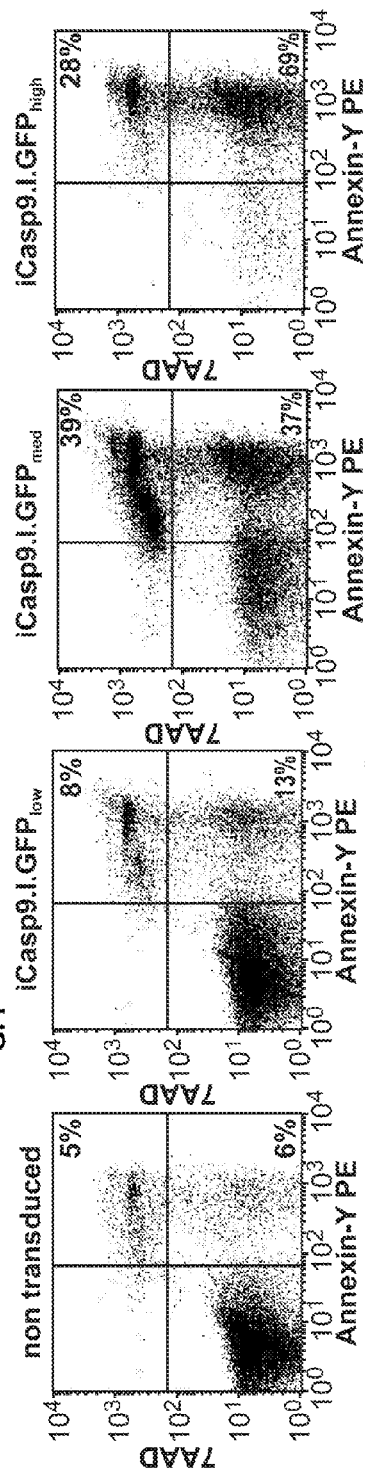
Figure 4C:
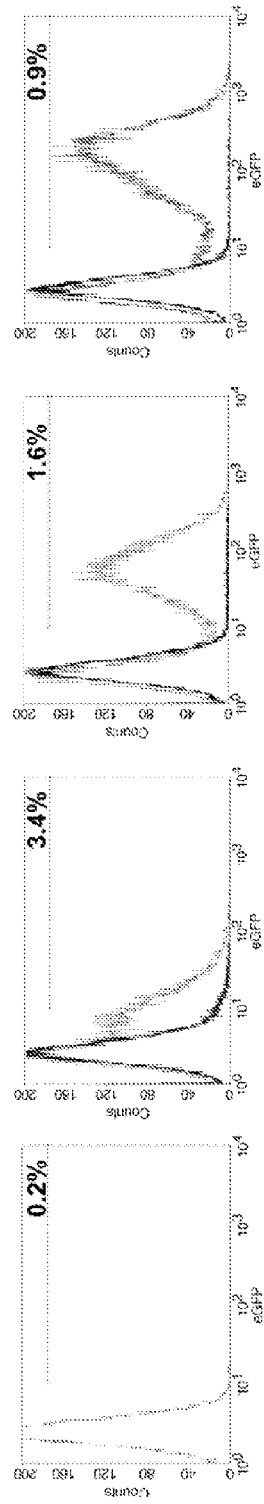

The number of transduced T cells eliminated increased with the level of GFP transgene expression (see FIGS. 4A, 4B and 4C). To determine the correlation between transgene expression and function of iCasp9$_M$, iCasp9$_M$ IRES.GFP-transduced EBV-CTL were selected for low (mean 21), intermediate (mean 80) and high (mean 189) GFP expression (see FIG. 4A). Selected T-cells were incubated overnight with 10 nM CID and subsequently stained with Annexin V and 7-AAD. Indicated are the percentages of Annexin V+/7-AAD– and Annexin V+/7-AAD+ T-cells (see FIG. 4B). Selected T-cells were mixed 1:1 with non-transduced T-cells and incubated with 10 nM CID following antigenic stimulation. Indicated is the percentage of residual GFP-positive T-cells on day 7 (see FIG. 4C).

For GFP$_{high}$-selected cells, 10 nM CID led to deletion of 99.1% (range, 98.7%-99.4%) of transduced cells (see FIG. 3A). On the day of antigen stimulation, F-Casp9$_M$.I.GFP-transduced CTLs were either untreated or treated with 10 nM CID. Seven days later, the response to CID was measured by flow cytometry for GFP. The percentage of transduced T cells was adjusted to 50% to allow for an accurate measurement of residual GFP+ cells after CID treatment. The responses to CID in unselected (top row of FIG. 3A) and GFP$_{high}$-selected CTLs (bottom row of FIG. 3A) was compared. The percentage of residual GFP+ cells is indicated (see FIG. 3A).

Figure 3B:
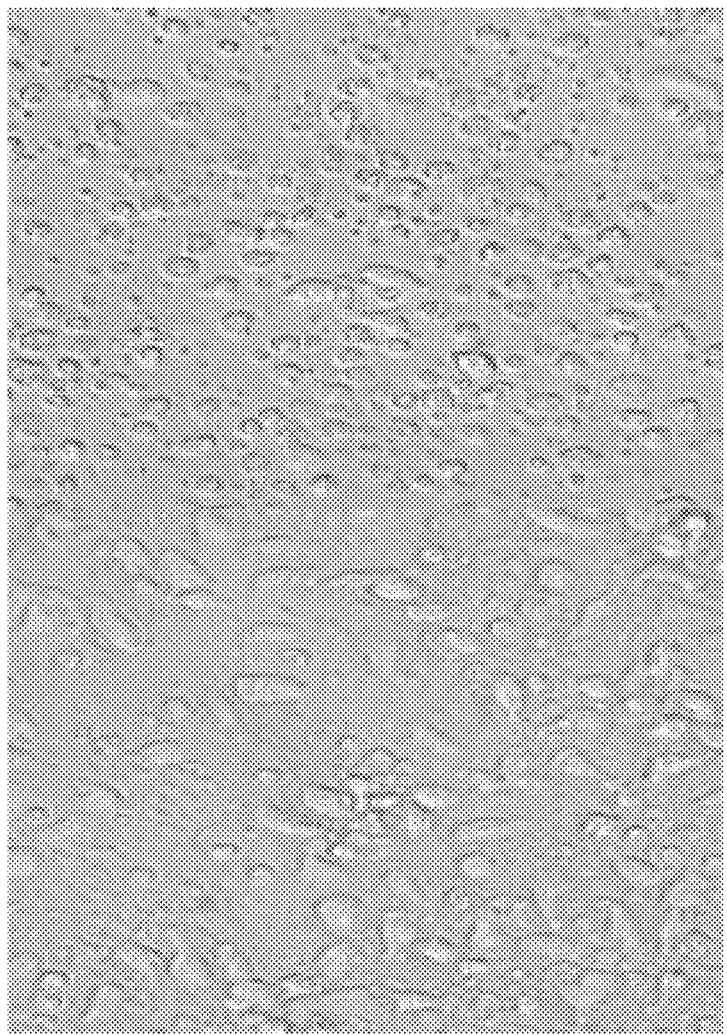
Figure 3C:
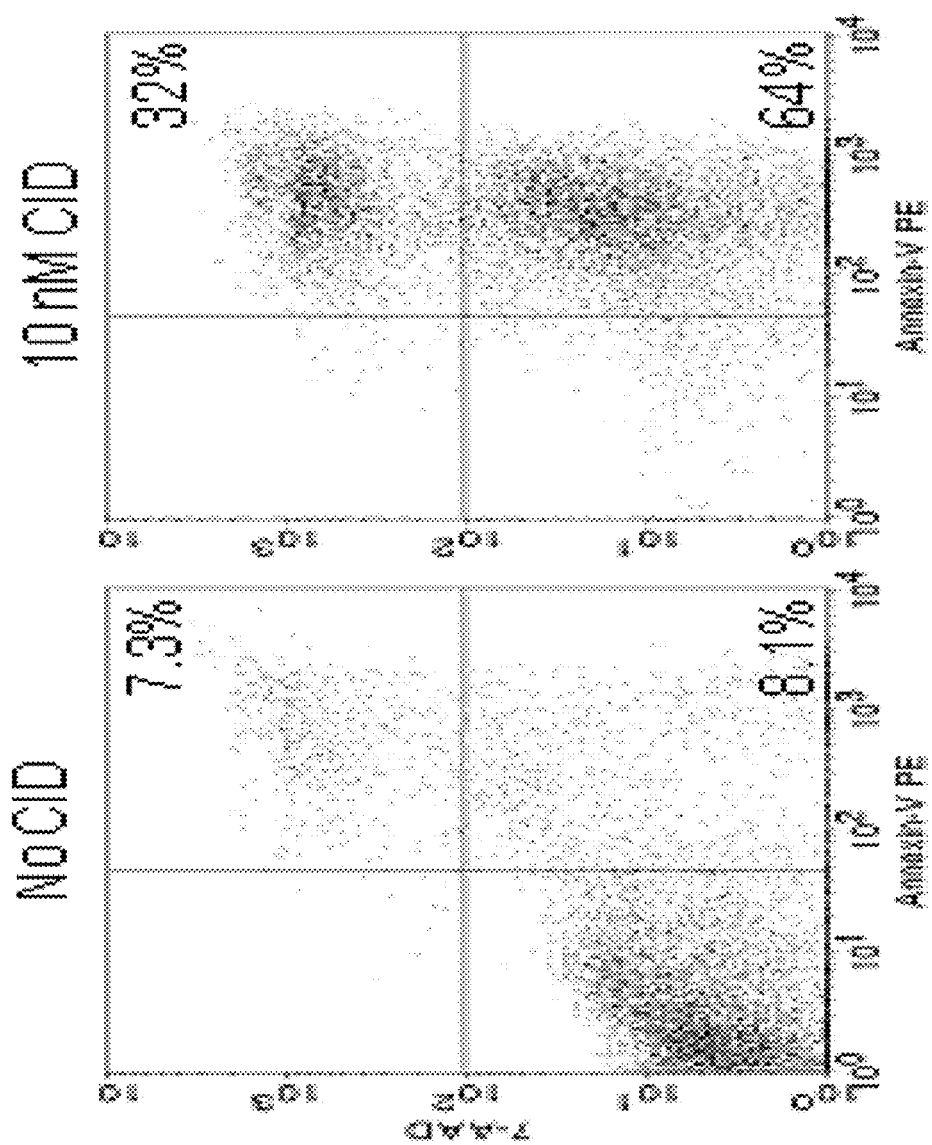

Rapid induction of apoptosis in the GFP$_{high}$-selected cells is demonstrated by apoptotic characteristics such as cell shrinkage and fragmentation within 14 hours of CID administration (see FIG. 3B). After overnight incubation with 10 nM CID, F-Casp9$_M$.I.GFP$_{high}$-transduced T cells had apoptotic characteristics such as cell shrinkage and fragmentation by microscopic evaluation. Of the T cells selected for high expression, 64% (range, 59%-69%) had an apoptotic (annexin-V+/7-AAD–) and 30% (range, 26%-32%) had a necrotic (annexinV+/7-AAD+) phenotype (see FIG. 3C). Staining with markers of apoptosis showed that 64% of T cells had an apoptotic phenotype (annexin V+, 7-AAD–, lower right quadrant) and 32% a necrotic phenotype (annexin V+, 7-AAD+, upper right quadrant). A representative example of 3 separate experiments is shown.

Figure 3D:
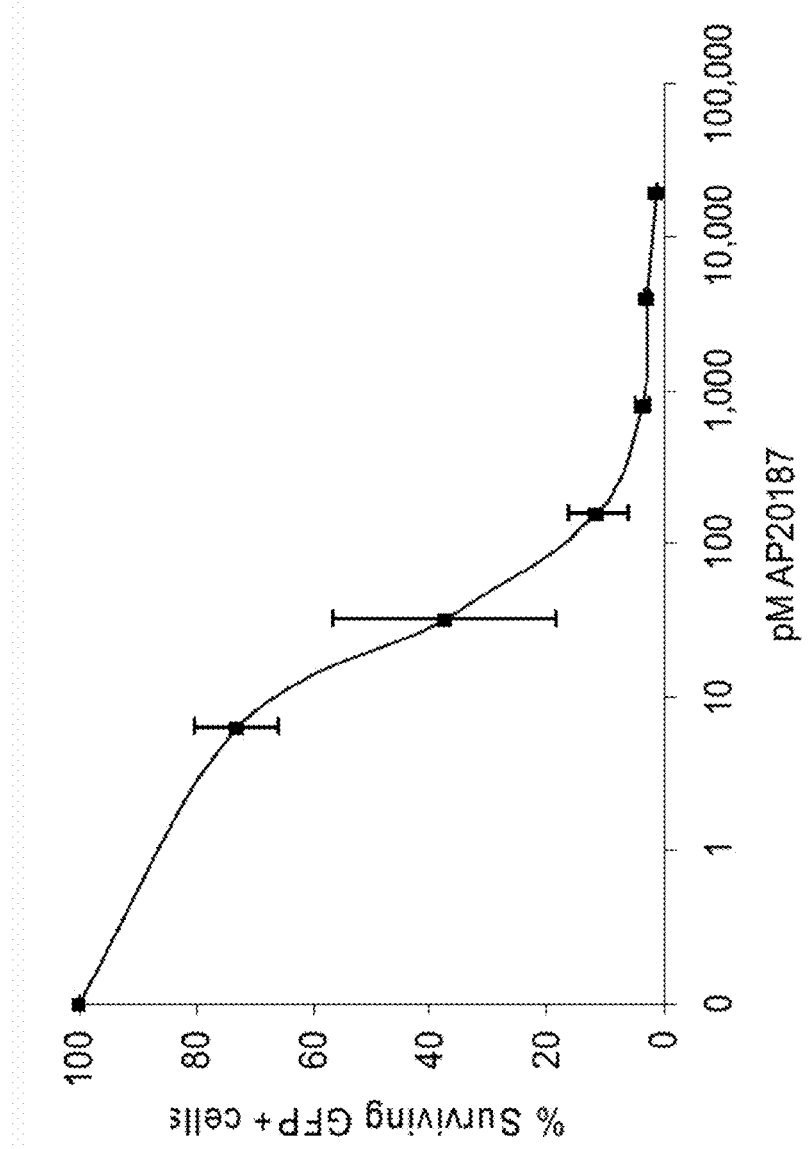
Figure 5A:
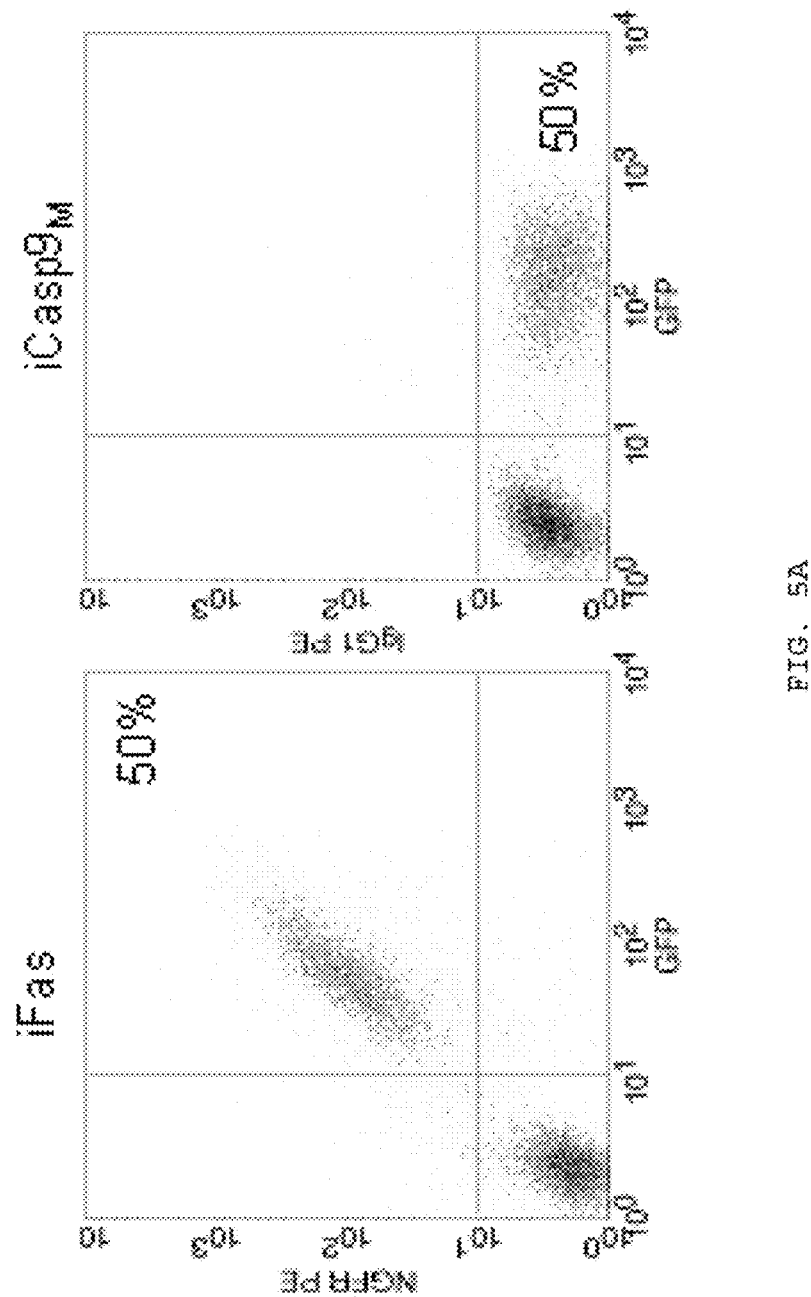
FIGS. 5A-5C illustrate the results of various experiments comparing the functionality of iFas and iCasp9 in T cells.

In contrast, the induction of apoptosis was significantly lower in T cells selected for intermediate or low GFP expression (see FIGS. 4A, 4B and 4C). For clinical applications therefore, versions of the expression constructs with selectable markers that allow selection for high copy number, high levels of expression, or both high copy number and high levels of expression may be desirable. CID-induced apoptosis was inhibited by the pancaspase inhibitor zVAD-fmk (100 µM for 1 hour prior to adding CID. Titration of CID showed that 1 nM CID was sufficient to obtain the maximal deletion effect (FIG. 3D). A dose-response curve using the indicated amounts of CID (AP20187) shows the sensitivity of F-Casp9$_M$.I.GFP$_{high}$ to CID. Survival of GFP+ cells is measured on day 7 after administration of the indicated amount of CID. The mean and standard deviation for each point are given. Similar results were obtained using another chemical inducer of dimerization (CID), AP1903, which was clinically shown to have substantially no adverse effects when administered to healthy volunteers. The dose response remained unchanged for at least 4 weeks after transduction.

iCasp9$_M$ is Functional in Malignant Cells that Express Antiapoptotic Molecules Caspase 9 was selected as an inducible proapoptotic molecule for clinical use rather than previously presented iFas and iFADD, because caspase 9 acts relatively late in apoptosis signaling and therefore is expected to be less susceptible to inhibition by apoptosis inhibitors. Thus, suicide function should be preserved not only in malignant, transformed T-cell lines that express antiapoptotic molecules, but also in subpopulations of normal T cells that express elevated antiapoptotic molecules as part of the process to ensure long-term preservation of memory cells. To further investigate the hypothesis, the function of iCasp9$_M$ and iFas was first compared in EBV-CTLs. To eliminate any potential vector based difference, inducible Fas also was expressed in the MSCV.IRES.GFP vector, like iCasp9. For these experiments both ΔNGFR.iFas.I.GFP and iCasp9$_M$.I.GFP-transduced CTLs were sorted for GFP$_{high}$ expression and mixed with nontransduced CTLs at a 1:1 ratio to obtain cell populations that expressed either iFas or iCasp9$_M$ at equal proportions and at similar levels (see FIG. 5A). EBV-CTLs transduced with ΔNGFR-iFas.I.GFP are shown in the left panel of FIG. 5A. EBV-CTLs transduced with iCasp9$_M$.I.GFP are shown in the right panel of FIG. 5A. The EBV-CTLs were sorted for high GFP expression and mixed 1:1 with nontransduced CTLs as presented. The percentages of ΔNGFR+/GFP+ and GFP+ T cells are indicated.

Figure 5B:
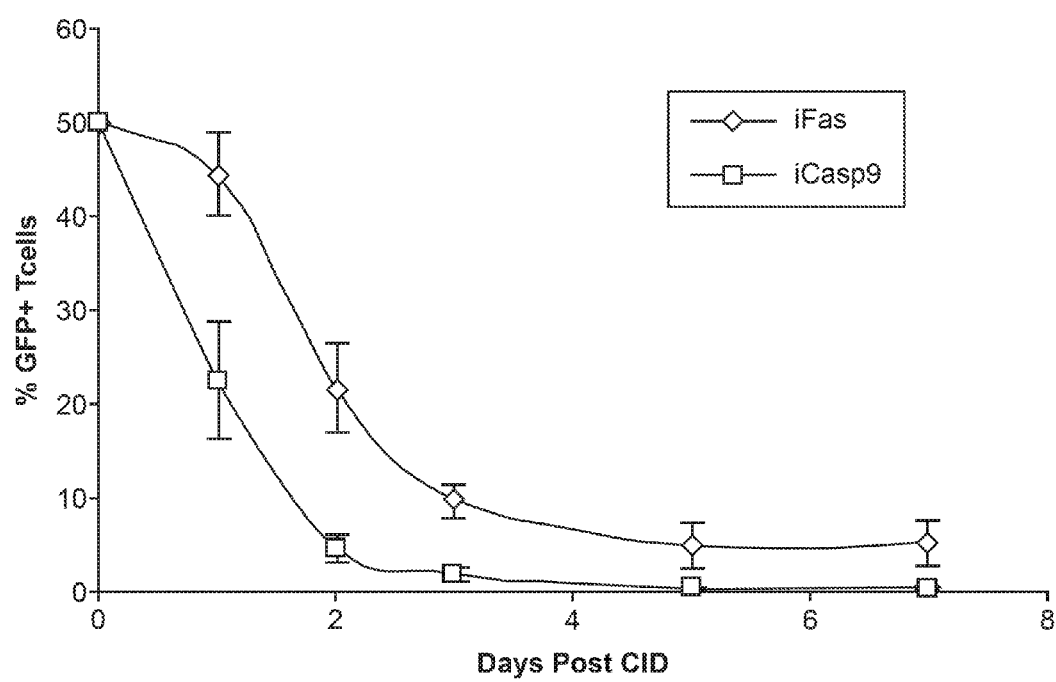

Elimination of GFP+ cells after administration of 10 nM CID was more rapid and more efficient in iCasp9$_M$ than in iFas-transduced CTLs (99.2%+/−0.14% of iCasp9$_M$-transduced cells compared with 89.3%+/−4.9% of iFas-transduced cells at day 7 after CID; P<0.05; see FIG. 5B). On the day of LCL stimulation, 10 nM CID was administered, and GFP was measured at the time points indicated to determine the response to CID. Black diamonds represent data for ΔNGFR-iFas.I.GFP; black squares represent data for iCasp9$_M$.I.GFP. Mean and standard deviation of 3 experiments are shown.

The function of iCasp9M and iFas was also compared in 2 malignant T-cell lines: Jurkat, an apoptosis-sensitive T-cell leukemia line, and MT-2, an apoptosis-resistant T-cell line, due to c-FLIP and bcl-xL expression. Jurkat cells and MT-2 cells were transduced with iFas and iCasp9$_M$ with similar efficiencies (92% vs 84% in Jurkat, 76% vs 70% in MT-2) and were cultured in the presence of 10 nM CID for 8 hours. Annexin-V staining showed that although iFas and iCasp9$_M$ induced apoptosis in an equivalent number of Jurkat cells (56.4%+/−15.6% and 57.2%+/−18.9%, respectively), only activation of iCasp9$_M$ resulted in apoptosis of MT-2 cells (19.3%+/−8.4% and 57.9%+/−11.9% for iFas and iCasp9$_M$, respectively; see FIG. 5C).

Figure 5C:
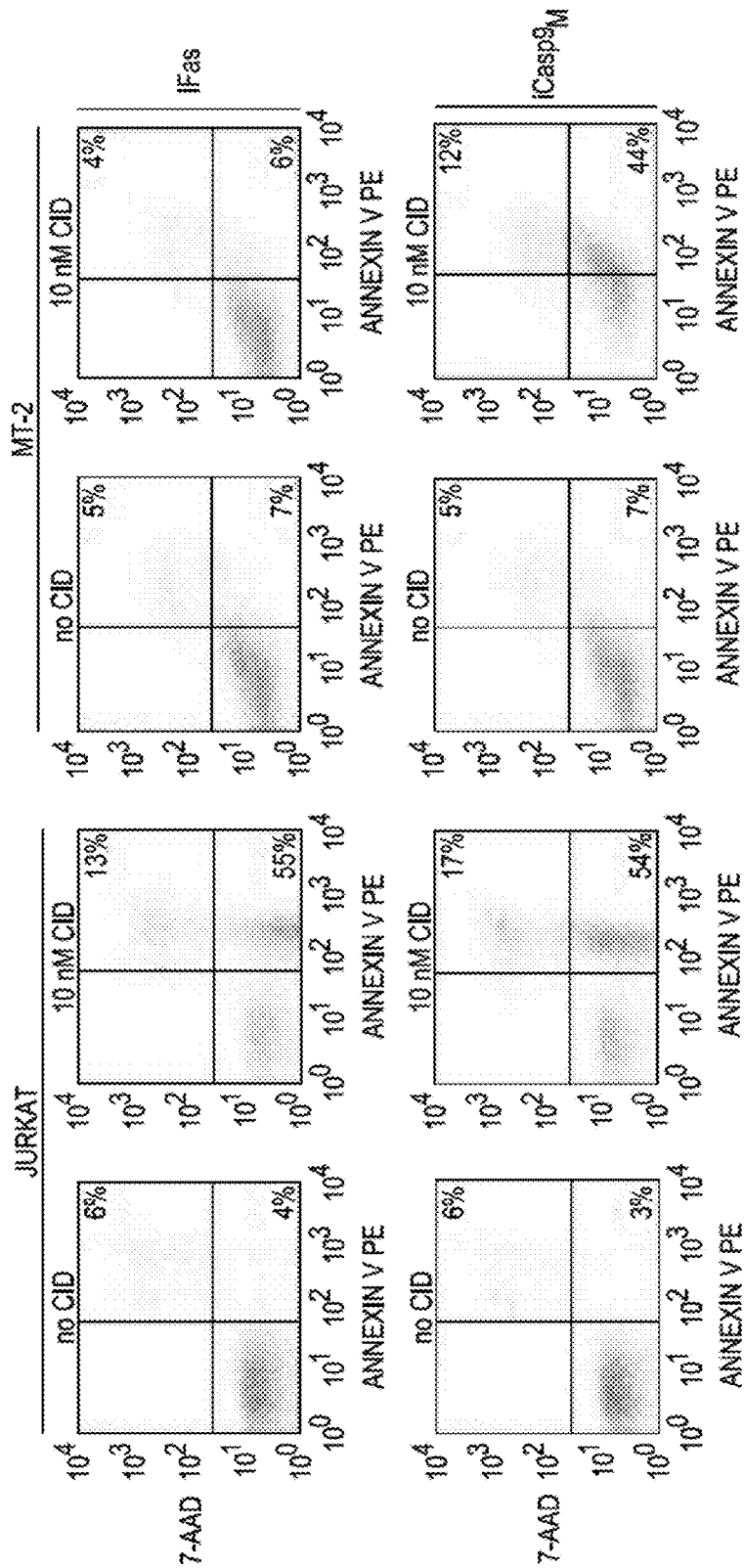
Figure 6:
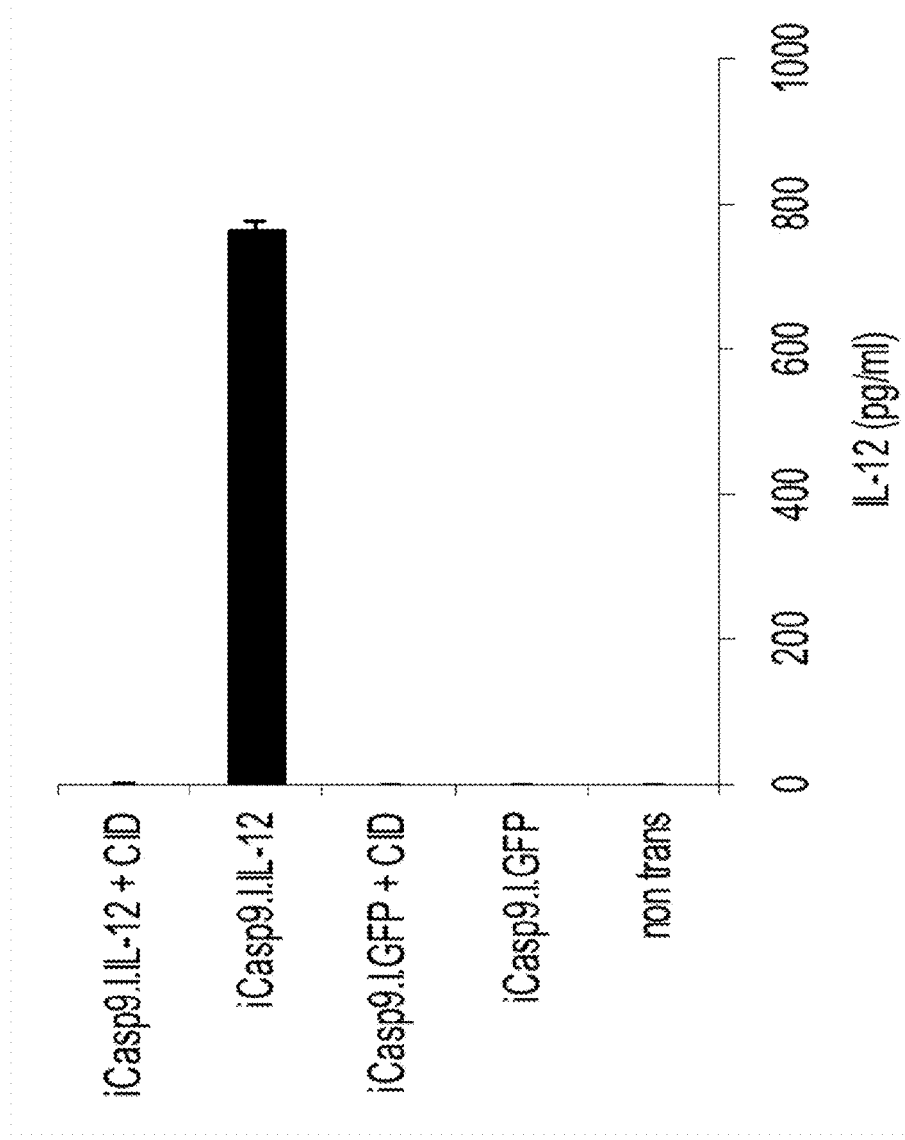
FIG. 6 graphically illustrates the function of iCasp9 when co-expressed with Il-2.

The human T-cell lines Jurkat (left) and MT-2 (right) were transduced with ΔNGFR-iFas.I.GFP (top row of FIG. 5C) or iCasp9$_M$.I.GFP (bottom row of FIG. 5C). An equal percentage of T cells were transduced with each of the suicide genes: 92% for ΔNGFR-iFas.I.GFP versus 84% for iCasp9$_M$.I.GFP in Jurkat, and 76% for ΔNGFR-iFas.I.GFP versus 70% for iCasp9$_M$.I.GFP in MT-2. T cells were either nontreated or incubated with 10 nM CID. Eight hours after exposure to CID, apoptosis was measured by staining for annexin V and 7-AAD. Representative example of 3 experiments is shown. PE indicates phycoerythrin. These results demonstrate that in T cells overexpressing apoptosis-inhibiting molecules, the function of iFas can be blocked, while iCasp9$_M$ can still effectively induce apoptosis.

iCasp9M-Mediated Elimination of T Cells Expressing an Immunomodulatory transgene To determine whether iCasp9M could effectively destroy cells genetically modified to express an active transgene product, the ability of iCasp9$_M$ to eliminate EBV-CTLs stably expressing IL-12 was measured. While IL-12 was undetectable in the supernatant of nontransduced and iCasp9$_M$.IRES.GFP-transduced CTLs, the supernatant of iCasp9$_M$.IRES.IL-12-transduced cells contained 324 pg/mL to 762 pg/mL IL-12. After administration of 10 nM CID, however, the IL-12 in the supernatant fell to undetectable levels (<7.8 pg/mL). Thus, even without prior sorting for high transgene expressing cells, activation of iCasp9$_M$ is sufficient to completely eliminate all T cells producing biologically relevant levels of IL-12 (FIG. 6). The function of iCasp9M when coexpressed with IL-12 is graphically represented by bar graphs in FIG. 6. The marker gene GFP in the iCasp9$_M$.I.GFP constructs was replaced by flexi IL-12, encoding the p40 and p35 subunits of human IL-12. iCasp9$_M$.I.GFP- and iCasp9$_M$.I.IL-12-transduced EBV-CTLs were stimulated with LCLs, and then left untreated or exposed to 10 nM CID. Three days after a second antigenic stimulation, the levels of IL-12 in the culture supernatant were measured by IL-12 ELISA (detection limit of this assay is 7.8 pg/mL). The mean and standard deviation of triplicate wells are indicated. Results of 1 of 2 experiments with CTLs from 2 different donors are shown.

Elimination of More than 99% of T Cells Selected for High Transgene Expression In Vivo The function of iCasp9$_M$ also was evaluated in transduced EBV-CTLs in vivo. A SCID mouse-human xenograft model was used for adoptive immunotherapy. After intravenous infusion of a 1:1 mixture of nontransduced and iCasp9$_M$.IRES.GFP$_{high}$-transduced CTLs into SCID mice bearing an autologous LCL xenograft, mice were treated either with a single dose of CID or carrier only. Three days after CID/carrier administration, tumors were analyzed for human CD3+/GFP+ cells. Detection of the nontransduced component of the infusion product, using human anti-CD3 antibodies, confirmed the success of the tail-vein infusion in mice that received CID. In mice treated with CID, there was more than a 99% reduction in the number of human CD3+/GFP+ T cells, compared with infused mice treated with carrier alone, demonstrating equally high sensitivity of iCasp9$_M$-transduced T cells in vivo and in vitro (see FIG. 7).

Figure 7:
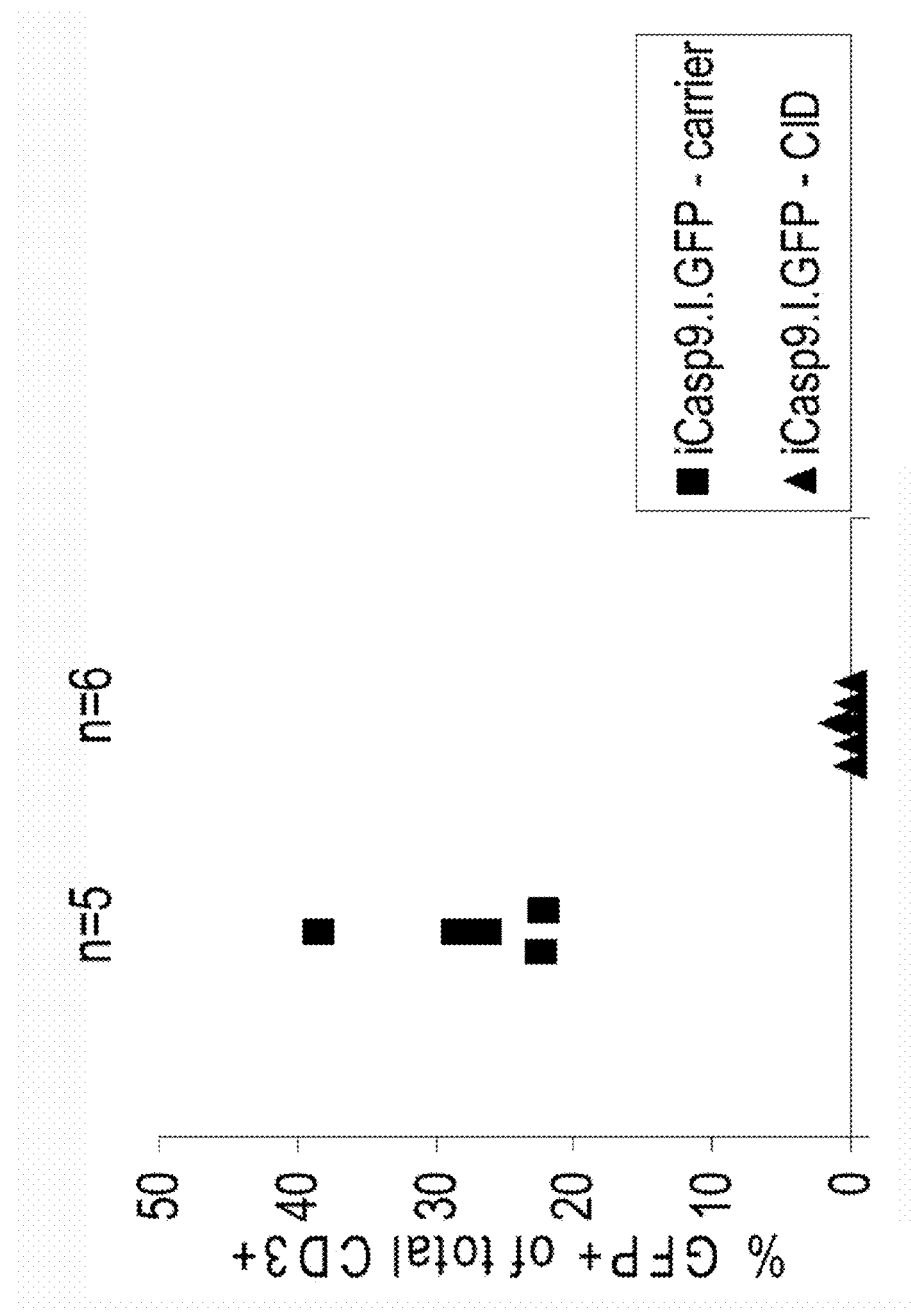
FIG. 7 graphically illustrates the function of iCasp9 in vivo. Further discussion of experimental conditions and results are presented in the Examples.

The function of iCasp9$_M$ in vivo, is graphically illustrated in FIG. 7. NOD/SCID mice were irradiated and injected subcutaneously with 10×10$^6$ to 15×10$^6$ LCLs. After 14 days, mice bearing tumors of 0.5 cm in diameter received a total of 15×10$^6$ EBV-CTLs (50% of these cells were nontransduced and 50% were transduced with iCasp9$_M$.I.GFP and sorted for high GFP expression). On day 3 after CTL administration, mice received either CID (50 µg AP20187; (black diamonds, n=6) or carrier only (black squares, n=5) and on day 6 the presence of human CD3+/GFP+ T cells in the tumors was analyzed. Human CD3+ T cells isolated from the tumors of a control group of mice that received only nontransduced CTLs (15×10$^6$ CTLs; n=4) were used as a negative control for the analysis of CD3+/GFP+ T cells within the tumors.

Discussion

Presented herein are expression vectors expressing suicide genes suitable for eliminating gene-modified T cells in vivo, in some embodiments. Suicide gene expression vectors presented herein have certain non-limiting advantageous features including stable coexpression in all cells carrying the modifying gene, expression at levels high enough to elicit cell death, low basal activity, high specific activity, and minimal susceptibility to endogenous antiapoptotic molecules. Presented herein, in certain embodiments, is an inducible caspase 9, iCasp9$_M$, which has low basal activity allowing stable expression for more than 4 weeks in human T cells. A single 10-nM dose of a small molecule chemical inducer of dimerization (CID) is sufficient to kill more than 99% of iCasp9$_M$-transduced cells selected for high transgene expression both in vitro and in vivo. Moreover, when coexpressed with Th1 cytokine IL-12, activation of iCasp9$_M$ eliminated all detectable IL-12-producing cells, even without selection for high transgene expression. Caspase 9 acts downstream of most antiapoptotic molecules, therefore a high sensitivity to CID is preserved regardless of the presence of increased levels of antiapoptotic molecules of the bcl-2 family. Thus, iCasp9$_M$ also may prove useful for inducing destruction even of transformed T cells and memory T cells that are relatively resistant to apoptosis.

Unlike other caspase molecules, proteolysis does not appear sufficient for activation of caspase 9. Crystallographic and functional data indicate that dimerization of inactive caspase 9 monomers leads to conformational change-induced activation. The concentration of pro-caspase 9, in a physiologic setting, is in the range of about 20 nM, well below the threshold needed for dimerization.

Without being limited by theory, it is believed the energetic barrier to dimerization can be overcome by homophilic interactions between the CARD domains of Apaf-1 and caspase 9, driven by cytochrome C and ATP. Overexpression of caspase 9 joined to 2 FKBPs may allow spontaneous dimerization to occur and can account for the observed toxicity of the initial full length caspase 9 construct. A decrease in toxicity and an increase in gene expression was observed following removal of one FKBP, most likely due to a reduction in toxicity associated with spontaneous dimerization. While multimerization often is involved in activation of surface death receptors, dimerization of caspase 9 should be sufficient to mediate activation. Data presented herein indicates that iCasp9 constructs with a single FKBP function as effectively as those with 2 FKBPs. Increased sensitivity to CID by removal of the CARD domain may represent a reduction in the energetic threshold of dimerization upon CID binding.

The persistence and function of virus- or bacteria-derived lethal genes, such as HSV-TK and cytosine deaminase, can be impaired by unwanted immune responses against cells expressing the virus or bacteria derived lethal genes. The FKBPs and proapoptotic molecules that form the components of iCasp9$_M$ are human-derived molecules and are therefore less likely to induce an immune response. Although the linker between FKBP and caspase 9 and the single point mutation in the FKBP domain introduce novel amino acid sequences, the sequences were not immunologically recognized by macaque recipients of iFas-transduced T cells. Additionally, because the components of iCasp9$_M$ are human-derived molecules, no memory T cells specific for the junction sequences should be present in a recipient, unlike virus-derived proteins such as HSV-TK, thereby reducing the risk of immune response-mediated elimination of iCasp9$_M$-transduced T cells.

Previous studies using inducible Fas or the death effector domains (DED) of Fas associated death domain proteins (FADD) showed that approximately 10% of transduced cells were unresponsive to activation of the destructive gene. As observed in experiments presented here, a possible explanation for unresponsiveness to CID is low expression of the transgene. The iCasp9$_M$-transduced T cells in our study and iFas-transduced T cells in studies by others that survived after CID administration had low levels of transgene expression. In an attempt to overcome a perceived retroviral "positional effect", increased levels of homogeneous expression of the transgene were achieved by flanking retroviral integrants with the chicken beta-globin chromatin insulator. Addition of the chromatin insulator dramatically increased the homogeneity of expression in transduced 293T cells, but had no significant effect in transduced primary T cell. Selection of T cells with high expression levels minimized variability of response to the dimerizer. Over 99% of transduced T cells sorted for high GFP expression were eliminated after a single 10-nM CID dose. This demonstration supports the hypothesis that cells expressing high levels of suicide gene can be isolated using a selectable marker.

A very small number of resistant residual cells may cause a resurgence of toxicity, a deletion efficiency of up to 2 logs will significantly decrease this possibility. For clinical use, coexpression with a nonimmunogenic selectable marker such as truncated human NGFR, CD20, or CD34 (e.g., instead of GFP) will allow for selection of high transgene-expressing T cells. Coexpression of the suicide switch (e.g., iCASP9$_M$) and a suitable selectable marker (e.g., truncated human NGFR, CD20, CD34, the like and combinations thereof) can be obtained using either an internal ribosome entry site (IRES) or posttranslational modification of a fusion protein containing a self-cleaving sequence (eg, 2A). In contrast, in situations where the sole safety concern is the transgene-mediated toxicity (eg, artificial T-cell receptors, cytokines, the like or combinations thereof), this selection step may be unnecessary, as tight linkage between iCasp9$_M$ and transgene expression enables elimination of substantially all cells expressing biologically relevant levels of the therapeutic transgene. This was demonstrated by coexpressing iCasp9$_M$ with IL-12. Activation of iCasp9$_M$ substantially eliminated any measurable IL-12 production. The success of transgene expression and subsequent activation of the "suicide switch" may depend on the function and the activity of the transgene.

Another possible explanation for unresponsiveness to CID is that high levels of apoptosis inhibitors may attenuate CID-mediated apoptosis. Examples of apoptosis inhibitors include c-FLIP, bcl-2 family members and inhibitors of apoptosis proteins (IAPs), which normally regulate the balance between apoptosis and survival. For instance, upregulation of c-FLIP and bcl-2 render a subpopulation of T cells, destined to establish the memory pool, resistant to activation-induced cell death in response to cognate target or antigen-presenting cells. In several T-lymphoid tumors, the physiologic balance between apoptosis and survival is disrupted in favor of cell survival. A suicide gene should delete substantially all transduced T cells including memory and malignantly transformed cells. Therefore, the chosen inducible suicide gene should retain a significant portion if not substantially all of its activity in the presence of increased levels of antiapoptotic molecules.

The apical location of iFas (or iFADD) in the apoptosis signaling pathway may leave it especially vulnerable to inhibitors of apoptosis, thus making these molecules less well suited to being the key component of an apoptotic safety switch. Caspase 3 or 7 would seem well suited as terminal effector molecules, however neither could be expressed at functional levels in primary human T cells. Therefore caspase 9, was chosen as the suicide gene, because capsase 9 functions late enough in the apoptosis pathway that it bypasses the inhibitory effects of c-FLIP and antiapoptotic bcl-2 family members, and capsase 9 also could be expressed stably at functional levels. Although X-linked inhibitor of apoptosis (XIAP) could in theory reduce spontaneous caspase 9 activation, the high affinity of AP20187 (or AP1903) for FKBP$_{v36}$ may displace this noncovalently associated XIAP. In contrast to iFas, iCasp9$_M$ remained functional in a transformed T-cell line that overexpresses antiapoptotic molecules, including bcl-xL.

Presented herein is an inducible safety switch, designed specifically for expression from an oncoretroviral vector by human T cells. iCasp9$_M$ can be activated by AP1903 (or analogs), a small chemical inducer of dimerization that has proven safe at the required dose for optimum deletional effect, and unlike ganciclovir or rituximab has no other biologic effects in vivo. Therefore, expression of this suicide gene in T cells for adoptive transfer can increase safety and also may broaden the scope of clinical applications.

Example 2

Using the iCasp9 Suicide Gene to Improve the Safety of Allodepleted T Cells after Haploidentical Stem Cell Transplantation Presented in this example are expression constructs and methods of using the expression constructs to improve the safety of allodepleted T cells after haploidentical stem cell transplantation. A retroviral vector encoding iCasp9 and a selectable marker (truncated CD19) was generated as a safety switch for donor T cells. Even after allodepletion (using anti-CD25 immunotoxin), donor T cells could be efficiently transduced, expanded, and subsequently enriched by CD19 immunomagnetic selection to >90% purity. The engineered cells retained anti-viral specificity and functionality, and contained a subset with regulatory phenotype and function. Activating iCasp9 with a small-molecule dimerizer rapidly produced >90% apoptosis. Although transgene expression was down-regulated in quiescent T cells, iCasp9 remained an efficient suicide gene, as expression was rapidly upregulated in activated (alloreactive) T cells.

Materials and Methods

Generation of Allodepleted T Cells

Allodepleted cells were generated from healthy volunteers as previously presented. Briefly, peripheral blood mononuclear cells (PBMCs) from healthy donors were co-cultured with irradiated recipient Epstein Barr virus (EBV)-transformed lymphoblastoid cell lines (LCL) at responder-to-stimulator ratio of 40:1 in serum-free medium (AIM V; Invitrogen, Carlsbad, Calif.). After 72 hours, activated T cells that expressed CD25 were depleted from the co-culture by overnight incubation in RFT5-SMPT-dgA immunotoxin. Allodepletion was considered adequate if the residual CD3$^+$ CD25+ population was <1% and residual proliferation by 3H-thymidine incorporation was <10%.

Plasmid and Retrovirus

SFG.iCasp9.2A.CD19 consists of inducible caspase 9 (iCasp9) linked, via a cleavable 2A-like sequence, to truncated human CD19 (CD 19; see FIG. 8A). iCasp9 consists of a human FK506-binding protein (FKBP12; GenBank AH002 818) with an F36V mutation, connected via a Ser-Gly-Gly-Gly-Ser (SEQ ID NO: 21) linker to human caspase 9 (CASP9; GenBank NM 001229). The F36V mutation increases the binding affinity of FKBP12 to the synthetic homodimerizer, AP20187 or AP1903. The caspase recruitment domain (CARD) has been deleted from the human caspase 9 sequence because its physiological function has been replaced by FKBP12, and its removal increases transgene expression and function. The 2A-like sequence encodes an 20 amino acid peptide from Thosea asigna insect virus, which mediates >99% cleavage between a glycine and terminal proline residue, resulting in 19 extra amino acids in the C terminus of iCasp9, and one extra proline residue in the N terminus of CD19. CD19 consists of full-length CD19 (GenBank NM 001770) truncated at amino acid 333 (TDPTRRF) (SEQ ID NO: 22), which shortens the intracytoplasmic domain from 242 to 19 amino acids, and removes all conserved tyrosine residues that are potential sites for phosphorylation.

A stable PG13 clone producing Gibbon ape leukemia virus (Gal-V) pseudotyped retrovirus was made by transiently transfecting Phoenix Eco cell line (ATCC product #SD3444; ATCC, Manassas, Va.) with SFG.iCasp9.2A.CD19. This produced Eco-pseudotyped retrovirus. The PG13 packaging cell line (ATCC) was transduced three times with Eco-pseudotyped retrovirus to generate a producer line that contained multiple SFG.iCasp9.2A.CD19 proviral integrants per cell. Single cell cloning was performed, and the PG13 clone that produced the highest titer was expanded and used for vector production.

Retroviral Transduction

Figures 8A, 8B:
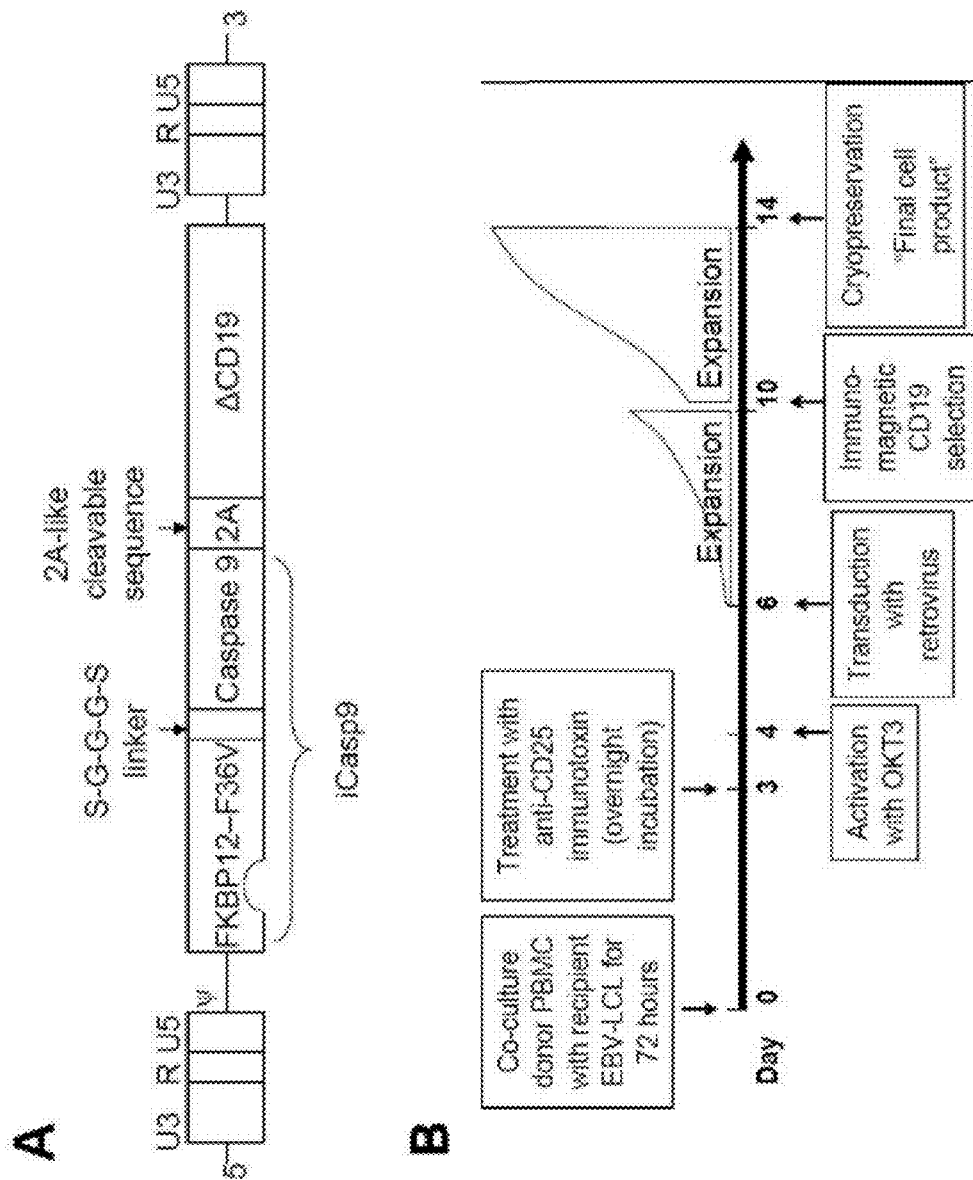
FIGS. 8A-8B illustrates the structure of the iCasp9 expression construct SFG.iCasp9.2A.ΔCD19.

Culture medium for T cell activation and expansion consisted of 45% RPMI 1640 (Hyclone, Logan, Utah), 45% Clicks (Irvine Scientific, Santa Ana, Calif.) and 10% fetal bovine serum (FBS; Hyclone). Allodepleted cells were activated by immobilized anti-CD3 (OKT3; Ortho Biotech, Bridgewater, N.J.) for 48 hours before transduction with retroviral vector (see FIG. 8B). FIG. 8B presents an overview of the process for production of the "final cell product" that express the transduced transgene. Selective allodepletion was performed by co-culturing donor PBMC with recipient EBV-LCL to activate alloreactive cells: activated cells expressed CD25 and were subsequently eliminated by anti-CD25 immunotoxin. The allodepleted cells were activated by OKT3 and transduced with the retroviral vector 48 hours later. Immunomagnetic selection was performed on day 4 of transduction; the positive fraction was expanded for a further 4 days and cryopreserved.

In small-scale experiments, non-tissue culture-treated 24-well plates (Becton Dickinson, San Jose, Calif.) were coated with OKT3 1 g/ml for 2 to 4 hours at 37° C. Allodepleted cells were added at $1 \times 10^6$ cells per well. At 24 hours, 100 U/ml of recombinant human interleukin-2 (IL-2) (Proleukin; Chiron, Emeryville, Calif.) was added. Retroviral transduction was performed 48 hours after activation. Non-tissue culture-treated 24-well plates were coated with 3.5 $\mu$g/cm$^2$ recombinant fibronectin fragment (CH-296; Retronectin; Takara Mirus Bio, Madison, Wis.) and the wells loaded twice with retroviral vector-containing supernatant at 0.5 ml per well for 30 minutes at 37° C., following which OKT3-activated cells were plated at $5 \times 10^5$ cells per well in fresh retroviral vector-containing supernatant and T cell culture medium at a ratio of 3:1, supplemented with 100 U/ml IL-2. Cells were harvested after 2 to 3 days and expanded in the presence of 50 U/ml IL-2.

Scaling-Up Production of Gene-Modified Allodepleted Cells

Scale-up of the transduction process for clinical application used non-tissue culture-treated T75 flasks (Nunc, Rochester, N.Y.), which were coated with 10 ml of OKT3 1 µg/ml or 10 ml of fibronectin 7 µg/ml at 4° C. overnight. Fluorinated ethylene propylene bags corona-treated for increased cell adherence (2PF-0072AC, American Fluoroseal Corporation, Gaithersburg, Md.) were also used. Allodepleted cells were seeded in OKT3-coated flasks at $1 \times 10^6$ cells/ml. 100 U/ml IL-2 was added the next day. For retroviral transduction, retronectin-coated flasks or bags were loaded once with 10 ml of retrovirus-containing supernatant for 2 to 3 hours. OKT3-activated T cells were seeded at $1 \times 10^6$ cells/ml in fresh retroviral vector-containing medium and T cell culture medium at a ratio of 3:1, supplemented with 100 U/ml IL-2. Cells were harvested the following morning and expanded in tissue-culture treated T75 or T175 flasks in culture medium supplemented with between about 50 to 100 U/ml IL-2 at a seeding density of between about $5 \times 10^5$ cells/ml to $8 \times 10^5$ cells/ml.

CD19 Immunomagnetic Selection

Immunomagnetic selection for CD19 was performed 4 days after transduction. Cells were labeled with paramagnetic microbeads conjugated to monoclonal mouse anti-human CD19 antibodies (Miltenyi Biotech, Auburn, Calif.) and selected on MS or LS columns in small scale experiments and on a CliniMacs Plus automated selection device in large scale experiments. CD19-selected cells were expanded for a further 4 days and cryopreserved on day 8 post transduction. These cells were referred to as "gene-modified allodepleted cells".

Immunophenotyping and Pentamer Analysis

Flow cytometric analysis (FACSCalibur and CellQuest software; Becton Dickinson) was performed using the following antibodies: CD3, CD4, CD8, CD19, CD25, CD27, CD28, CD45RA, CD45RO, CD56 and CD62L. CD19-PE (Clone 4G7; Becton Dickinson) was found to give optimum staining and was used in all subsequent analysis. A Non-transduced control was used to set the negative gate for CD19. An HLA-pentamer, HLA-B8-RAKFKQLL (SEQ ID NO: 20) (Proimmune, Springfield, Va.) was used to detect T cells recognizing an epitope from EBV lytic antigen (BZLF1). HLA-A2-NLVPMVATV pentamer (SEQ ID NO: 23) was used to detect T cells recognizing an epitope from CMV-pp65 antigen.

Interferon-ELISPOT Assay for Anti-Viral Response

Interferon-ELISPOT for assessment of responses to EBV, CMV and adenovirus antigens was performed using known methods. Gene-modified allodepleted cells cryopreserved at 8 days post transduction were thawed and rested overnight in complete medium without IL-2 prior to use as responder cells. Cryopreserved PBMCs from the same donor were used as comparators. Responder cells were plated in duplicate or triplicate in serial dilutions of $2 \times 10^5$, $1 \times 10^5$, $5 \times 10^4$ and $2.5 \times 10^4$ cells per well. Stimulator cells were plated at $1 \times 10^5$ per well. For response to EBV, donor-derived EBV-LCLs irradiated at 40Gy were used as stimulators. For response to adenovirus, donor-derived activated monocytes infected with Ad5f35 adenovirus were used.

Briefly, donor PBMCs were plated in X-Vivo 15 (Cambrex, Walkersville, Md.) in 24-well plates overnight, harvested the next morning, infected with Ad5f35 at a multiplicity of infection (MOI) of 200 for 2 hours, washed, irradiated at 30Gy, and used as stimulators. For anti-CMV response, a similar process using Ad5f35 adenovirus encoding the CMV pp65 transgene (Ad5f35-pp65) at an MOI of 5000 was used. Specific spot-forming units (SFU) were calculated by subtracting SFU from responder-alone and stimulator-alone wells from test wells. Response to CMV was the difference in SFU between Ad5f35-pp65 and Ad5f35 wells.

EBV-Specific Cytotoxicity

Gene-modified allodepleted cells were stimulated with 40Gy-irradiated donor-derived EBVLCL at a responder: stimulator ratio of 40:1. After 9 days, the cultures were restimulated at a responder: stimulator ratio of 4:1. Restimulation was performed weekly as indicated. After two or three rounds of stimulation, cytotoxicity was measured in a 4-hour 51 Cr-release assay, using donor EBV-LCL as target cells and donor OKT3 blasts as autologous controls. NK activity was inhibited by adding 30-fold excess of cold K562 cells.

Induction of Apoptosis with Chemical Inducer of Dimerization, AP20187

Suicide gene functionality was assessed by adding a small molecule synthetic homodimerizer, AP20187 (Ariad Pharmaceuticals; Cambridge, Mass.), at 10 nM final concentration the day following CD19 immunomagnetic selection. Cells were stained with annexin V and 7-amino-actinomycin (7-AAD)(BD Pharmingen) at 24 hours and analyzed by flow cytometry. Cells negative for both Annexin V and 7-AAD were considered viable, cells that were annexin V positive were apoptotic, and cells that were both annexin V and 7-AAD positive were necrotic. The percentage killing induced by dimerization was corrected for baseline viability as follows: Percentage killing=100%−(% Viability in AP20187-treated cells÷% Viability in nontreated cells).

Assessment of Transgene Expression Following Extended Culture and Reactivation

Cells were maintained in T cell medium containing 50 U/ml IL-2 until 22 days after transduction. A portion of cells was reactivated on 24-well plates coated with 1 g/ml OKT3 and 1 µg/ml anti-CD28 (Clone CD28.2, BD Pharmingen, San Jose, Calif.) for 48 to 72 hours. CD19 expression and suicide gene function in both reactivated and non-reactivated cells were measured on day 24 or 25 post transduction.

In some experiments, cells also were cultured for 3 weeks post transduction and stimulated with 30G-irradiated allogeneic PBMC at a responder:stimulator ratio of 1:1. After 4 days of co-culture, a portion of cells was treated with 10 nM AP20187. Killing was measured by annexin V/7-AAD staining at 24 hours, and the effect of dimerizer on bystander virus-specific T cells was assessed by pentamer analysis on AP20187-treated and untreated cells.

Regulatory T Cells

CD4, CD25 and Foxp3 expression was analyzed in gene-modified allodepleted cells using flow cytometry. For human Foxp3 staining, the eBioscience (San Diego, Calif.) staining set was used with an appropriate rat IgG2a isotype control. These cells were co-stained with surface CD25-FITC and CD4-PE. Functional analysis was performed by co-culturing CD4$^+$25$^+$ cells selected after allodepletion and gene modification with carboxyfluorescein diacetate N-succinimidyl ester (CFSE)-labeled autologous PBMC. CD4$^+$25$^+$ selection was performed by first depleting CD8$^+$ cells using anti-CD 8 microbeads (Miltenyi Biotec, Auburn, Calif.), followed by positive selection using anti-CD25 microbeads (Miltenyi Biotec, Auburn, Calif.). CFSE-labeling was performed by incubating autologous PBMC at 2×10$^7$/ml in phosphate buffered saline containing 1.5 µM CFSE for 10 minutes. The reaction was stopped by adding an equivalent volume of FBS and incubating for 10 minutes at 37° C. Cells were washed twice before use. CFSE-labeled PBMCs were stimulated with OKT3 500 ng/ml and 40G-irradiated allogeneic PBMC feeders at a PBMC:allogeneic feeder ratio of 5:1. The cells were then cultured with or without an equal number of autologous CD4$^+$25$^+$ gene-modified allodepleted cells. After 5 days of culture, cell division was analyzed by flow cytometry; CD19 was used to gate out non-CFSE-labeled CD4$^+$CD25$^+$ gene-modified T cells.

Statistical Analysis

Paired, 2-tailed Student's t test was used to determine the statistical significance of differences between samples. All data are represented as mean±1 standard deviation.

Results

Selectively allodepleted T cells can be efficiently transduced with iCasp9 and expanded Selective allodepletion was performed in accordance with clinical protocol procedures. Briefly, ⅗ to ⅚ HLA-mismatched PBMC and lymphoblastoid cell lines (LCL) were co-cultured. RFT5-SMPT-dgA immunotoxin was applied after 72 hours of co-culture and reliably produced allodepleted cells with <10% residual proliferation (mean 4.5±2.8%; range 0.74 to 9.1%; 10 experiments) and containing<1% residual CD3$^+$CD25$^+$ cells (mean 0.23±0.20%; range 0.06 to 0.73%; 10 experiments), thereby fulfilling the release criteria for selective allodepletion, and serving as starting materials for subsequent manipulation.

Figure 9:
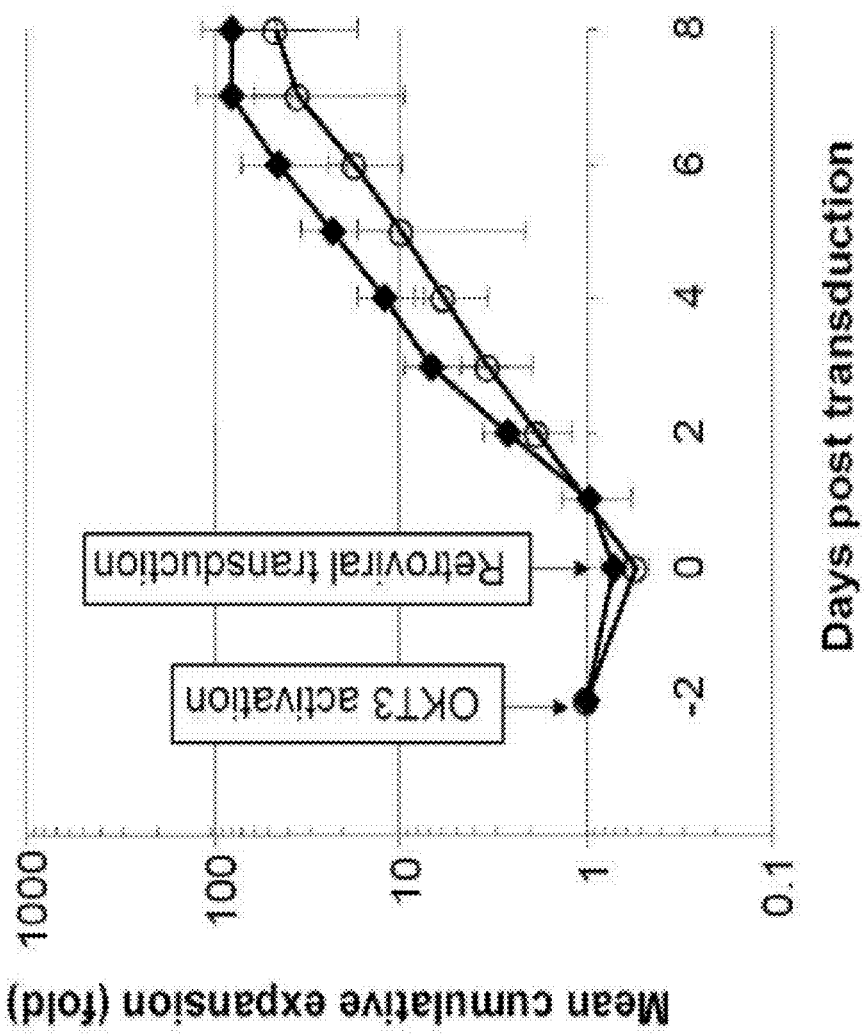
FIG. 9 graphically illustrates that allodepleted cells could be successfully expanded following transduction.

Allodepleted cells activated on immobilized OKT3 for 48 hours could be efficiently transduced with Gal-V pseudotyped retrovirus vector encoding SFG.iCasp9.2A.CD19. Transduction efficiency assessed by FACS analysis for CD19 expression 2 to 4 days after transduction was about 53%±8%, with comparable results for small-scale (24-well plates) and large-scale (T75 flasks) transduction (about 55±8% versus about 50%±10% in 6 and 4 experiments, respectively). Cell numbers contracted in the first 2 days following OKT3 activation such that only about 61%±12% (range of about 45% to 80%) of allodepleted cells were recovered on the day of transduction (see FIG. 9). Illustrated in FIG. 9 are graphical results of experiments performed to determine if allodepleted cells could be successfully expanded following transduction. Black diamonds denote large scale experiments performed in flasks and bags. Open circles denote small-scale experiments performed in 24 well plates. Thereafter, the cells showed significant expansion, with a mean expansion in the range of about 94±46-fold (range of about 40 to about 153) over the subsequent 8 days, resulting in a net 58±33-fold expansion. Cell expansion in both small- and large-scale experiments was similar, with net expansion of about 45±29 fold (range of about 25 to about 90) in 5 small-scale experiments and about 79±34 fold (range of about 50 to about 116) in 3 large-scale experiments.

ΔCD19 Enables Efficient and Selective Enrichment of Transduced Cells on Immunomagnetic Columns The efficiency of suicide gene activation sometimes depends on the functionality of the suicide gene itself, and sometimes on the selection system used to enrich for gene-modified cells. The use of CD19 as a selectable marker was investigated to determine if CD19 selection enabled the selection of gene-modified cells with sufficient purity and yield, and whether selection had any deleterious effects on subsequent cell growth. Small-scale selection was performed according to manufacturer's instruction; however, it was determined that large-scale selection was optimum when 10l of CD19 microbeads was used per 1.3×10$^7$ cells. FACS analysis was performed at 24 hours after immunomagnetic selection to minimize interference from anti-CD19 microbeads.

Figure 10:
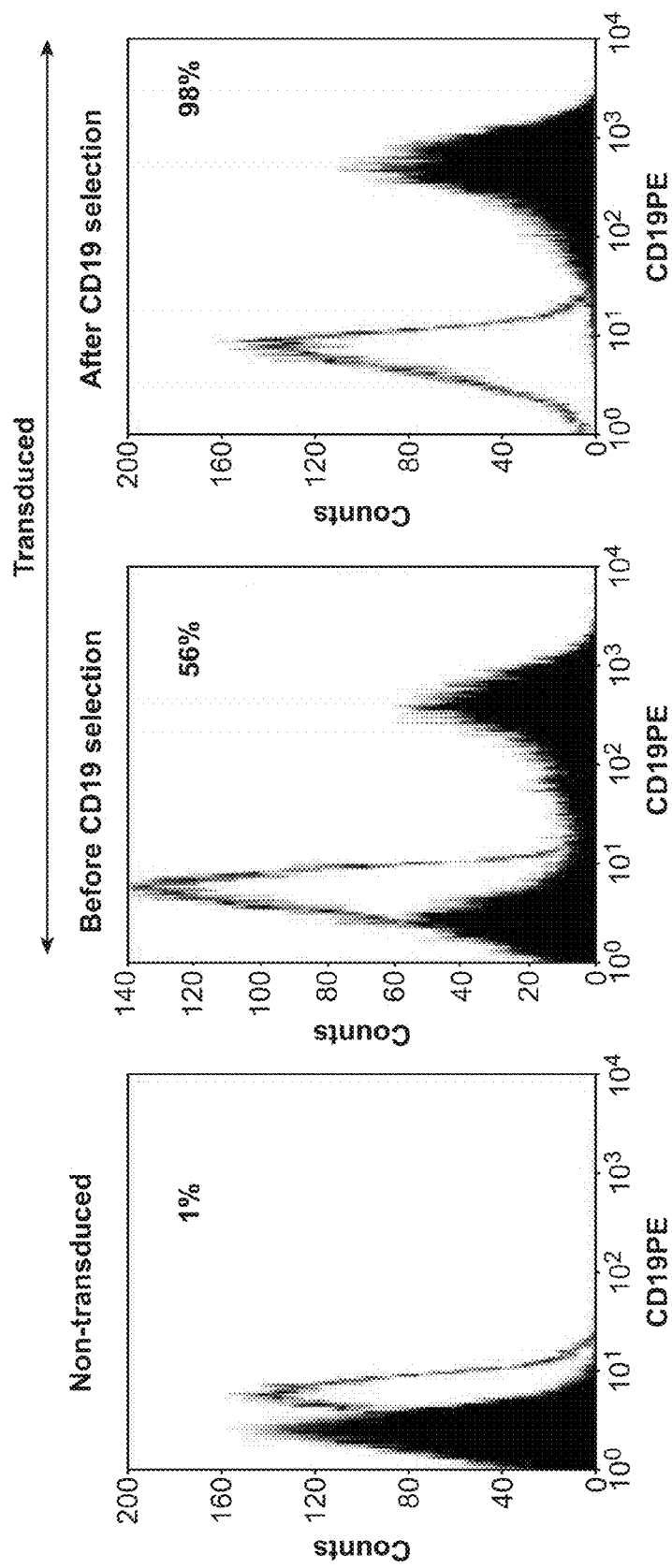
FIG. 10 shows that cells transduced with the suicide gene construct could be enriched to high purity by CD19 immunomagnetic selection. Further discussion of experimental conditions and results are presented in the Examples.

The purity of the cells after immunomagnetic selection was consistently greater than 90%: mean percentage of CD19+ cells was in the range of about 98.3%±0.5% (n=5) in small-scale selections and in the range of about 97.4%±0.9% (n=3) in large-scale CliniMacs selections (see FIG. 10). Shown in FIG. 10 are representative FACS analysis traces of the immunomagnetic selection performed 2 days post-transduction.

The absolute yield of small- and large-scale selections were about 31%±11% and about 28%±6%, respectively; after correction for transduction efficiency. The mean recovery of transduced cells was about 54%±14% in small-scale and about 72%±18% in large-scale selections. The selection process did not have any discernable deleterious effect on subsequent cell expansion. In 4 experiments, the mean cell expansion over 3 days following CD19 immunomagnetic selection was about 3.5 fold for the CD19 positive fraction versus about 4.1 fold for non-selected transduced cells (p=0.34) and about 3.7 fold for non-transduced cells (p=0.75).

Immunophenotype of Gene-Modified Allodepleted Cells

The final cell product (gene-modified allodepleted cells that had been cryopreserved 8 days after transduction) was immunophenotyped and was found to contain both CD4 and CD8 cells, with CD8 cells predominant, at 62%±11% $CD8^+$ versus 23%±8% $CD4^+$, as shown in the table below. NS=not significant, SD=standard deviation.

|  | Unmanipulated PBMC (mean % ± SD) | Gene-modified allodepleted cells (mean % ± SD) |  |
| --- | --- | --- | --- |
| T cells: Total $CD3^+$ | 82 ± 6 | 95 ± 6 | NS |
| CD3+ 4+ | 54 ± 5 | 23 ± 8 | p < 0.01 |
| CD3+ 8+ | 26 ± 9 | 62 ± 11 | p < 0.001 |
| NK cells: $CD3^-$ 56+ | 6 ± 3 | 2 ± 1 | NS |
| Memory phenotype |  |  |  |
| $CD45RA^+$ | 66 ± 3 | 10 ± 5 | p < 0.001 |
| $CD45RO^+$ | 26 ± 2 | 78 ± 7 | p < 0.001 |
| $CD45RA^- CD62L^+$ | 19 ± 1 | 24 ± 7 | NS |
| $CD45RA^- CD62L^-$ | 9 ± 1 | 64 ± 7 | p < 0.001 |
| $CD27^+ CD28^+$ | 67 ± 7 | 19 ± 9 | p < 0.001 |
| $CD27^+ CD28^-$ | 7 ± 3 | 9 ± 4 | NS |
| $CD27^- CD28^+$ | 4 ± 1 | 19 ± 8 | p < 0.05 |
| $CD27^- CD28^-$ | 22 ± 8 | 53 ± 18 | p < 0.05 |

The majority of cells were $CD45RO^+$ and had the surface immunophenotype of effector memory T cells. Expression of memory markers, including CD62L, CD27 and CD28, was heterogeneous. Approximately 24% of cells expressed CD62L, a lymph node-homing molecule predominantly expressed on central memory cells.

Figures 11A, 11B:
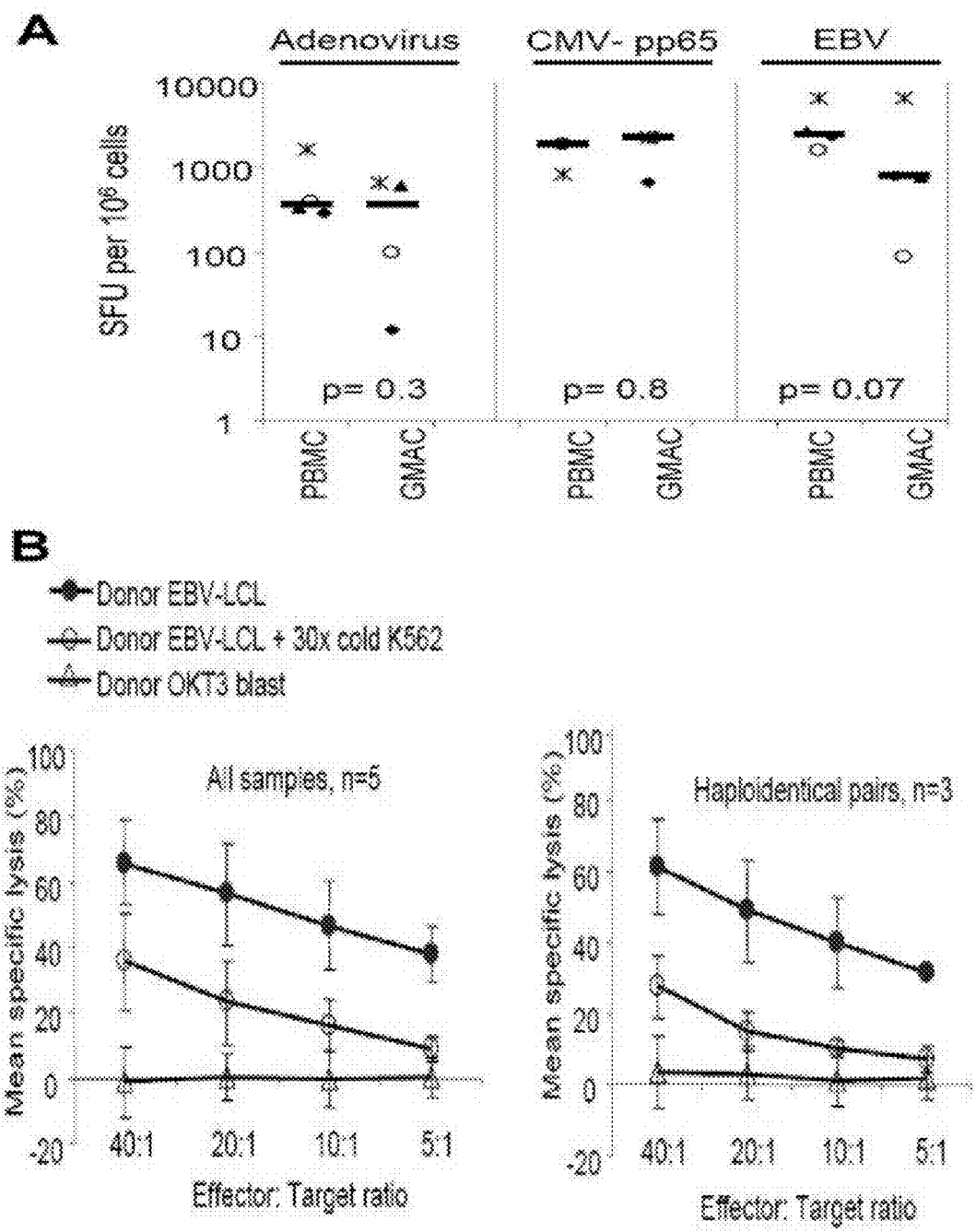
FIGS. 11A-11C illustrate the results of various experiments performed to show that gene modified allodepleted cells retain their anti-viral repertoire and functionality.

Gene-Modified Allodepleted Cells Retained Antiviral Repertoire and Functionality The ability of end-product cells to mediate antiviral immunity was assessed by interferon-ELISPOT, cytotoxicity assay, and pentamer analysis. The cryopreserved gene-modified allodepleted cells were used in all analyses, since they were representative of the product currently being evaluated for use in a clinical study. Interferon-γ secretion in response to adenovirus, CMV or EBV antigens presented by donor cells was preserved although there was a trend towards reduced anti-EBV response in gene-modified allodepleted cells versus unmanipulated PBMC (see FIG. 11A). Illustrated in FIG. 11A are the results of the interferon secretion studies. The response to viral antigens was assessed by ELISPOT in 4 pairs of unmanipulated PBMC and gene-modified allodepleted cells (GMAC). Adenovirus and CMV antigens were presented by donor-derived activated monocytes through infection with Ad5f35 null vector and Ad5f35-pp65 vector, respectively. EBV antigens were presented by donor EBV-LCL. The number of spot-forming units (SFU) were corrected for stimulator- and responder-alone wells. Only three of four donors were evaluable for CMV response, one seronegative donor was excluded. In FIG. 11A the horizontal bars represent the median.

Cytotoxicity was assessed using donor-derived EBV-LCL as targets. Gene-modified allodepleted cells that had undergone 2 or 3 rounds of stimulation with donor-derived EBV-LCL could efficiently lyse virus-infected autologous target cells (see FIG. 11B). Presented in FIG. 11B are the results of the cytotoxicity assay. Gene-modified allodepleted cells were stimulated with donor EBV-LCL for 2 or 3 cycles. $^{51}Cr$ release assay was performed using donor-derived EBV-LCL and donor OKT3 blasts as targets. NK activity was blocked with 30-fold excess cold K562. The left panel shows results from 5 independent experiments using totally or partially mismatched donor-recipient pairs. The right panel shows results from 3 experiments using unrelated HLA haploidentical donor-recipient pairs. Error bars indicate standard deviation.

Figure 11C:
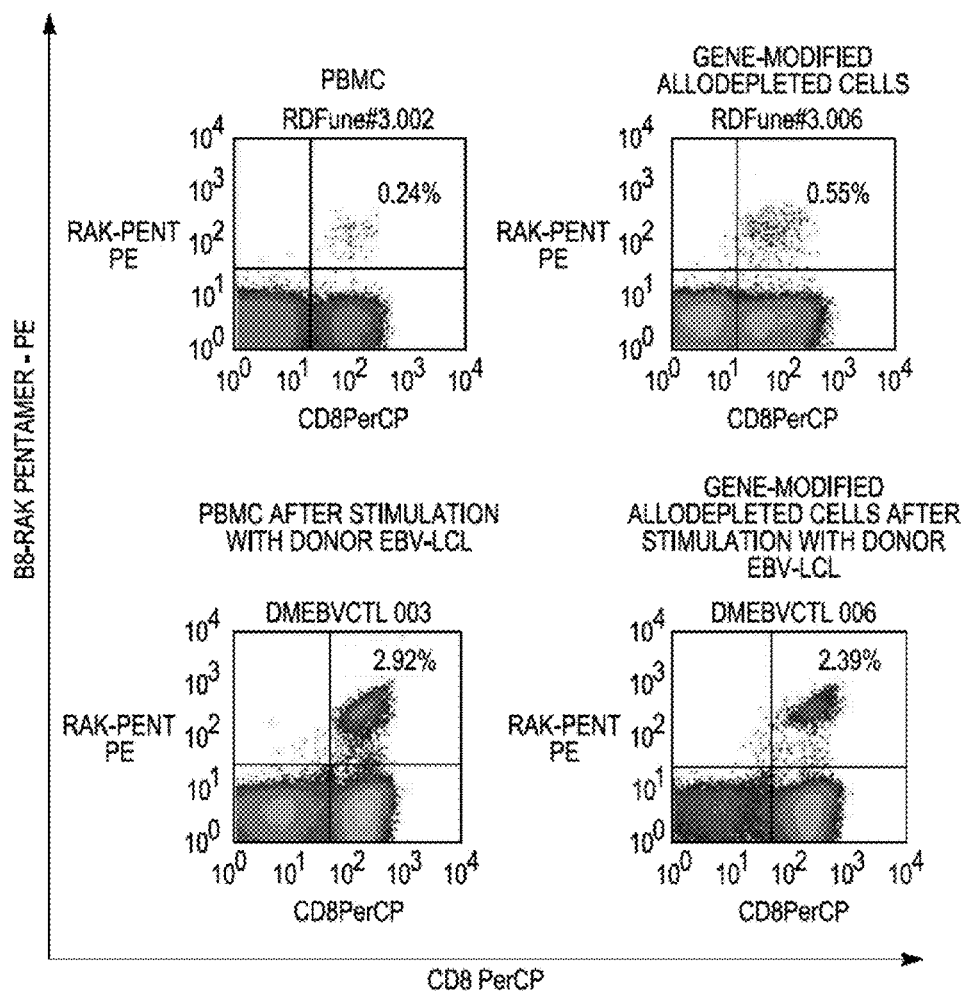

EBV-LCLs were used as antigen-presenting cells during selective allodepletion, therefore it was possible that EBV-specific T cells could be significantly depleted when the donor and recipient were haploidentical. To investigate this hypothesis, three experiments using unrelated HLA-haploidentical donor-recipient pairs were included, and the results showed that cytotoxicity against donor-derived EBV-LCL was retained. The results were corroborated by pentamer analysis for T cells recognizing HLA-B8-RAKFKQLL (SEQ ID NO: 20), an EBV lytic antigen (BZLF1) epitope, in two informative donors following allodepletion against HLA-B8 negative haploidentical recipients (see FIG. 11C). FIG. 11C illustrates the frequency of T cells specific for the BZLF1 epitope. Unmanipulated PBMC were used as comparators. The RAK-pentamer positive population was retained in gene-modified allodepleted cells and could be expanded following several rounds of in vitro stimulation with donor-derived EBV-LCL. The percentages shown in graph presented in FIG. 11C indicate percentage of pentamer positive cells within the CD8 population. Together, these results indicate that gene-modified allodepleted cells retained significant anti-viral functionality.

Regulatory T Cells in the Gene-Modified Allodepleted Cell Population

Figures 12A, 12B:
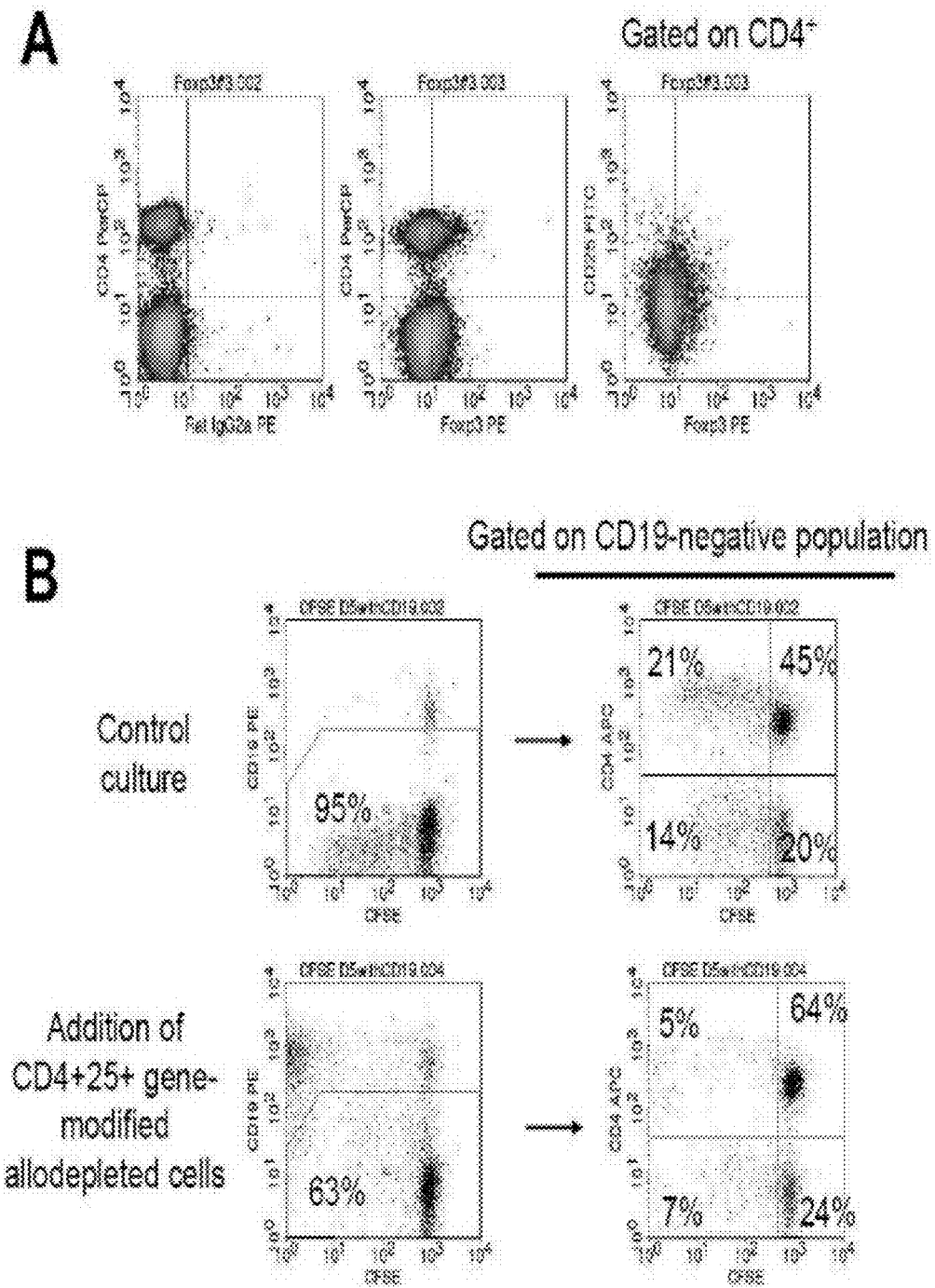
FIGS. 12A and 12B illustrate the results of various experiments performed to show that regulatory T cells could be isolated from gene modified end product cells despite initial allodepletion using CD25 immunotoxin.

Flow cytometry and functional analysis were used to determine whether regulatory T cells were retained in our allodepleted, gene modified, T cell product. A Foxp3+CD4+25+ population was found, as shown in FIG. 12A. Following immunomagnetic separation, the $CD4^+CD25^+$ enriched fraction demonstrated suppressor function when co-cultured with CFSE-labeled autologous PBMC in the presence of OKT3 and allogeneic feeders (see FIG. 12B). FIG. 12B illustrates the results of a $CD4^+CD25^+$ functional assay. Donor-derived PBMC was labeled with CFSE and stimulated with OKT3 and allogeneic feeders. CD4+CD25+ cells were immunomagnetically selected from the gene-modified cell population and added at 1:1 ratio to test wells. Flow cytometry was performed after 5 days. Gene-modified T cells were gated out by CD19 expression. The addition of CD4+CD25+ gene-modified cells (bottom panel) significantly reduced cell proliferation. Thus, allodepleted T cells may reacquire regulatory phenotype even after exposure to a CD25 depleting immunotoxin.

Figure 13A:
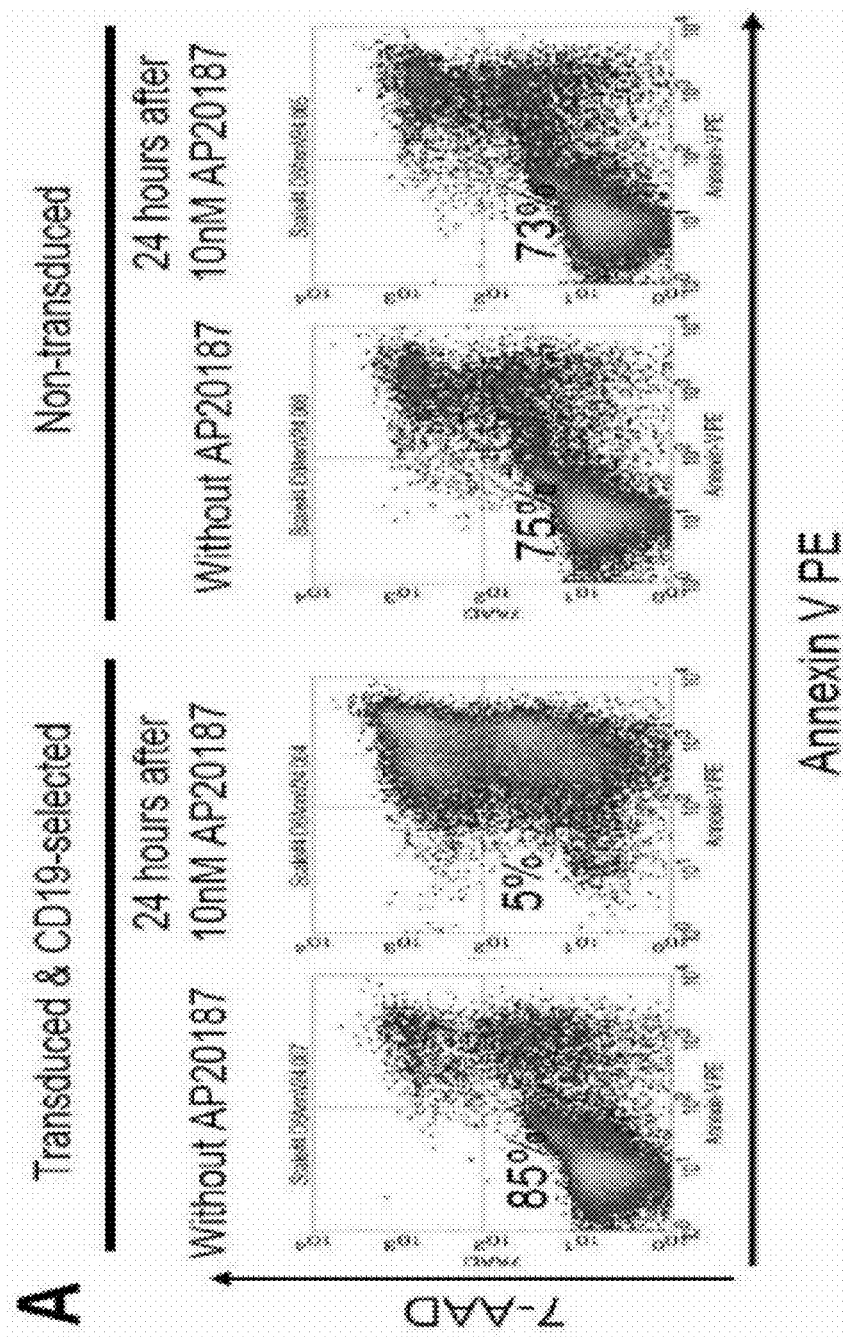
FIGS. 13A-13CB illustrate the results of various experiments performed to show that gene modified allodepleted cells are rapidly and efficiently eliminated by AP20187, and that transgene expression and killing efficiency diminished with extended culture, and could be restored upon T cell reactivation.

Gene-Modified Allodepleted Cells were Efficiently and Rapidly Eliminated by Addition of Chemical Inducer of Dimerization The day following immunomagnetic selection, 10 nM of the chemical inducer of dimerization, AP20187, was added to induce apoptosis, which appeared within 24 hours. FACS analysis with annexin V and 7-AAD staining at 24 hours showed that only about 5.5%±2.5% of AP20187-treated cells remained viable, whereas about 81.0%±9.0% of untreated cells were viable (see FIG. 13A). Killing efficiency after correction for baseline viability was about 92.9%±3.8%. Large-scale CD19 selection produced cells that were killed with similar efficiency as small-scale selection: mean viability with and without AP20187, and percentage killing, in large and small scale were about 3.9%, about 84.0%, about 95.4% (n=3) and about 6.6%, about 79.3%, about 91.4% (n=5) respectively. AP20187 was non-toxic to non-transduced cells: viability with and without AP20187 was about 86%±9% and 87%±8% respectively (n=6).

Figure 13B:
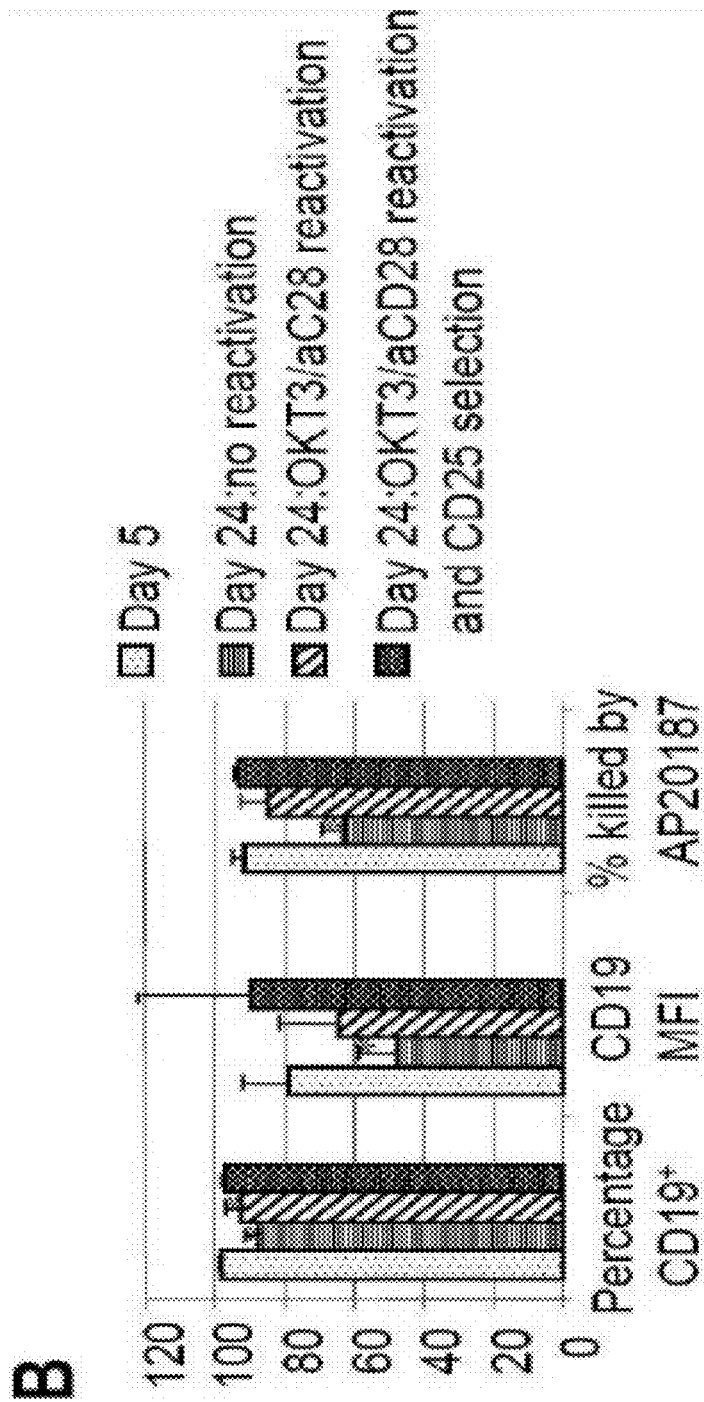

Transgene Expression and Function Decreased with Extended Culture but were Restored Upon Cell Reactivation To assess the stability of transgene expression and function, cells were maintained in T cell culture medium and low dose IL-2 (50 U/ml) until 24 days after transduction. A portion of cells was then reactivated with OKT3/anti-CD28. CD19 expression was analyzed by flow cytometry 48 to 72 hours later, and suicide gene function was assessed by treatment with 10 nM AP20187. The results shown in FIG. 13B are for cells from day 5 post transduction (ie, 1 day after CD 19 selection) and day 24 post transduction, with or without 48-72 hours of reactivation (5 experiments). In 2 experiments, CD25 selection was performed after OKT3/aCD28 activation to further enrich activated cells. Error bars represent standard deviation. * indicates p<0.05 when compared to cells from day 5 post transduction. By day 24, surface CD19 expression fell from about 98%±1% to about 88%±4% (p<0.05) with a parallel decrease in mean fluorescence intensity (MFI) from 793±128 to 478±107 (p<0.05) (see FIG. 13B). Similarly, there was a significant reduction in suicide gene function: residual viability was 19.6±5.6% following treatment with AP20187; after correction for baseline viability of 54.8±20.9%, this equated to killing efficiency of only 63.1±6.2%.

Figure 13C:
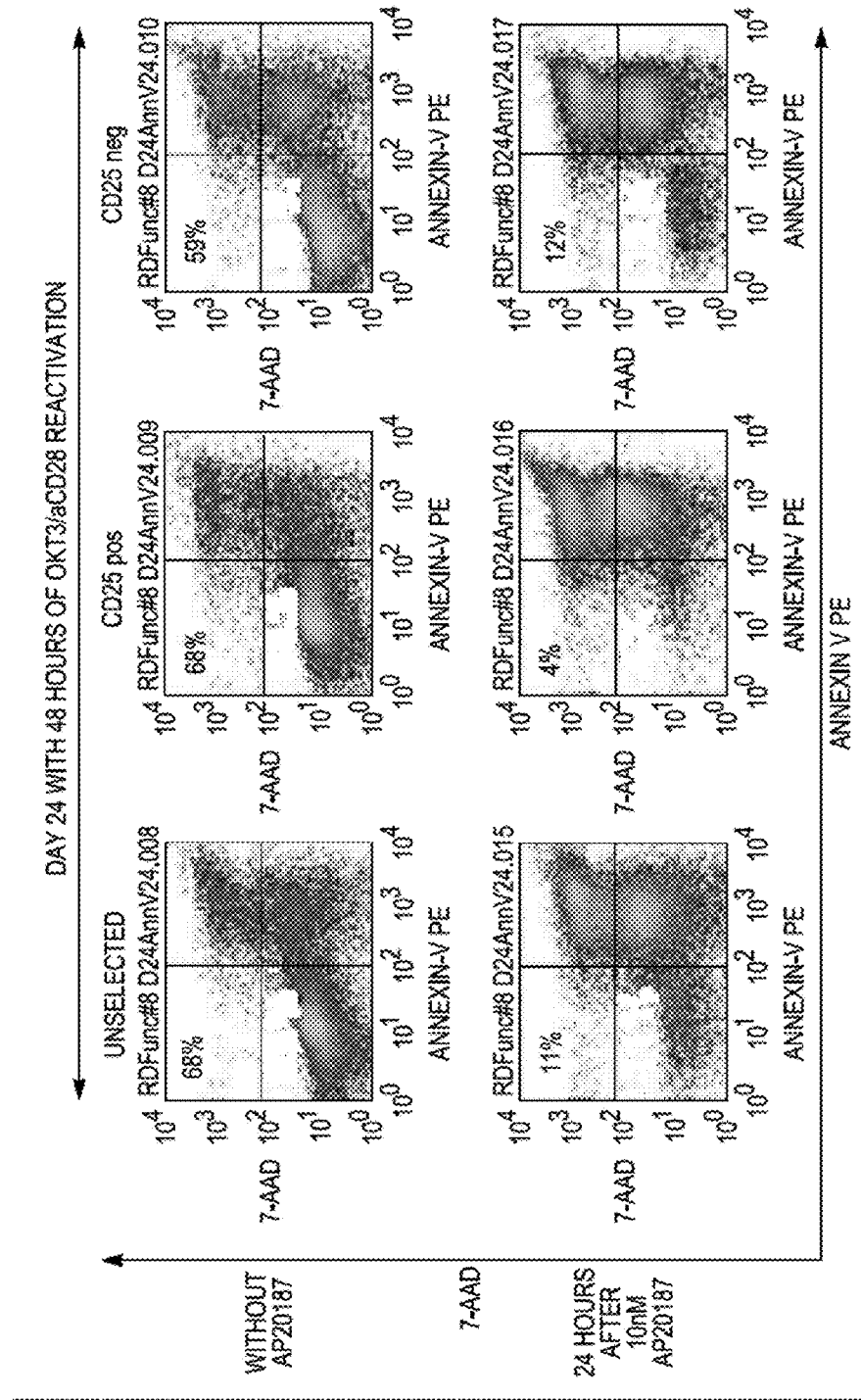

To determine whether the decrease in transgene expression with time was due to reduced transcription following T cell quiescence or to elimination of transduced cells, a portion of cells were reactivated on day 22 post transduction with OKT3 and anti-CD28 antibody. At 48 to 72 hours (day 24 or 25 post transduction), OKT3/aCD28-reactivated cells had significantly higher transgene expression than non-reactivated cells. CD19 expression increased from about 88%±4% to about 93%±4% (p<0.01) and CD19 MFI increased from 478±107 to 643±174 (p<0.01). Additionally, suicide gene function also increased significantly from about a 63.1%±6.2% killing efficiency to about a 84.6%±8.0% (p<0.01) killing efficiency. Furthermore, killing efficiency was completely restored if the cells were immunomagnetically sorted for the activation marker CD25: killing efficiency of CD25 positive cells was about 93%. 2±1.2%, which was the same as killing efficiency on day 5 post transduction (93.1±3.5%) (see FIG. 13C). Killing of the CD25 negative fraction was 78.6±9.1%. Illustrated in FIG. 13C are representative FACS plots showing the effect of extended culture and T cell activation on suicide gene function.

Figures 14A, 14B:
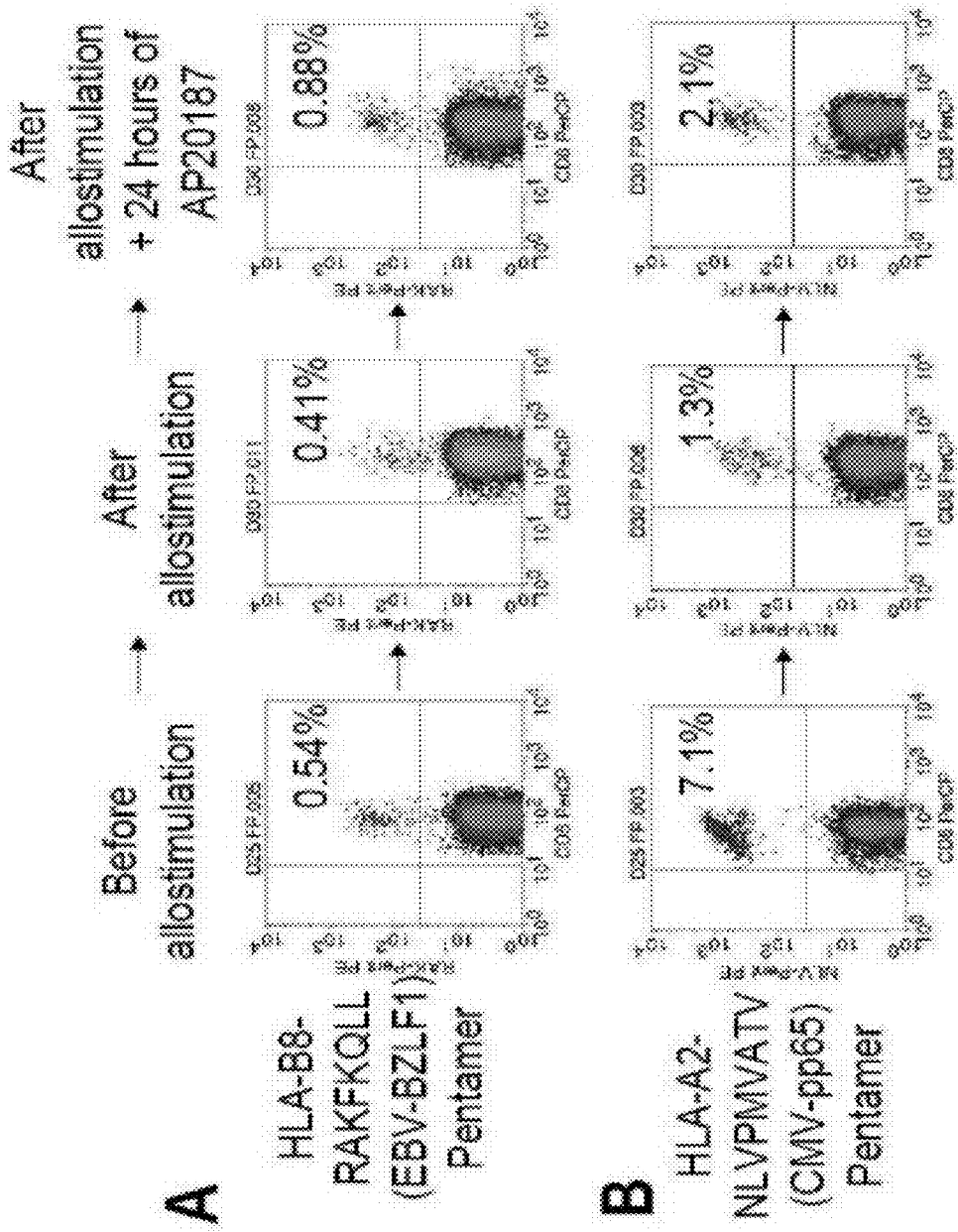
FIGS. 14A and 14B illustrate the results of various experiments performed to show that viral-specific T cells are partially retained after treatment of allostimulated cells with dimerizer.

An observation of note was that many virus-specific T cells were spared when dimerizer was used to deplete gene-modified cells that have been re-activated with allogeneic PBMC, rather than by non-specific mitogenic stimuli. After 4 days reactivation with allogeneic cells, as shown in FIGS. 14A and 14B, treatment with AP20187 spares (and thereby enriches) viral reactive subpopulations, as measured by the proportion of T cells reactive with HLA pentamers specific for peptides derived from EBV and CMV. Gene-modified allodepleted cells were maintained in culture for 3 weeks post-transduction to allow transgene down-modulation. Cells were stimulated with allogeneic PBMC for 4 days, following which a portion was treated with 10 nM AP20187. The frequency of EBV-specific T cells (see FIG. 14A) and CMV-specific T cells (see FIG. 14B) were quantified by pentamer analysis before allostimulation, after allostimulation, and after treatment of allostimulated cells with dimerizer. The percentage of virus-specific T cells decreased after allostimulation. Following treatment with dimerizer, virus-specific T cells were partially and preferentially retained.

Discussion

The feasibility of engineering allogeneic T cells with two distinct safety mechanisms, selective allodepletion and suicide gene-modification has been demonstrated herein. In combination, these modifications can enhance and/or enable addback of substantial numbers of T cells with anti-viral and anti-tumor activity, even after haploidentical transplantation. The data presented herein show that the suicide gene, iCasp9, functions efficiently (>90% apoptosis after treatment with dimerizer) and that down-modulation of transgene expression that occurred with time was rapidly reversed upon T cell activation, as would occur when alloreactive T cells encountered their targets. Data presented herein also show that CD19 is a suitable selectable marker that enabled efficient and selective enrichment of transduced cells to >90% purity. Furthermore the data presented herein indicate that these manipulations had no discernable effects on the immunological competence of the engineered T cells with retention of antiviral activity, and regeneration of a $CD4^+CD25^+Foxp3^+$ population with Treg activity.

Given that the overall functionality of suicide genes depends on both the suicide gene itself and the marker used to select the transduced cells, translation into clinical use requires optimization of both components, and of the method used to couple expression of the two genes. The two most widely used selectable markers, currently in clinical practice, each have drawbacks. Neomycin phosphotransferase (neo) encodes a potentially immunogenic foreign protein and requires a 7-day culture in selection medium, which not only increases the complexity of the system, but is also potentially damaging to virus-specific T cells. A widely used surface selection marker, LNGFR, has recently had concerns raised, regarding its ocogenic potential and potential correlation with leukemia, in a mouse model, despite its apparent clinical safety. Furthermore, LNGFR selection is not widely available, because it is used almost exclusively in gene therapy. A number of alternative selectable markers have been suggested. CD34 has been well-studied in vitro, but the steps required to optimize a system configured primarily for selection of rare hematopoietic progenitors, and more critically, the potential for altered in vivo T cell homing, make CD34 sub-optimal for use as a selectable marker for a suicide switch expression construct. CD19 was chosen as an alternative selectable marker, since clinical grade CD19 selection is readily available as a method for B-cell depletion of stem cell autografts. The results presented herein demonstrated that CD19 enrichment could be performed with high purity and yield and, furthermore, the selection process had no discernable effect on subsequent cell growth and functionality.

The effectiveness of suicide gene activation in CD19-selected iCasp9 cells compared very favorably to that of neo- or LNGFR-selected cells transduced to express the HSVtk gene. The earlier generations of HSVtk constructs provided 80-90% suppression of $^3$H-thymidine uptake and showed similar reduction in killing efficiency upon extended in vitro culture, but were nonetheless clinically efficacious. Complete resolution of both acute and chronic GVHD has been reported with as little as 80% in vivo reduction in circulating gene-modified cells. These data support the hypothesis that transgene down-modulation seen in vitro is unlikely to be an issue because activated T cells responsible for GVHD will upregulate suicide gene expression and will therefore be selectively eliminated in vivo. Whether this effect is sufficient to allow retention of virus- and leukemia-specific T cells in vivo will be tested in a clinical setting. By combining in vitro selective allodepletion prior to suicide gene modification, the need to activate the suicide gene mechanism may be significantly reduced, thereby maximizing the benefits of addback T cell based therapies.

The high efficiency of iCasp9-mediated suicide seen in vitro has been replicated in vivo. In a SCID mouse-human xenograft model, more than 99% of iCasp9-modified T cells were eliminated after a single dose of dimerizer. AP1903, which has extremely close functional and chemical equivalence to AP20187, and currently is proposed for use in a clinical application, has been safety tested on healthy human volunteers and shown to be safe. Maximal plasma level of between about 10 ng/ml to about 1275 ng/ml AP1903 (equivalent to between about 7 nM to about 892 nM) was attained over a 0.01 mg/kg to 1.0 mg/kg dose range administered as a 2-hour intravenous infusion. There were substantially no significant adverse effects. After allowing for rapid plasma redistribution, the concentration of dimerizer used in vitro remains readily achievable in vivo.

Optimal culture conditions for maintaining the immunological competence of suicide gene-modified T cells must be determined and defined for each combination of safety switch, selectable marker and cell type, since phenotype, repertoire and functionality can all be affected by the stimulation used for polyclonal T cell activation, the method for selection of transduced cells, and duration of culture. The addition of CD28 co-stimulation and the use of cell-sized paramagnetic beads to generate gene modified-cells that more closely resemble unmanipulated PBMC in terms of CD4:CD8 ratio, and expression of memory subset markers including lymph node homing molecules CD62L and CCR7, may improve the in vivo functionality of gene-modified T cells. CD28 co-stimulation also may increase the efficiency of retroviral transduction and expansion. Interestingly however, the addition of CD28 co-stimulation was found to have no impact on transduction of allodepleted cells, and the degree of cell expansion demonstrated was higher when compared to the anti-CD3 alone arm in other studies. Furthermore, iCasp9-modified allodepleted cells retained significant anti-viral functionality, and approximately one fourth retained CD62L expression. Regeneration of CD4$^+$CD25$^+$ Foxp3$^+$ regulatory T cells, was also seen. The allodepleted cells used as the starting material for T cell activation and transduction may have been less sensitive to the addition of anti-CD28 antibody as co-stimulation. CD25-depleted PBMC/EBV-LCL co-cultures contained T cells and B cells that already express CD86 at significantly higher level than unmanipulated PBMC and may themselves provide co-stimulation. Depletion of CD25$^+$ regulatory T cells prior to polyclonal T cell activation with anti-CD3 has been reported to enhance the immunological competence of the final T cell product. In order to minimize the effect of in vitro culture and expansion on functional competence, a relatively brief culture period was used in some experiments presented herein, whereby cells were expanded for a total of 8 days post-transduction with CD19-selection being performed on day 4.

Finally, scaled up production was demonstrated such that sufficient cell product can be produced to treat adult patients at doses of up to $10^7$ cells/kg: allodepleted cells can be activated and transduced at $4 \times 10^7$ cells per flask, and a minimum of 8-fold return of CD19-selected final cell product can be obtained on day 8 post-transduction, to produce at least $3 \times 10^8$ allodepleted gene-modified cells per original flask. The increased culture volume is readily accommodated in additional flasks or bags.

The allodepletion and iCasp9-modification presented herein may significantly improve the safety of adding back T cells, particularly after haploidentical stem cell allografts. This should in turn enable greater dose-escalation, with a higher chance of producing an anti-leukemia effect.

Example 3

Figure 22:
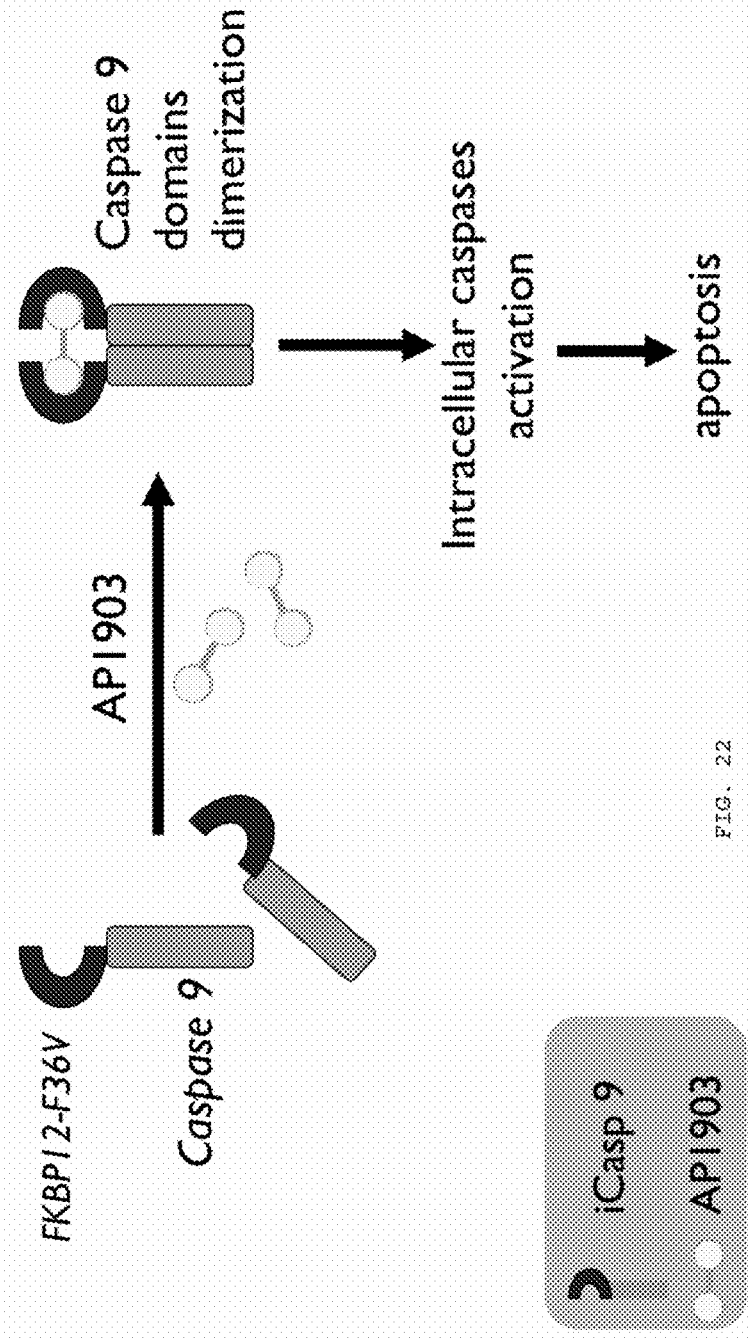
FIG. 22 shows how the suicide gene product and the CID interact to cause apoptosis.
Figure 23:
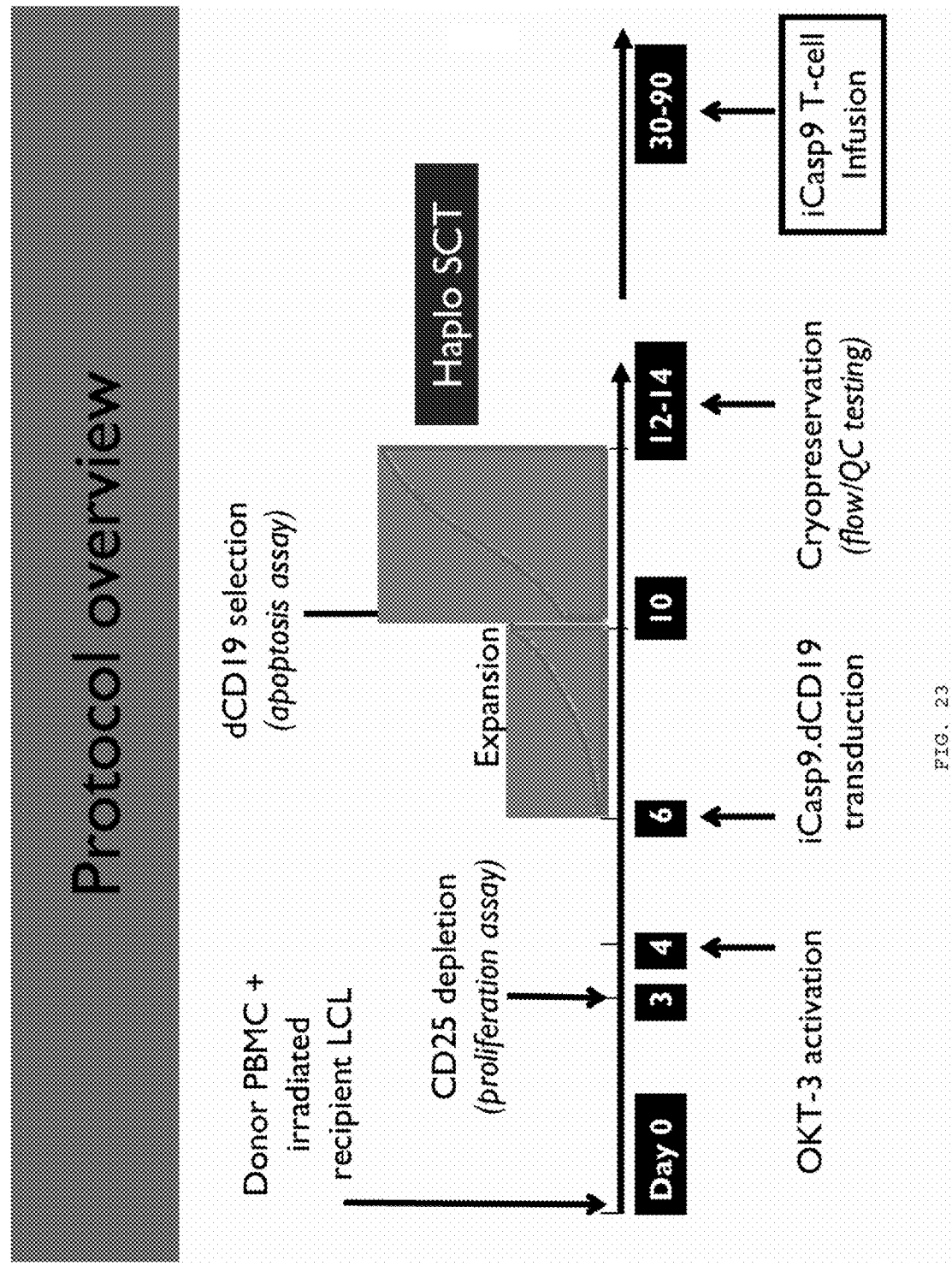
FIG. 23 illustrates an overview of the protocol used for production of suicide gene modified allodepleted cells.

CASPALLO—Phase I Clinical Trial of Allodepleted T Cells Transduced with Inducible Caspase 9 Suicide Gene after Haploidentical Stem Cell Transplantation This example presents results of a phase 1 clinical trial using the alternative suicide gene strategy illustrated in FIG. 22. Briefly, donor peripheral blood mononuclear cells were co-cultured with recipient irradiated EBV-transformed lymphoblastoid cells (40:1) for 72 hrs, allodepleted with a CD25 immunotoxin and then transduced with a retroviral supernatant carrying the iCasp9 suicide gene and a selection marker (ΔCD19); ΔCD19 allowed enrichment to >90% purity via immunomagnetic selection., as illustrated in FIG. 23.

A detailed protocol for generation of the cell therapy product is provided herein.

Source Material

Up to 240 ml (in 2 collections) of peripheral blood was obtained from the transplant donor according to established protocols. In some cases, dependent on the size of donor and recipient, a leukopheresis was performed to isolate sufficient T cells. 10 cc-30 cc of blood also was drawn from the recipient and was used to generate the Epstein Barr virus (EBV)-transformed lymphoblastoid cell line used as stimulator cells. In some cases, dependent on the medical history and/or indication of a low B cell count, the LCLs were generated using appropriate 1st degree relative (e.g., parent, sibling, or offspring) peripheral blood mononuclear cells.

Generation of Allodepleted Cells

Allodepleted cells were generated from the transplant donors as presented herein. Peripheral blood mononuclear cells (PBMCs) from healthy donors were co-cultured with irradiated recipient Epstein Barr virus (EBV)-transformed lymphoblastoid cell lines (LCL) at responder-to-stimulator ratio of 40:1 in serum-free medium (AIM V; Invitrogen, Carlsbad, Calif.). After 72 hours, activated T cells that express CD25 were depleted from the co-culture by overnight incubation in RFT5-SMPT-dgA immunotoxin. Allodepletion is considered adequate if the residual CD3$^+$CD25$^+$ population was <1% and residual proliferation by $^3$H-thymidine incorporation was <10%.

Retroviral Production

A retroviral producer line clone was generated for the iCasp9-CD19 construct. A master cell-bank of the producer also was generated. Testing of the master-cell bank was performed to exclude generation of replication competent retrovirus and infection by Mycoplasma, HIV, HBV, HCV and the like. The producer line was grown to confluency, supernatant harvested, filtered, aliquoted and rapidly frozen and stored at −80C. Additional testing was performed on all batches of retroviral supernatant to exclude Replication Competent Retrovirus (RCR) and issued with a certificate of analysis, as per protocol.

Transduction of Allodepleted Cells

Allodepleted T-lymphocytes were transduced using Fibronectin. Plates or bags were coated with recombinant Fibronectin fragment CH-296 (Retronectin™, Takara Shuzo, Otsu, Japan). Virus was attached to retronectin by incubating producer supernatant in coated plates or bags. Cells were then transferred to virus coated plates or bags. After transduction allodepleted T cells were expanded, feeding them with IL-2 twice a week to reach the sufficient number of cells as per protocol.

CD19 Immunomagnetic Selection

Figure 24:
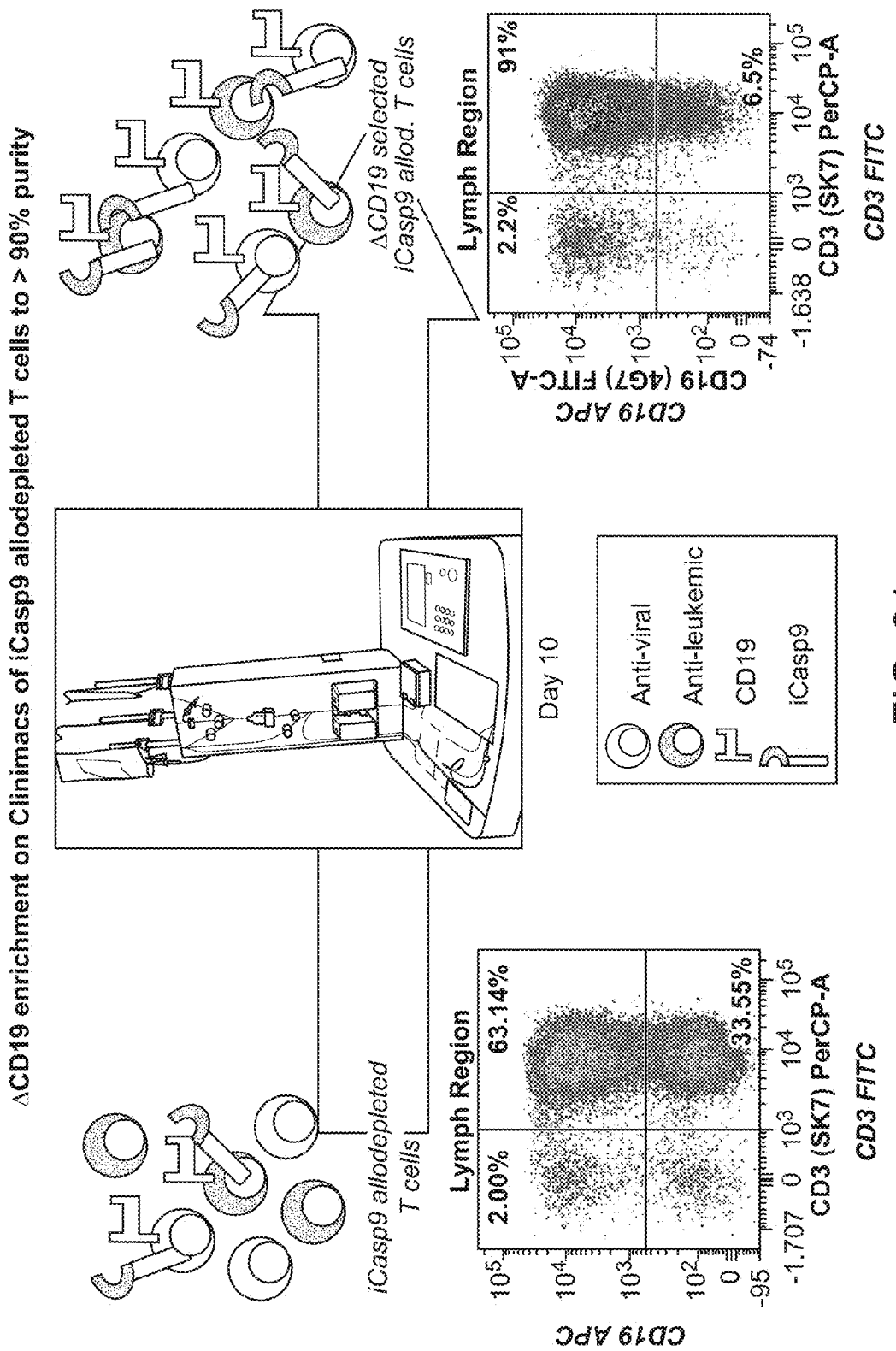
FIG. 24 describes the use of immunomagnetic enrichment of iCasp9 expressing allodepleted T cells.

Immunomagnetic selection for CD19 was performed 4 days after transduction. Cells are labeled with paramagnetic microbeads conjugated to monoclonal mouse anti-human CD19 antibodies (Miltenyi Biotech, Auburn, Calif.) and selected on a CliniMacs Plus automated selection device (see FIG. 24). Depending upon the number of cells required for clinical infusion cells were either cryopreserved after the CliniMacs selection or further expanded with IL-2 and cryopreserved on day 6 or day 8 post transduction.

Freezing

Aliquots of cells were removed for testing of transduction efficiency, identity, phenotype and microbiological culture as required for final release testing by the FDA. The cells were cryopreserved prior to administration according to protocol.

Study Drugs

RFT5-SMPT-dgA

RFT5-SMPT-dgA is a murine IgG1 anti-CD25 (IL-2 receptor alpha chain) conjugated via a hetero-bifunctional crosslinker [N-succinimidyloxycarbonyl-alpha-methyl-d-(2-pyridylthio) toluene] (SMPT) to chemically deglycosylated ricin A chain (dgA). RFT5-SMPT-dgA is formulated as a sterile solution at 0.5 mg/ml.

Synthetic Homodimerizer, AP1903

Mechanism of Action: AP1903-inducible cell death is achieved by expressing a chimeric protein comprising the intracellular portion of the human (Caspase 9 protein) receptor, which signals apoptotic cell death, fused to a drug-binding domain derived from humanFK506-binding protein (FKBP). This chimeric protein remains quiescent inside cells until administration of AP1903, which cross-links the FKBP domains, initiating Caspase signaling and apoptosis.

Toxicology: AP1903 has been evaluated as an Investigational New Drug (IND) by the FDA and has successfully completed a phase I clinical safety study. No significant adverse effects were noted when API 903 was administered over a 0.01 mg/kg to 1.0 mg/kg dose range.

Pharmacology/Pharmacokinetics: Patients received 0.4 mg/kg of AP1903 as a 2 h infusion—based on published Pk data which show plasma concentrations of 10 ng/mL-1275 ng/mL over the 0.01 mg/kg to 1.0 mg/kg dose range with plasma levels falling to 18% and 7% of maximum at 0.5 and 2 hrs post dose.

Side Effect Profile in Humans: No serious adverse events occurred during the Phase 1 study in volunteers. The incidence of adverse events was very low following each treatment, with all adverse events being mild in severity. Only one adverse event was considered possibly related to AP1903. This was an episode of vasodilatation, presented as "facial flushing" for 1 volunteer at the 1.0 mg/kg AP1903 dosage. This event occurred at 3 minutes after the start of infusion and resolved after 32 minutes duration. All other adverse events reported during the study were considered by the investigator to be unrelated or to have improbable relationship to the study drug. These events included chest pain, flu syndrome, halitosis, headache, injection site pain, vasodilatation, increased cough, rhinitis, rash, gum hemorrhage, and ecchymosis.

Patients developing grade 1 GVHD were treated with 0.4 mg/kg AP1903 as a 2-hour infusion. Protocols for administration of AP1903 to patients grade 1 GVHD were established as follows. Patients developing GvHD after infusion of allodepleted T cells are biopsied to confirm the diagnosis and receive 0.4 mg/kg of AP1903 as a 2 h infusion. Patients with Grade I GVHD received no other therapy initially, however if they showed progression of GvHD conventional GvHD therapy was administered as per institutional guidelines. Patients developing grades 2-4 GVHD were administered standard systemic immunosuppressive therapy per institutional guidelines, in addition to the AP1903 dimerizer drug.

Instructions for preparation and infusion: AP1903 for injection is obtained as a concentrated solution of 2.33 ml in a 3 ml vial, at a concentration of 5 mg/mi, (i.e., 10.66 mg per vial). Prior to administration, the calculated dose was diluted to 100 mL in 0.9% normal saline for infusion. AP1903 for injection (0.4 mg/kg) in a volume of 100 ml was administered via IV infusion over 2 hours, using a non-DEHP, non-ethylene oxide sterilized infusion set and infusion pump.

Figure 25:
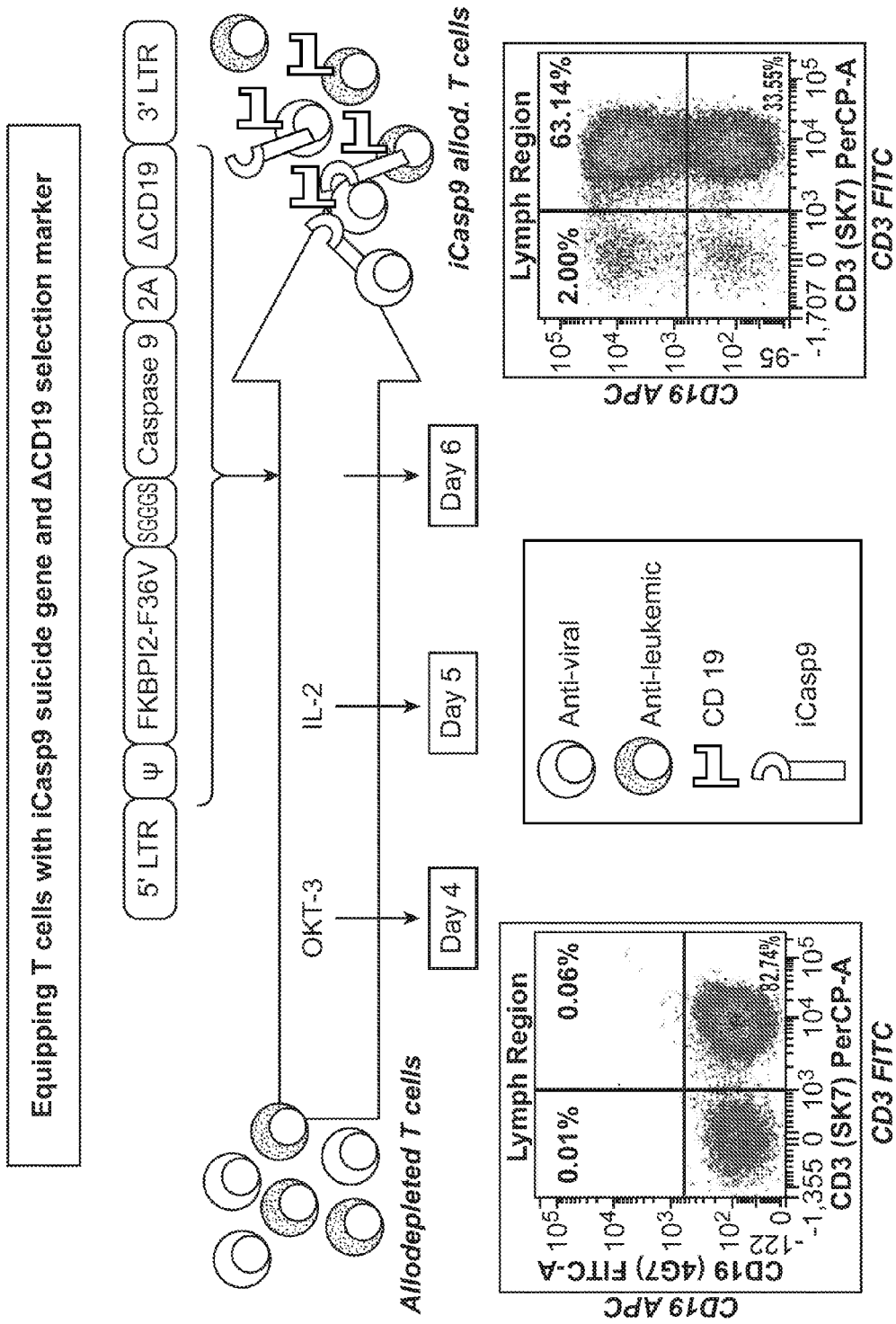
FIG. 25 illustrates the iCasp9-ΔCD19 expression construct and the method of transducing cells to harbor the expression construct.
Figure 26:
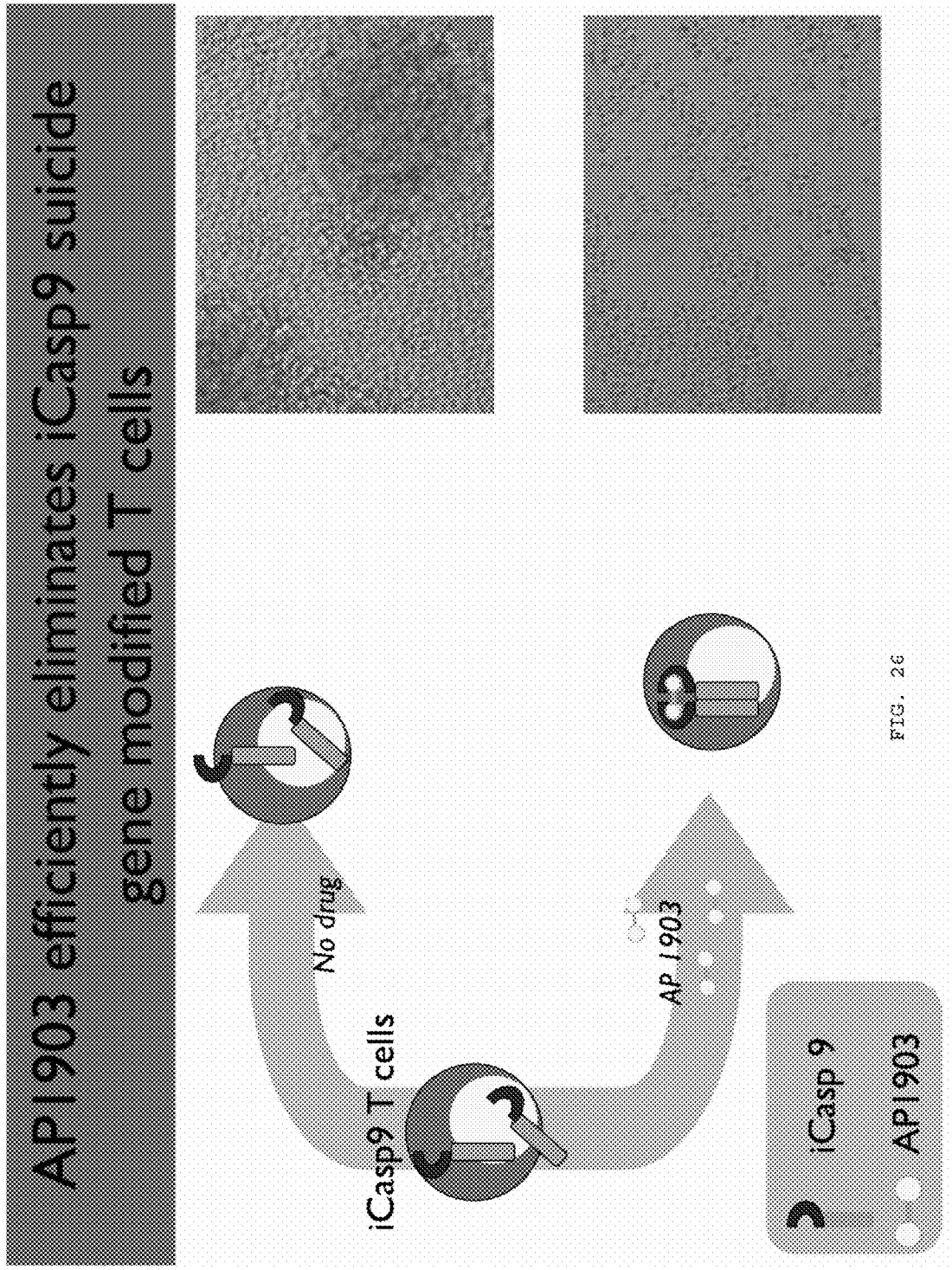
FIG. 26 shows the effect of CID treatment on gene modified T cells (e.g., iCasp9 expressing cells).

The iCasp9 suicide gene expression construct (e.g., SFG.iCasp9.2A.ACD19), shown in FIG. 25, consists of inducible caspase 9 (iCasp9) linked, via a cleavable 2A-like sequence, to truncated human CD19 (ACD19). iCasp9 includes a human FK506-binding protein (FKBP12; GenBank AH002 818) with an F36V mutation, connected via a Ser-Gly-Gly-Gly-Ser linker (SEQ ID NO: 21) to human caspase 9 (CASP9; GenBank NM 001229). The F36V mutation may increase the binding affinity of FKBP12 to the synthetic homodimerizer, AP20187 or AP1903. The caspase recruitment domain (CARD) has been deleted from the human caspase 9 sequence and its physiological function has been replaced by FKBP12. The replacement of CARD with FKBP12 increases transgene expression and function. The 2A-like sequence encodes an 18 amino acid peptide from Thosea Asigna insect virus, which mediates >99% cleavage between a glycine and terminal proline residue, resulting in 17 extra amino acids in the C terminus of iCasp9, and one extra proline residue in the N terminus of CD19. ΔCD19 consists of full length CD19 (GenBank NM 001770) truncated at amino acid 333 (TDPTRRF) (SEQ ID NO: 22), which shortens the intracytoplasmic domain from 242 to 19 amino acids, and removes all conserved tyrosine residues that are potential sites for phosphorylation. Illustrated in FIG. 26 is the result of iCasp9 and AP1903 in eliminating gene modified T cells carrying the iCasp9 suicide switch.

In Vivo Studies

Three patients received iCasp9+ T cells after haplo-CD34+ stem cell transplantation (SCT), at dose levels between about $1\times10^6$ to about $3\times10^6$ cells/kg.

Characteristics of the patients and clinical outcome.

| Patient # | Sex (age (yr)) | Diagnosis | Disease status at SCT | Days from SCT to T-cell infusion | Number of cells infused per kg | Acute GvHD | Clinical outcome |
|---|---|---|---|---|---|---|---|
| P1 | M(3) | MDS/AML | CR2 | 63 | $1 \times 10^6$ | Grade ½ (skin, liver) | Alive in CR > 12 months No GvHD |
| P2 | F(17) | B-ALL | CR2 | 80 and 112 | $(1 \times 10^6)2$ | Grade 1 (skin) | Alive in CR > 12 months No GvHD |
| P3 | M(8) | T-ALL | PIF/CR1 | 93 | $3 \times 10^6$ | None | Alive in CR > 12 No GvHD |
| P4 | F(4) | T-ALL | Active disease | 30 | $3 \times 10^6$ | Grade 1 (skin) | Alive in CR > 12 No GvHD |

Figure 28:
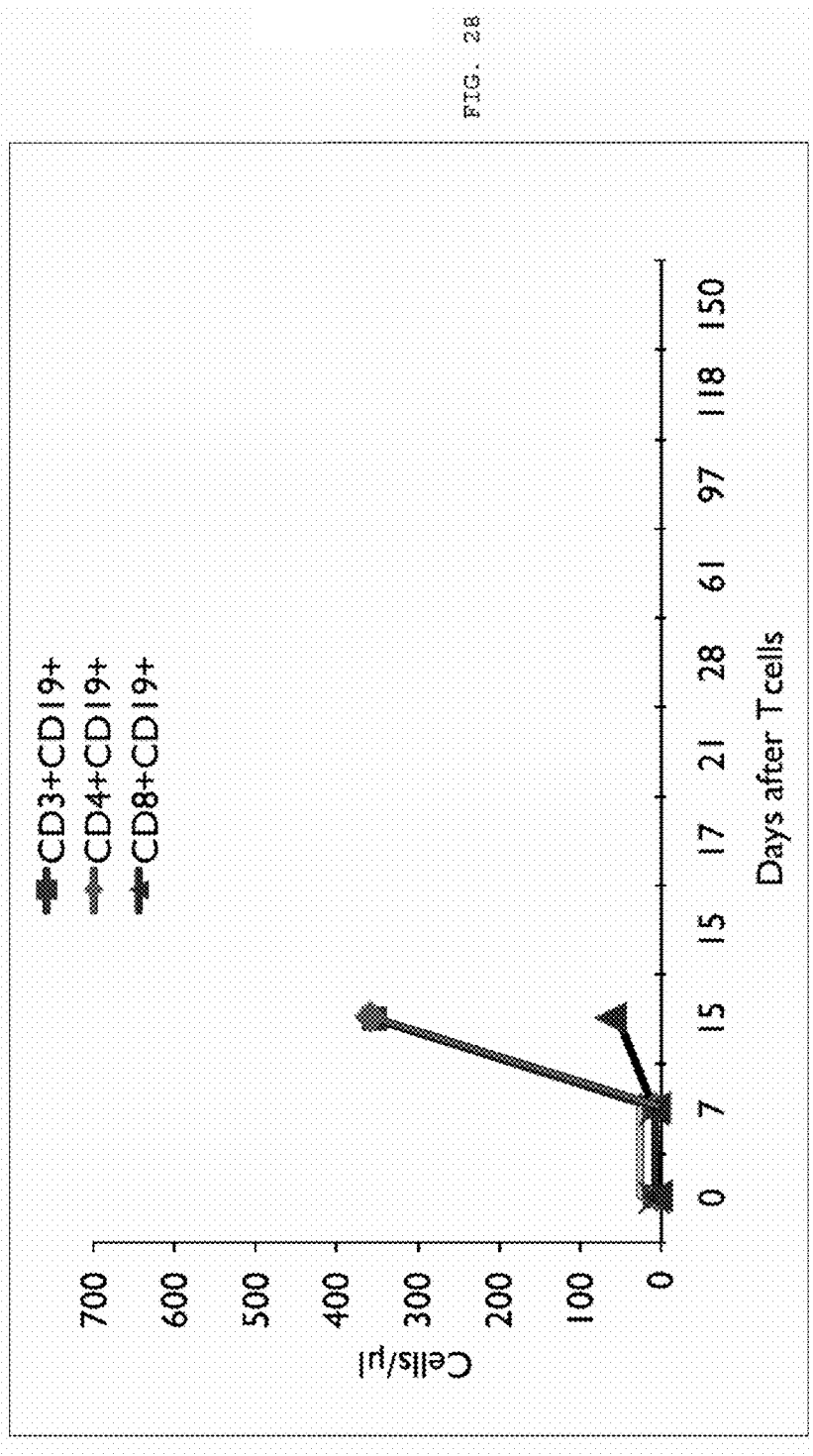
FIGS. 28 and 29 graphically illustrate cell lineage expansion of transduced iCasp9 T cells, as indicated by cell surface markers.
Figure 29:
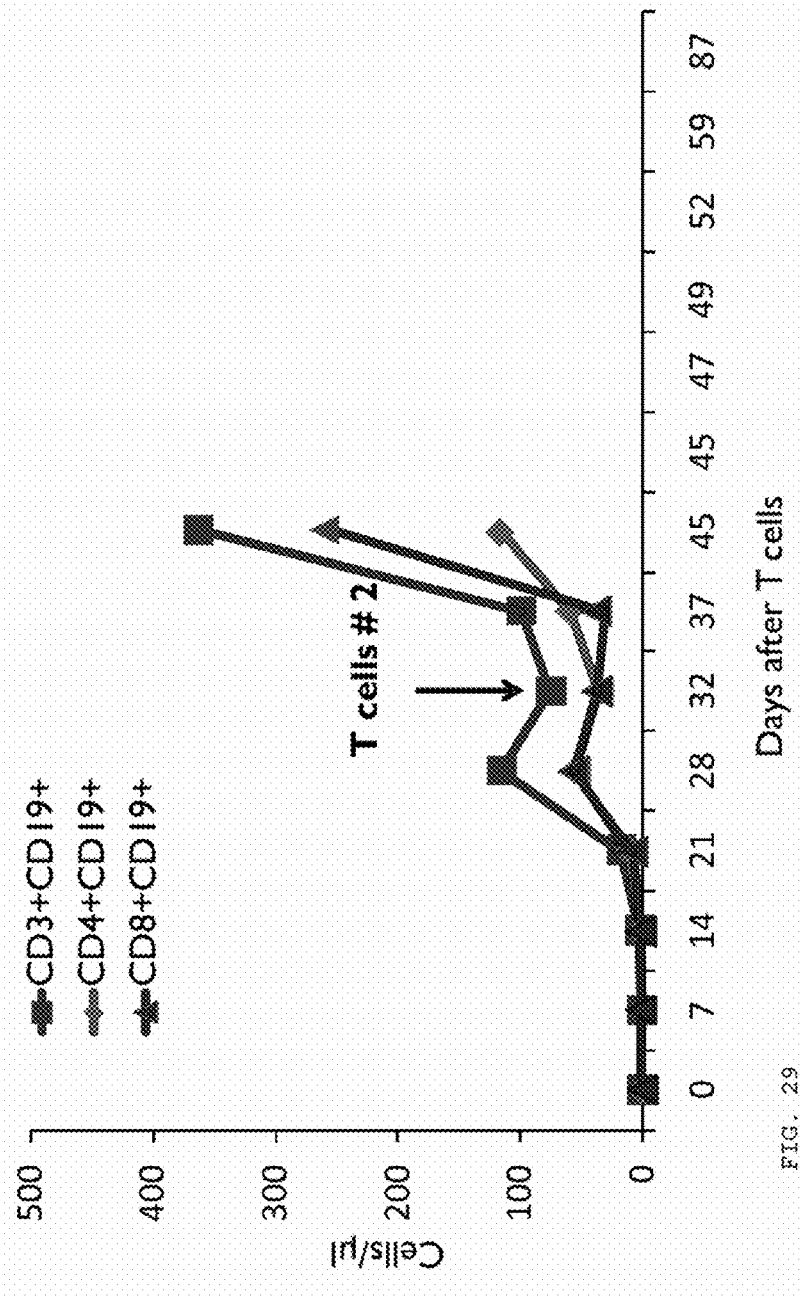
Figure 30A:
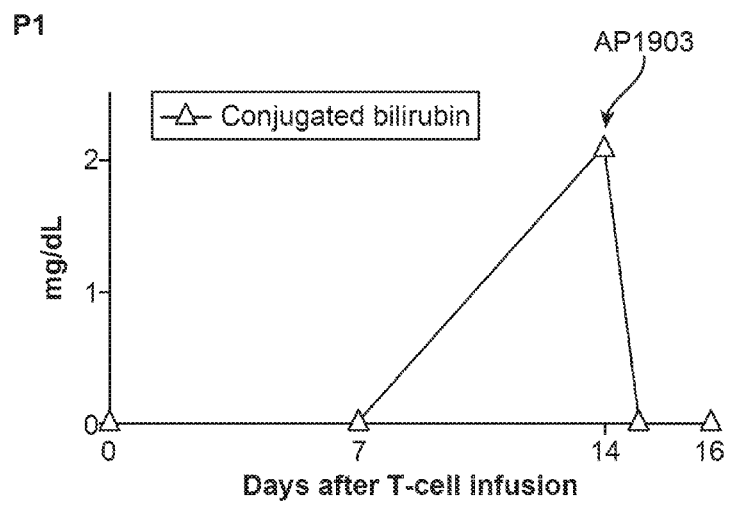
FIGS. 30A-30C provide a graph and photographs of the rapid reversal of GvHD after treatment with the dimerizing drug AP1903.
Figures 30B, 30C:
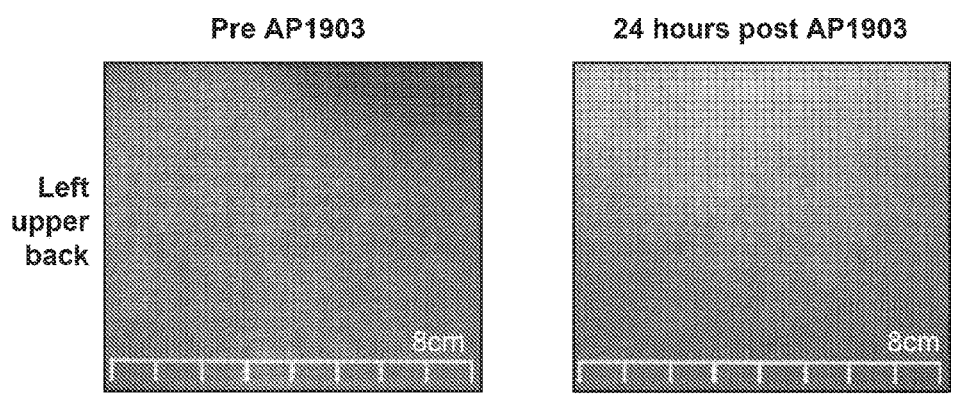
Figure 31:
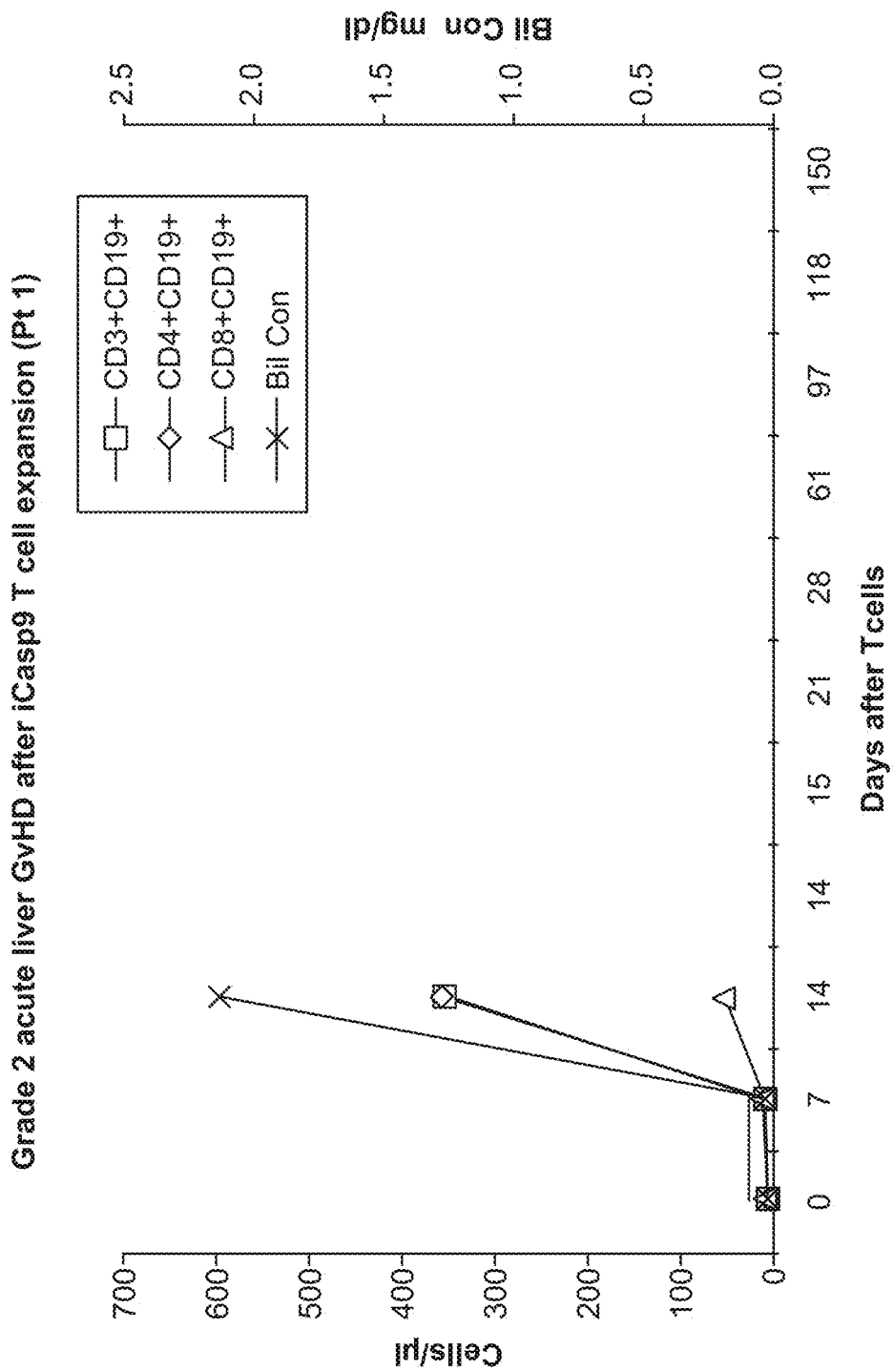
FIGS. 31 and 32 graphically illustrate the onset of acute liver GvHD (grade 2) after iCasp9 T cell expansion.
Figure 32:
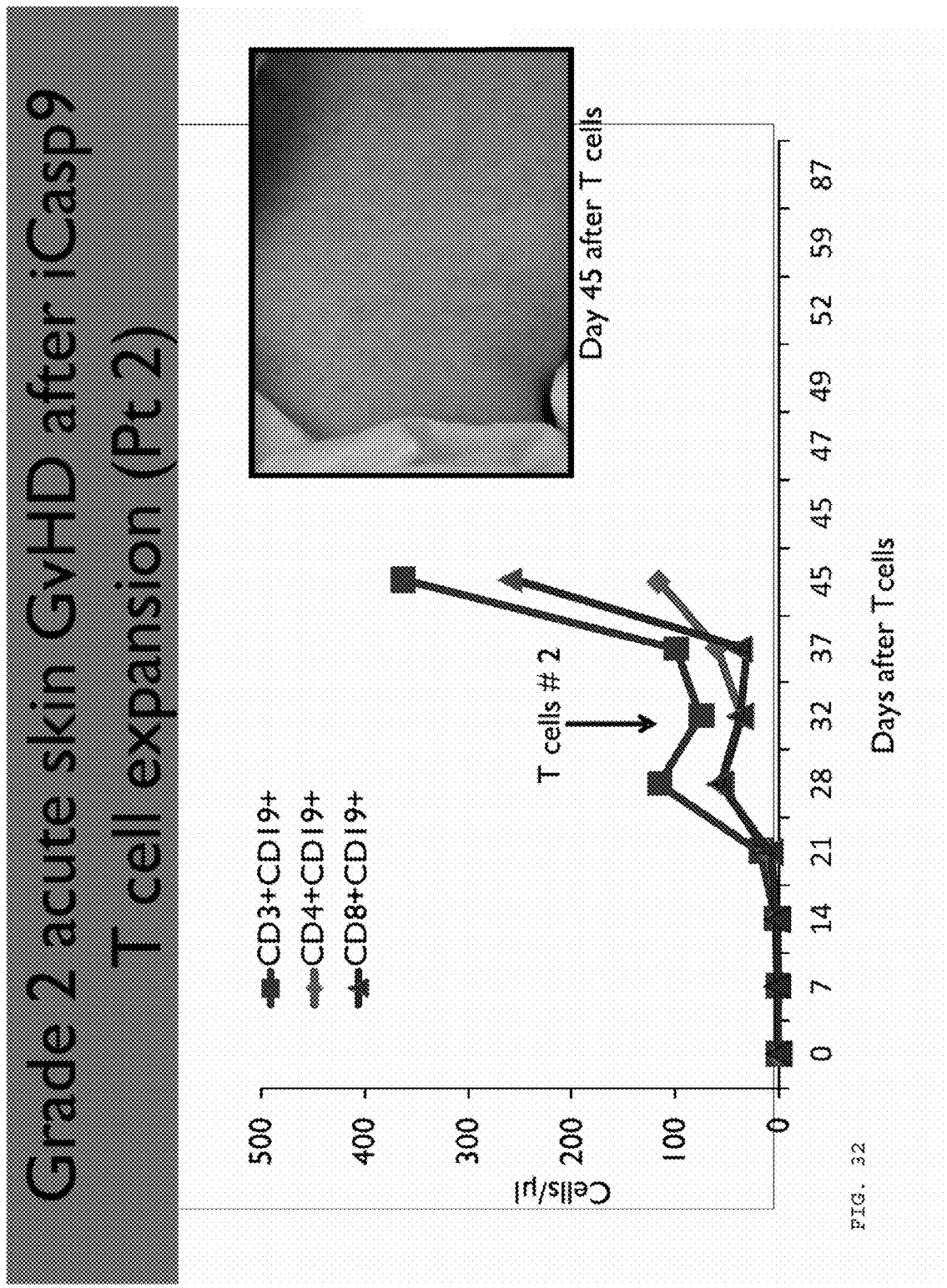
Figure 33:
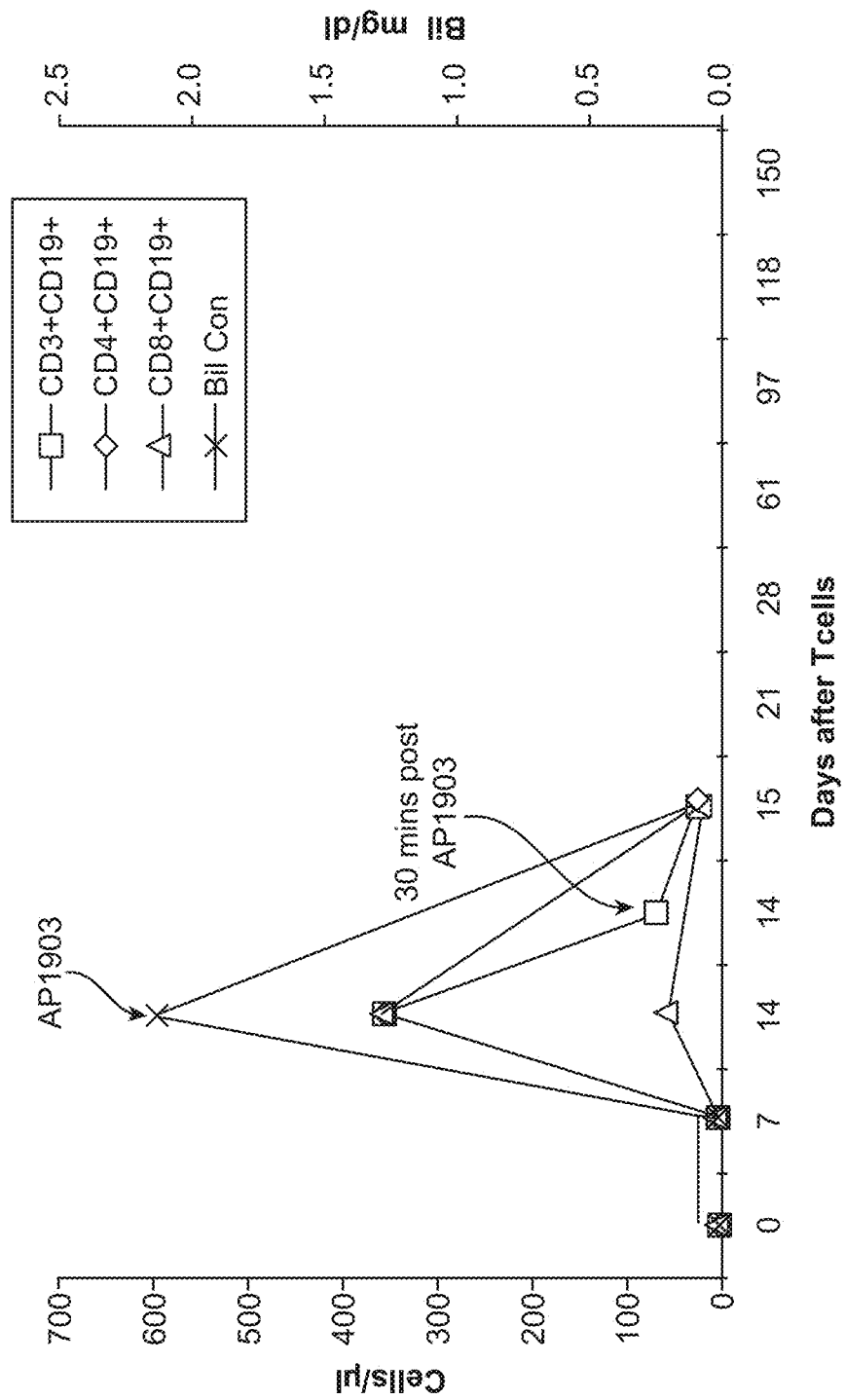
FIGS. 33-34 show the rapid and efficient elimination of iCasp9 T cells after AP1903 (e.g., the CID) is administered to patients.
Figure 34:
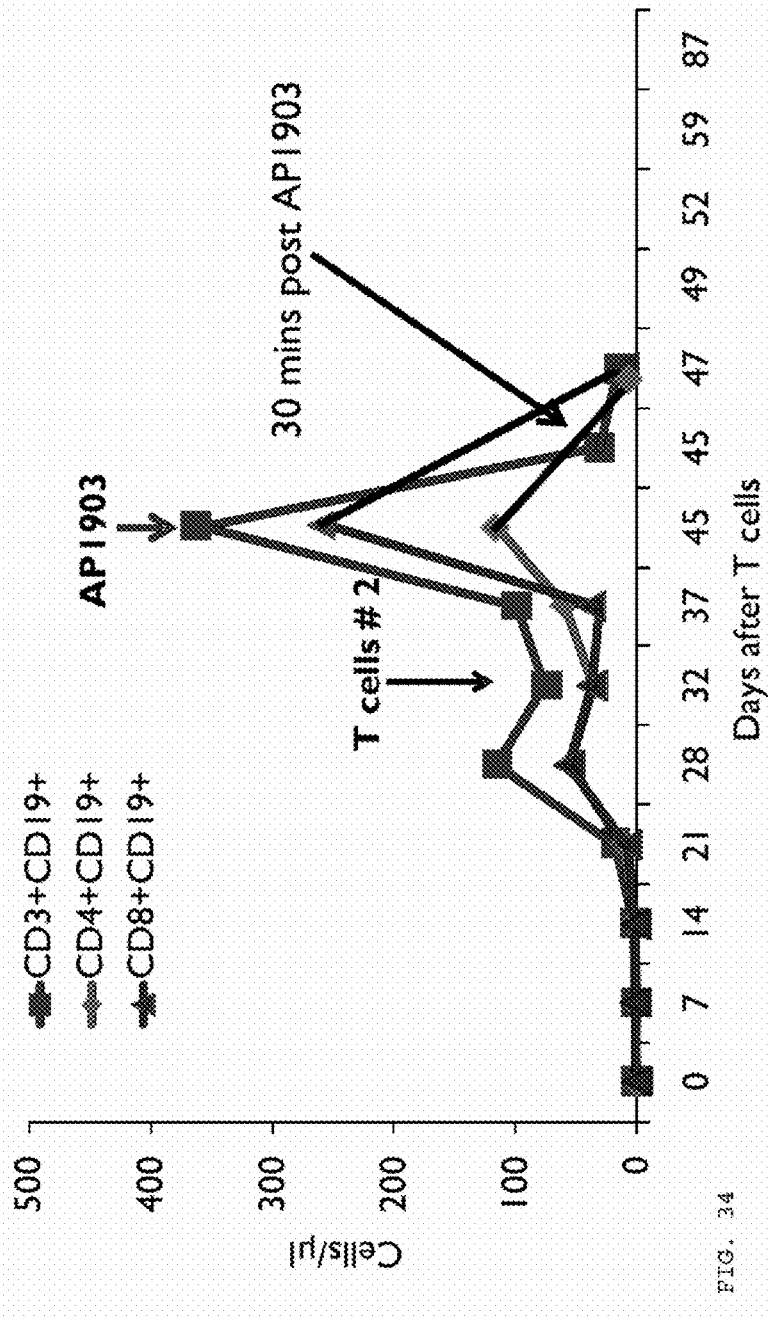
Figure 35A:
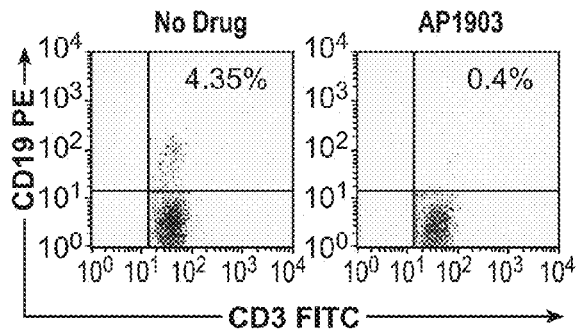
FIGS. 35A-35C provides graphs showing the persistence of drug sensitivity and antiviral function of CD3$^+$ CD19$^+$ precursors after treatment with AP1903 in vivo. (A) CD3$^+$ CD19$^+$ T cells remain within the CD3$^+$ population in the peripheral blood 5 months after treatment with AP1903 (patient 2). These CD3$^+$ CD19$^+$ cells retain sensitivity to AP1903 in vitro as assessed both by reduction of CD3$^+$CD19$^+$ cell number on FACS analysis and (B) by quantitative PCR analysis of the icasp9 gene before and after exposure to the dimerizing drug. (C) CD3$^+$ CD19$^+$ gene-modified T cells collected from patient 2 were responsive to CMV peptide mixtures at 6 days prior to AP1903, but not to negative control surviving peptide mixtures, as shown by the presence of IFN-gamma-positive CD3$^+$ CD19$^+$ T cells in the CMV-stimulated cultures. Assessment of the recovering CD3$^+$CD19$^+$ population at 6 and 14 days after AP1903 infusion to treat GvHD showed the persistence of virus-specific cells in the absence of recurrent GvHD.
Figure 35B:
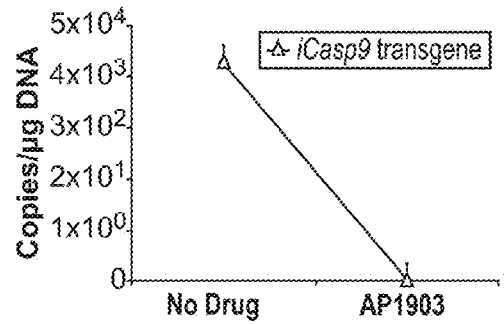
Figure 35C:
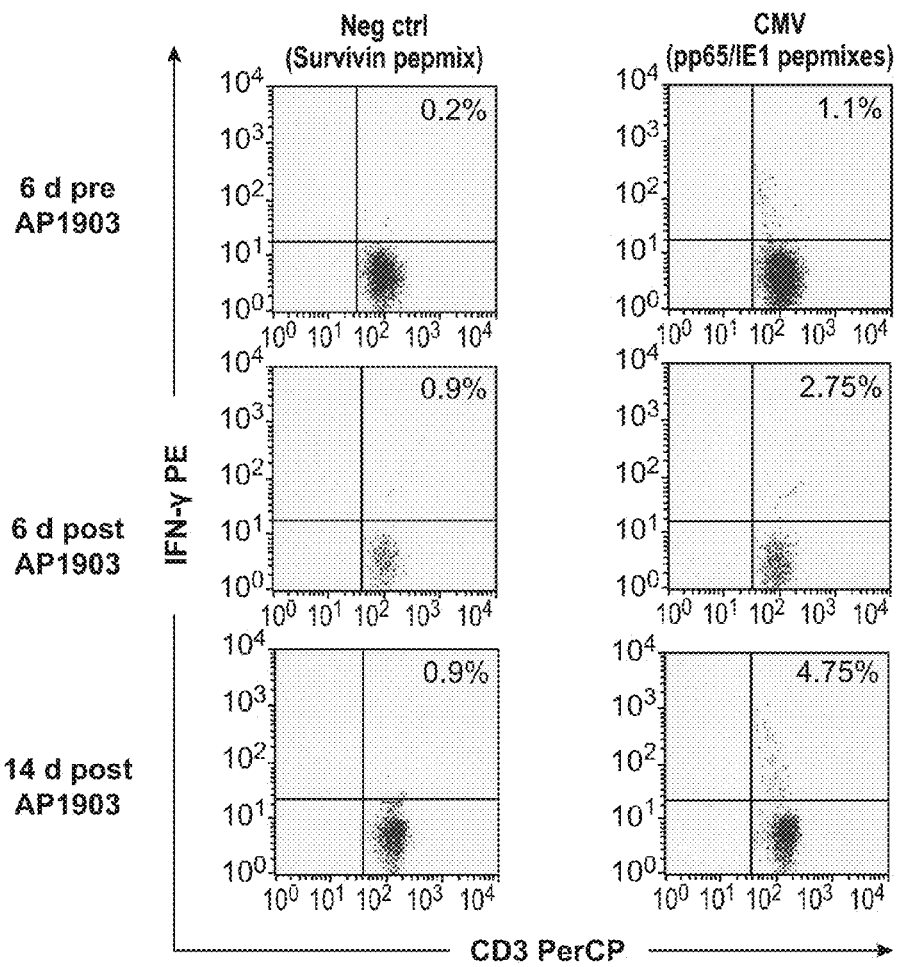
Figure 36:
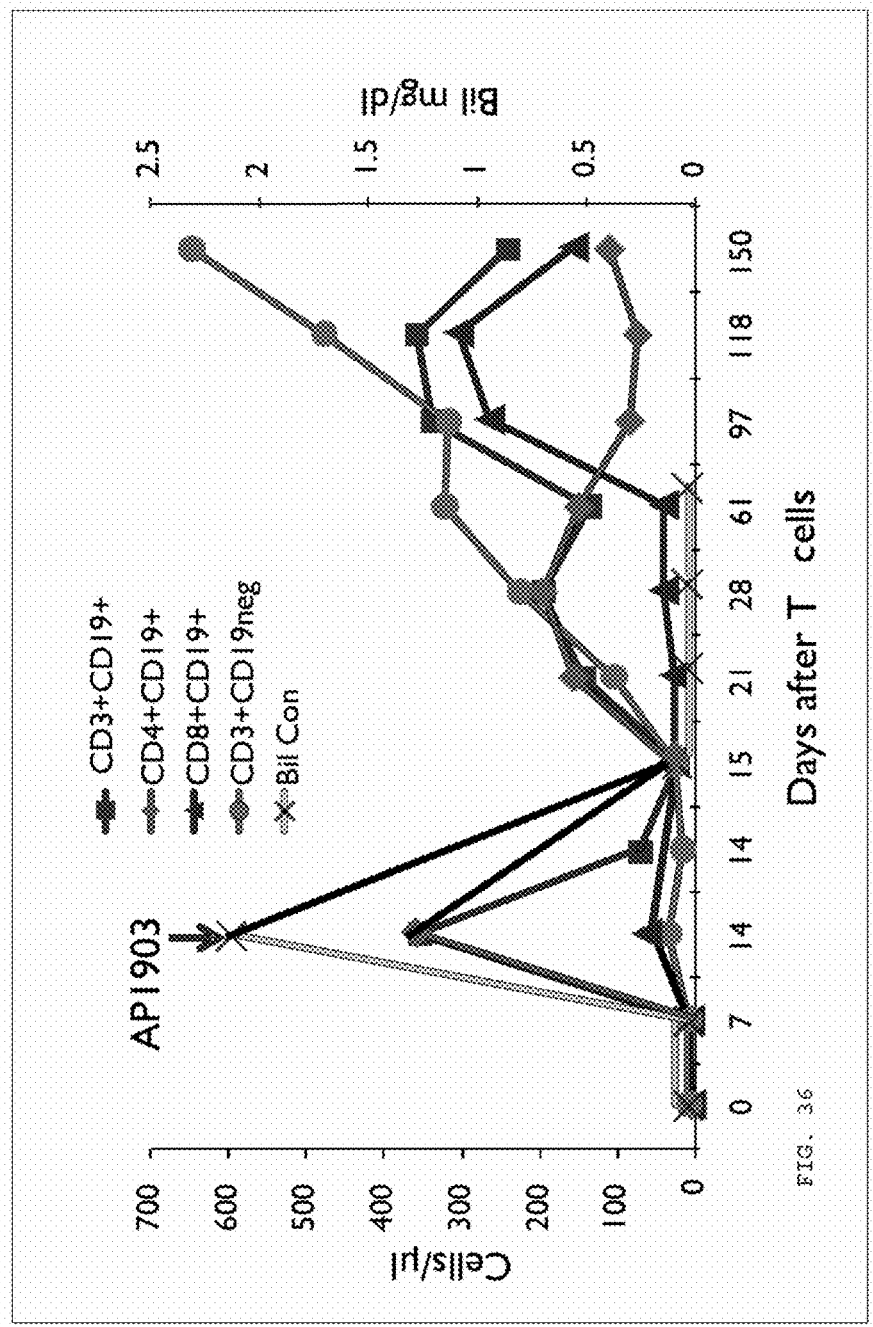
FIG. 36 graphically illustrates that iCasp9 allodepleted cells are able to expand after AP1903 treatment without signs of GvHD.
Figure 37:
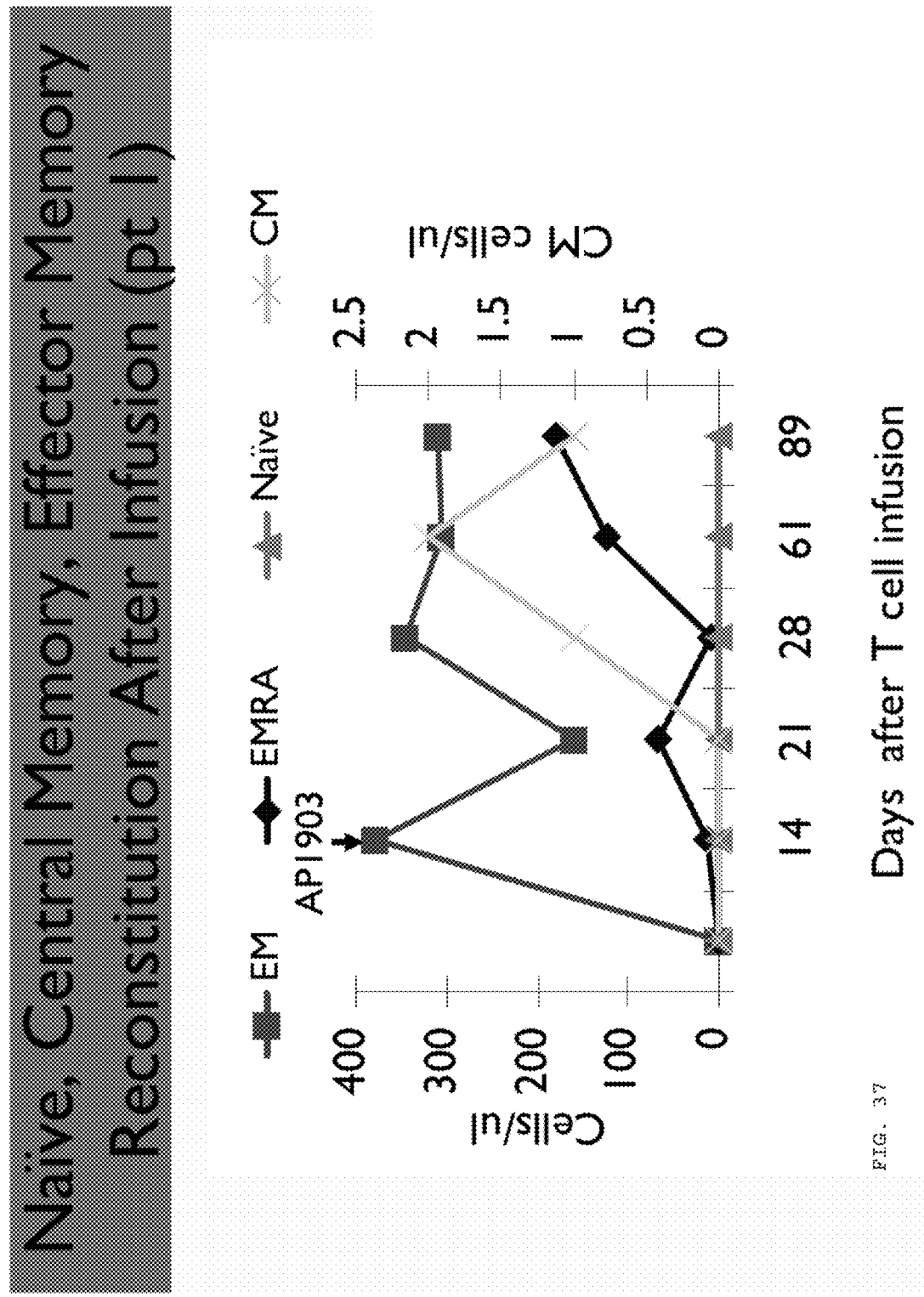
FIG. 37 shows reconstitution of naïve, central memory and effector memory T cell after AP1903 treatment.
Figure 38:
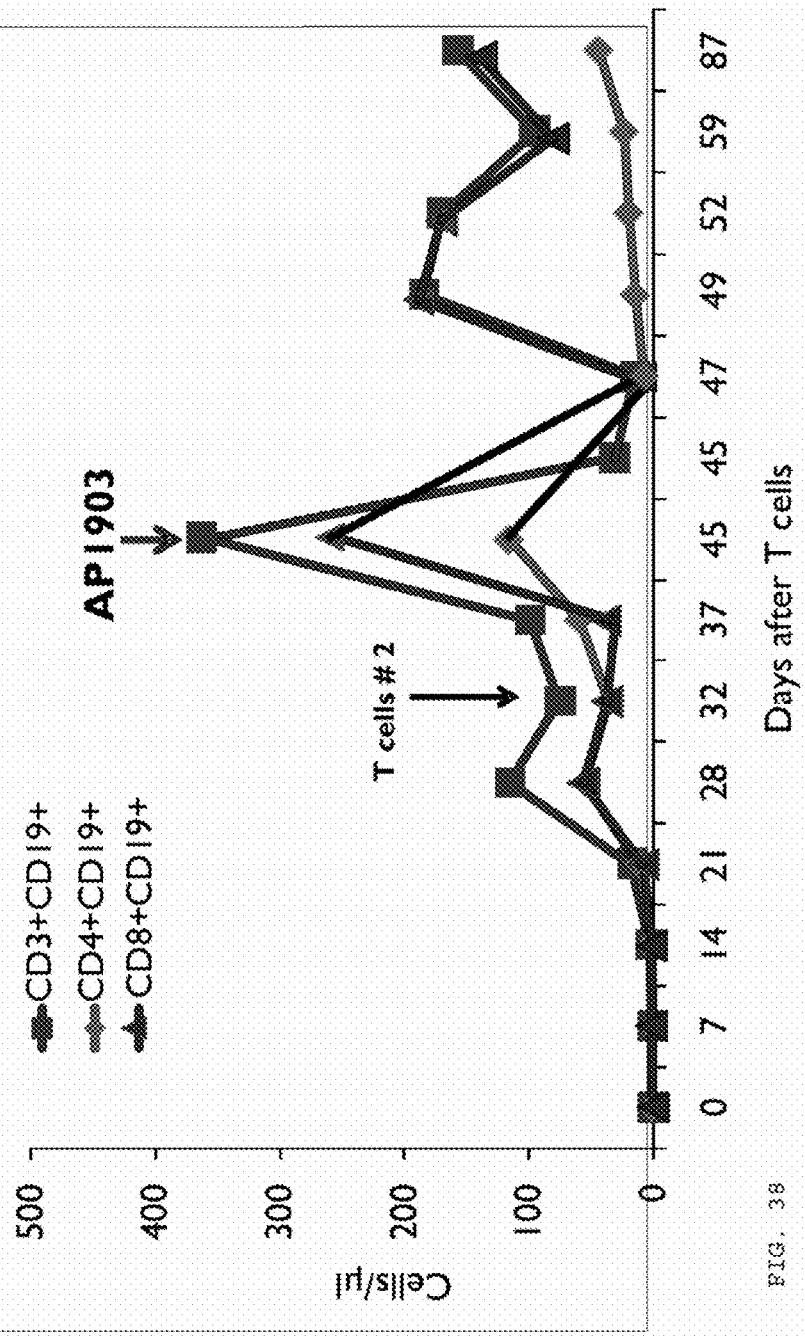
FIG. 38 graphically illustrates that iCasp9 allodepleted cells are able to expand after AP1903 treatment without signs of GvHD.
Figure 39:
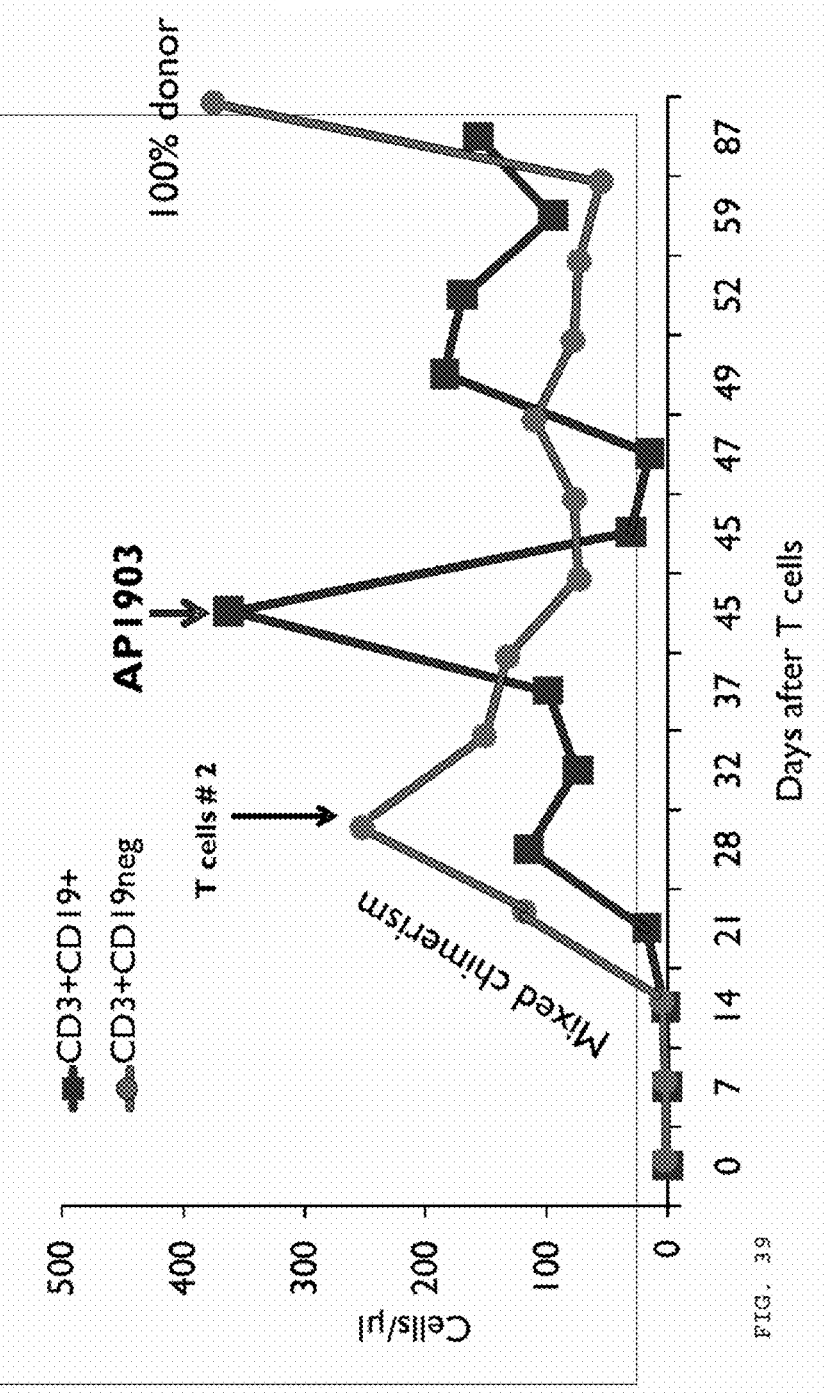
FIG. 39 graphically illustrates iCasp9 allodepleted T cell expansion and restoration of donor chimerism. Further discussion of experimental conditions and results are presented in the Examples.
Figure 40:
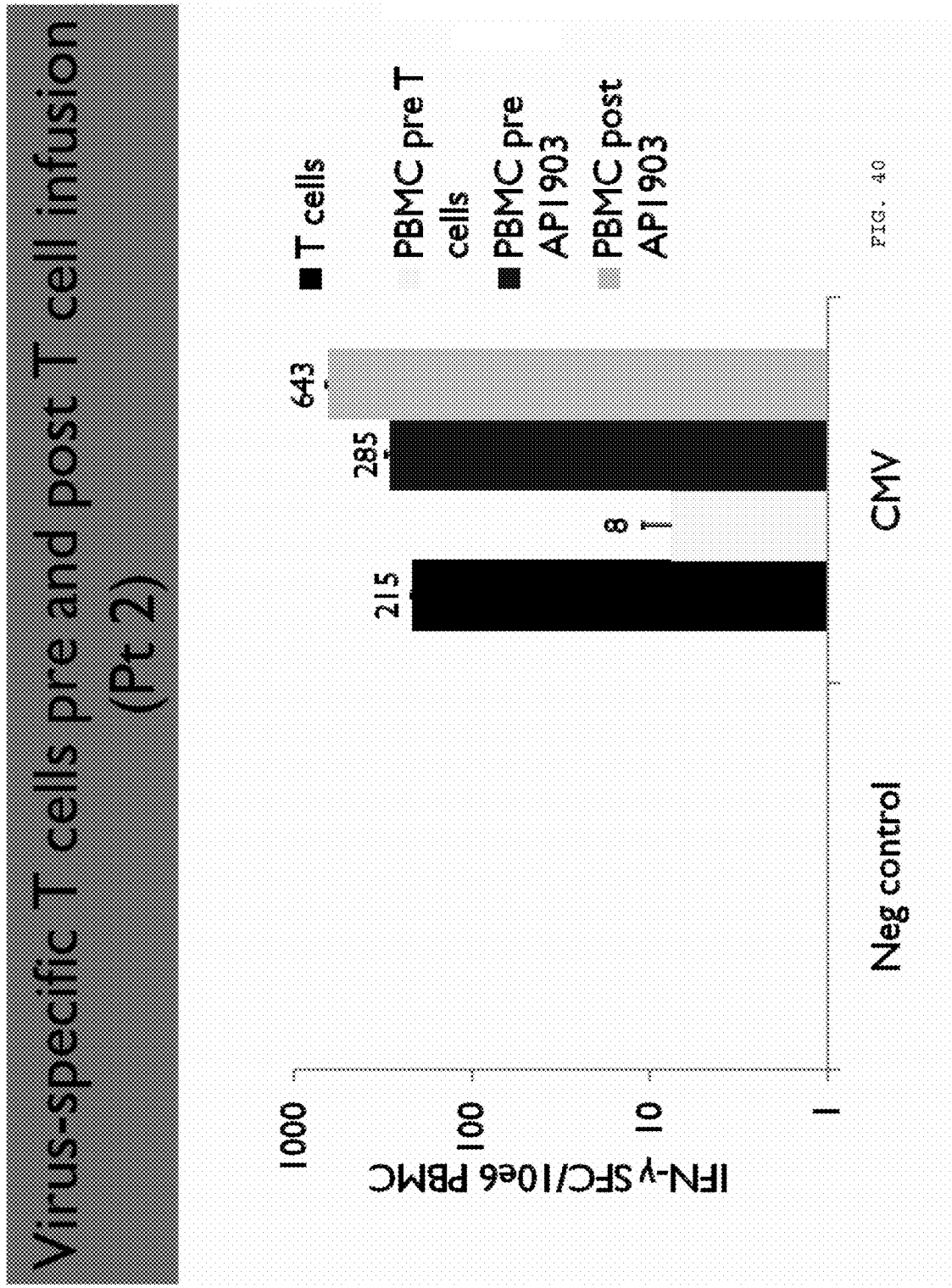
FIG. 40 graphically illustrates virus specific T cells pre and post T cell infusion.
Figure 41:
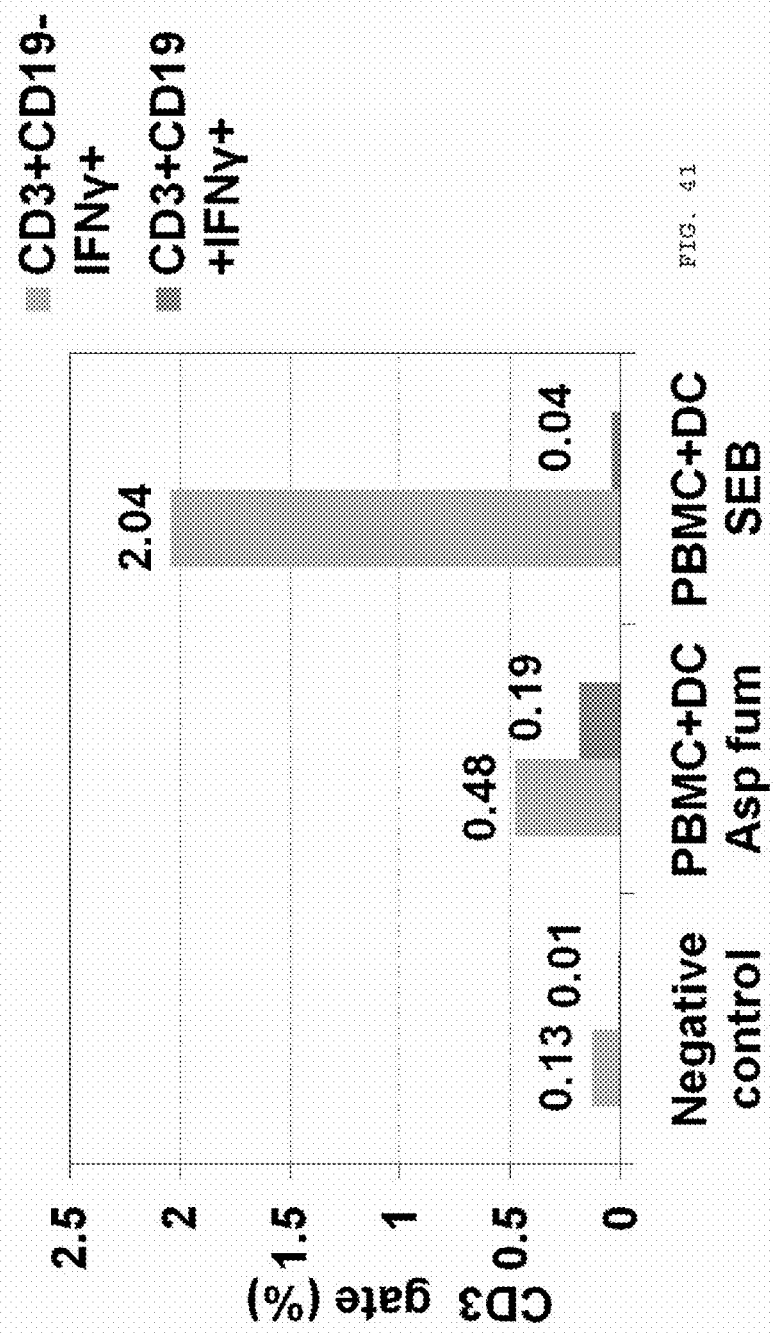
FIG. 41 graphically illustrates the levels of intracellular IFN-g production by Pt PBMC in response to *aspergillus* antigen.
Figure 42:
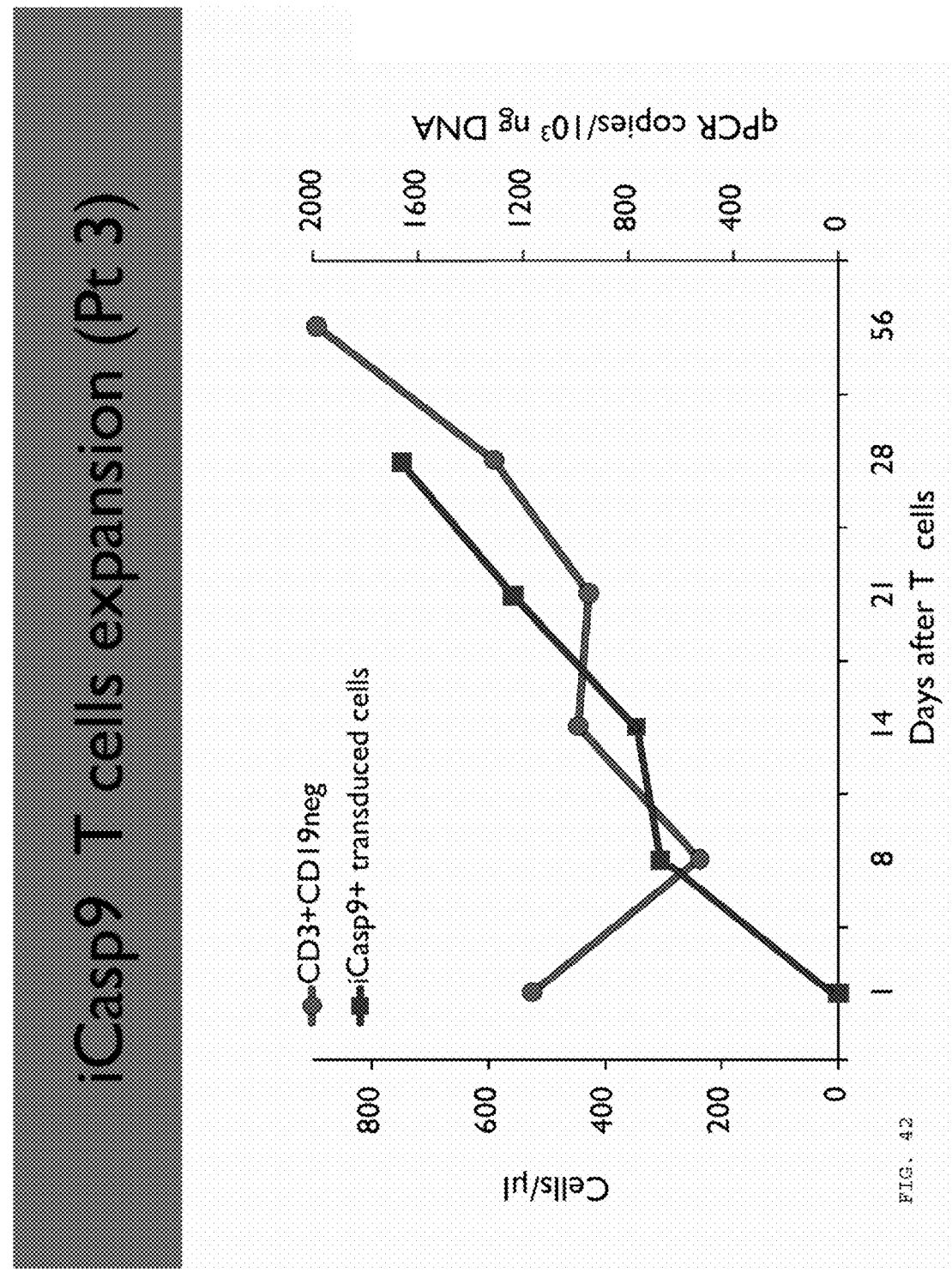
FIG. 42 graphically illustrates iCasp T cells expansion. Further discussion of experimental conditions and results are presented in the Examples.

Infused T cells were detected in vivo by flow cytometry (CD3+ΔCD19+) or qPCR as early as day 7 after infusion, with a maximum fold expansion of 170±5 (day 29±9 after infusion), as illustrated in FIGS. 27, 28, and 29. Two patients developed grade I/II aGVHD (see FIGS. 31-32) and AP1903 administration caused >90% ablation of CD3+ΔCD19+ cells, within 30 minutes of infusion (see FIGS. 30, 33, and 34), with a further log reduction within 24 hours, and resolution of skin and liver aGvHD within 24 hrs (see FIG. 35), showing that iCasp9 transgene was functional in vivo.

Patients with GvHD (dose level 1)

| Patient | SCT to GvHD (days) | T cells to GvHD (days) | GvHD (grade/site) |
|---|---|---|---|
| 1 | 77 | 14 | 2 (liver, skin) |
| 2 | 124 | 45/13 | 2 (skin) |

Ex vivo experiments confirmed this data. Furthermore, the residual allodepleted T cells were able to expand and were reactive to viruses (CMV) and fungi (*Aspergillus fumigatus*) (IFN-γ production), as shown in FIGS. 36-42. These in vivo studies found that a single dose of dimerizer drug can reduce or eliminate the subpopulation of T cells causing GvHD, but can spare virus specific CTLs, which can then re-expand.

Immune Reconstitution

Depending on availability of patient cells and reagents, immune reconstitution studies (Immunophenotyping, T and B cell function) may be obtained at serial intervals after transplant. Several parameters measuring immune reconstitution resulting from iCaspase transduced allodepleted T cells will be analyzed. The analysis includes repeated measurements of total lymphocyte counts, T and CD19 B cell numbers, and FACS analysis of T cell subsets (CD3, CD4, CD8, CD16, CD19, CD27, CD28, CD44, CD62L, CCR7, CD56, CD45RA, CD45RO, alpha/beta and gamma/delta T cell receptors). Depending on the availability of a patients T cells T regulatory cell markers such as CD41CD251FoxP3 also are analyzed. Approximately 10-60 ml of patient blood is taken, when possible, 4 hours after infusion, weekly for 1 month, monthly×9 months, and then at 1 and 2 years. The amount of blood taken is dependent on the size of the recipient and does not exceed 1-2 cc/kg in total (allowing for blood taken for clinical care and study evaluation) at any one blood draw.

Persistence and Safety of Transduced Allodepleted T Cells

The following analysis also was performed on the peripheral blood samples o monitor function, persistence and safety of transduced T-cells at time-points indicated in the study calendar.

Phenotype to detect the presence of transgenic cells

RCR testing by PCR.

Quantitative real-time PCR for detecting retroviral integrants.

RCR testing by PCR is performed pre study, at 3, 6, and 12 months, and then yearly for a total of 15 years. Tissue, cell, and serum samples are archived for use in future studies for RCR as required by the FDA.

Statistical Analysis and Stopping Rules.

The MTD is defined to be the dose which causes grade III/IV acute GVHD in at most 25% of eligible cases. The determination is based on a modified continual reassessment method (CRM) using a logistic model with a cohort of size 2. Three dose groups are being evaluated namely, $1 \times 10^6$, $3 \times 10^6$, $1 \times 10^7$ with prior probabilities of toxicity estimated at 10%, 15%, and 30%, respectively. The proposed CRM design, employs modifications to the original CRM by accruing more than one subject in each cohort, limiting dose escalation to no more than one dose level, and starting patient enrollment at the lowest dose level shown to be safe for non-transduced cells. Toxicity outcome in the lowest dose cohort is used to update the dose-toxicity curve. The next patient cohort is assigned to the dose level with an associated probability of toxicity closest to the target probability of 25%. This process continues until at least 10 patients have been accrued into this dose-escalation study. Depending on patient availability, at most 18 patients may be enrolled into the Phase I trial or until 6 patients have been treated at the current MTD. The final MTD will be the dose with probability closest to the target toxicity rate at these termination points.

Simulations were performed to determine the operating characteristics of the proposed design and compared this with a standard 3+3 dose-escalation design. The proposed design delivers better estimates of the MTD based on a higher probability of declaring the appropriate dose level as the MTD, afforded smaller number of patients accrued at lower and likely ineffective dose levels, and maintained a lower average total number of patients required for the trial. A shallow dose-toxicity curve is expected over the range of doses proposed herein and therefore accelerated dose-escalations can be conducted without comprising patient safety. The simulations performed indicate that the modified CRM design does not incur a larger average number of total toxicities when compared to the standard design (total toxicities equal to 1.9 and 2.1, respectively.).

Grade III/IV GVHD that occurs within 45 days after initial infusion of allodepleted T cells will be factored into the CRM calculations to determine the recommended dose for the subsequent cohort. Real-time monitoring of patient toxicity outcome is performed during the study in order to implement estimation of the dose-toxicity curve and determine dose level for the next patient cohort using one of the pre-specified dose levels.

Treatment limiting toxicities will include
a) grade 4 reactions related to infusion,
b) graft failure (defined as a subsequent decline in the ANC to <5001 mm³ for three consecutive measurements on different days, unresponsive to growth factor therapy that persists for at least 14 days.) occurring within 30 days after infusion of TC-T c) grade 4 nonhematologic and noninfectious adverse events, occurring within 30 days after infusion d) grades 3-4 acute GVHD by 45 days after infusion of TC-T e) treatment-related death occurring within 30 days after infusion GVHD rates are summarized using descriptive statistics along with other measures of safety and toxicity. Likewise, descriptive statistics will be calculated to summarize the clinical and biologic response in patients who receive AP1903 due to great than Grade 1 GVHD.

Several parameters measuring immune reconstitution resulting from iCaspase transduced allodepleted T cells will be analyzed. These include repeated measurements of total lymphocyte counts, T and CD19 B cell numbers, and FACS analysis of T cell subsets (CD3, CD4, CD5, CD16, CD19, CD27, CD44, CD62L, CCR7, CD56, CD45RA, CD45RO, alpha/beta and gamma/delta T cell receptors). If sufficient T cells remain for analysis, T regulatory cell markers such as CD4/CD25/FoxP3 will also be analyzed. Each subject will be measured pre-infusion and at multiple time points post-infusion as presented above.

Descriptive summaries of these parameters in the overall patient group and by dose group as well as by time of measurement will be presented. Growth curves representing measurements over time within a patient will be generated to visualize general patterns of immune reconstitution. The proportion of iCasp9 positive cells will also be summarized at each time point. Pairwise comparisons of changes in these endpoints over time compared to pre-infusion will be implemented using paired t-tests or Wilcoxon signed-ranks test.

Longitudinal analysis of each repeatedly-measured immune reconstitution parameter using the random coefficients model, will be performed. Longitudinal analysis allows construction of model patterns of immune reconstitution per patient while allowing for varying intercepts and slopes within a patient. Dose level as an independent variable in the model to account for the different dose levels received by the patients will also be used. Testing whether there is a significant improvement in immune function over time and estimates of the magnitude of these improvements based on estimates of slopes and its standard error will be possible using the model presented herein. Evaluation of any indication of differences in rates of immune reconstitution across different dose levels of CTLs will also be performed. The normal distribution with an identity link will be utilized in these models and implemented using SAS MIXED procedure. The normality assumption of the immune reconstitution parameters will be assessed and transformations (e.g. log, square root) can be performed, if necessary to achieve normality.

A strategy similar to the one presented above can be employed to assess kinetics of T cell survival, expansion and persistence. The ratio of the absolute T cell numbers with the number of marker gene positive cells will be determined and modeled longitudinally over time. A positive estimate of the slope will indicate increasing contribution of T cells for immune recovery. Virus-specific immunity of the iCasp9 T cells will be evaluated by analysis of the number of T cells releasing IFN gamma based on ex-vivo stimulation virus-specific CTLs using longitudinal models. Separate models will be generated for analysis of EBV, CMV and adenovirus evaluations of immunity.

Finally, overall and disease-free survival in the entire patient cohort will be summarized using the Kaplan-Meier product-limit method. The proportion of patients surviving and who are disease-free at 100 days and 1 year post transplant can be estimated from the Kaplan-Meier curves.

In conclusion, addback of iCasp9+ allodepleted T cells after haplo CD34+SCT allows a significant expansion of functional donor lymphocytes in vivo and a rapid clearance of alloreactive T cells with resolution of aGvHD.

Example 4

In Vivo T Cell Allodepletion

The protocols provided in Examples 1-3 may also be modified to provide for in vivo T cell allodepletion. To extend the approach to a larger group of subjects who might benefit from immune reconstitution without actute GvHD, the protocol may be simplified, by providing for an in vivo method of T cell depletion. In the pre-treatment allodepletion method, as discussed herein, EBV-transformed lymphoblastoid cell lines are first prepared from the recipient, which then act as alloantigen presenting cells. This procedure can take up to 8 weeks, and may fail in extensively pre-treated subjects with malignancy, particularly if they have received rituximab as a component of their initial therapy. Subsequently, the donor T cells are co-cultured with recipient EBV-LCL, and the alloreactive T cells (which express the activation antigen CD25) are then treated with CD25-ricin conjugated monoclonal antibody. This procedure may take many additional days of laboratory work for each subject.

The process may be simplified by using an in vivo method of allodepletion, building on the observed rapid in vivo depletion of alloreactive T cells by dimerizer drug and the sparing of unstimulated but virus/fungus reactive T cells.

If there is development of Grade I or greater acute GvHD, a single dose of dimerizer drug is administered, for example at a dose of 0.4 mg/kg of AP1903 as a 2 hour intravenous infusion. Up to 3 additional doses of dimerizer drug may be administered at 48 hour intervals if acute GvHD persists. In subjects with Grade II or greater acute GvHD, these additional doses of dimerizer drug may be combined with steroids. For patients with persistent GVHD who cannot receive additional doses of the dimerizer due to a Grade III or IV reaction to the dimerizer, the patient may be treated with steroids alone, after either 0 or 1 doses of the dimerizer.

Generation of Therapeutic T cells

Up to 240 ml (in 2 collections) of peripheral blood is obtained from the transplant donor according to the procurement consent. If necessary, a leukapheresis is used to obtain sufficient T cells; (either prior to stem cell mobilization or seven days after the last dose of G-CSF). An extra 10-30 mls of blood may also be collected to test for infectious diseases such as hepatitis and HIV.

Peripheral blood mononuclear cells are be activated using anti-human CD3 antibody (e.g. from Orthotech or Miltenyi) on day 0 and expanded in the presence of recombinant human interleukin-2 (rhIL-2) on day 2. CD3 antibody-activated T cells are transduced by the iCaspase 9 retroviral vector on flasks or plates coated with recombinant Fibronectin fragment CH-296 (Retronectin™, Takara Shuzo, Otsu, Japan). Virus is attached to retronectin by incubating producer supernatant in retronectin coated plates or flasks. Cells are then transferred to virus coated tissue culture devices. After transduction T cells are expanded by feeding them with rhIL-2 twice a week to reach the sufficient number of cells as per protocol.

To ensure that the majority of infused T cells carry the suicide gene, a selectable marker, truncated human CD19

(ΔCD19) and a commercial selection device, may be used to select the transduced cells to >90% purity. Immunomagnetic selection for CD19 may be performed 4 days after transduction. Cells are labeled with paramagnetic microbeads conjugated to monoclonal mouse anti-human CD19 antibodies (Miltenyi Biotech, Auburn, Calif.) and selected on a CliniMacs Plus automated selection device. Depending upon the number of cells required for clinical infusion cells might either be cryopreserved after the CliniMacs selection or further expanded with IL-2 and cryopreserved as soon as sufficient cells have expanded (up to day 14 from product initiation).

Aliquots of cells may be removed for testing of transduction efficiency, identity, phenotype, autonomous growth and microbiological examination as required for final release testing by the FDA. The cells are be cryopreserved prior to administration.

Administration of T Cells

The transduced T cells are administered to patients from, for example, between 30 and 120 days following stem cell transplantation. The cryopreserved T cells are thawed and infused through a catheter line with normal saline. For children, premedications are dosed by weight. Doses of cells may range from, for example, from about $1\times10^4$ cells/Kg to $1\times10^8$ cells/Kg, for example from about $1\times10^5$ cells/Kg to $1\times10^7$ cells/Kg, from about $1\times10^6$ cells/Kg to $5\times10^6$ cells/Kg, from about $1\times10^4$ cells/Kg to $5\times10^6$ cells/Kg, for example, about $1\times10^4$, about $1\times10^5$, about $2\times10^5$, about $3\times10^5$, about $5\times10^5$, $6\times10^5$, about $7\times10^5$, about $8\times10^5$, about $9\times10^5$, about $1\times10^6$, about $2\times10^6$, about $3\times10^6$, about $4\times10^6$, or about $5\times10^6$ cells/Kg.

Treatment of GvHD

Patients who develop grade ≥1 acute GVHD are treated with 0.4 mg/kg AP1903 as a 2-hour infusion. AP1903 for injection may be provided, for example, as a concentrated solution of 2.33 ml in a 3 ml vial, at a concentration of 5 mg/ml, (i.e 10.66 mg per vial). Prior to administration, the calculated dose will be diluted to 100 mL in 0.9% normal saline for infusion. AP1903 for Injection (0.4 mg/kg) in a volume of 100 ml may be administered via IV infusion over 2 hours, using a non-DEHP, non-ethylene oxide sterilized infusion set and an infusion pump.

Sample Treatment Schedule

| Time | Donor | Recipient |
| --- | --- | --- |
| Pre-transplant | Obtain up to 240 of blood or unstimulated leukapheresis from bone marrow transplant donor. Prepare T cells and donor LCLs for later immune reconstitution studies. | |
| Day 0 | Anti-CD3 activation of PBMC | |
| Day 2 | IL-2 feed | |
| Day 3 | Transduction | |
| Day 4 | Expansion | |
| Day 6 | CD19 selection. Cryopreservation (*if required dose is met) | |
| Day 8 | Assess transduction efficiency and iCaspase9 transgene functionality by phenotype. Cryopreservation (*if not yet performed) | |
| Day 10 or Day 12 to Day 14 | Cryopreservation (if not yet performed) | |
| From 30 to 120 days post transplant | | Thaw and infuse T cells 30 to 120 days post stem cell infusion. |

Other methods may be followed for clinical therapy and assessment as provided in, for example, Examples 1-3 herein.

Example 5

Using the iCasp9 Suicide Gene to Improve the Safety of Mesenchymal Stromal Cell Therapies Mesenchymal stromal cells (MSCs) have been infused into hundreds of patients to date with minimal reported deleterious side effects. The long term side effects are not known due to limited follow-up and a relatively short time since MSCs have been used in treatment of disease. Several animal models have indicated that there exists the potential for side effects, and therefore a system allowing control over the growth and survival of MSCs used therapeutically is desirable. The inducible caspase 9 suicide switch expression vector construct presented herein was investigated as a method of eliminating MSC's in vivo and in vitro.

Materials and Methods

MSC isolation

MSCs were isolated from healthy donors. Briefly, post-infusion discarded healthy donor bone marrow collection bags and filters were washed with RPMI 1640 (HyClone, Logan, Utah) and plated on tissue culture flasks in DMEM (Invitrogen, Carlsbad, Calif.) with 10% fetal bovine serum (FBS), 2 mM alanyl-glutamine (Glutamax, Invitrogen), 100 units/mL penicillin and 100 µg/mL streptomycin (Invitrogen). After 48 hours, the supernatant was discarded and the cells were cultured in complete culture medium (CCM): α-MEM (Invitrogen) with 16.5% FBS, 2 mM alanyl-glutamine, 100 units/mL penicillin and 100 µg/mL streptomycin. Cells were grown to less then 80% confluence and replated at lower densities as appropriate.

Immunophenotyping

Phycoerythrin (PE), fluorescein isothiocyanate (FITC), peridinin chlorophyll protein (PerCP) or allophycocyanin (APC)-conjugated CD14, CD34, CD45, CD73, CD90, CD105 and CD133 monoclonal antibodies were used to stain MSCs. All antibodies were from Becton Dickinson-Pharmingen (San Diego, Calif.), except where indicated. Control samples labeled with an appropriate isotype-matched antibody were included in each experiment. Cells were analyzed by fluorescence-activated cell sorting FACScan (Becton Dickinson) equipped with a filter set for 4 fluorescence signals.

Differentiation Studies In Vitro

Adipocytic differentiation. MSCs ($7.5\times10^4$ cells) were plated in wells of 6-well plates in NH AdipoDiff Medium (Miltenyi Biotech, Auburn, Calif.). Medium was changed every third day for 21 days. Cells were stained with Oil Red O solution (obtained by diluting 0.5% w/v Oil Red O isopropanol with water at a 3:2 ratio), after fixation with 4% formaldehyde in phosphate buffered saline (PBS).

Osteogenic differentiation. MSCs ($4.5\times10^4$ cells) were plated in 6-well plates in NH OsteoDiff Medium (Miltenyi Biotech). Medium was changed every third day for 10 days. Cells were stained for alkaline phosphatase activity using Sigma Fast BCIP/NBT substrate (Sigma-Aldrich, St. Louis, Mo.) as per manufacturer instructions, after fixation with cold methanol.

Chondroblastic differentiation. MSC pellets containing $2.5\times10^5$ to $5\times10^5$ cells were obtained by centrifugation in 15 mL or 1.5 mL polypropylene conical tubes and cultured in NH ChondroDiff Medium (Miltenyi Biotech). Medium was changed every third day for a total of 24 days. Cell pellets were fixed in 4% formalin in PBS and processed for routine paraffin sectioning. Sections were stained with alcian blue or using indirect immunofluorescence for type II collagen (mouse anti-collagen type II monoclonal antibody MAB8887, Millipore, Billerica, Mass.) after antigen retrieval with pepsin (Thermo Scientific, Fremont, Calif.).

iCasp9-ΔCD19 Retrovirus Production and Transduction of MSCs

The SFG.iCasp9.2A.ΔCD19 (iCasp-ΔCD19) retrovirus consists of iCasp9 linked, via a cleavable 2A-like sequence, to truncated human CD19 (ΔCD19). As noted above, iCasp9 is a human FK506-binding protein (FKBP12) with an F36V mutation, which increases the binding affinity of the protein to a synthetic homodimerizer (AP20187 or AP1903), connected via a Ser-Gly-Gly-Gly-Ser linker (SEQ ID NO: 21) to human caspase 9, whose recruitment domain (CARD) has been deleted, its function replaced by FKBP12.

The 2A-like sequence encodes a 20 amino acid peptide from Thosea Asigna insect virus, which mediates more than 99% cleavage between a glycine and terminal proline residue, to ensure separation of iCasp9 and ΔCD19 upon translation. ΔCD19 consists of human CD19 truncated at amino acid 333, which removes all conserved intracytoplasmic tyrosine residues that are potential sites for phosphorylation. A stable PG13 clone producing Gibbon ape leukemia virus (Gal-V) pseudotyped retrovirus was made by transiently transfecting Phoenix Eco cell line (ATCC product #SD3444; ATCC, Manassas, Va.) with SFG.iCasp9.2A.ΔCD19, which yielded Eco-pseudotyped retrovirus. The PG13 packaging cell line (ATCC) was transduced 3 times with Eco-pseudotyped retrovirus to generate a producer line that contained multiple SFG.iCasp9.2A.ΔCD19 proviral integrants per cell. Single-cell cloning was performed, and the PG13 clone that produced the highest titer was expanded and used for vector production. Retroviral supernatant was obtained via culture of the producer cell lines in IMDM (Invitrogen) with 10% FBS, 2 mM alanyl-glutamine, 100 units/mL penicillin and 100 µg/mL streptomycin. Supernatant containing the retrovirus was collected 48 and 72 hours after initial culture. For transduction, approximately $2 \times 10^4$ MSCs/cm$^2$ were plated in CM in 6-well plates, T75 or T175 flasks. After 24 hours, medium was replaced by viral supernatant diluted 10-fold together with polybrene (final concentration 5 µg/mL) and the cells were incubated at 37° C. in 5% CO2 for 48 hours, after which cells were maintained in complete medium.

Cell Enrichment

For inducible iCasp9-ΔCD19-positive MSC selection for in vitro experiments, retrovirally transduced MSC were enriched for CD19-positive cells using magnetic beads (Miltenyi Biotec) conjugated with anti-CD19 (clone 4G7), per manufacturer instructions. Cell samples were stained with PE- or APC-conjugated CD19 (clone SJ25C1) antibody to assess the purity of the cellular fractions.

Apoptosis Studies In Vitro

Undifferentiated MSCs. The chemical inducer of dimerization (CID) (AP20187; ARIAD Pharmaceuticals, Cambridge, Mass.) was added at 50 nM to iCasp9-transduced MSCs cultures in complete medium. Apoptosis was evaluated 24 hours later by FACS analysis, after cell harvest and staining with annexin V-PE and 7-AAD in annexin V binding buffer (BD Biosciences, San Diego, Calif.). Control iCasp9-transduced MSCs were maintained in culture without exposure to CID.

Differentiated MSCs. Transduced MSCs were differentiated as presented above. At the end of the differentiation period, CID was added to the differentiation media at 50 nM. Cells were stained appropriately for the tissue being studied, as presented above, and a contrast stain (methylene azur or methylene blue) was used to evaluate the nuclear and cytoplasmic morphology. In parallel, tissues were processed for terminal deoxynucleotidyl-transferase dUTP nick end labeling (TUNEL) assay as per manufacturer instructions (In Situ Cell Death Detection Kit, Roche Diagnostics, Mannheim, Germany). For each time point, four random fields were photographed at a final magnification of 40x and the images were analyzed with ImageJ software version 1.43o (NIH, Bethesda, Md.). Cell density was calculated as the number of nuclei (DAPI positivity) per unit of surface area (in mm$^2$). The percentage of apoptotic cells was determined as the ratio of the number of nuclei with positive TUNEL signal (FITC positivity) to the total number of nuclei. Controls were maintained in culture without CID.

In Vivo Killing Studies in Murine Model

All mouse experiments were performed in accordance with the Baylor College of Medicine animal husbandry guidelines. To assess the persistence of modified MSCs in vivo, a SCID mouse model was used in conjunction with an in vivo imaging system. MSCs were transduced with retroviruses coding for the enhanced green fluorescent protein-firefly luciferase (eGFP-FFLuc) gene alone or together with the iCasp9-ΔCD19 gene. Cells were sorted for eGFP positivity by fluorescence activated cell sorting using a MoFlo flow cytometer (Beckman Coulter, Fullerton, Calif.). Doubly transduced cells were also stained with PE-conjugated anti-CD19 and sorted for PE-positivity. SCID mice (8-10 weeks old) were injected subcutaneously with $5 \times 10^5$ MSCs with and without iCasp9-ΔCD19 in opposite flanks. Mice received two intraperitoneal injections of 50 µg of CID 24 hours apart starting a week later. For in vivo imaging of MSCs expressing eGFP-FFLuc, mice were injected intraperitoneally with D-luciferin (150 mg/kg) and analyzed using the Xenogen-IVIS Imaging System. Total luminescence (a measurement proportional to the total labeled MSCs deposited) at each time point was calculated by automatically defining regions-of-interest (ROIs) over the MSC implantation sites. These ROIs included all areas with luminescence signals at least 5% above background. Total photon counts were integrated for each ROI and an average value calculated. Results were normalized so that time zero would correspond to 100% signal.

In a second set of experiments, a mixture of $2.5 \times 10^6$ eGFP-FFLuc-labeled MSCs and $2.5 \times 10^6$ eGFP-FFLuc-labeled, iCasp9-ΔCD19-transduced MSCs was injected subcutaneously in the right flank, and the mice received two intraperitoneal injections of 50 µg of CID 24 h apart starting 7 days later. At several time points after CID injection, the subcutaneous pellet of MSCs was harvested using tissue luminescence to identify and collect the whole human specimen and to minimize mouse tissue contamination. Genomic DNA was then isolated using QIAmp® DNA Mini (Qiagen, Valencia, Calif.). Aliquots of 100 ng of DNA were used in a quantitative PCR (qPCR) to determine the number of copies of each transgene using specific primers and probes (for the eGFP-FFLuc construct: forward primer 5'-TCCGCCCTGAG-CAAAGAC-3' (SEQ ID NO: 24), reverse 5'-ACGAACTC-CAGCAGGACCAT-3' (SEQ ID NO: 25), probe 5' FAM, 6-carboxyfluorescein-ACGAGAAGCGCGATC-3' (SEQ ID NO: 26) MGBNFQ, minor groove binding non-fluorescent quencher; iCasp9-ΔCD19: forward 5'-CTGGAATCTG-GCGGTGGAT-3' (SEQ ID NO: 27), reverse 5'-CAAACTCT-CAAGAGCACCGACAT-3' (SEQ ID NO: 28), probe 5' FAM-CGGAGTCGACGGATT-3' MGBNFQ (SEQ ID NO: 29)). Known numbers of plasmids containing single copies of each transgene were used to establish standard curves. It was determined that approximately 100 ng of DNA isolated from "pure" populations of singly eGFP-FFLuc- or doubly eGFP- FFLuc- and iCasp9-transduced MSCs had similar numbers of eGFP-FFLuc gene copies (approximately $3.0 \times 10^4$), as well as zero and $1.7 \times 10^3$ of iCasp9-ΔCD19 gene copies, respectively.

Untransduced human cells and mouse tissues had zero copies of either gene in 100 ng of genomic DNA. Because the copy number of the eGFP gene is the same on identical amounts of DNA isolated from either population of MSCs (iCasp9-negative or positive), the copy number of this gene in DNA isolated from any mixture of cells will be proportional to the total number of eGFP-FFLuc-positive cells (iCasp9-positive plus negative MSCs). Moreover, because iCasp9-negative tissues do not contribute to the iCasp9 copy number, the copy number of the iCasp9 gene in any DNA sample will be proportional to the total number of iCasp9-positive cells. Therefore, if G is the total number of GFP-positive and iCasp9-negative cells and C the total number of GFP-positive and iCasp9-positive cells, for any DNA sample then $N_{eGFP}=g\cdot(C+G)$ and $N_{icasp9}=k\cdot C$, where N represents gene copy number and g and k are constants relating copy number and cell number for the eGFP and iCasp9 genes, respectively. Thus $N_{icasp9}/N_{eGFP}=(k/g)\cdot[C/(C+G)]$, i.e., the ratio between iCasp9 copy number and eGFP copy number is proportional to the fraction of doubly transduced (iCasp9-positive) cells among all eGFP positive cells. Although the absolute values of $N_{icasp9}$ and $N_{eGFP}$ will decrease with increasing contamination by murine cells in each MSC explant, for each time point the ratio will be constant regardless of the amount of murine tissue included, since both types of human cells are physically mixed. Assuming similar rates of spontaneous apoptosis in both populations (as documented by in vitro culture) the quotient between $N_{icasp9}/N_{eGFP}$ at any time point and that at time zero will represent the percentage of surviving iCasp9-positive cells after exposure to CID. All copy number determinations were done in triplicate.

Statistical Analysis

Paired 2-tailed Student's t-test was used to determine the statistical significance of differences between samples. All numerical data are represented as mean±1 standard deviation.

Results

Figures 15A, 15B:
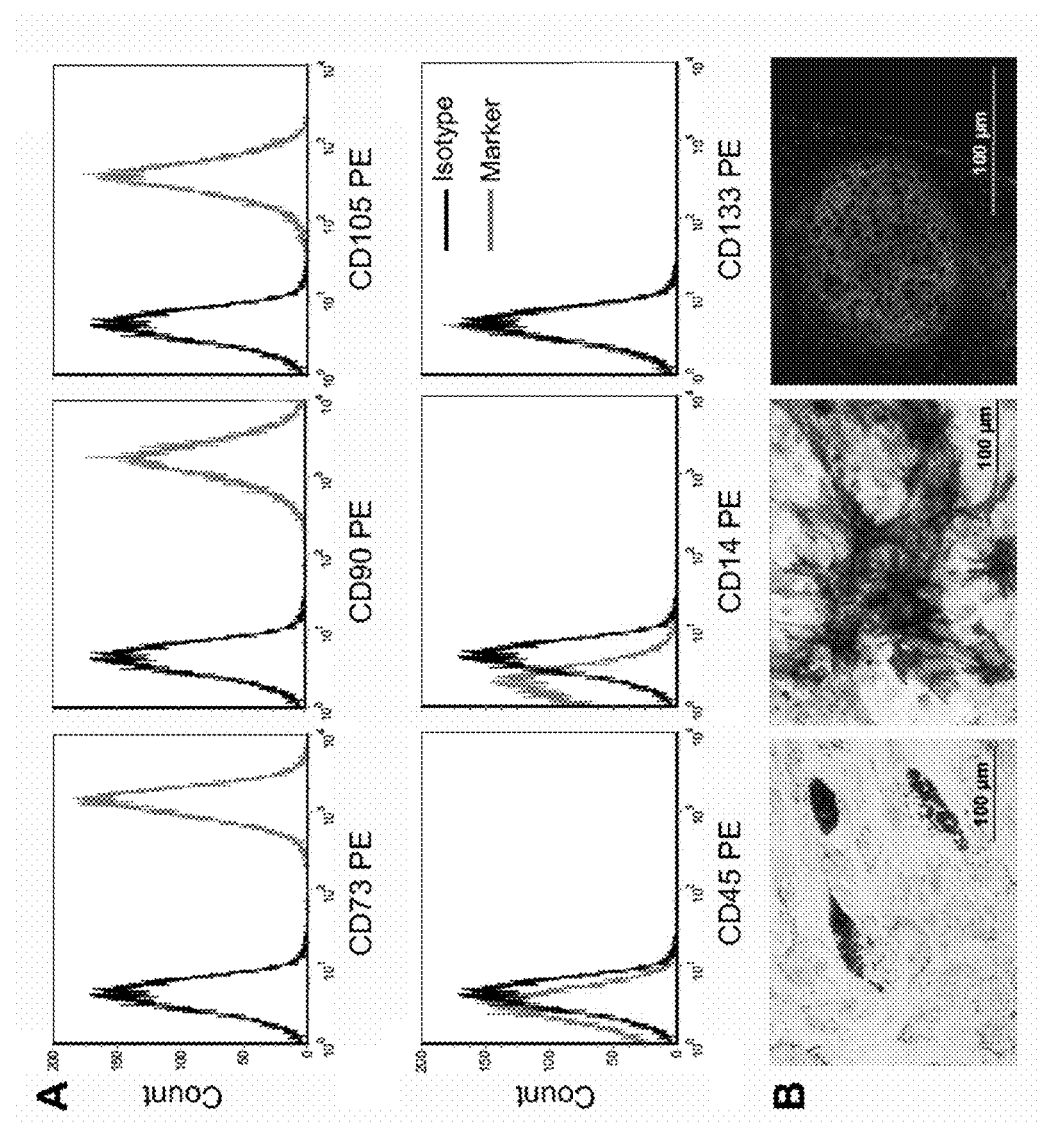
FIGS. 15A and 15B illustrate an analysis of mesenchymal stromal cells (MSCs) from healthy individuals.

MSCs are Readily Transduced with iCasp9-ΔCD19 and Maintain their Basic Phenotype Flow cytometric analysis of MSCs from 3 healthy donors showed they were uniformly positive for CD73, CD90 and CD105 and negative for the hematopoietic markers CD45, CD14, CD133 (FIG. 15A) and CD34. The mononuclear adherent fraction isolated from bone marrow was homogenously positive for CD73, CD90 and CD105 and negative for hematopoietic markers. The differentiation potential, of isolated MSCs, into adipocytes, osteoblasts and chondroblasts was confirmed in specific assays (see FIG. 15B), demonstrating that these cells are bona fide MSCs. FIG. 15B illustrates the results of differentiation studies, the isolated MSCs were able to differentiate into adipocytes (left, oil red and methylene blue), osteoblasts (center, alkaline phosphatase-bromochloroindolyl phosphate/nitroblue tetrazolium and methylene blue) and chondroblasts (right, anti-type II collagen antibody-Texas red and DAPI) when cultured in appropriate media.

Figures 16A, 16B:
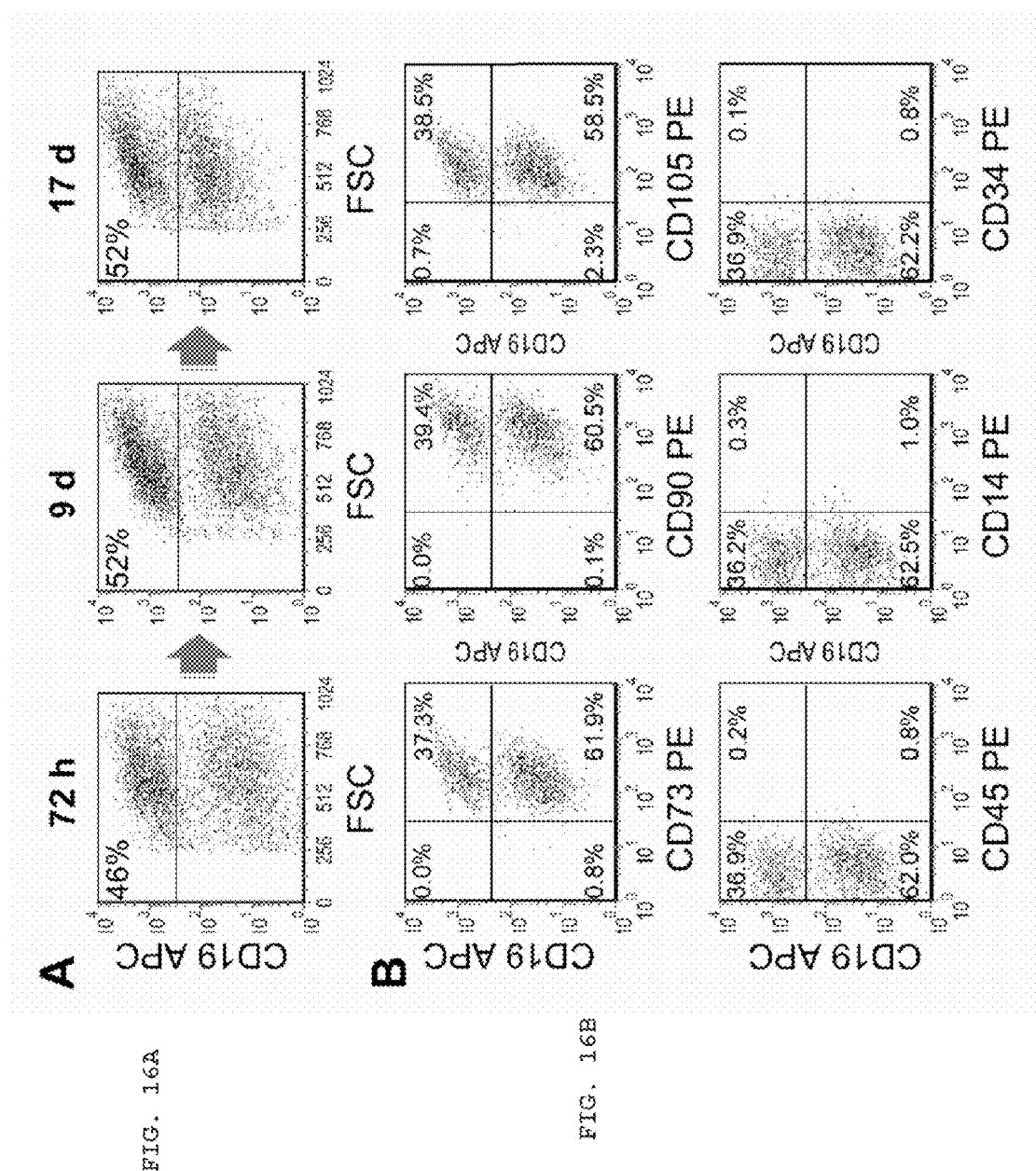
FIGS. 16A and 16B illustrate the results of experiments performed to show that human MSCs are readily transformed with iCasp9-ΔCD19 and maintain their phenotype.
Figures 17A, 17B:
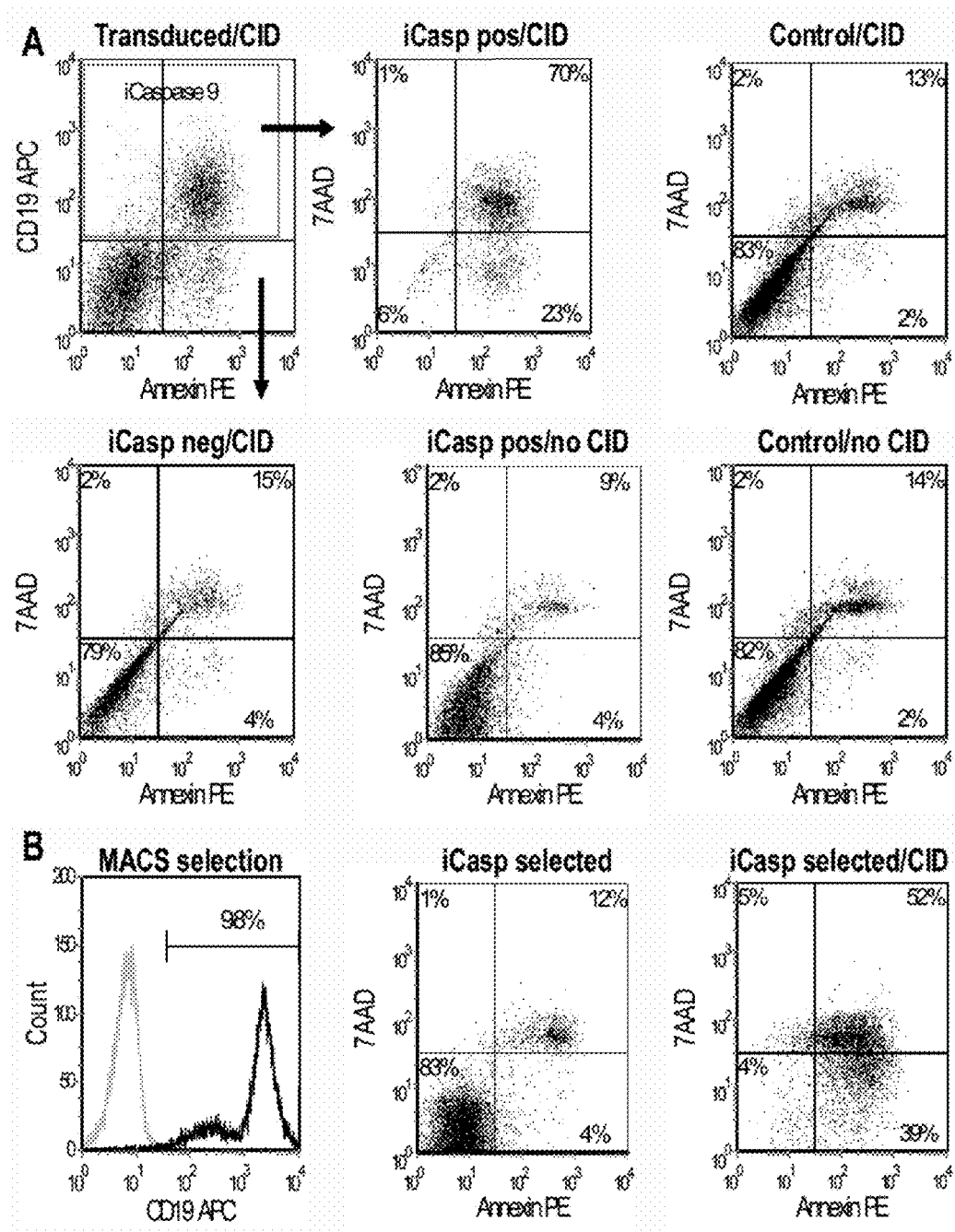
FIGS. 17A and 17B illustrate the results of experiments performed to show that human MSCs expressing iCasp9 are selectively driven to apoptosis in vitro after exposure to the CID.

Early passage MSCs were transduced with an iCasp9-ΔCD19 retroviral vector, encoding an inducible form of caspase 9. Under optimal single transduction conditions, 47±6% of the cells expressed CD19, a truncated form of which is transcribed in cis with iCasp9, serving as a surrogate for successful transduction and allowing selection of transduced cells. The percentage of cells positive for CD19 was stable for more than two weeks in culture, suggesting no deleterious or growth advantageous effects of the construct on MSCs, as shown in FIG. 16A. FIG. 9A illustrates the results of MSCs that underwent a single round of transduction with iCasp9-ΔCD19 retrovirus. The percentage of CD19-positive cells, a surrogate for successful transduction with iCasp9, remains constant for more than 2 weeks. To further address the stability of the construct, a population of iCasp9-positive cells purified by a fluorescence activated cell sorter (FACS) was maintained in culture: no significant difference in the percentage of CD19-positive cells was observed over six weeks (96.5±1.1% at baseline versus 97.4±0.8% after 43 days, P=0.46). The phenotype of the iCasp9-CD19-positive cells was otherwise substantially identical to that of untransduced cells, with virtually all cells positive for CD73, CD90 and CD105 and negative for hematopoietic markers, as illustrated in FIG. 16B), confirming that the genetic manipulation of MSCs did not modify their basic characteristics.

iCasp9-ΔCD19 Transduced MSCs Undergo Selective Apoptosis after Exposure to CID In Vitro The proapoptotic gene product iCasp9 can activated by a small chemical inducer of dimerization (CID), AP20187, an analogue of tacrolimus that binds the FK506-binding domain present in the iCasp9 product. Non-transduced MSCs have a spontaneous rate of apoptosis in culture of approximately 18% (±7%) as do iCasp9-positive cells at baseline (15±6%, P=0.47). Addition of CID (50 nM) to MSC cultures after transduction with iCasp9-ΔCD19 results in the apoptotic death of more than 90% of iCasp9-positive cells within 24 hrs (93±1%, P<0.0001), while iCasp9-negative cells retain an apoptosis index similar to that of non-transduced controls (20±7%, P=0.99 and P=0.69 vs. non-transduced controls with or without CID respectively) (see FIGS. 17A and 70B). After transduction of MSCs with iCasp9, the chemical inducer of dimerization (CID) was added at 50 nM to cultures in complete medium. Apoptosis was evaluated 24 hours later by FACS analysis, after cell harvest and staining with annexin V-PE and 7-AAD. Ninety-three percent of the iCasp9-CD19-positive cells (iCasp pos/CID) became annexin positive versus only 19% of the negative population (iCasp neg/CID), a proportion comparable to non-transduced control MSC exposed to the same compound (Control/CID, 15%) and to iCasp9-CD19-positive cells unexposed to CID (iCasp pos/no CID, 13%), and similar to the baseline apoptotic rate of non-transduced MSCs (Control/no CID, 16%). Magnetic immunoselection of iCap9-CD19-positive cells can be achieved to high degree of purity. More than 95% of the selected cells become apoptotic after exposure to CID.

Figure 18:
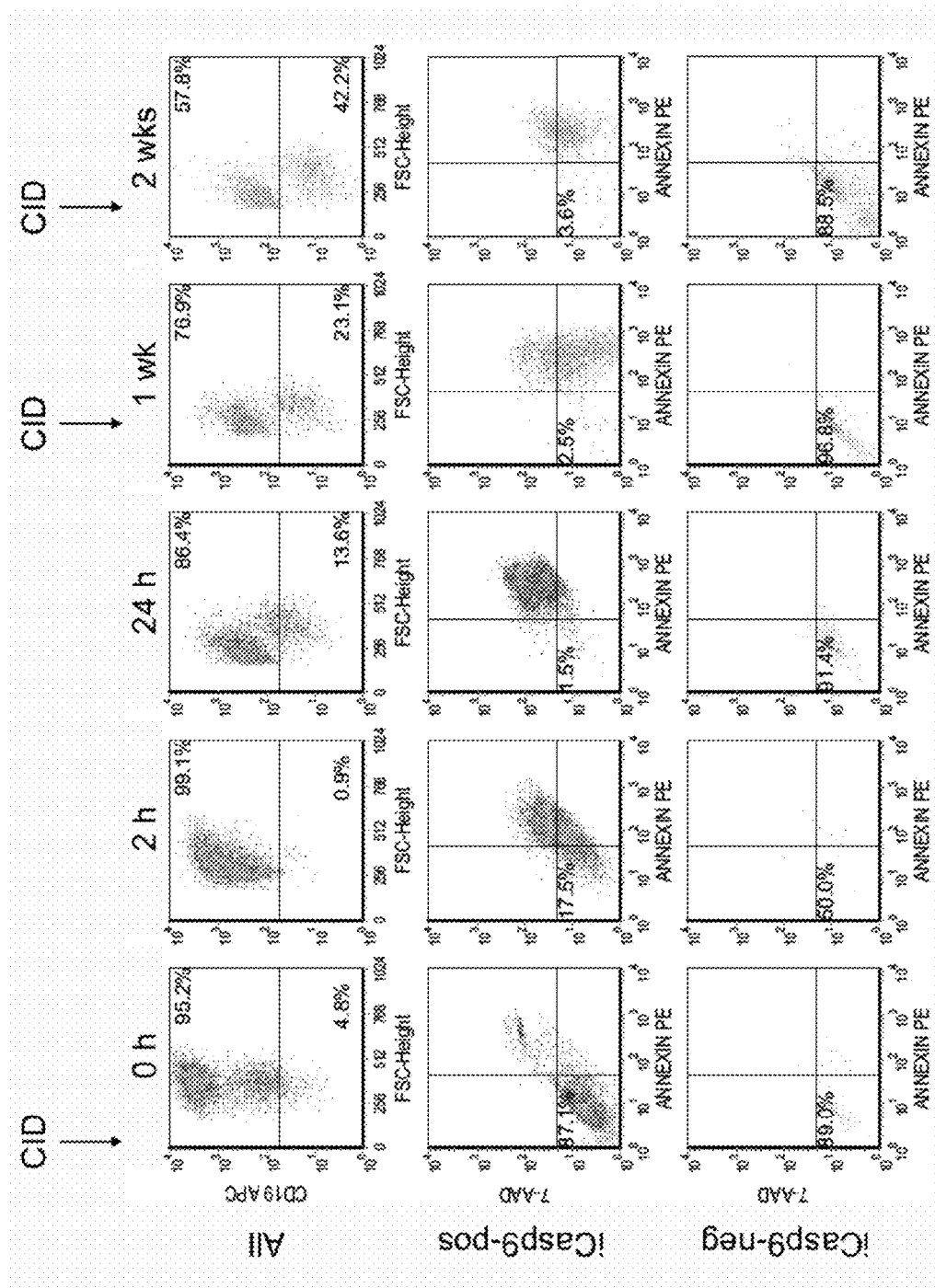
FIG. 18 illustrates the results of experiments performed to determine the efficacy of apoptosis and identify apoptosis resistant populations.
Figure 19:
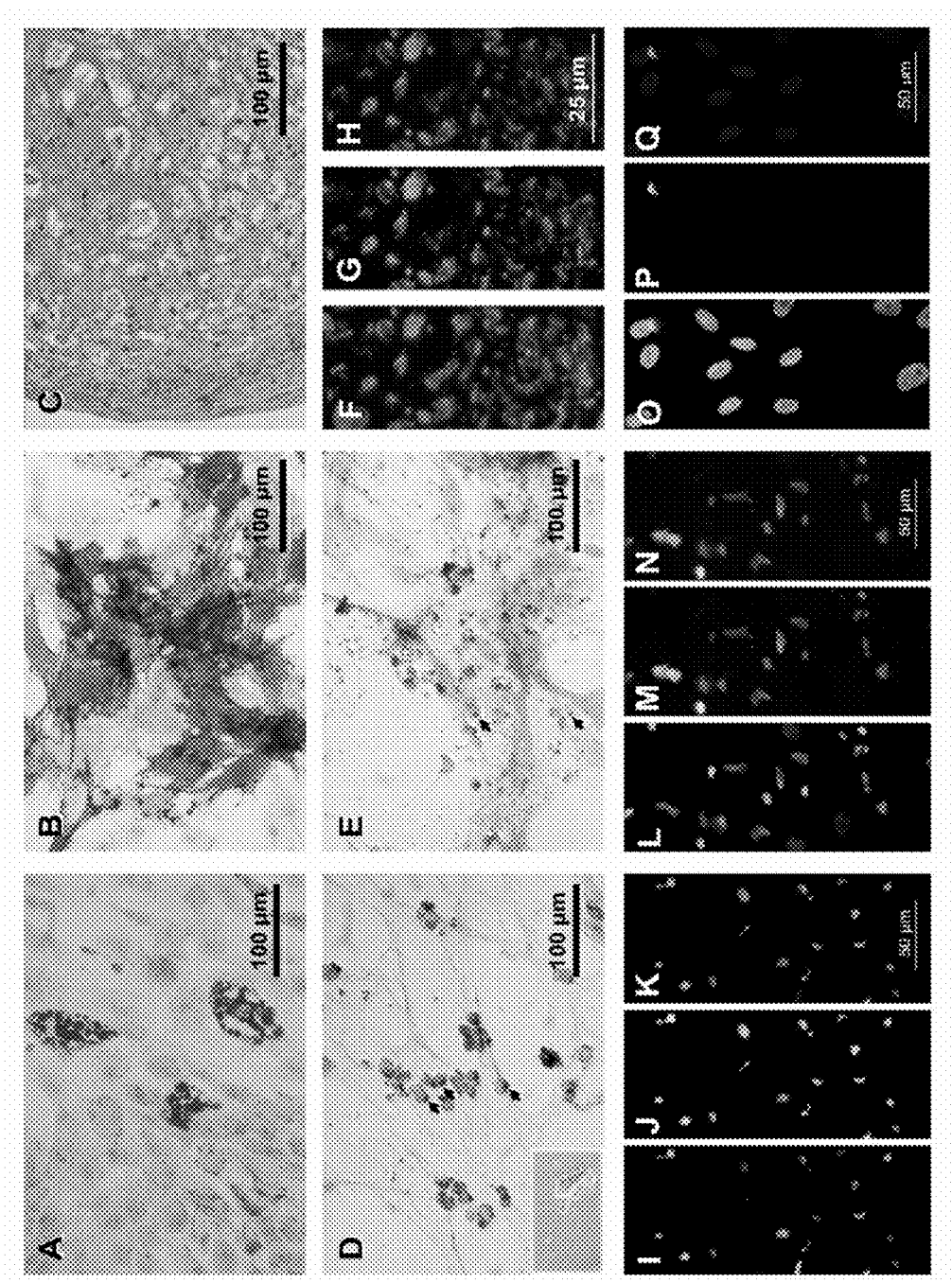
FIG. 19, panels A-Q illustrate human MSCs expressing iCasp9 stained to highlight specific cell lineages, showing that the transduced cells retain the differentiation potential of unmodified MSCs. Further discussion of experimental conditions and results are presented in the Examples.

Analysis of a highly purified iCasp9-positive population at later time points after a single exposure to CID shows that the small fraction of iCasp9-negative cells expands and that a population of iCasp9-positive cells remains, but that the latter can be killed by re-exposure to CID. Thus, no iCasp9-positive population resistant to further killing by CID was detected (see FIG. 18). A population of iCasp9-CD19-negative MSCs emerges as early as 24 hours after CID introduction. A population of iCasp9-CD19-negative MSCs is expected since achieving a population with 100% purity is unrealistic and because the MSCs are being cultured in conditions that favor their rapid expansion in vitro. A fraction of iCasp9-CD19-positive population persists, as predicted by the fact that killing is not 100% efficient (assuming, for example, 99% killing of a 99% pure population, the resulting population would have 49.7% iCasp9-positive and 50.3% iCasp9-negative cells). The surviving cells, however, can be killed at later time points by re-exposure to CID.

iCasp9-ΔCD19 Transduced MSCs Maintain the Differentiation Potential of Unmodified MSCs and their Progeny is Killed by Exposure to CID To determine if the CID can selectively kill the differentiated progeny of iCasp9-positive MSCs, immunomagnetic selection for CD19 was used to increase the purity of the modified population (>90% after one round of selection, see FIG. 16B). The iCasp9-positive cells thus selected were able to differentiate in vivo into all connective tissue lineages studied (see FIGS. 19A-19Q). Human MSCs were immunomagnetically selected for CD19 (thus iCasp9) expression, with a purity greater than 91%. After culture in specific differentiation media, iCasp9-positive cells were able to give rise to adipocytic (A, oil red and methylene azur), osteoblastic (B, alkaline phosphatase-BCIP/NBT and methylene blue) and chondroblastic lineages (C, alcian blue and nuclear red) lineages. These differentiated tissues are driven to apoptosis by exposure to 50 nM CID (D-N). Note numerous apoptotic bodies (arrows), cytoplasmic membrane blebbing (inset) and loss of cellular architecture (D and E); widespread TUNEL positivity in chondrocytic nodules (F-H), and adipogenic (I-K) and osteogenic (L-N) cultures, in contrast to that seen in untreated iCasp9-transduced controls (adipogenic condition shown, O-Q) (F, I, L, O, DAPI; G, J, M, P, TUNEL-FITC; H, K, N, Q, overlay).

Figure 20:
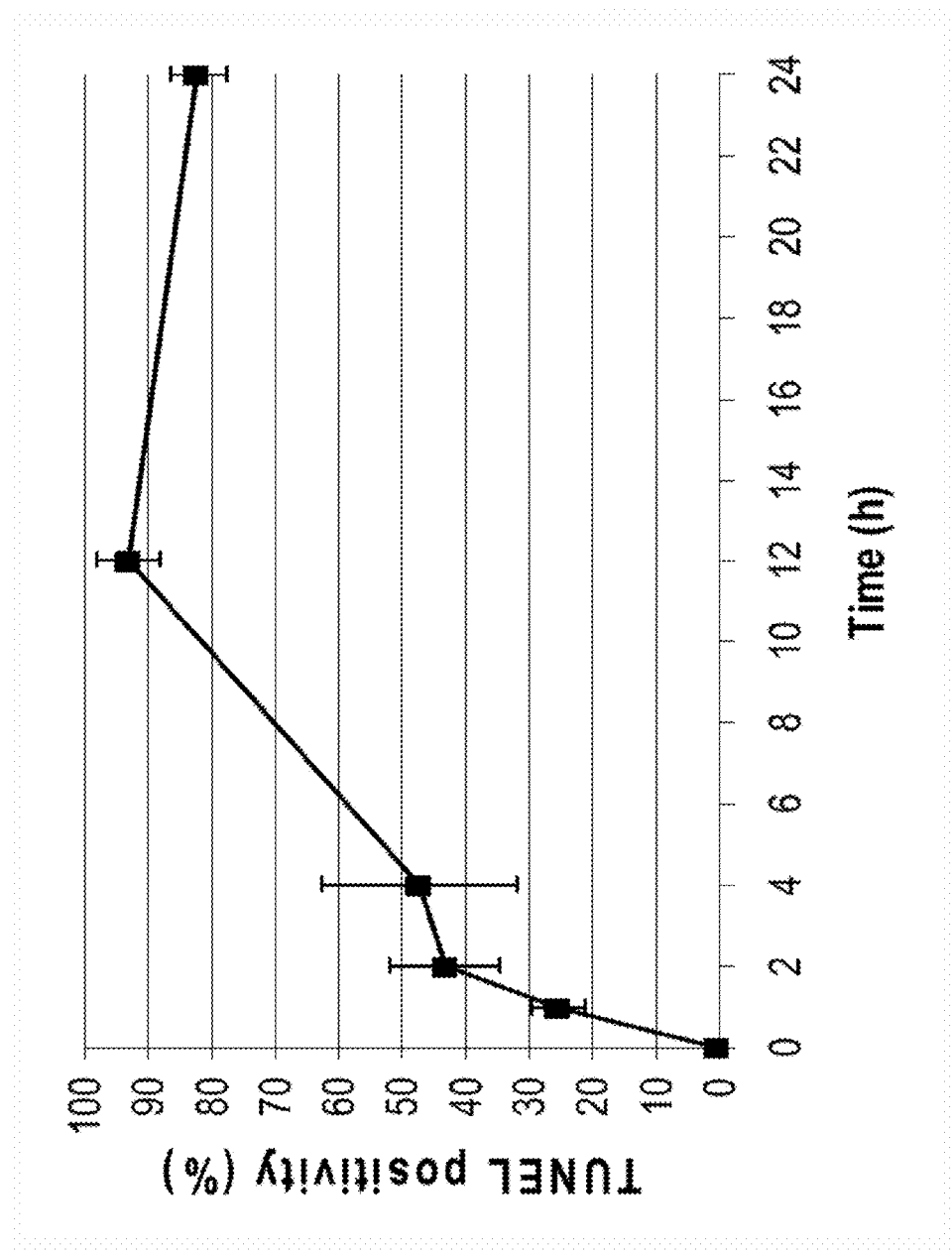
FIG. 20 graphically illustrates that the differentiated progeny of human MSCs expressing iCasp9 are killed by exposure to CID in vitro.

After 24 hours of exposure to 50 nM of CID, microscopic evidence of apoptosis was observed with membrane blebbing, cell shrinkage and detachment, and presence of apoptotic bodies throughout the adipogenic and osteogenic cultures. A TUNEL assay showed widespread positivity in adipogenic and osteogenic cultures and the chondrocytic nodules (see FIGS. 19A-19Q), which increased over time (see FIG. 20). After culture in adipocytic differentiation media, iCasp9-positive cells gave rise to adipocytes. After exposure to 50 nM CID, progressive apoptosis was observed as evidenced by an increasing proportion of TUNEL-positive cells. After 24 hours, there was a significant decrease in cell density (from 584 cells/mm2 to <14 cells/mm2), with almost all apoptotic cells having detached from the slides, precluding further reliable calculation of the proportion of apoptotic cells. Thus, iCasp9 remained functional even after MSC differentiation, and its activation results in the death of the differentiated progeny.

iCasp9-ΔCD19 Transduced MSCs Undergo Selective Apoptosis after In Vivo Exposure to CID Although intravenously injected MSC already appear to have a short in vivo survival time, cells injected locally may survive longer and produce correspondingly more profound adverse effects. To assess the in vivo functionality of the iCasp9 suicide system in such a setting, SCID mice were subcutaneously injected with MSCs. MSCs were doubly transduced with the eGFP-FFLuc (previously presented) and iCasp9-ΔCD19 genes. MSCs were also singly transduced with eGFP-FFLuc. The eGFP-positive (and CD19-positive, where applicable) fractions were isolated by fluorescence activated cell sorting, with a purity >95%. Each animal was injected subcutaneously with iCasp9-positive and control MSCs (both eGFP-FFLuc-positive) in opposite flanks. Localization of the MSCs was evaluated using the Xenogen-IVIS Imaging System. In another set of experiments, a 1:1 mixture of singly and doubly transduced MSCs was injected subcutaneously in the right flank and the mice received CID as above. The subcutaneous pellet of MSCs was harvested at different time points, genomic DNA was isolated and qPCR was used to determine copy numbers of the eGFP-FFLuc and iCasp9-ΔCD19 genes. Under these conditions, the ratio of the iCasp9 to eGFP gene copy numbers is proportional to the fraction of iCasp9-positive cells among total human cells (see Methods above for details). The ratios were normalized so that time zero corresponds to 100% of iCasp9-positive cells. Serial examination of animals after subcutaneous inoculation of MSCs (prior to CID injection) shows evidence of spontaneous apoptosis in both cell populations (as demonstrated by a fall in the overall luminescence signal to ~20% of the baseline). This has been previously observed after systemic and local delivery of MSCs in xenogeneic models.

Figures 21A, 21B, 21C:
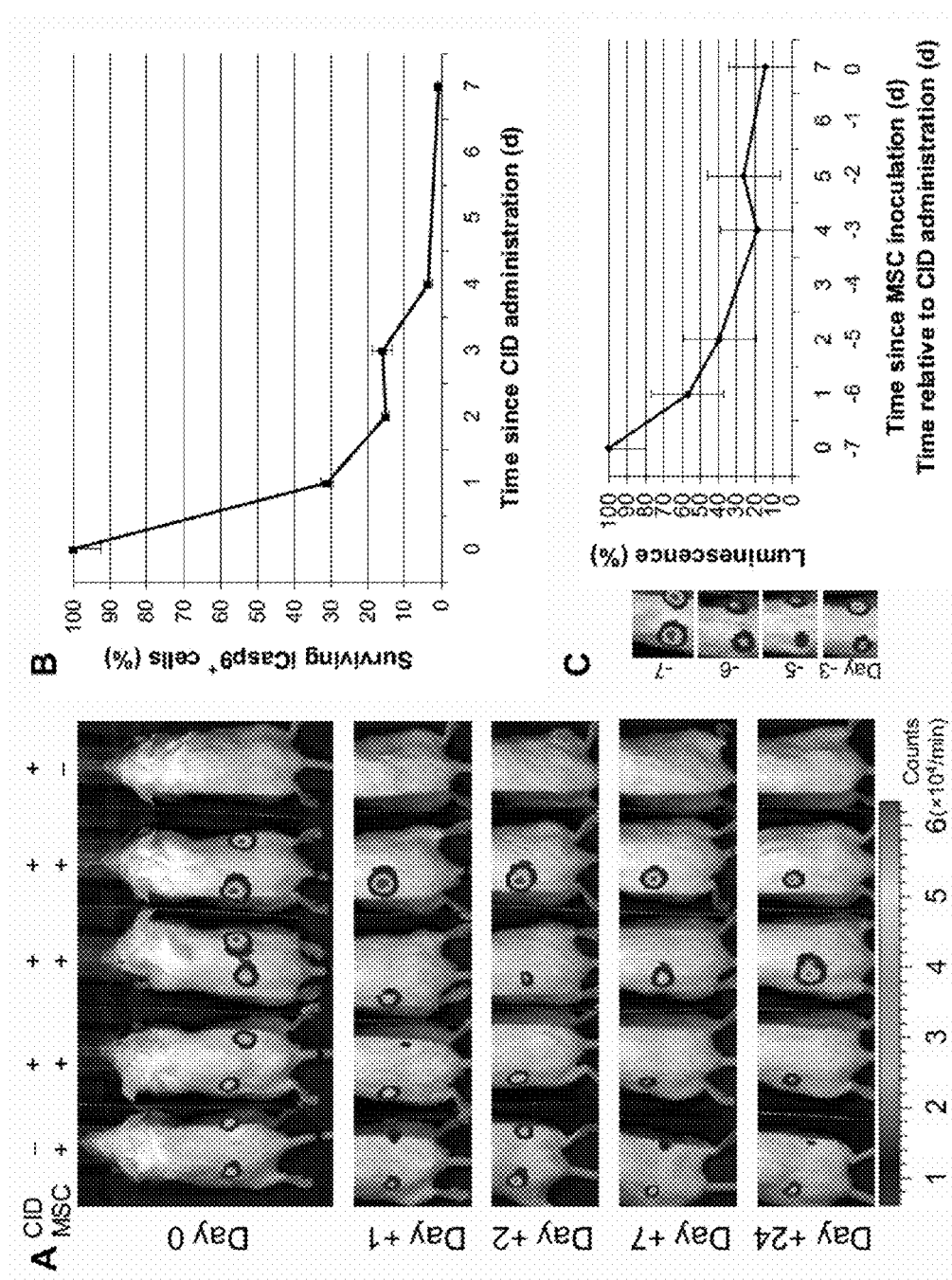
FIGS. 21A-21C illustrate the results of experiments performed to show that human MSCs expressing iCasp9 are selectively killed in vivo after exposure to CID.

The luminescence data showed a substantial loss of human MSCs over the first 96 h (see FIG. 21C) after local delivery of MSCs, even before administration of CID, with only approximately 20% cells surviving after one week. From that time point onward, however, there were significant differences between the survival of icasp9-positive MSCs with and without dimerizer drug. Seven days after MSC implantation, animals were given two injections of 50 µg of CID, 24 hours apart. As illustrated in FIG. 21A, the MSCs transduced with iCasp9 were quickly killed by the drug, as demonstrated by the disappearance of their luminescence signal. Cells negative for iCasp9 were not affected by the drug. Animals not injected with the drug showed persistence of signal in both populations up to a month after MSC implantation. To further quantify cell killing, qPCR assays were developed to measure copy numbers of the eGFP-FFLuc and iCasp9-ΔCD19 genes. Mice were injected subcutaneously with a 1:1 mixture of doubly and singly transduced MSCs and administered CID as above, one week after MSC implantation. MSCs explants were collected at several time points, genomic DNA isolated from the samples and qPCR assays performed on substantially identical amounts of DNA. Under these conditions (see Methods), at any time point, the ratio of iCasp9-ΔCD19 to eGFP-FFLuc copy numbers is proportional to the fraction of viable iCasp9-positive cells. Progressive killing of iCasp9-positive cells was observed (>99%) so that the proportion of surviving iCasp9-positive cells was reduced to 0.7% of the original population after one week (see FIG. 21B). Therefore, MSCs transduced with iCasp9 can be selectively killed in vivo after exposure to CID, but otherwise persist.

Discussion

The feasibility of engineering human MSCs to express a safety mechanism using an inducible suicide protein is demonstrated herein. The date presented herein show that MSC can be readily transduced with the suicide gene iCasp9 coupled to the selectable surface maker CD19. Expression of the co-transduced genes is stable both in MSCs and their differentiated progeny, and does not evidently alter their phenotype or potential for differentiation. These transduced cells can be killed in vitro and in vivo when exposed to the appropriate small molecule chemical inducer of dimerization that binds to the iCasp9.

For a cell based therapy to be successful, transplanted cells must survive the period between their harvest and their ultimate in vivo clinical application. Additionally, a safe cell based therapy also should include the ability to control the unwanted growth and activity of successfully transplanted cells. Although MSCs have been administered to many patients without notable side effects, recent reports indicate additional protections, such as the safety switch presented herein, may offer additional methods of control over cell based therapies as the potential of transplanted MSC to be genetically and epigenetically modified to enhance their functionality, and to differentiate into lineages including bone and cartilage is further investigated and exploited. Subjects receiving MSCs that have been genetically modified to release biologically active proteins might particularly benefit from the added safety provided by a suicide gene.

The suicide system presented herein offers several potential advantages over other known suicide systems. Strategies involving nucleoside analogues, such as those combining Herpes Simplex Virus thymidine kinase (HSV-tk) with gancyclovir (GCV) and bacterial or yeast cytosine deaminase (CD) with 5-fluoro-cytosine (5-FC), are cell-cycle dependent and are unlikely to be effective in the post-mitotic tissues that may be formed during the application of MSCs to regenerative medicine. Moreover, even in proliferating tissues the mitotic fraction does not comprise all cells, and a significant portion of the graft may survive and remain dysfunctional. In some instance, the prodrugs required for suicide may themselves have therapeutic uses that are therefore excluded (e.g. GCV), or may be toxic (e.g. 5-FC), either as a result of their metabolism by non-target organs (e.g., many cytochrome P450 substrates), or due to diffusion to neighboring tissues after activation by target cells (e.g. CB1954, a substrate for bacterial nitroreductase).

In contrast, the small molecule chemical inducers of dimerization presented herein have shown no evidence of toxicities even at doses ten fold higher than those required to activate the iCasp9. Additionally, nonhuman enzymatic systems, such as HSV-tk and DC, carry a high risk of destructive immune responses against transduced cells. Both the iCasp9 suicide gene and the selection marker CD19, are of human origin, and thus should be less likely to induce unwanted immune responses. Although linkage of expression of the selectable marker to the suicide gene by a 2A-like cleavable peptide of nonhuman origin could pose problems, the 2A-like linker is 20 amino acids long, and is likely less immunogenic than a nonhuman protein. Finally, the effectiveness of suicide gene activation in iCasp9-positive cells compares favorably to killing of cells expressing other suicide systems, with 90% or more of iCasp9-modified T cells eliminated after a single dose of dimerizer, a level that is likely to be clinically efficacious.

The iCasp9 system presented herein also may avoid additional limitations seen with other cell based and/or suicide switch based therapies. Loss of expression due to silencing of the transduced construct is frequently observed after retroviral transduction of mammalian cells. The expression constructs presented herein showed no evidence of such an effect. No decrease in expression or induced death was evident, even after one month in culture.

Another potential problem sometimes observed in other cell based and/or suicide switch based therapies, is the development of resistance in cells that have upregulated anti-apoptotic genes. This effect has been observed in other suicide systems involving different elements of the programmed cell death pathways such as Fas. iCasp9 was chosen as the suicide gene for the expression constructs presented herein because it was less likely to have this limitation. Compared to other members of the apoptotic cascade, activation of caspase 9 occurs late in the apoptotic pathway and therefore should bypass the effects of many if not all anti-apoptotic regulators, such as c-FLIP and bcl-2 family members.

A potential limitation specific to the system presented herein may be spontaneous dimerization of iCasp9, which in turn could cause unwanted cell death and poor persistence. This effect has been observed in certain other inducible systems that utilize Fas. The observation of low spontaneous death rate in transduced cells and long term persistence of transgenic cells in vivo indicate this possibility is not a significant consideration when using iCasp9 based expression constructs.

Integration events deriving from retroviral transduction of MSCs may potentially drive deleterious mutagenesis, especially when there are multiple insertions of the retroviral vector, causing unwanted copy number effects and/or other undesirable effects. These unwanted effects could offset the benefit of a retrovirally transduced suicide system. These effects often can be minimized using clinical grade retroviral supernatant obtained from stable producer cell lines and similar culture conditions to transduce T lymphocytes. The T cells transduced and evaluated herein contain in the range of about 1 to 3 integrants (the supernatant containing in the range of about $1 \times 10^6$ viral particles/mL). The substitution of lentiviral for retroviral vectors could further reduce the risk of genotoxicity, especially in cells with high self-renewal and differentiation potential.

While a small proportion of iCasp9-positive MSCs persists after a single exposure to CID, these surviving cells can subsequently be killed following re-exposure to CID. In vivo, there is >99% depletion with two doses, but it is likely that repeated doses of CID will be needed for maximal depletion in the clinical setting. Additional non-limiting methods of providing extra safety when using an inducible suicide switch system include additional rounds of cell sorting to further increase the purity of the cell populations administered and the use of more than one suicide gene system to enhance the efficiency of killing.

The CD19 molecule, which is physiologically expressed by B lymphocytes, was chosen as the selectable marker for transduced cells, because of its potential advantages over other available selection systems, such as neomycin phosphotransferase (neo) and truncated low affinity nerve growth factor receptor (ΔLNGFR). neo encodes a potentially immunogenic foreign protein and requires a 7-day culture in selection medium, increasing the complexity of the system and potentially damaging the selected cells. ΔLNGFR expression should allow for isolation strategies similar to other surface markers, but these are not widely available for clinical use and a lingering concern remains about the oncogenic potential of ΔLNGFR. In contrast, magnetic selection of iCasp9-positive cells by CD19 expression using a clinical grade device is readily available and has shown no notable effects on subsequent cell growth or differentiation.

The procedure used for preparation and administration of mesenchymal stromal cells comprising the caspase 9 safety switch may also be used for the preparation of embryonic stem cells and inducible pluripotent stem cells. Thus for the procedures outlined in the present example, either embryonic stem cells or inducible pluripotent stem cells may be substituted for the mesenchymal stromal cells provided in the example. In these cells, retroviral and lentiviral vectors may be used, with, for example, CMV promoters, or the ronin promoter.

Example 6

Examples of Particular Nucleic Acid and Amino Acid Sequences

Figure 43:
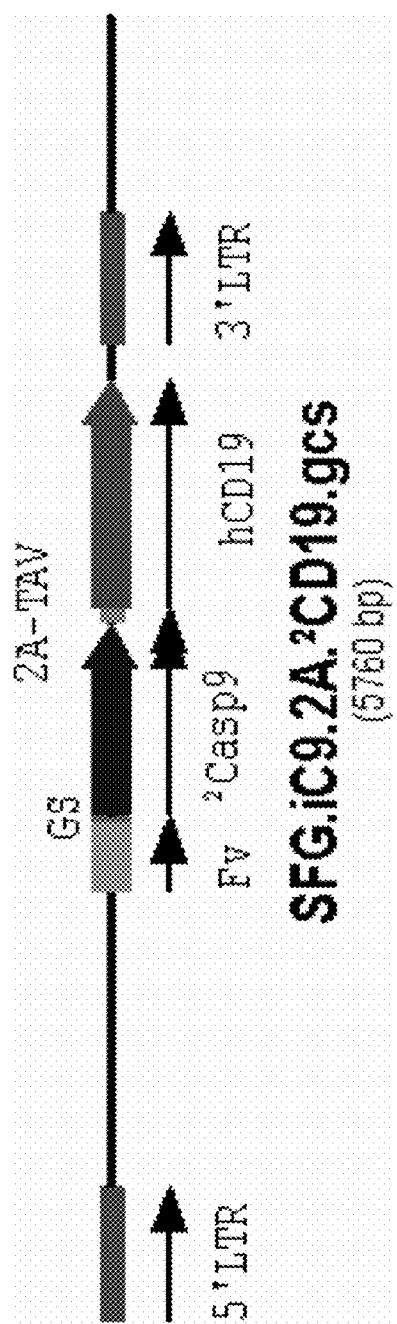
FIG. 43 graphically illustrates the portion of the expression construct coding for the chimeric iCaspase9 and CD19 polypeptides.

FIG. 43 presents an example of a construct that may be used for expression of the chimeric protein and CD19 marker. The figure presents the SFG.iC9.2A.²CD19.gcs construct

```
nucleotide sequence of 5'LTR sequence
                                               SEQ ID NO: 1
TGAAAGACCCCACCTGTAGGTTTGGCAAGCTAGCTTAAGTAACGCCAT

TTTGCAAGGCATGGAAAAATACATAACTGAGAATAGAAAAGTTCAGAT
```

-continued
```
CAAGGTCAGGAACAGATGGAACAGCTGAATATGGGCCAAACAGGATAT

CTGTGGTAAGCAGTTCCTGCCCCGGCTCAGGGCCAAGAACAGATGGAA

CAGCTGAATATGGGCCAAACAGGATATCTGTGGTAAGCAGTTCCTGCC

CCGGCTCAGGGCCAAGAACAGATGGTCCCCAGATGCGGTCCAGCCCTC

AGCAGTTTCTAGAGAACCATCAGATGTTTCCAGGGTGCCCCAAGGACC

TGAAATGACCCTGTGCCTTATTTGAACTAACCAATCAGTTCGCTTCTC

GCTTCTGTTCGCGCGCTTATGCTCCCCGAGCTCAATAAAAGAGCCCAC

AACCCCTCACTCGGGGCGCCAGTCCTCCGATTGACTGAGTCGCCCGGG

TACCCGTGTATCCAATAAACCCTCTTGCAGTTGCATCCGACTTGTGGT

CTCGCTGTTCCTTGGGAGGGTCTCCTCTGAGTGATTGACTACCCGTCA

GCGGGGGTCTTTCA
``` nucleotide sequence of Fv (human FKBP12v36)
SEQ ID NO: 2
```
GGAGTGCAGGTGGAAACCATCTCCCCAGGAGACGGGCGCACCTTCCCC

AAGCGCGGCCAGACCTGCGTGGTGCACTACACCGGGATGCTTGAAGAT

GGAAAGAAAGTTGATTCCTCCCGGGACAGAAACAAGCCCTTTAAGTTT

ATGCTAGGCAAGCAGGAGGTGATCCGAGGCTGGGAAGAAGGGGTTGCC

CAGATGAGTGTGGGTCAGAGAGCCAAACTGACTATATCTCCAGATTAT

GCCTATGGTGCCACTGGGCACCCAGGCATCATCCCACCACATGCCACT

CTCGTCTTCGATGTGGAGCTTCTAAAACTGGAA
``` amino acid sequence of Fv (human FKBP12v36)
SEQ ID NO: 3
G V Q V E T I S P G D G R T F P K R G Q T C V V
H Y T G M L E D G K K V D S S R D R N K P F K F
M L G K Q E V I R G W E E G V A Q M S V G Q R A
K L T I S P D Y A Y G A T G H P G I I P P H A T
L V F D V E L L K L E GS linker nucleotide sequence
SEQ ID NO: 4
TCTGGCGGTGGATCCGGA GS linker amino acid sequence
SEQ ID NO: 5
S G G G S G linker nucleotide sequence (between GS linker and Casp 9)
SEQ ID NO: 6
GTCGAC linker amino acid sequence (between GS linker and Casp 9)
SEQ ID NO: 7
V D Casp 9 (truncated) nucleotide sequence
SEQ ID NO: 8
```
GGATTTGGTGATGTCGGTGCTCTTGAGAGTTTGAGGGGAAATGCAGAT

TTGGCTTACATCCTGAGCATGGAGCCCTGTGGCCACTGCCTCATTATC

AACAATGTGAACTTCTGCCGTGAGTCCGGGCTCCGCACCCGCACTGGC

TCCAACATCGACTGTGAGAAGTTGCGGCGTCGCTTCTCCTCGCTGCAT

TTCATGGTGGAGGTGAAGGGCGACCTGACTGCCAAGAAAATGGTGCTG

GCTTTGCTGGAGCTGGCGCAGCAGGACCACGGTGCTCTGGACTGCTGC

GTGGTGGTCATTCTCTCTCACGGCTGTCAGGCCAGCCACCTGCAGTTC

CCAGGGGCTGTCTACGGCACAGATGGATGCCCTGTGTCGGTCGAGAAG

ATTGTGAACATCTTCAATGGGACCAGCTGCCCCAGCCTGGGAGGGAAG

CCCAAGCTCTTTTTCATCCAGGCCTGTGGTGGGGAGCAGAAAGACCAT

GGGTTTGAGGTGGCCTCCACTTCCCCTGAAGACGAGTCCCCTGGCAGT

AACCCCGAGCCAGATGCCACCCCGTTCCAGGAAGGTTTGAGGACCTTC

GACCAGCTGGACGCCATATCTAGTTTGCCCACACCCAGTGACATCTTT

GTGTCCTACTCTACTTTCCCAGGTTTTGTTTCCTGGAGGGACCCCAAG

AGTGGCTCCTGGTACGTTGAGACCCTGGACGACATCTTTGAGCAGTGG

GCTCACTCTGAAGACCTGCAGTCCCTCCTGCTTAGGGTCGCTAATGCT

GTTTCGGTGAAAGGGATTTATAAACAGATGCCTGGTTGCTTTAATTTC

CTCCGGAAAAAACTTTTCTTTAAAACATCA
```

Caspase 9 (truncated) amino acid sequence- CARD domain deleted
SEQ ID NO: 9
G F G D V G A L E S L R G N A D L A Y I L S M E
P C G H C L I I N N V N F C R E S G L R T R T G
S N I D C E K L R R R F S S L H F M V E V K G D
L T A K K M V L A L L E L A Q Q D H G A L D C C
V V V I L S H G C Q A S H L Q F P G A V Y G T D
G C P V S V E K I V N I F N G T S C P S L G G K
P K L F F I Q A C G G E Q K D H G F E V A S T S
P E D E S P G S N P E P D A T P F Q E G L R T F
D Q L D A I S S L P T P S D I F V S Y S T F P G
F V S W R D P K S G S W Y V E T L D D I F E Q W
A H S E D L Q S L L L R V A N A V S V K G I Y K
Q M P G C F N F L R K K L F F K T S linker nucleotide sequence (between caspase 9 and 2A)
SEQ ID NO: 10
GCTAGCAGA linker amino acid sequence (between caspase 9 and 2A)
SEQ ID NO: 11
A S R Thosea asigna virus-2A from capsid protein precursor nucleotide sequence
SEQ ID NO: 12
GCCGAGGGCAGGGGAAGTCTTCTAACATGCGGGGACGTGGAGGAAAAT
CCCGGGCCC Thosea asigna virus-2A from capsid protein precursor amino acid sequence
SEQ ID NO: 13
A E G R G S L L T C G D V E E N P G P human CD19 (Δ cytoplasmic domain) nucleotide sequence (transmembrane domain in bold)
SEQ ID NO: 14
ATGCCACCTCCTCGCCTCCTCTTCTTCCTCCTCTTCCTCACCCCCATG

GAAGTCAGGCCCGAGGAACCTCTAGTGGTGAAGGTGGAAGAGGGAGAT

```
AACGCTGTGCTGCAGTGCCTCAAGGGGACCTCAGATGGCCCCACTCAG
CAGCTGACCTGGTCTCGGGAGTCCCCGCTTAAACCCTTCTTAAAACTC
AGCCTGGGGCTGCCAGGCCTGGGAATCCACATGAGGCCCCTGGCCATC
TGGCTTTTCATCTTCAACGTCTCTCAACAGATGGGGGGCTTCTACCTG
TGCCAGCCGGGGCCCCCCTCTGAGAAGGCCTGGCAGCCTGGCTGGACA
GTCAATGTGGAGGGCAGCGGGGAGCTGTTCCGGTGGAATGTTTCGGAC
CTAGGTGGCCTGGGCTGTGGCCTGAAGAACAGGTCCTCAGAGGGCCCC
AGCTCCCCTTCCGGGAAGCTCATGAGCCCCAAGCTGTATGTGTGGGCC
AAAGACCGCCCTGAGATCTGGGAGGGAGAGCCTCCGTGTCTCCCACCG
AGGGACAGCCTGAACCAGAGCCTCAGCCAGGACCTCACCATGGCCCCT
GGCTCCACACTCTGGCTGTCCTGTGGGGTACCCCCTGACTCTGTGTCC
AGGGGCCCCCTCTCCTGGACCCATGTGCACCCCAAGGGGCCTAAGTCA
TTGCTGAGCCTAGAGCTGAAGGACGATCGCCCGGCCAGAGATATGTGG
GTAATGGAGACGGGTCTGTTGTTGCCCCGGGCCACAGCTCAAGACGCT
GGAAAGTATTATTGTCACCGTGGCAACCTGACCATGTCATTCCACCTG
GAGATCACTGCTCGGCCAGTACTATGGCACTGGCTGCTGAGGACTGGT
GGCTGGAAG**GTCTCAGCTGTGACTTTGGCTTATCTGATCTTCTGCCTG
TGTTCCCTTGTGGGCATTCTTCATCTT**CAAAGAGCCCTGGTCCTGAGG
AGGAAAAGAAAGCGAATGACTGACCCCACCAGGAGATTC
``` human CD19 (Δ cytoplasmic domain) amino acid sequence
SEQ ID NO: 15
```
M P P P R L L F F L L F L T P M E V R P E E P L
V V K V E E G D N A V L Q C L K G T S D G P T Q
Q L T W S R E S P L K P F L K L S L G L P G L G
I H M R P L A I W L F I F N V S Q Q M G G F Y L
C Q P G P P S E K A W Q P G W T V N V E G S G E
L F R W N V S D L G G L G C G L K N R S S E G P
S S P S G K L M S P K L Y V W A K D R P E I W E
G E P P C L P P R D S L N Q S L S Q D L T M A P
G S T L W L S C G V P P D S V S R G P L S W T H
V H P K G P K S L L S L E L K D D R P A R D M W
V M E T G L L L P R A T A Q D A G K Y Y C H R G
N L T M S F H L E I T A R P V L W H W L L R T G
G W K V S A V T L A Y L I F C L C S L V G I L H
L Q R A L V L R R K R K M T D P T R R F
```

3'LTR nucleotide sequence
SEQ ID NO: 16
```
TGAAAGACCCCACCTGTAGGTTTGGCAAGCTAGCTTAAGTAACGCCAT
TTTGCAAGGCATGGAAAAATACATAACTGAGAATAGAGAAGTTCAGAT
CAAGGTCAGGAACAGATGGAACAGCTGAATATGGGCCAAACAGGATAT
CTGTGGTAAGCAGTTCCTGCCCCGGCTCAGGGCCAAGAACAGATGGAA
CAGCTGAATATGGGCCAAACAGGATATCTGTGGTAAGCAGTTCCTGCC
CCGGCTCAGGGCCAAGAACAGATGGTCCCCAGATGCGGTCCAGCCCTC
AGCAGTTTCTAGAGAACCATCAGATGTTTCCAGGGTGCCCCAAGGACC
TGAAATGACCCTGTGCCTTATTTGAACTAACCAATCAGTTCGCTTCTC
GCTTCTGTTCGCGCGCTTCTGCTCCCCGAGCTCAATAAAAGAGCCCAC
AACCCCTCACTCGGGGCGCCAGTCCTCCGATTGACTGAGTCGCCCGGG
TACCCGTGTATCCAATAAACCCTCTTGCAGTTGCATCCGACTTGTGGT
CTCGCTGTTCCTTGGGAGGGTCTCCTCTGAGTGATTGACTACCCGTCA
GCGGGGGTCTTTCA
```

Expression vector construct nucleotide sequence- nucleotide sequence coding for the chimeric protein and 5' and 3' LTR sequences, and additional vector sequence.
SEQ ID NO: 17
```
TGAAAGACCCCACCTGTAGGTTTGGCAAGCTAGCTTAAGTAACGCCAT
TTTGCAAGGCATGGAAAAATACATAACTGAGAATAGAAAAGTTCAGAT
CAAGGTCAGGAACAGATGGAACAGCTGAATATGGGCCAAACAGGATAT
CTGTGGTAAGCAGTTCCTGCCCCGGCTCAGGGCCAAGAACAGATGGAA
CAGCTGAATATGGGCCAAACAGGATATCTGTGGTAAGCAGTTCCTGCC
CCGGCTCAGGGCCAAGAACAGATGGTCCCCAGATGCGGTCCAGCCCTC
AGCAGTTTCTAGAGAACCATCAGATGTTTCCAGGGTGCCCCAAGGACC
TGAAATGACCCTGTGCCTTATTTGAACTAACCAATCAGTTCGCTTCTC
GCTTCTGTTCGCGCGCTTATGCTCCCCGAGCTCAATAAAAGAGCCCAC
AACCCCTCACTCGGGGCGCCAGTCCTCCGATTGACTGAGTCGCCCGGG
TACCCGTGTATCCAATAAACCCTCTTGCAGTTGCATCCGACTTGTGGT
CTCGCTGTTCCTTGGGAGGGTCTCCTCTGAGTGATTGACTACCCGTCA
GCGGGGGTCTTTCATTTGGGGGCTCGTCCGGGATCGGGAGACCCCTGC
CCAGGGACCACCGACCCACCACCGGGAGGTAAGCTGGCCAGCAACTTA
TCTGTGTCTGTCCGATTGTCTAGTGTCTATGACTGATTTTATGCGCCT
GCGTCGGTACTAGTTAGCTAACTAGCTCTGTATCTGGCGGACCCGTGG
TGGAACTGACGAGTTCGGAACACCCGGCCGCAACCCTGGGAGACGTCC
CAGGGACTTCGGGGGCCGTTTTGTGGCCCGACCTGAGTCCTAAAATC
CCGATCGTTTAGGACTCTTTGGTGCACCCCCCTTAGAGGAGGGATATG
TGGTTCTGGTAGGAGACGAGAACCTAAAACAGTTCCCGCCTCCGTCTG
AATTTTTGCTTTCGGTTTGGGACCGAAGCCGCGCCGCGCGTCTTGTCT
GCTGCAGCATCGTTCTGTGTTGTCTCTGTCTGACTGTGTTTCTGTATT
TGTCTGAAAATATGGGCCCGGGCTAGCCTGTTACCACTCCCTTAAGTT
TGACCTTAGGTCACTGGAAAGATGTCGAGCGGATCGCTCACAACCAGT
CGGTAGATGTCAAGAAGAGACGTTGGGTTACCTTCTGCTCTGCAGAAT
GGCCAACCTTTAACGTCGGATGGCCGCGAGACGGCACCTTTAACCGAG
ACCTCATCACCCAGGTTAAGATCAAGGTCTTTTCACCTGGCCCGCATG
GACACCCAGACCAGGTGGGGTACATCGTGACCTGGGAAGCCTTGGCTT
TTGACCCCCTCCCTGGGTCAAGCCCTTTGTACACCCTAAGCCTCCGC
CTCCTCTTCCTCCATCCGCCCCGTCTCTCCCCCTTGAACCTCCTCGTT
```

-continued

```
CGACCCCGCCTCGATCCTCCCTTTATCCAGCCCTCACTCCTTCTCTAG
GCGCCCCCATATGGCCATATGAGATCTTATATGGGGCACCCCCGCCCC
TTGTAAACTTCCCTGACCCTGACATGACAAGAGTTACTAACAGCCCCT
CTCTCCAAGCTCACTTACAGGCTCTCTACTTAGTCCAGCACGAAGTCT
GGAGACCTCTGGCGGCAGCCTACCAAGAACAACTGGACCGACCGGTGG
TACCTCACCCTTACCGAGTCGGCGACACAGTGTGGGTCCGCCGACACC
AGACTAAGAACCTAGAACCTCGCTGGAAAGGACCTTACACAGTCCTGC
TGACCACCCCCACCGCCCTCAAAGTAGACGGCATCGCAGCTTGGATAC
ACGCCGCCCACGTGAAGGCTGCCGACCCCGGGGGTGGACCATCCTCTA
GACTGCCATGCTCGAGGGAGTGCAGGTGGAAACCATCTCCCCAGGAGA
CGGGCGCACCTTCCCCAAGCGCGGCCAGACCTGCGTGGTGCACTACAC
CGGGATGCTTGAAGATGGAAAGAAAGTTGATTCCTCCCGGGACAGAAA
CAAGCCCTTTAAGTTTATGCTAGGCAAGCAGGAGGTGATCCGAGGCTG
GGAAGAAGGGGTTGCCCAGATGAGTGTGGGTCAGAGAGCCAAACTGAC
TATATCTCCAGATTATGCCTATGGTGCCACTGGGCACCCAGGCATCAT
CCCACCACATGCCACTCTCGTCTTCGATGTGGAGCTTCTAAAACTGGA
ATCTGGCGGTGGATCCGGAGTCGACGGATTTGGTGATGTCGGTGCTCT
TGAGAGTTTGAGGGGAAATGCAGATTTGGCTTACATCCTGAGCATGGA
GCCCTGTGGCCACTGCCTCATTATCAACAATGTGAACTTCTGCCGTGA
GTCCGGGCTCCGCACCCGCACTGGCTCCAACATCGACTGTGAGAAGTT
GCGGCGTCGCTTCTCCTCGCTGCATTTCATGGTGGAGGTGAAGGGCGA
CCTGACTGCCAAGAAAATGGTGCTGGCTTTGCTGGAGCTGGCGCAGCA
GGACCACGGTGCTCTGGACTGCTGCGTGGTGGTCATTCTCTCTCACGG
CTGTCAGGCCAGCCACCTGCAGTTCCCAGGGGCTGTCTACGGCACAGA
TGGATGCCCTGTGTCGGTCGAGAAGATTGTGAACATCTTCAATGGGAC
CAGCTGCCCCAGCCTGGGAGGGAAGCCCAAGCTCTTTTTCATCCAGGC
CTGTGGTGGGGAGCAGAAAGACCATGGGTTTGAGGTGGCCTCCACTTC
CCCTGAAGACGAGTCCCCTGGCAGTAACCCCGAGCCAGATGCCACCCC
GTTCCAGGAAGGTTTGAGGACCTTCGACCAGCTGGACGCCATATCTAG
TTTGCCCACACCCAGTGACATCTTTGTGTCCTACTCTACTTTCCCAGG
TTTTGTTTCCTGGAGGGACCCCAAGAGTGGCTCCTGGTACGTTGAGAC
CCTGGACGACATCTTTGAGCAGTGGGCTCACTCTGAAGACCTGCAGTC
CCTCCTGCTTAGGGTCGCTAATGCTGTTTCGGTGAAAGGGATTTATAA
ACAGATGCCTGGTTGCTTTAATTTCCTCCGGAAAAAACTTTTCTTTAA
AACATCAGCTAGCAGAGCCGAGGGCAGGGGAAGTCTTCTAACATGCGG
GGACGTGGAGGAAAATCCCGGGCCCATGCCACCTCCTCGCCTCCTCTT
CTTCCTCCTCTTCCTCACCCCCATGGAAGTCAGGCCCGAGGAACCTCT
AGTGGTGAAGGTGGAAGAGGGAGATAACGCTGTGCTGCAGTGCCTCAA
GGGGACCTCAGATGGCCCCACTCAGCAGCTGACCTGGTCTCGGGAGTC
CCCGCTTAAACCCTTCTTAAAACTCAGCCTGGGGCTGCCAGGCCTGGG
AATCCACATGAGGCCCCTGGCCATCTGGCTTTTCATCTTCAACGTCTC
```

-continued

```
TCAACAGATGGGGGGCTTCTACCTGTGCCAGCCGGGGCCCCCCTCTGA
GAAGGCCTGGCAGCCTGGCTGGACAGTCAATGTGGAGGGCAGCGGGGA
GCTGTTCCGGTGGAATGTTTCGGACCTAGGTGGCCTGGGCTGTGGCCT
GAAGAACAGGTCCTCAGAGGGCCCCAGCTCCCCTTCCGGGAAGCTCAT
GAGCCCCAAGCTGTATGTGTGGGCCAAAGACCGCCCTGAGATCTGGGA
GGGAGAGCCTCCGTGTCTCCCACCGAGGGACAGCCTGAACCAGAGCCT
CAGCCAGGACCTCACCATGGCCCCTGGCTCCACACTCTGGCTGTCCTG
TGGGGTACCCCCTGACTCTGTGTCCAGGGGCCCCCTCTCCTGGACCCA
TGTGCACCCCAAGGGGCCTAAGTCATTGCTGAGCCTAGAGCTGAAGGA
CGATCGCCCGGCCAGAGATATGTGGGTAATGGAGACGGGTCTGTTGTT
GCCCCGGGCCACAGCTCAAGACGCTGGAAAGTATTATTGTCACCGTGG
CAACCTGACCATGTCATTCCACCTGGAGATCACTGCTCGGCCAGTACT
ATGGCACTGGCTGCTGAGGACTGGTGGCTGGAAGGTCTCAGCTGTGAC
TTTGGCTTATCTGATCTTCTGCCTGTGTTCCCTTGTGGGCATTCTTCA
TCTTCAAAGAGCCCTGGTCCTGAGGAGGAAAAGAAAGCGAATGACTGA
CCCCACCAGGAGATTCTAACGCGTCATCATCGATCCGGATTAGTCCAA
TTTGTTAAAGACAGGATATCAGTGGTCCAGGCTCTAGTTTTGACTCAA
CAATATCACCAGCTGAAGCCTATAGAGTACGAGCCATAGATAAAATAA
AAGATTTTATTTAGTCTCCAGAAAAAGGGGGAATGAAAGACCCCACC
TGTAGGTTTGGCAAGCTAGCTTAAGTAACGCCATTTTGCAAGGCATGG
AAAAATACATAACTGAGAATAGAGAAGTTCAGATCAAGGTCAGGAACA
GATGGAACAGCTGAATATGGGCCAAACAGGATATCTGTGGTAAGCAGT
TCCTGCCCCGGCTCAGGGCCAAGAACAGATGGAACAGCTGAATATGGG
CCAAACAGGATATCTGTGGTAAGCAGTTCCTGCCCCGGCTCAGGGCCA
AGAACAGATGGTCCCCAGATGCGGTCCAGCCCTCAGCAGTTTCTAGAG
AACCATCAGATGTTTCCAGGGTGCCCCAAGGACCTGAAATGACCCTGT
GCCTTATTTGAACTAACCAATCAGTTCGCTTCTCGCTTCTGTTCGCGC
GCTTCTGCTCCCCGAGCTCAATAAAAGAGCCCACAACCCCTCACTCGG
GGCGCCAGTCCTCCGATTGACTGAGTCGCCCGGGTACCCGTGTATCCA
ATAAACCCTCTTGCAGTTGCATCCGACTTGTGGTCTCGCTGTTCCTTG
GGAGGGTCTCCTCTGAGTGATTGACTACCCGTCAGCGGGGGTCTTTCA
CACATGCAGCATGTATCAAAATTAATTTGGTTTTTTTTCTTAAGTATT
TACATTAAATGGCCATAGTACTTAAAGTTACATTGGCTTCCTTGAAAT
AAACATGGAGTATTCAGAATGTGTCATAAATATTTCTAATTTTAAGAT
AGTATCTCCATTGGCTTTCTACTTTTTCTTTTATTTTTTTTGTCCTC
TGTCTTCCATTTGTTGTTGTTGTTGTTTGTTTGTTTGTTGTTGGTTG
GTTGGTTAATTTTTTTTAAAGATCCTACACTATAGTTCAAGCTAGAC
TATTAGCTACTCTGTAACCCAGGGTGACCTTGAAGTCATGGGTAGCCT
GCTGTTTTAGCCTTCCCACATCTAAGATTACAGGTATGAGCTATCATT
TTTGGTATATTGATTGATTGATTGATTGATGTGTGTGTGTGATTGT
```

```
GTTTGTGTGTGTGACTGTGAAAATGTGTGTATGGGTGTGTGTGAATGT
GTGTATGTATGTGTGTGTGAGTGTGTGTGTGTGTGTGCATGTGT
GTGTGTGTGACTGTGTCTATGTGTATGACTGTGTGTGTGTGTGTGT
GTGTGTGTGTGTGTGTGTGTGTGTTGTGAAAAAATATTCTATGG
TAGTGAGAGCCAACGCTCCGGCTCAGGTGTCAGGTTGGTTTTTGAGAC
AGAGTCTTTCACTTAGCTTGGAATTCACTGGCCGTCGTTTTACAACGT
CGTGACTGGGAAAACCCTGGCGTTACCCAACTTAATCGCCTTGCAGCA
CATCCCCCTTTCGCCAGCTGGCGTAATAGCGAAGAGGCCCGCACCGAT
CGCCCTTCCCAACAGTTGCGCAGCCTGAATGGCGAATGGCGCCTGATG
CGGTATTTTCTCCTTACGCATCTGTGCGGTATTTCACACCGCATATGG
TGCACTCTCAGTACAATCTGCTCTGATGCCGCATAGTTAAGCCAGCCC
CGACACCCGCCAACACCCGCTGACGCGCCCTGACGGGCTTGTCTGCTC
CCGGCATCCGCTTACAGACAAGCTGTGACCGTCTCCGGGAGCTGCATG
TGTCAGAGGTTTTCACCGTCATCACCGAAACGCGCGATGACGAAAGGG
CCTCGTGATACGCCTATTTTTATAGGTTAATGTCATGATAATAATGGT
TTCTTAGACGTCAGGTGGCACTTTTCGGGGAAATGTGCGCGGAACCCC
TATTTGTTTATTTTTCTAAATACATTCAAATATGTATCCGCTCATGAG
ACAATAACCCTGATAAATGCTTCAATAATATTGAAAAAGGAAGAGTAT
GAGTATTCAACATTTCCGTGTCGCCCTTATTCCCTTTTTTGCGGCATT
TTGCCTTCCTGTTTTTGCTCACCCAGAAACGCTGGTGAAAGTAAAAGA
TGCTGAAGATCAGTTGGGTGCACGAGTGGGTTACATCGAACTGGATCT
CAACAGCGGTAAGATCCTTGAGAGTTTTCGCCCCGAAGAACGTTTTCC
AATGATGAGCACTTTTAAAGTTCTGCTATGTGGCGCGGTATTATCCCG
TATTGACGCCGGGCAAGAGCAACTCGGTCGCCGCATACACTATTCTCA
GAATGACTTGGTTGAGTACTCACCAGTCACAGAAAAGCATCTTACGGA
TGGCATGACAGTAAGAGAATTATGCAGTGCTGCCATAACCATGAGTGA
TAACACTGCGGCCAACTTACTTCTGACAACGATCGGAGGACCGAAGGA
GCTAACCGCTTTTTTGCACAACATGGGGGATCATGTAACTCGCCTTGA
TCGTTGGGAACCGGAGCTGAATGAAGCCATACCAAACGACGAGCGTGA
CACCACGATGCCTGTAGCAATGGCAACAACGTTGCGCAAACTATTAAC
TGGCGAACTACTTACTCTAGCTTCCCGGCAACAATTAATAGACTGGAT
GGAGGCGGATAAAGTTGCAGGACCACTTCTGCGCTCGGCCCTTCCGGC
TGGCTGGTTTATTGCTGATAAATCTGGAGCCGGTGAGCGTGGGTCTCG
CGGTATCATTGCAGCACTGGGGCCAGATGGTAAGCCCTCCCGTATCGT
AGTTATCTACACGACGGGGAGTCAGGCAACTATGGATGAACGAAATAG
ACAGATCGCTGAGATAGGTGCCTCACTGATTAAGCATTGGTAACTGTC
AGACCAAGTTTACTCATATATACTTTAGATTGATTTAAAACTTCATTT
TTAATTTAAAAGGATCTAGGTGAAGATCCTTTTTGATAATCTCATGAC
CAAAATCCCTTAACGTGAGTTTTCGTTCCACTGAGCGTCAGACCCCGT
AGAAAAGATCAAAGGATCTTCTTGAGATCCTTTTTTTCTGCGCGTAAT
CTGCTGCTTGCAAACAAAAAAACCACCGCTACCAGCGGTGGTTTGTTT
GCCGGATCAAGAGCTACCAACTCTTTTTCCGAAGGTAACTGGCTTCAG
CAGAGCGCAGATACCAAATACTGTCCTTCTAGTGTAGCCGTAGTTAGG
CCACCACTTCAAGAACTCTGTAGCACCGCCTACATACCTCGCTCTGCT
AATCCTGTTACCAGTGGCTGCTGCCAGTGGCGATAAGTCGTGTCTTAC
CGGGTTGGACTCAAGACGATAGTTACCGGATAAGGCGCAGCGGTCGGG
CTGAACGGGGGGTTCGTGCACACAGCCCAGCTTGGAGCGAACGACCTA
CACCGAACTGAGATACCTACAGCGTGAGCATTGAGAAAGCGCCACGCT
TCCCGAAGGGAGAAAGGCGGACAGGTATCCGGTAAGCGGCAGGGTCGG
AACAGGAGAGCGCACGAGGGAGCTTCCAGGGGGAAACGCCTGGTATCT
TTATAGTCCTGTCGGGTTTCGCCACCTCTGACTTGAGCGTCGATTTTT
GTGATGCTCGTCAGGGGGCGGAGCCTATGGAAAAACGCCAGCAACGC
GGCCTTTTTACGGTTCCTGGCCTTTTGCTGGCCTTTTGCTCACATGTT
CTTTCCTGCGTTATCCCCTGATTCTGTGGATAACCGTATTACCGCCTT
TGAGTGAGCTGATACCGCTCGCCGCAGCCGAACGACCGAGCGCAGCGA
GTCAGTGAGCGAGGAAGCGGAAGAGCGCCCAATACGCAAACCGCCTCT
CCCCGCGCGTTGGCCGATTCATTAATGCAGCTGGCACGACAGGTTTCC
CGACTGGAAAGCGGGCAGTGAGCGCAACGCAATTAATGTGAGTTAGCT
CACTCATTAGGCACCCCAGGCTTTACACTTTATGCTTCCGGCTCGTAT
GTTGTGTGGAATTGTGAGCGGATAACAATTTCACACAGGAAACAGCTA
TGACCATGATTACGCCAAGCTTTGCTCTTAGGAGTTTCCTAATACATC
CCAAACTCAAATATATAAAGCATTTGACTTGTTCTATGCCCTAGGGGG
CGGGGGGAAGCTAAGCCAGCTTTTTTTAACATTTAAAATGTTAATTCC
ATTTTAAATGCACAGATGTTTTTATTTCATAAGGGTTTCAATGTGCAT
GAATGCTGCAATATTCCTGTTACCAAAGCTAGTATAAATAAAAATAGA
TAAACGTGGAAATTACTTAGAGTTTCTGTCATTAACGTTTCCTTCCTC
AGTTGACAACATAAATGCGCTGCTGAGCAAGCCAGTTTGCATCTGTCA
GGATCAATTTCCCATTATGCCAGTCATATTAATTACTAGTCAATTAGT
TGATTTTTATTTTTGACATATACATGTGAA (nucleotide sequence of Fv'Fvls with XhoI/SalI
linkers, (wobbled codons lowercase in Fv'))
                                    SEQ ID NO: 18
ctcgagGGcGTcCAagTcGAaACcATtagtCCcGGcGAtGGcaGaACa
TTtCCtAAaaGgGGaCAaACaTGtGTcGTcCAtTAtACaGGcATGtTg
GAgGAcGGcAAaAAgGTgGAacagtagtaGaGAtcGcAAtAAaCCtTTc
AAaTTcATGtTgGGaAAaCAaGAaGTcATtaGgGGaTGGGaGAgGGc
GTgGCtCAaATGtccGTcGGcCAacGcGCtAAgCTcACcATcagcCCc
GAcTAcGCaTAcGGcGCtACcGGaCAtCCcGGaATtATtCCcCCtCAc
GCtACctTgGTgTTtGAcGTcGAaCTgtTgAAgCTcGAagtcgaggga
gtgcaggtggaaaccatctcccaggagacgggcgccttccccaag
cgcggccagacctgcgtggtgcactacaccgggatgcttgaagatgga
aagaaagttgattcctcccgggacagaaacaagcccttaagtttatg
ctaggcaagcaggaggtgatccgaggctgggaagaaggggttgcccag
```

-continued

```
atgagtgtgggtcagagagccaaactgactatatctccagattatgcc tatggtgccactgggcacccaggcatcatcccaccacatgccactctc gtcttcgatgtggagcttctaaaactggaatctggcggtggatccgga gtcgag
```

(FV'FVLS amino acid sequence)

SEQ ID NO: 19

GlyValGlnValGluThrIleSerProGlyAspGlyArgThrPhePro

LysArgGlyGlnThrCysValValHisTyrThrGlyMetLeuGluAsp

GlyLysLysValAspSerSerArgAspArgAsnLysProPheLysPhe

MetLeuGlyLysGlnGluValIleArgGlyTrpGluGluGlyValAla

GlnMetSerValGlyGlnArgAlaLysLeuThrIleSerProAspTyr

AlaTyrGlyAlaThrGlyHisProGlyIleIleProProHisAlaThr

LeuValPheAspValGluLeuLeuLysLeuGlu (ValGlu)

GlyValGlnValGluThrIleSerProGlyAspGlyArgThrPhePro

LysArgGlyGlnThrCysValValHisTyrThrGlyMetLeuGluAsp

GlyLysLysValAspSerSerArgAspArgAsnLysProPheLysPhe

MetLeuGlyLysGlnGluValIleArgGlyTrpGluGluGlyValAla

GlnMetSerValGlyGlnArgAlaLysLeuThrIleSerProAspTyr

AlaTyrGlyAlaThrGlyHisProGlyIleIleProProHisAlaThr

LeuValPheAspValGluLeuLeuLysLeuGluSerGlyGlyGlySer

Gly

Example 7

Representative Embodiments

Provided hereafter are examples of certain embodiments of the technology.

A1. A method of administering donor T cells to a human patient, comprising
  a) transfecting or transducing human donor T cells in a donor cell culture with a nucleic acid including a promoter region and a nucleotide sequence that encodes a chimeric protein comprising a multimeric ligand binding region and a caspase 9 polypeptide; and
  b) administering the transduced or transfected donor T cells to the human patient.

A2. A method of reducing the effect of graft versus host disease in a human patient following donor T cell transplantation, comprising
  a) transfecting or transducing human donor T cells in a donor cell culture with a nucleic acid including a promoter region and a nucleotide sequence that encodes a chimeric protein comprising a multimeric ligand binding region and a caspase 9 polypeptide;
  b) administering the transduced or transfected donor T cells to the patient;
  c) detecting the presence or absence of graft versus host disease in the patient after (b); and
  d) administering a multimeric ligand that binds to the multimeric ligand binding region to a patient for whom the presence of graft versus host disease is detected.

A3. A method of stem cell transplantation, comprising
  a) administering a haploidentical stem cell transplant to a human patient; and
  b) administering haploidentical donor T cells to the patient, wherein the T cells are transfected or transduced in a haploidentical donor cell culture with a nucleic acid including a promoter region and a nucleotide sequence that encodes a chimeric protein comprising a multimeric ligand binding region and a caspase 9 polypeptide.

A4. The method of embodiment A3, wherein the haploidentical stem cell transplant is a CD34+ haploidentical stem cell transplant.

A5. The method of any of embodiments A1-A4 wherein the human donor T cells are haploidentical to the patient's T cells.

A6 The method of any of embodiments A1-A5, or A59, wherein the patient has cancer.

A7 The method of any of embodiments A1-A6, or A58, wherein the patient has a solid tumor.

A8 The method of embodiments A8, or A59, wherein the cancer is present in the blood or bone marrow of the patient.

A9 The method of any of embodiments A1-A8, or A59, wherein the patient has a blood or bone marrow disease.

A10 The method of any of embodiments A1-9, or A59, wherein the patient has been diagnosed with any condition or disorder that can be alleviated by stem cell transplantation.

A11 The method of any of embodiments A1-A10, or A59, wherein the patient has been diagnosed with sickle cell anemia or metachromatic leukodystrophy.

A12 The method of any of embodiments A1-A11, wherein the promoter is activated in activated T cells.

A13. The method of any of embodiments A1-A12, wherein the promoter comprises a 5' LTR sequence.

A14. The method of any of embodiments A1-A13, or A59, wherein the chimeric protein further comprises a marker polypeptide.

A15. The method of embodiment A14, wherein the marker polypeptide is a CD19 polypeptide.

A16. The method of embodiment A14, further comprising a selection step, wherein cells that express the marker are selected for administration to the patient.

A17. The method of embodiment A14, wherein the cells are selected by immunomagnetic selection.

A18. The method of any of embodiments A1-A17, or A59, wherein the caspase 9 polypeptide is a truncated caspase 9 polypeptide.

A19. The method of embodiment A18, wherein the caspase 9 polypeptide lacks the caspase recruitment domain.

A20. The method of embodiment A18, wherein the caspase 9 polypeptide comprises the amino acid sequence of SEQ ID NO: 9, or a fragment thereof, or is encoded by the nucleotide sequence of SEQ ID NO: 8, or a fragment thereof.

A21. The method of any of embodiments A1-A20, wherein the donor cell culture is prepared from a bone marrow sample.

A22 The method of any of embodiments A1-A20, wherein the donor cell culture is prepared from peripheral blood.

A23. The method of embodiment A22, wherein the donor cell culture is prepared from donor peripheral blood mononuclear cells.

A24. The method of any of embodiments A1-A23, wherein the donor T cells are allodepleted from the donor cell culture before transfection or transduction.

A25. The method of any of embodiments A1-A24, wherein the transduced or transfected T cells are cultured in the presence of IL-2 before administration to the patient.

A26. The method of any of embodiments A1-A25, further comprising administering a multimeric ligand that binds to the multimeric ligand binding region.

A27. The method of any of embodiments A1-A26, or A59, wherein the multimeric ligand binding region is selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof.

A28. The method of any of embodiments A1-A27, or A59, wherein the multimeric ligand binding region is an FKBP12 region.

A29. The method of embodiments A26 or A59, wherein the multimeric ligand is an FK506 dimer or a dimeric FK506 analog ligand.

A30. The method of embodiments A26 or A59, wherein the multimeric ligand is AP1903.

A31. The method of embodiments A26 or A59, wherein the multimeric ligand is administered to treat graft versus host disease.

A32. The method of any of embodiments A1-A31, wherein the patient exhibits graft versus host disease symptoms before the multimeric ligand is administered.

A33. The method of embodiments A32 or A59, wherein the patient exhibits one or more Stage 0 graft versus host disease symptoms.

A34 The method of embodiments A32 or A59, wherein the patient exhibits one or more Stage 1 graft versus host disease symptoms.

A35 The method of embodiments A32 or A59, wherein the patient exhibits one or more Stage 2 graft versus host disease symptoms.

A36 The method of embodiments A32 or A59, wherein the patient exhibits one or more Stage 3 graft versus host disease symptoms.

A37 The method of embodiments A32 or A59, wherein the patient exhibits one or more Stage 4 graft versus host disease symptoms.

A38. The method of embodiment A32 or A59, wherein more than one dose of the multimeric ligand is administered.

A39. The method of embodiment A32, wherein after administration of the multimeric ligand, the number of alloreactive T cells is reduced.

A40. The method of any of embodiments A31-A39, wherein the alloreactive T cells express the marker and CD3.

A41. The method of any of embodiments A31-A40, wherein the number of alloreactive T cells is reduced by about 90% or more after administration of the multimeric ligand.

A42. The method of any of embodiments A31-A41, wherein after administration of the multimeric ligand, donor T cells survive in the patient that are able to expand and are reactive to viruses and fungi.

A43. The method of any of embodiments A31-A42, wherein after administration of the multimeric ligand, donor T cells survive in the patient that are able to expand and are reactive to tumor cells in the patient.

A44. The method of any of embodiments A1-A43, wherein the patients have received haplo-CD34+ stem cell transplants before or at the same time as administration of the donor T cells.

A45. The method of any of embodiments A1-A44, wherein the donor T cells are transduced or transfected with a retroviral vector.

A46. The method of embodiment A45, wherein the retroviral vector is a murine leukemia virus vector.

A47. The method of embodiment A45, wherein the retroviral vector is an SFG vector.

A48 The method of any of embodiments A1-A47, wherein the transfected or transduced cells are further transfected or transduced with a gene expression vector.

A49. The method of any of embodiments A31-A48, or A59, further comprising determining whether to administer an additional dose or additional doses of the multimeric ligand to the patient based upon the appearance of graft versus host disease symptoms in the patient.

A50. The method of any of embodiments A31-A48, or A59, further comprising determining whether to administer an additional dose or additional doses of the multimeric ligand to the patient, wherein the determination is based upon the amount or concentration of marker and CD3 positive T cells in the patient.

A51. The method of any of embodiments A1-A50, wherein at least $1 \times 10^6$ transduced or transfected donor T cells are administered to the patient.

A52. The method of any of embodiments A1-A50, wherein at least $1 \times 10^7$ transduced or transfected donor T cells are administered to the patient.

A53. The method of any of embodiments A1-A50, wherein at least $1 \times 10^8$ transduced or transfected donor T cells are administered to the patient.

A54. The method of any of embodiments A1-A53, further comprising
identifying the presence, absence or stage of graft versus host disease in the patient, and
administering a multimeric ligand that binds to the multimeric ligand binding region, maintaining a subsequent dosage of the multimeric ligand, or adjusting a subsequent dosage of the multimeric ligand to the patient based on the presence, absence or stage of the graft versus host disease identified in the patient.

A55. The method of any of embodiments A1-A53, further comprising
identifying the presence, absence or stage of graft versus host disease in the patient, and
determining whether a multimeric ligand that binds to the multimeric ligand binding region should be administered to the patient, or the dosage of the multimeric ligand subsequently administered to the patient is adjusted based on the presence, absence or stage of the graft versus host disease identified in the patient.

A56. The method of any of embodiments A1-A53, or A59, further comprising
receiving information comprising the presence, absence or stage of graft versus host disease in the patient; and
administering a multimeric ligand that binds to the multimeric ligand binding region, maintaining a subsequent dosage of the multimeric ligand, or adjusting a subsequent dosage of the multimeric ligand to the patient based on the presence, absence or stage of the graft versus host disease identified in the patient.

A57. The method of any of embodiments A1-A53, or A59, further comprising
identifying the presence, absence or stage of graft versus host disease in the patient, and
transmitting the presence, absence or stage of the graft versus host disease to a decision maker who administers a multimeric ligand that binds to the multimeric ligand binding region, maintains a subsequent dosage of the multimeric ligand, or adjusts a subsequent dosage of the multimeric ligand administered to the patient based on the presence, absence or stage of the graft versus host disease identified in the subject.

A58. The method of any of embodiments A1-A53, or A59, further comprising
identifying the presence, absence or stage of graft versus host disease in the patient, and
transmitting an indication to administer a multimeric ligand that binds to the multimeric binding region, maintain a subsequent dosage of the multimeric ligand or adjust a subsequent dosage of the multimeric ligand administered to the patient based on the presence, absence or stage of the graft versus host disease identified in the subject.

A59. A method of treating graft versus host disease in a patient who has undergone cell therapy, wherein one or more of the cells introduced for the therapy expresses a chimeric protein, wherein the chimeric protein comprises a multimeric ligand binding region and a caspase 9 polypeptide, comprising administering a multimeric ligand that binds to the multimeric ligand binding region to the patient.

A60. The method of any of embodiments A1-A59, wherein after administration of the multimeric ligand that binds to the multimeric binding region, the number of alloreactive T cells is reduced.

A61. The method of embodiment A60, wherein alloreactive T cells that are not undergoing cell division are ablated.

A62. The method of embodiment A60, wherein within 2 hours of administration of the multimeric ligand, at least 90% of CD3+ΔCD19+ cells are ablated.

A63. The method of embodiment A60, wherein within 1 hour of administration of the multimeric ligand, at least 90% of CD3+ΔCD19+ cells are ablated.

A64. The method of embodiment A60, wherein within 30 minutes of administration of the multimeric ligand, at least 90% of CD3+ΔCD19+ cells are ablated.

A65. The method of any of embodiments A62-A64, wherein within 24 hours of administration of the multimeric ligand, there is a further log reduction of CD3+ΔCD19+ cells compared to the amount of CD3+ΔCD19+ cells at 30 minutes after administration of the multimeric ligand.

A66. The method of any of embodiments A62-A65, further comprising a resolution of skin and liver GvHD within 24 hours after administration of the multimeric ligand.

B1. A method of controlling the survival of transplanted therapeutic cells in a patient, comprising
a) preparing or obtaining therapeutic cells;
b) transfecting or transducing the therapeutic cells with a nucleic acid including a promoter region and a nucleotide sequence that encodes a chimeric protein comprising a multimeric ligand binding region and a caspase 9 polypeptide;
c) transplanting the transduced or transfected therapeutic cells into the patient; and
d) after step c), administering a multimeric ligand to the patient, wherein the multimeric ligand binds to the multimeric ligand binding region wherein transplanted therapeutic cells that express the caspase 9 polypeptide are killed following administration of the multimeric ligand.

B2. A method of transplanting therapeutic cells in a human patient, comprising
a) preparing or obtaining cells for transplantation;
b) transfecting or transducing the cells with a nucleic acid including a promoter region and a nucleotide sequence that encodes a chimeric protein comprising a multimeric ligand binding region and a caspase 9 polypeptide; and
c) transplanting the transduced or transfected therapeutic cells into the human patient.

B3. A method of preparing progenitor therapeutic cells for transplantation in a patient, comprising
a) preparing or obtaining cells for transplantation; and
b) transfecting or transducing the cells with a nucleic acid including a promoter region and a nucleotide sequence that encodes a chimeric protein comprising a multimeric ligand binding region and a caspase 9 polypeptide.

B4. The method of embodiment B1 or B3, wherein the patient is a human patient.

B5. The method of embodiment B2, wherein a multimeric ligand is administered to the patient, wherein the multimeric ligand binds to the multimeric ligand binding region.

B6. The method of embodiment B1 or B3, wherein the multimeric ligand is administered to kill transplanted therapeutic cells.

B7. The method of any of embodiments B1-B6, wherein the therapeutic cells are obtained or prepared from bone marrow.

B8. The method of any of embodiments B1-B6, wherein the therapeutic cells are obtained or prepared from umbilical cord blood.

B9. The method of any of embodiments B1-B2, wherein the therapeutic cells are obtained or prepared from peripheral blood.

B10. The method of embodiment B9, wherein the therapeutic cells are obtained or prepared from peripheral blood mononuclear cells.

B11. The method of any of embodiments B1-B10, wherein the therapeutic cells are progenitor cells.

B12. The method of any of embodiments B1-B11, wherein the therapeutic cells are hematopoietic progenitor cells.

B13. The method of any of embodiments B1-B12, wherein the therapeutic cells are selected from the group consisting of mesenchymal stromal cells, embryonic stem cells, and inducible pluripotent stem cells.

B14. The method of any of embodiments B1-B13, wherein the promoter is developmentally regulated and the caspase 9 polypeptide is expressed in developmentally differentiated cells.

B15. The method of any of embodiments B1-B13, wherein the promoter is tissue specific and the caspase 9 polypeptide is expressed in the specific tissue.

B16 The method of any of embodiments B1-B15, wherein the patient has cancer.

B17 The method of any of embodiments B1-B16, wherein the patient has a solid tumor.

B18 The method of any of embodiments B1-B17, wherein the cancer is present in the blood or bone marrow of the patient.

B19 The method of any of embodiments B1-B18, wherein the patient has a blood or bone marrow disease.

B20 The method of any of embodiments B1-B19, wherein the patient has any condition or disorder that can be alleviated by stem cell transplantation.

B21 The method of any of embodiments B1-B19, wherein the patient has been diagnosed with sickle cell anemia or metachromatic leukodystrophy.

B22. The method of any of embodiments B1-B21, wherein the chimeric protein further comprises a marker polypeptide.

B23. The method of any of embodiments B1-B22, wherein the marker polypeptide is a CD19 polypeptide.

B24. The method of any of embodiments B1-B23, further comprising a selection step, wherein cells that express the marker are selected for administration to the patient.

B25. The method of any of embodiments B1-B24, wherein the cells are selected by immunomagnetic selection.

B26. The method of any of embodiments B1-B25, wherein the caspase 9 polypeptide is a truncated caspase 9 polypeptide.

B27. The method of embodiment B26, wherein the caspase 9 polypeptide lacks the caspase recruitment domain.

B28. The method of embodiment B26, wherein the caspase 9 polypeptide comprises the amino acid sequence of SEQ ID NO: 9, or a fragment thereof, or is encoded by the nucleotide sequence of SEQ ID NO: 8, or a fragment thereof.

B29. The method of any of embodiments B1-B28, wherein the multimeric ligand binding region is selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof.

B30. The method of any of embodiments B1-B29, wherein the multimeric ligand binding region is an FKBP12 region.

B31. The method of embodiment B1 or B5, wherein the multimeric ligand is an FK506 dimer or a dimeric FK506 analog ligand.

B32. The method of embodiment B1 or B5, wherein the multimeric ligand is AP1903.

B33. The method of embodiment B1 or B5, wherein more than one dose of the multimeric ligand is administered.

B34. The method of any of embodiments B1-B33, wherein the therapeutic cells are transduced or transfected with a retroviral vector.

B35. The method of embodiment B34, wherein the retroviral vector is a murine leukemia virus vector.

B36. The method of embodiment B34, wherein the retroviral vector is an SFG vector.

B37. The method of any of embodiments B1-B36, wherein the transfected or transduced cells are further transfected or transduced with a gene expression vector.

B38. The method of any of embodiments B1 or B2, further comprising
identifying a presence or absence of a condition in the patient that requires the removal of transfected or transduced therapeutic cells from the patient; and
administering a multimeric ligand that binds to the multimeric ligand binding region, maintaining a subsequent dosage of the multimeric ligand, or adjusting a subsequent dosage of the multimeric ligand to the patient based on the presence or absence of the condition identified in the patient.

B39. The method of any of embodiments B1 or B2 further comprising
identifying a presence or absence of a condition in the patient that requires the removal of transfected or transduced therapeutic cells from the patient; and
determining whether a multimeric ligand that binds to the multimeric ligand binding region should be administered to the patient, or the dosage of the multimeric ligand subsequently administered to the patient is adjusted based on the presence or absence of the condition identified in the patient.

B40. The method of any of embodiments B1 or B2, further comprising
receiving information comprising presence or absence of a condition in the patient that requires the removal of transfected or transduced therapeutic cells from the patient; and
administering a multimeric ligand that binds to the multimeric ligand binding region, maintaining a subsequent dosage of the multimeric ligand, or adjusting a subsequent dosage of the multimeric ligand to the patient based on the presence or absence of the condition identified in the patient.

B41. The method of any of embodiments B1 or B2, further comprising
identifying a presence or absence of a condition in the patient that requires the removal of transfected or transduced therapeutic cells from the patient; and
transmitting the presence, absence or stage of the condition identified in the patient to a decision maker who administers a multimeric ligand that binds to the multimeric ligand binding region, maintains a subsequent dosage of the multimeric ligand, or adjusts a subsequent dosage of the multimeric ligand administered to the patient based on the presence, absence or stage of the condition identified in the patient.

B42. The method of any of embodiments B1 or B2, further comprising
identifying a presence or absence of a condition in the patient that requires the removal of transfected or transduced therapeutic cells from the patient; and
transmitting an indication to administer a multimeric ligand that binds to the multimeric ligand binding region, maintains a subsequent dosage of the multimeric ligand, or adjusts a subsequent dosage of the multimeric ligand administered to the patient based on the presence, absence or stage of the condition identified in the patient.

B43. The method of any of embodiments B1-42, wherein the therapeutic cells are transduced or transfected with a second nucleic acid that encodes a second heterologous protein.

B44. The method of any of embodiments B1-42, wherein the therapeutic cells are transduced with a heterologous gene that expresses a chimeric antigen receptor.

B45. The method of any of embodiments B1-B42, wherein the therapeutic cells are transduced with a heterologous gene that expresses a modified TGF-beta receptor.

B46. The method of embodiments B43, B44, or B45, wherein the therapeutic cells are transduced with the heterologous gene before, at the same time as, or after being transduced with the nucleic acid encoding the chimeric protein comprising a multimeric ligand binding region and a caspase 9 polypeptide;

C1. A cell, comprising a nucleic acid including a promoter region and a nucleotide sequence that encodes a chimeric protein comprising a multimeric ligand binding region and a caspase 9 polypeptide, wherein the cell is obtained or prepared from bone marrow or umbilical cord blood.

C2. The cell of embodiment C1, wherein the cell is a human cell.

C3. The cell of any of embodiments C1-C2, wherein cell is a progenitor cell.

C4. The cell of any of embodiments C1-C2, wherein the cell is a hematopoietic progenitor cell.

C5. The cell of any of embodiments C1-C4, wherein the cell is selected from the group consisting of mesenchymal stromal cells, embryonic stem cells, and inducible pluripotent stem cells.

C6. The cell of any of embodiments C1-05, wherein the promoter is developmentally regulated and the caspase 9 polypeptide is expressed in developmentally differentiated cells.

C7. The cell of any of embodiments C1-05, wherein the promoter is tissue-specific and the caspase 9 polypeptide is expressed in the specific tissue.

C8. The cell of any of embodiments C1-C7, wherein the chimeric protein further comprises a marker polypeptide.

C9. The cell of embodiment C8, wherein the marker polypeptide is a CD19 polypeptide.

C10. The cell of any of embodiments C1-C9, wherein the caspase 9 polypeptide is a truncated caspase 9 polypeptide.

C11. The cell of embodiment C10, wherein the caspase 9 polypeptide lacks the caspase recruitment domain.

C12. The cell of embodiment C11, wherein the caspase 9 polypeptide comprises the amino acid sequence of SEQ ID NO: 9, or a fragment thereof, or is encoded by the nucleotide sequence of SEQ ID NO: 8, or a fragment thereof.

C13. The cell of any of embodiments C1-C12, wherein the multimeric ligand binding region is selected from the group consisting of FKBP, cyclophilin receptor, steroid receptor, tetracycline receptor, heavy chain antibody subunit, light chain antibody subunit, single chain antibodies comprised of heavy and light chain variable regions in tandem separated by a flexible linker domain, and mutated sequences thereof.

C14. The cell of any of embodiments C1-C13, wherein the multimeric ligand binding region is an FKBP12 region.

C15. The cell of any of embodiments C1-C14, wherein the cells are transduced or transfected with a retroviral vector.

C16. The cell of embodiment C15, wherein the retroviral vector is a murine leukemia virus vector.

C17. The cell of embodiment C16, wherein the retroviral vector is an SFG vector.

C18. The cell of any of embodiments C1-C17, wherein the transfected or transduced cells are further transfected or transduced with a gene expression vector.

D1. A method of administering donor T cells to a human patient, comprising
  a) transfecting or transducing non-allodepleted human donor T cells in a donor cell culture with a nucleic acid including a promoter region and a nucleotide sequence that encodes a chimeric protein comprising a multimeric ligand binding region and a caspase 9 polypeptide; and
  b) administering the transduced or transfected donor T cells to the human patient.

D2. A method of reducing the effect of graft versus host disease in a human patient following donor T cell transplantation, comprising
  a) transfecting or transducing non-allodepleted human donor T cells in a donor cell culture with a nucleic acid including a promoter region and a nucleotide sequence that encodes a chimeric protein comprising a multimeric ligand binding region and a caspase 9 polypeptide;
  b) administering the transduced or transfected donor T cells to the patient;
  c) detecting the presence or absence of graft versus host disease in the patient after (b); and
  d) administering a multimeric ligand that binds to the multimeric ligand binding region to a patient for whom the presence of graft versus host disease is detected.

D3. A method of stem cell transplantation, comprising
  a) administering a haploidentical stem cell transplant to a human patient; and
  b) administering non-allodepleted haploidentical donor T cells to the patient, wherein the T cells are transfected or transduced in a haploidentical donor cell culture with a nucleic acid including a promoter region and a nucleotide sequence that encodes a chimeric protein comprising a multimeric ligand binding region and a caspase 9 polypeptide.

D4. The method of any of embodiments D1-D3, wherein at least $1 \times 10^6$ cells/Kg body weight are administered to the patient.

D5. The method of any of embodiments D1-D3, wherein at least $3 \times 10^6$ cells/Kg body weight are administered to the patient.

D6. The method of any of embodiments D1-D3, wherein at least $5 \times 10^6$ cells/Kg body weight are administered to the patient.

D7. The method of any of embodiments D1-D3, wherein at least $7 \times 10^6$ cells/Kg body weight are administered to the patient.

D8. The method of any of embodiments D1-D3, wherein at least $9 \times 10^6$ cells/Kg body weight are administered to the patient.

E1. The method of any of embodiments A1-A66, B1-B46, or D1-D8, wherein the chimeric protein comprises a caspase 1, caspase 3, or caspase 8 polypeptide and not a caspase 9 polypeptide.

E2. The method of embodiment E1, wherein the caspase 1, caspase 3 or caspase 8 polypeptide is truncated.

E3. The method of embodiment E2, wherein the caspase 1, caspase 3, or caspase 8 polypeptide lacks the caspase recruitment domain.

E4. The cell of any of embodiments C1-C18, wherein the chimeric protein comprises a caspase 1, caspase 3, or caspase 8 polypeptide and not a caspase 9 polypeptide.

E5. The cell of embodiment E4, wherein the caspase 1, caspase 3 pr caspase 8 polypeptide is truncated.

E6. The cell of embodiment E5, wherein the caspase 1, caspase 3, or caspase 8 polypeptide lacks the caspase recruitment domain.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method of controlling the survival of therapeutic cells in a human patient, comprising administering a multimeric ligand to a human patient to whom therapeutic cells have been administered, wherein:
the therapeutic cells have been transfected or transduced with a nucleic acid comprising (i) a promoter region, and (ii) a polynucleotide that encodes a chimeric protein comprising a multimeric ligand binding region and a caspase 9 polypeptide;
the promoter region is operatively linked to the polynucleotide;
the multimeric ligand binds to the multimeric ligand binding region;
the multimeric ligand binding region comprises a modified FKBP12 polypeptide;
the modified FKBP12 polypeptide binds with higher affinity to the multimeric ligand than the wild type FKBP12 polypeptide;
the modified FKBP12 polypeptide comprises an amino acid substation at position 36;
the number of therapeutic cells that express the caspase 9 polypeptide is reduced at least 90% within 24 hours following administration of the multimeric ligand.

2. The method of claim 1, wherein therapeutic cells that are not undergoing cell division are killed following administration of the multimeric ligand.

3. The method of claim 1, wherein the multimeric ligand is AP1903.

4. The method of claim 1, wherein the multimeric ligand is AP20187.

5. The method of claim 1, wherein the therapeutic cells are allogeneic T cells.

6. The method of claim 1, wherein the therapeutic cells are non-allodepleted.

7. The method of claim 1, wherein the caspase-9 polypeptide is a truncated caspase-9 polypeptide.

8. The method of claim 1, wherein the modified FKBP12 polypeptide binds with higher affinity to AP1903 than the wild type FKBP12 polypeptide.

9. The method of claim 1, wherein the FKBP12 polypeptide comprises a valine at position 36.

10. The method of claim 1, further comprising administering a haploidentical stem cell transplant to the patient.

11. The method of claim 1, wherein the chimeric protein further comprises a marker polypeptide.

12. The method of claim 1, wherein the number of therapeutic cells is reduced at least 90% within 30 minutes following administration of the multimeric ligand.

13. The method of claim 1, wherein the FKBP12 polypeptide is encoded by a wobbled nucleotide sequence.

14. The method of claim 1, comprising administering a composition comprising the therapeutic cells to the patient prior to administering the multimeric ligand to the patient.

15. The method of claim 14, wherein the therapeutic cells are allogeneic T cells.

16. The method of claim 15, wherein the T cells are not in an active state when administered to the patient.

17. The method of claim 15, wherein the composition comprising the T cells is over 90% pure.

18. A method of controlling the survival of therapeutic cells in a human patient, comprising administering a multimeric ligand to a human patient to whom therapeutic cells have been administered, wherein:
the therapeutic cells have been transfected or transduced with a nucleic acid comprising (i) a promoter region, and (ii) a polynucleotide that encodes a chimeric protein comprising a multimeric ligand binding region and a caspase 9 polypeptide;
the promoter region is operatively linked to the polynucleotide;
the multimeric ligand binds to the multimeric ligand binding region;
the multimeric ligand is AP20187 or AP1903;
the multimeric ligand binding region comprises a modified FKBP12 polypeptide;
the modified FKBP12 polypeptide binds with higher affinity to the multimeric ligand than the wild type FKBP12 polypeptide; and
the number of therapeutic cells that express the caspase 9 polypeptide is reduced at least 90% within 24 hours following administration of the multimeric ligand.

19. The method of claim 18, wherein therapeutic cells that are not undergoing cell division are killed following administration of the multimeric ligand.

20. The method of claim 18, wherein the multimeric ligand is AP1903.

21. The method of claim 18, wherein the multimeric ligand is AP20187.

22. The method of claim 18, wherein the therapeutic cells are allogeneic T cells.

23. The method of claim 18, wherein the therapeutic cells are non-allodepleted.

24. The method of claim 18, wherein the caspase-9 polypeptide is a truncated caspase-9 polypeptide.

25. The method of claim 18, wherein the modified FKBP12 polypeptide binds with higher affinity to AP1903 than the wild type FKBP12 polypeptide.

26. The method of claim 18, wherein the FKBP12 polypeptide comprises a valine at position 36.

27. The method of claim 18, further comprising administering a haploidentical stem cell transplant to the patient.

28. The method of claim 18, wherein the chimeric protein further comprises a marker polypeptide.

29. The method of claim 18, wherein the number of therapeutic cells is reduced at least 90% within 30 minutes following administration of the multimeric ligand.

30. The method of claim 18, wherein the FKBP12 polypeptide is encoded by a wobbled nucleotide sequence.

31. The method of claim 18, comprising administering a composition comprising the therapeutic cells to the patient prior to administering the multimeric ligand to the patient.

32. The method of claim 31, wherein the therapeutic cells are allogeneic T cells.

33. The method of claim 32, wherein the T cells are not in an active state when administered to the patient.

34. The method of claim 33, wherein the composition comprising the T cells is over 90% pure.

* * * * *

```
                        SEQUENCE LISTING

<160> NUMBER OF SEQ ID NOS: 29

<210> SEQ ID NO 1
<211> LENGTH: 590
<212> TYPE: DNA
<213> ORGANISM: Unknown
<220> FEATURE:
<223> OTHER INFORMATION: Description of Unknown: 5' Long terminal repeat
      viral genomic polynucleotide

<400> SEQUENCE: 1
tgaaagaccc cacctgtagg tttggcaagc tagcttaagt aacgccattt tgcaaggcat      60
ggaaaaatac ataactgaga atagaaaagt tcagatcaag gtcaggaaca gatggaacag     120
ctgaatatgg gccaaacagg atatctgtgg taagcagttc ctgccccggc tcagggccaa     180
gaacagatgg aacagctgaa tatgggccaa acaggatatc tgtggtaagc agttcctgcc     240
ccggctcagg gccaagaaca gatggtcccc agatgcggtc cagccctcag cagtttctag     300
agaaccatca gatgtttcca gggtgcccca aggacctgaa atgaccctgt gccttatttg     360
aactaaccaa tcagttcgct tctcgcttct gttcgcgcgc ttatgctccc cgagctcaat     420
aaaagagccc acaaccccte actcggggcg ccagtcctcc gattgactga gtcgcccggg     480
tacccgtgta tccataaaac cctcttgcag ttgcatccga cttgtggtct cgctgttcct     540
tgggagggtc tcctctgagt gattgactac ccgtcagcgg gggtctttca                 590

<210> SEQ ID NO 2
<211> LENGTH: 321
<212> TYPE: DNA
<213> ORGANISM: Homo sapiens

<400> SEQUENCE: 2
ggagtgcagg tggaaaccat ctccccagga gacgggcgca ccttccccaa gcgcggccag      60
acctgcgtgg tgcactacac cgggatgctt gaagatggaa agaaagttga ttcctcccgg     120
gacagaaaca agcccttta gtttatgcta ggcaagcagg aggtgatccg aggctgggaa     180 gaagggggttg cccagatgag tgtgggtcag agagccaaac tgactatatc tccagattat     240
gcctatggtg ccactgggca cccaggcatc atcccaccac atgccactct cgtcttcgat     300
gtggagcttc taaaactgga a                                                321

<210> SEQ ID NO 3
<211> LENGTH: 107
<212> TYPE: PRT
<213> ORGANISM: Homo sapiens

<400> SEQUENCE: 3

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
                20                  25                  30

Gly Lys Lys Val Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
        50                  55                  60
```

```
Gln Met Ser Val Gly Gln Arg Ala Lys Leu Thr Ile Ser Pro Asp Tyr
 65                  70                  75                  80

Ala Tyr Gly Ala Thr Gly His Pro Gly Ile Ile Pro Pro His Ala Thr
                 85                  90                  95

Leu Val Phe Asp Val Glu Leu Leu Lys Leu Glu
            100                 105

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tctggcggtg gatccgga                                              18

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Gly Gly Gly Ser Gly
1               5

<210> SEQ ID NO 6
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 gtcgac                                                            6

<210> SEQ ID NO 7
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Asp
1

<210> SEQ ID NO 8
<211> LENGTH: 846
<212> TYPE: DNA
<213> ORGANISM: Homo sapiens

<400> SEQUENCE: 8
ggatttggtg atgtcggtgc tcttgagagt ttgaggggaa atgcagattt ggcttacatc    60
ctgagcatgg agccctgtgg ccactgcctc attatcaaca atgtgaactt ctgccgtgag   120
tccgggctcc gcacccgcac tggctccaac atcgactgtg agaagttgcg gcgtcgcttc   180
tcctcgctgc atttcatggt ggaggtgaag ggcgacctga ctgccaagaa aatggtgctg   240
```

```
gctttgctgg agctggcgca gcaggaccac ggtgctctgg actgctgcgt ggtggtcatt    300
ctctctcacg gctgtcaggc cagccacctg cagttcccag gggctgtcta cggcacagat    360
ggatgccctg tgtcggtcga aagattgtg aacatcttca atgggaccag ctgccccagc    420
ctgggaggga agcccaagct cttttcatc caggcctgtg gtgggagca aaagaccat      480 gggtttgagg tggcctccac ttcccctgaa gacgagtccc ctggcagtaa ccccgagcca    540
gatgccaccc cgttccagga aggtttgagg accttcgacc agctggacgc catatctagt    600
ttgcccacac ccagtgacat ctttgtgtcc tactctactt tcccaggttt tgtttcctgg    660 agggaccca agagtggctc ctggtacgtt gagaccctgg acgacatctt tgagcagtgg    720
gctcactctg aagacctgca gtccctcctg cttagggtcg ctaatgctgt ttcggtgaaa    780
gggatttata aacagatgcc tggttgcttt aatttcctcc ggaaaaaact tttctttaaa    840
acatca                                                              846
```

<210> SEQ ID NO 9
<211> LENGTH: 282
<212> TYPE: PRT
<213> ORGANISM: Homo sapiens

<400> SEQUENCE: 9

```
Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
                20                  25                  30

Asn Asn Val Asn Phe Cys Arg Glu Ser Gly Leu Arg Thr Arg Thr Gly
            35                  40                  45

Ser Asn Ile Asp Cys Glu Lys Leu Arg Arg Arg Phe Ser Ser Leu His
        50                  55                  60

Phe Met Val Glu Val Lys Gly Asp Leu Thr Ala Lys Lys Met Val Leu
65                  70                  75                  80

Ala Leu Leu Glu Leu Ala Gln Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
    210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255
```

```
            Val Ser Val Lys Gly Ile Tyr Lys Gln Met Pro Gly Cys Phe Asn Phe
                    260                 265                 270

Leu Arg Lys Lys Leu Phe Phe Lys Thr Ser
                    275                 280

<210> SEQ ID NO 10
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10 gctagcaga                                                                  9

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ser Arg
1

<210> SEQ ID NO 12
<211> LENGTH: 57
<212> TYPE: DNA
<213> ORGANISM: Thosea asigna virus

<400> SEQUENCE: 12
gccgagggca ggggaagtct tctaacatgc ggggacgtgg aggaaaatcc cggccc         57

<210> SEQ ID NO 13
<211> LENGTH: 19
<212> TYPE: PRT
<213> ORGANISM: Thosea asigna virus

<400> SEQUENCE: 13

Ala Glu Gly Arg Gly Ser Leu Leu Thr Cys Gly Asp Val Glu Glu Asn
1               5                   10                  15

Pro Gly Pro

<210> SEQ ID NO 14
<211> LENGTH: 999
<212> TYPE: DNA
<213> ORGANISM: Homo sapiens

<400> SEQUENCE: 14
atgccacctc ctcgcctcct cttcttcctc ctcttcctca cccccatgga agtcaggccc    60
gaggaacctc tagtggtgaa ggtggaagag ggagataacg ctgtgctgca gtgcctcaag   120
gggacctcag atggccccac tcagcagctg acctggtctc gggagtcccc gcttaaaccc   180
ttcttaaaac tcagcctggg gctgccaggc ctggaatcc acatgaggcc cctggccatc    240
tggcttttca tcttcaacgt ctctcaacag atgggggct tctacctgtg ccagccgggg   300
cccccctctg agaaggcctg gcagcctggc tggacagtca atgtggaggg cagcggggag   360
ctgttccggt ggaatgtttc ggacctaggt ggcctgggct gtggcctgaa gaacaggtcc   420
tcagagggcc ccagctcccc ttccgggaag ctcatgagcc ccaagctgta tgtgtgggcc   480
```

-continued

```
aaagaccgcc ctgagatctg ggagggagag cctccgtgtc tcccaccgag ggacagcctg      540
aaccagagcc tcagccagga cctcaccatg gcccctggct ccacactctg gctgtcctgt      600
ggggtacccc ctgactctgt gtccaggggc cccctctcct ggacccatgt gcaccccaag      660
gggcctaagt cattgctgag cctagagctg aaggacgatc gcccggccag agatatgtgg      720
gtaatggaga cgggtctgtt gttgccccgg ccacagctc aagacgctgg aaagtattat       780
tgtcaccgtg caacctgac catgtcattc cacctggaga tcactgctcg gccagtacta       840
tggcactggc tgctgaggac tggtggctgg aaggtctcag ctgtgacttt ggcttatctg      900
atcttctgcc tgtgttccct tgtgggcatt cttcatcttc aaagagccct ggtcctgagg      960
aggaaaagaa agcgaatgac tgaccccacc aggagattc                             999
```

<210> SEQ ID NO 15
<211> LENGTH: 333
<212> TYPE: PRT
<213> ORGANISM: Homo sapiens

<400> SEQUENCE: 15

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
```

```
            275                 280                 285
Gly Trp Lys Val Ser Ala Val Thr Leu Ala Tyr Leu Ile Phe Cys Leu
        290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe
                325                 330
```

<210> SEQ ID NO 16
<211> LENGTH: 590
<212> TYPE: DNA
<213> ORGANISM: Unknown
<220> FEATURE:
<223> OTHER INFORMATION: Description of Unknown: 3' Long terminal repeat
      viral genomic polynucleotide

<400> SEQUENCE: 16

| | | | | | |
|---|---|---|---|---|---|
| tgaaagaccc | cacctgtagg | tttggcaagc | tagcttaagt | aacgccattt | tgcaaggcat | 60 |
| ggaaaaatac | ataactgaga | atagagaagt | tcagatcaag | gtcaggaaca | gatggaacag | 120 |
| ctgaatatgg | gccaaacagg | atatctgtgg | taagcagttc | ctgccccggc | tcagggccaa | 180 |
| gaacagatgg | aacagctgaa | tatgggccaa | acaggatatc | tgtggtaagc | agttcctgcc | 240 |
| ccggctcagg | gccaagaaca | gatggtcccc | agatgcggtc | cagccctcag | cagtttctag | 300 |
| agaaccatca | gatgtttcca | gggtgcccca | aggacctgaa | atgaccctgt | gccttatttg | 360 |
| aactaaccaa | tcagttcgct | tctcgcttct | gttcgcgcgc | ttctgctccc | cgagctcaat | 420 |
| aaaagagccc | acaacccctc | actcggggcg | ccagtcctcc | gattgactga | gtcgcccggg | 480 |
| tacccgtgta | tccaataaac | cctcttgcag | ttgcatccga | cttgtggtct | cgctgttcct | 540 |
| tgggagggtc | tcctctgagt | gattgactac | ccgtcagcgg | gggtctttca | | 590 |

<210> SEQ ID NO 17
<211> LENGTH: 8622
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

| | | | | | |
|---|---|---|---|---|---|
| tgaaagaccc | cacctgtagg | tttggcaagc | tagcttaagt | aacgccattt | tgcaaggcat | 60 |
| ggaaaaatac | ataactgaga | atagaaaagt | tcagatcaag | gtcaggaaca | gatggaacag | 120 |
| ctgaatatgg | gccaaacagg | atatctgtgg | taagcagttc | ctgccccggc | tcagggccaa | 180 |
| gaacagatgg | aacagctgaa | tatgggccaa | acaggatatc | tgtggtaagc | agttcctgcc | 240 |
| ccggctcagg | gccaagaaca | gatggtcccc | agatgcggtc | cagccctcag | cagtttctag | 300 |
| agaaccatca | gatgtttcca | gggtgcccca | aggacctgaa | atgaccctgt | gccttatttg | 360 |
| aactaaccaa | tcagttcgct | tctcgcttct | gttcgcgcgc | ttatgctccc | cgagctcaat | 420 |
| aaaagagccc | acaacccctc | actcggggcg | ccagtcctcc | gattgactga | gtcgcccggg | 480 |
| tacccgtgta | tccaataaac | cctcttgcag | ttgcatccga | cttgtggtct | cgctgttcct | 540 |
| tgggagggtc | tcctctgagt | gattgactac | ccgtcagcgg | gggtctttca | tttggggct | 600 |
| cgtccgggat | cgggagaccc | ctgcccaggg | accaccgacc | caccaccggg | aggtaagctg | 660 |
| gccagcaact | tatctgtgtc | tgtccgattg | tctagtgtct | atgactgatt | ttatgcgcct | 720 |
| gcgtcggtac | tagttagcta | actagctctg | tatctggcgg | acccgtggtg | gaactgacga | 780 |

-continued

```
gttcggaaca cccggccgca accctgggag acgtcccagg gacttcgggg gccgttttg     840
tggcccgacc tgagtcctaa aatcccgatc gtttaggact cttggtgca cccccttag      900
aggagggata tgtggttctg gtaggagacg agaacctaaa acagttcccg cctccgtctg    960
aattttgct ttcggtttgg gaccgaagcc gcgccgcgcg tcttgtctgc tgcagcatcg    1020
ttctgtgttg tctctgtctg actgtgtttc tgtatttgtc tgaaaatatg ggcccgggct   1080
agcctgttac cactcccta agtttgacct taggtcactg gaaagatgtc gagcggatcg    1140
ctcacaacca gtcggtagat gtcaagaaga gacgttgggt taccttctgc tctgcagaat   1200
ggccaacctt taacgtcgga tggccgcgag acggcacctt taaccgagac ctcatcaccc   1260
aggttaagat caaggtcttt tcacctggcc cgcatggaca cccagaccag gtggggtaca   1320
tcgtgacctg ggaagccttg cttttgacc cccctccctg ggtcaagccc tttgtacacc    1380
ctaagcctcc gcctcctctt cctccatccg ccccgtctct cccccttgaa cctcctcgtt   1440
cgaccccgcc tcgatcctcc ctttatccag ccctcactcc ttctctaggc gcccccatat   1500
ggccatatga gatcttatat ggggcacccc cgccccttgt aaacttccct gaccctgaca   1560
tgacaagagt tactaacagc ccctctctcc aagctcactt acaggctctc tacttagtcc   1620
agcacgaagt ctggagacct ctggcggcag cctaccaaga acaactggac cgaccggtgg   1680
tacctcaccc ttaccgagtc ggcgacacag tgtgggtccg ccgacaccag actaagaacc   1740
tagaacctcg ctggaaagga ccttacacag tcctgctgac caccccccacc gccctcaaag  1800
tagacggcat cgcagcttgg atacacgccg cccacgtgaa ggctgccgac cccggggtg    1860
gaccatcctc tagactgcca tgctcgaggg agtgcaggtg gaaaccatct ccccaggaga   1920
cgggcgcacc ttccccaagc gcggccagac ctgcgtggtg cactacaccg ggatgcttga   1980
agatggaaag aaagttgatt cctcccggga cagaaacaag cccttaagt ttatgctagg    2040
caagcaggag gtgatccgag gctgggaaga aggggttgcc cagatgagtg tgggtcagag   2100
agccaaactg actatatctc cagattatgc ctatggtgcc actgggcacc caggcatcat   2160
cccaccacat gccactctcg tcttcgatgt ggagcttcta aaactggaat ctggcggtgg   2220
atccggagtc gacggatttg gtgatgtcgg tgctcttgag agtttgaggg gaaatgcaga   2280
tttggcttac atcctgagca tggagccctg tggccactgc ctcattatca acaatgtgaa   2340
cttctgccgt gagtccgggc tccgcacccg cactggctcc aacatcgact gtgagaagtt   2400
gcggcgtcgc ttctcctcgc tgcatttcat ggtggaggtg aagggcgacc tgactgccaa   2460
gaaaatggtg ctggctttgc tggagctggc gcagcaggac cacggtgctc tggactgctg   2520
cgtggtggtc attctctctc acggctgtca ggccagccac ctgcagttcc cagggctgt    2580
ctacggcaca gatggatgcc ctgtgtcggt cgagaagatt gtgaacatct tcaatgggac   2640
cagctgcccc agcctgggag ggaagcccaa gctcttttc atccaggcct gtggtgggga   2700
gcagaaagac catgggtttg aggtggcctc cacttcccct gaagacgagt ccctggcag    2760
taaccccgag ccagatgcca ccccgttcca ggaaggtttg aggaccttcg accagctgga   2820
cgccatatct agtttgccca cacccagtga catctttgtg tcctactcta ctttcccagg   2880
ttttgtttcc tggagggacc ccaagagtgg ctcctggtac gttgagaccc tggacgacat   2940
ctttgagcag tgggctcact ctgaagacct gcagtccctc ctgcttaggg tcgctaatgc   3000
tgtttcggtg aaagggattt ataaacagat gcctggttgc tttaatttcc tccggaaaaa   3060
acttttcttt aaaacatcag ctagcagagc cgagggcagg ggaagtcttc taacatgcgg   3120
ggacgtggag gaaaatcccg ggcccatgcc acctcctcgc ctcctcttct tcctcctctt   3180
```

```
cctcaccccc atggaagtca ggcccgagga acctctagtg gtgaaggtgg aagagggaga    3240
taacgctgtg ctgcagtgcc tcaaggggac ctcagatggc cccactcagc agctgacctg    3300
gtctcgggag tccccgctta aaccttctt  aaaactcagc ctggggctgc caggcctggg    3360
aatccacatg aggcccctgg ccatctggct tttcatcttc aacgtctctc aacagatggg    3420
gggcttctac ctgtgccagc cggggccccc ctctgagaag gcctggcagc ctggctggac    3480
agtcaatgtg gagggcagcg gggagctgtt ccggtggaat gtttcggacc taggtggcct    3540
gggctgtggc ctgaagaaca ggtcctcaga gggccccagc tccccttccg ggaagctcat    3600
gagccccaag ctgtatgtgt gggccaaaga ccgccctgag atctgggagg gagagcctcc    3660
gtgtctccca ccgagggaca gcctgaacca gagcctcagc caggacctca ccatggcccc    3720
tggctccaca ctctggctgt cctgtggggt accccctgac tctgtgtcca ggggccccct    3780
ctcctggacc catgtgcacc ccaaggggcc taagtcattg ctgagcctag agctgaagga    3840
cgatcgcccg gccagagata tgtgggtaat ggagacgggt ctgttgttgc cccggggccac   3900
agctcaagac gctggaaagt attattgtca ccgtggcaac ctgaccatgt cattccacct    3960
ggagatcact gctcggccag tactatggca ctggctgctg aggactggtg gctgaaggt     4020
ctcagctgtg actttggctt atctgatctt ctgcctgtgt tcccttgtgg gcattcttca    4080
tcttcaaaga gccctggtcc tgaggaggaa aagaaagcga atgactgacc ccaccaggag    4140
attctaacgc gtcatcatcg atccggatta gtccaatttg ttaaagacag gatatcagtg    4200
gtccaggctc tagttttgac tcaacaatat caccagctga gcctataga  gtacgagcca    4260
tagataaaat aaaagatttt atttagtctc cagaaaagg  ggggaatgaa agaccccacc    4320
tgtaggtttg gcaagctagc ttaagtaacg ccattttgca aggcatggaa aaatacataa    4380
ctgagaatag agaagttcag atcaaggtca ggaacagatg gaacagctga atatgggcca    4440
aacaggatat ctgtggtaag cagttcctgc cccggctcag ggccaagaac agatggaaca    4500
gctgaatatg ggccaaacag gatatctgtg gtaagcagtt cctgccccgg ctcagggcca    4560
agaacagatg gtccccagat gcggtccagc cctcagcagt ttctagagaa ccatcagatg    4620
tttccagggt gccccaagga cctgaaatga ccctgtgcct tatttgaact aaccaatcag    4680
ttcgcttctc gcttctgttc gcgcgcttct gctccccgag ctcaataaaa gagcccacaa    4740
cccctcactc ggggcgccag tcctccgatt gactgagtcg cccgggtacc cgtgtatcca    4800
ataaaccctc ttgcagttgc atccgacttg tggtctcgct gttccttggg agggtctcct    4860
ctgagtgatt gactacccgt cagcggggt  ctttcacaca tgcagcatgt atcaaaatta    4920
atttggtttt ttttcttaag tatttacatt aaatggccat agtacttaaa gttacattgg    4980
cttccttgaa ataaacatgg agtattcaga atgtgtcata atatttcta  attttaagat    5040
agtatctcca ttggctttct acttttcctt ttatttttt  ttgtcctctg tcttccattt    5100
gttgttgttg ttgtttgttt gtttgtttgt tggttggttg gttaattttt ttttaaagat    5160
cctacactat agttcaagct agactattag ctactctgta acccagggtg accttgaagt    5220
catgggtagc ctgctgttt  agccttccca catctaagat tacaggtatg agctatcatt    5280
tttggtatat tgattgattg attgattgat gtgtgtgtgt gtgattgtgt ttgtgtgtgt    5340
gactgtgaaa atgtgtgtat gggtgtgtgt gaatgtgtgt atgtatgtgt gtgtgtgagt    5400
gtgtgtgtgt gtgtgtgcat gtgtgtgtgt gtgactgtgt ctatgtgtat gactgtgtgt    5460
gtgtgtgtgt gtgtgtgtgt gtgtgtgtgt tgtgaaaaaa tattctatgg                5520
```

```
tagtgagagc caacgctccg gctcaggtgt caggttggtt tttgagacag agtctttcac    5580
ttagcttgga attcactggc cgtcgtttta caacgtcgtg actgggaaaa ccctggcgtt    5640
acccaactta atcgccttgc agcacatccc cctttcgcca gctggcgtaa tagcgaagag    5700
gcccgcaccg atcgcccttc ccaacagttg cgcagcctga atggcgaatg cgcctgatg    5760
cggtattttc tccttacgca tctgtgcggt atttcacacc gcatatggtg cactctcagt    5820
acaatctgct ctgatgccgc atagttaagc cagccccgac acccgccaac acccgctgac    5880
gcgccctgac gggcttgtct gctcccggca tccgcttaca gacaagctgt gaccgtctcc    5940
gggagctgca tgtgtcagag gttttcaccg tcatcaccga aacgcgcgat gacgaaaggg    6000
cctcgtgata cgcctatttt tataggttaa tgtcatgata taatggtttt cttagacgtc    6060
aggtggcact tttcgggaa atgtgcgcgg aaccccctatt tgtttatttt tctaaataca    6120
ttcaaatatg tatccgctca tgagacaata accctgataa atgcttcaat aatattgaaa    6180
aaggaagagt atgagtattc aacatttccg tgtcgccctt attccctttt ttgcggcatt    6240
ttgccttcct gtttttgctc acccagaaac gctggtgaaa gtaaagatg ctgaagatca    6300
gttgggtgca cgagtgggtt acatcgaact ggatctcaac agcggtaaga tccttgagag    6360
ttttcgcccc gaagaacgtt ttccaatgat gagcactttt aaagttctgc tatgtggcgc    6420
ggtattatcc cgtattgacg ccgggcaaga gcaactcggt cgccgcatac actattctca    6480
gaatgacttg gttgagtact caccagtcac agaaaagcat cttacggatg gcatgacagt    6540
aagagaatta tgcagtgctg ccataaccat gagtgataac actgcggcca acttacttct    6600
gacaacgatc ggaggaccga aggagctaac cgcttttttg cacaacatgg gggatcatgt    6660
aactcgcctt gatcgttggg aaccggagct gaatgaagcc ataccaaacg acgagcgtga    6720
caccacgatg cctgtagcaa tggcaacaac gttgcgcaaa ctattaactg gcgaactact    6780
tactctagct tcccggcaac aattaataga ctggatggag gcggataaag ttgcaggacc    6840
acttctgcgc tcggcccttc cggctggctg gtttattgct gataaatctg gagccggtga    6900
gcgtgggtct cgcggtatca ttgcagcact ggggccagat ggtaagccct cccgtatcgt    6960
agttatctac acgacgggga gtcaggcaac tatggatgaa cgaaatagac agatcgctga    7020
gataggtgcc tcactgatta agcattggta actgtcagac caagtttact catatatact    7080
ttagattgat ttaaaacttc attttttaatt taaaaggatc taggtgaaga tcctttttga    7140
taatctcatg accaaaatcc cttaacgtga gttttcgttc cactgagcgt cagaccccgt    7200
agaaaagatc aaaggatctt cttgagatcc tttttttctg cgcgtaatct gctgcttgca    7260
aacaaaaaaa ccaccgctac cagcggtggt ttgtttgccg gatcaagagc taccaactct    7320
ttttccgaag gtaactggct tcagcagagc gcagatacca aatactgtcc ttctagtgta    7380
gccgtagtta ggccaccact tcaagaactc tgtagcaccg cctacatacc tcgctctgct    7440
aatcctgtta ccagtggctg ctgccagtgg cgataagtcg tgtcttaccg ggttggactc    7500
aagacgatag ttaccggata aggcgcagcg gtcgggctga acggggggtt cgtgcacaca    7560
gcccagcttg gagcgaacga cctacaccga actgagatac ctacagcgtg agcattgaga    7620
aagcgccacg cttcccgaag ggagaaaggc ggacaggtat ccggtaagcg gcagggtcgg    7680
aacaggagag cgcacgaggg agcttccagg gggaaacgcc tggtatcttt atagtcctgt    7740
cgggtttcgc cacctctgac ttgagcgtcg atttttgtga tgctcgtcag ggggggcggag    7800
cctatgaaa aacgccagca acgcggcctt tttacggttc ctggcctttt gctggccttt    7860
tgctcacatg ttctttcctg cgttatcccc tgattctgtg gataaccgta ttaccgcctt    7920
```

```
tgagtgagct gataccgctc gccgcagccg aacgaccgag cgcagcgagt cagtgagcga    7980
ggaagcggaa gagcgcccaa tacgcaaacc gcctctcccc gcgcgttggc cgattcatta    8040
atgcagctgg cacgacaggt ttcccgactg gaaagcgggc agtgagcgca acgcaattaa    8100
tgtgagttag ctcactcatt aggcacccca ggctttacac tttatgcttc cggctcgtat    8160
gttgtgtgga attgtgagcg gataacaatt tcacacagga aacagctatg accatgatta    8220
cgccaagctt tgctcttagg agtttcctaa tacatcccaa actcaaatat ataaagcatt    8280
tgacttgttc tatgccctag ggggcggggg gaagctaagc cagcttttt taacatttaa     8340 aatgttaatt ccattttaaa tgcacagatg ttttatttc ataagggttt caatgtgcat     8400
gaatgctgca atattcctgt taccaaagct agtataaata aaaatagata aacgtggaaa    8460
ttacttagag tttctgtcat taacgtttcc ttcctcagtt gacaacataa atgcgctgct    8520
gagcaagcca gtttgcatct gtcaggatca atttcccatt atgccagtca tattaattac    8580
tagtcaatta gttgattttt attttgaca tatacatgtg aa                       8622
```

```
<210> SEQ ID NO 18
<211> LENGTH: 678
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
```

```
ctcgagggcg tccaagtcga aaccattagt cccggcgatg gcagaacatt tcctaaaagg      60
ggacaaacat gtgtcgtcca ttatacaggc atgttggagg acggcaaaaa ggtggacagt     120
agtagagatc gcaataaacc tttcaaattc atgttgggaa acaagaagt cattagggga     180 tgggaggagg gcgtggctca aatgtccgtc ggccaacgcg ctaagctcac catcagcccc    240
gactacgcat acgcgctac cggacatccc ggaattattc cccctcacgc taccttggtg    300
tttgacgtcg aactgttgaa gctcgaagtc gagggagtgc aggtggaaac catctcccca    360
ggagacgggc gcaccttccc caagcgcggc cagacctgcg tggtgcacta caccgggatg    420
cttgaagatg gaaagaaagt tgattcctcc cgggacagaa acaagcccctt taagtttatg    480 ctaggcaagc aggaggtgat ccgaggctgg gaagaagggg ttgcccagat gagtgtgggt    540
cagagagcca aactgactat atctccagat tatgcctatg gtgccactgg gcacccaggc    600
atcatcccac acatgccac tctcgtcttc gatgtggagc ttctaaaact ggaatctggc    660
ggtggatccg gagtcgag                                                  678
```

```
<210> SEQ ID NO 19
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45
```

Met Leu Gly Lys Gln Glu Val Ile Arg Gly Trp Glu Glu Gly Val Ala
            50                  55                  60

Gln Met Ser Val Gly Gln Arg Ala Lys Leu Thr Ile Ser Pro Asp Tyr
 65                  70                  75                  80

Ala Tyr Gly Ala Thr Gly His Pro Gly Ile Ile Pro Pro His Ala Thr
                 85                  90                  95

Leu Val Phe Asp Val Glu Leu Leu Lys Leu Glu Val Glu Gly Val Gln
            100                 105                 110

Val Glu Thr Ile Ser Pro Gly Asp Gly Arg Thr Phe Pro Lys Arg Gly
        115                 120                 125

Gln Thr Cys Val Val His Tyr Thr Gly Met Leu Glu Asp Gly Lys Lys
    130                 135                 140

Val Asp Ser Ser Arg Asp Arg Asn Lys Pro Phe Lys Phe Met Leu Gly
145                 150                 155                 160

Lys Gln Glu Val Ile Arg Gly Trp Glu Glu Gly Val Ala Gln Met Ser
                165                 170                 175

Val Gly Gln Arg Ala Lys Leu Thr Ile Ser Pro Asp Tyr Ala Tyr Gly
            180                 185                 190

Ala Thr Gly His Pro Gly Ile Ile Pro Pro His Ala Thr Leu Val Phe
        195                 200                 205

Asp Val Glu Leu Leu Lys Leu Glu Ser Gly Gly Ser Gly
    210                 215                 220

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ala Lys Phe Lys Gln Leu Leu
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Gly Gly Gly Ser
1               5

<210> SEQ ID NO 22
<211> LENGTH: 7
<212> TYPE: PRT
<213> ORGANISM: Homo sapiens

<400> SEQUENCE: 22

Thr Asp Pro Thr Arg Arg Phe
1               5

<210> SEQ ID NO 23
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 23

Asn Leu Val Pro Met Val Ala Thr Val
1               5

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tccgccctga gcaaagac                                                   18

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acgaactcca gcaggaccat                                                 20

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
acgagaagcg cgatc                                                      15

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctggaatctg gcggtggat                                                  19

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
caaactctca agagcaccga cat                                             23

<210> SEQ ID NO 29
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 29
cggagtcgac ggatt                                                    15
```